US011136381B2

(12) United States Patent
Duey et al.

(10) Patent No.: US 11,136,381 B2
(45) Date of Patent: Oct. 5, 2021

(54) ANTI-C3 ANTIBODIES

(71) Applicant: NGM Biopharmaceuticals, Inc., South San Francisco, CA (US)

(72) Inventors: Dana Yen Mei Duey, San Francisco, CA (US); Zhonghao Liu, Redwood City, CA (US); Jie Tang, Palo Alto, CA (US); Yan Wang, Foster City, CA (US); Yiyuan Yin, Fremont, CA (US); Wenwu Zhai, Redwood City, CA (US); Jared Martin Higbee, San Francisco, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 104 days.

(21) Appl. No.: 16/371,684

(22) Filed: Apr. 1, 2019

(65) Prior Publication Data

US 2019/0322730 A1    Oct. 24, 2019

Related U.S. Application Data

(60) Provisional application No. 62/652,253, filed on Apr. 3, 2018.

(51) Int. Cl.
*C07K 16/18* (2006.01)
*A61K 39/395* (2006.01)

(52) U.S. Cl.
CPC .......... *C07K 16/18* (2013.01); *C07K 2317/24* (2013.01); *C07K 2317/31* (2013.01); *C07K 2317/565* (2013.01); *C07K 2317/622* (2013.01); *C07K 2317/624* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,816,497 B2 | 10/2010 | Ambati | |
| 8,012,473 B2 | 9/2011 | Campagne | |
| 8,168,584 B2 | 5/2012 | Deschatelets et al. | |
| 8,192,742 B2 | 6/2012 | Bansal | |
| 8,377,437 B2 | 2/2013 | Campagne | |
| 9,291,622 B2 | 3/2016 | Zhang et al. | |
| 9,745,367 B2 | 8/2017 | Bansal | |
| 2008/0233113 A1 | 9/2008 | Bansal | |
| 2009/0004183 A1 | 1/2009 | Taylor et al. | |
| 2010/0291106 A1 | 11/2010 | Etemad-Gilbertson et al. | |
| 2011/0020237 A1 | 1/2011 | Glabe et al. | |
| 2012/0065124 A1 | 3/2012 | Morishita et al. | |
| 2013/0078245 A1 | 3/2013 | Holers et al. | |
| 2013/0177567 A1 | 7/2013 | Skjoedt et al. | |
| 2014/0050739 A1 | 2/2014 | Francois et al. | |
| 2016/0319002 A1 | 11/2016 | Bansal | |
| 2017/0355730 A1 | 12/2017 | Pei et al. | |
| 2018/0346531 A1 | 12/2018 | Pyles | |
| 2019/0015521 A1 | 1/2019 | Roizman | |

FOREIGN PATENT DOCUMENTS

| | | |
|---|---|---|
| WO | WO 2004/031240 | 4/2004 |
| WO | WO 2007/056227 | 5/2007 |
| WO | WO 2007/084765 | 7/2007 |
| WO | WO 2010/136311 | 12/2010 |
| WO | WO 2017/062879 | 4/2017 |

OTHER PUBLICATIONS

Rudikoff et al., Proc Natl Acad Sci USA 79: 1979-1983 (1982). (Year: 1982).*
Colman, Research in Immunology 145: 33-36 (1994.) (Year: 1994).*
Kussie et al., J. Immunol. 152: 146-152 (1994). (Year: 1994).*
Chen et al., EMBO J., 14: 2784-2794 (1995). (Year: 1995).*
D'Angelo et al., Many Routes to an Antibody Heavy-Chain CDR3: Necessary, Yet Insufficient, for Specific Binding; Frontiers in Immunology vol. 9, Article 395 Mar. 2018; doi:10.3389/fimmu.2018. 00395. (Year: 2018).*
Piche-Nicholas et al., Changes in complemetarity-determining regions significantly alter IgG binding to the neonatal Fc receptor (FcRN) and pharmacokinetics; MABS 2018, vol. 10, No. 1, 81-94, doi.org/ 10.1080/19420862.2017.1389355. (Year: 2018).*
PCT International Preliminary Report on Patentability in International Appl. No. PCT/US2019/025123, dated Oct. 6, 2020, 15 pages.
PCT Invitation to Pay Additional Fees and, Where Applicable, Protest Fee in International Appl. No. PCT/US2019/025123, dated Jul. 16, 2019, 20 pages.
PCT International Search Report and Written Opinion in International Appl. No. PCT/US2019/025123, dated Sep. 11, 2019, 26 pages.
Alcorlo et al, "Structural Insights on Complement Activation," FEBS Journal, 2015, 282:3883-3891.
Al-Zamil & Yassin, "Recent developments in age-related macular degeneration: a review," Clinical Interventions in Aging, 2017, 12:1313-1330.
Anderson et al, "The Pivotal Role of the Complement System in Aging and Age related Macular Degeneration: Hypothesis Revisited," Prog. Retin. Eye Res., Mar. 2010, 29(2):95-112.
Boyer et al, "The pathophysiology of geographic atrophy secondary to age-related macular degeneration and the complement pathway as a therapeutic target," Retina, May 2017, 37(5):819-835.
Campagne et al, "Age-related macular degeneration: Complement in action," Immunobiology, 2016, 221:733-739.

(Continued)

*Primary Examiner* — Phillip Gambel
(74) *Attorney, Agent, or Firm* — Fish & Richardson P.C.

(57) ABSTRACT

The present disclosure provides binding agents, such as antibodies (including single chain variable fragments), that specifically bind complement component C3, including human C3, compositions comprising same, and methods of their use. The disclosure also provides related polynucleotides and vectors encoding the binding agents and cells comprising same.

44 Claims, 6 Drawing Sheets

Specification includes a Sequence Listing.

(56) References Cited

OTHER PUBLICATIONS

Chi et al, "Chapter 9. Suppression of Drusen Formation by Compstatin, a Peptide Inhibitor of Complement C3 activation, on Cynomolgus Monkey with Early-Onset Macular Degeneration," Adv. Exp. Med. Biol., 2010, 703:127-135.

Danis et al, "Geographic atrophy in patients with advanced dry age-related macular degeneration: current challenges and future prospects," Clinical Ophthalmology, 2015, 9:2159-2174.

De Cogan al., "Topical Delivery of Anti-VEGF Drugs to the Ocular Posterior Segment Using Cell-Penetrating Peptides," Investigative Ophthalmology & Visual Science, 2017, 58(5):2578-2590.

Fernandez-Gordino et al, "A local complement response by RPE causes early-stage macular degeneration," Human Molecular Genetics, 2015, 1-15.

Fritsche et al, "A large genome-wide association study of age-related macular degeneration highlights contributions of rare and common variants," Nature Genetics, Feb. 2016, 48(2):134-146.

Fritsche et al, "Seven new loci associated with age-related macular degeneration," Nature Genetics, Apr. 2013, 45(4):433-441.

GenBank Accession No. XP 005587776.1, "Predicted: complement C3 [Macaca fascicularis]," dated Jan. 25, 2016, 3 pages.

Ghosh et al, "Long-acting protein drugs for the treatment of ocular diseases," Nature Communications, Mar. 2017, 8:14837, 10 pages.

Hidalgo et al, "Functional and structural characterization of four mouse monoclonal antibodies to complement C3 with potential therapeutic and diagnostic applications," Eur. J. Immunol., 2017, 47:504-515.

Janssen et al, "Structure of Compstatin in Complex with Complement Component C3c Reveals a New Mechanism of Complement Inhibition," Journal of Biological Chemistry, Oct. 2007, 282(40):29241-29247.

Johnson et al, "Cell culture model that mimics drusen formation and triggers complement activation associated with age-related macular degeneration," PNAS, Nov. 2011, 108(45): 18277-18282.

Kam et al, "Complement Component C3 Plays a Critical Role in Protecting the Aging Retina in a Murine Model of Age-Related Macular Degeneration," The American Journal of Pathology, Aug. 2013, 2:481-492.

Katschke et al, "Structural and Functional Analysis of a C3b-specific Antibody That Selectively Inhibits the Alternative Pathway of Complement," The Journal of Biological Chemistry, Apr. 2009, 284(16):10473-10479.

Kawa et al, "Complement System in Pathogenesis of AMD: Dual Player in Degeneration and Protection of Retinal Tissue," Journal of Immunology Research, 2014, 483960, 12 pages.

Kirschfink & Mollness, "Modern Complement Analysis," Clinical and Diagnostic Laboratory Immunology, Nov. 2003, 982-989.

Loyet et al, "Activation of the Alternative Complement Pathway in Vitreous is Controlled by Genetics in Age-Related Macular Degeneration," Investigative Ophthalmology & Visual Science, 53(10):6628-6637.

Loyet et al., "Complement inhibition in cynomolgus monkeys by anti-factor d antigen-binding fragment for the treatment of an advanced form of dry age-related macular degeneration," J Pharmacol and Exp Ther, 2014, 351(3):527-537.

Maller et al, "Variation in complement factor 3 is associated with risk of age related macular degeneration," Nature Genetics, Oct. 2007, 39(10):1200-1201.

Mastellos et al, "Compstatin: a C3-targeted complement inhibitor reaching its prime for bedside intervention," European Journal of Clinical Investigation, 2015, 45:423-440.

Mastellos et al, "From orphan drugs to adopted therapies: Advancing C3-targeted intervention to the clinical stage," Immunobiology, 2016, 221:1046-1057.

Merle et al, "Complement system part I—molecular mechanisms of activation and regulation," Priorities in Immunology, Jun. 2015, 6(262):1-30.

Merle et al, "Complement System part II: Role in Immunity," Frontiers in Immunology, May 2015, 6(257):1-26.

Mohan et al, "Peptide redesign for inhibition of the complement system: Targeting age-related macular degeneration," Molecular Vision, Oct. 2016, 22:1280-1290.

Morikis et al., "Solution structure of Compstatin, a potent complement inhibitor," Protein Science, 1998, 7(3):619-627.

Qu et al, "Novel analogues of the therapeutic complement inhibitor compstatin with significantly improved affinity and potency," Mol. Immunol., Jan. 2011, 48(4):481-489.

Querques et al, "Treatment of Dry Age-Related Macular Degeneration," Ophthalmic Res., Sep. 2014, 52:107-115.

Ricklin & Lambris, "Compstatin: A Complement Inhibitor on its Way to Clinical Application," Adv. Exp. Med. Biol., 2008, 632:273-292.

Rickman et al, "Dry Age-Related Macular Degeneration: Mechanisms, Therapeutic Targets, and Imaging," IOVS, Dec. 2013, 54(14):0RSF68, 13 pages.

Rother et al, "Discovery and development of the complement inhibitor eculizumab for the treatment of paroxysmal nocturnal hemoglobinuria," Nature Biotechnology, Nov. 2007, 25(11):1256-1264.

Sadda et al, "Clinical Endpoints for the Study of Geographic Atrophy Secondary to Age-Related Macular Degeneration," Clinical Endpoints in Geographic Atrophy, 2016, 36(10):1806-1822.

Sahu & Lambris, "Structure and biology of complement protein C3, a connecting link between innate and acquired immunity," Immunological Reviews, 2001, 180:35-48.

Sahu et al, "Compstatin, a peptide inhibitor of complement, exhibits species-specific binding to complement component C3," Molecular Immunology, 2003, 39:557-566.

Thakkinstian et al, "Systematic Review and Meta-Analysis of the Association Between Complement Component 3 and Age-related Macular Degeneration: a HuGE Review and Meta-Analysis," American Journal of Epidemiology, May 2011, 173(12):1365-1379.

Whitmore et al, "Complement activation and choriocapillaris loss in early AMD: Implications for pathophysiology and therapy," Prog. Retin. Eye Res., Mar. 2015, 71 pages.

Xu & Chen, "Targeting the complement system for the management of retinal inflammatory and degenerative diseases," European Journal of Pharmacology, 2016, 787:94-104.

Yanagisawa et al, "A Common Complement C3 Variant Is Associated with Protection against Wet Age-Related Macular Degeneration in a Japanese Population," PLoS One, Dec. 2011, 6(12):e28847, 7 pages.

Yates et al, "Complement C3 Variant and the Risk of Age-Related Macular Degeneration," The New England Journal of Medicine, Aug. 2007, 357-553-561.

\* cited by examiner

SEQUENCE LISTING

<160> NUMBER OF SEQ ID NOS: 232

<210> SEQ ID NO 1
<211> LENGTH: 1663
<212> TYPE: PRT
<213> ORGANISM: Homo sapiens

<400> SEQUENCE: 1

```
Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Leu Val Ser Leu Gln Ser Gly
            115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
            195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365
```

```
Pro Phe Asp Leu Met Val Phe Val Thr Asn Pro Asp Gly Ser Pro Ala
    370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
        435                 440                 445
Val Gly Asn Ser Asn Asn Tyr Leu His Leu Ser Val Leu Arg Thr Glu
450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
            500                 505                 510
Asp Leu Val Val Leu Pro Leu Ser Ile Thr Thr Asp Phe Ile Pro Ser
            515                 520                 525
Phe Arg Leu Val Ala Tyr Tyr Thr Leu Ile Gly Ala Ser Gly Gln Arg
    530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
            580                 585                 590
Val Val Leu Val Ala Val Asp Lys Gly Val Phe Val Leu Asn Lys Lys
        595                 600                 605
Asn Lys Leu Thr Gln Ser Lys Ile Trp Asp Val Val Glu Lys Ala Asp
    610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Ser Gly Gln Gln Thr Ala Gln
                645                 650                 655
Arg Ala Glu Leu Gln Cys Pro Gln Pro Ala Ala Arg Arg Arg Arg Ser
            660                 665                 670
Val Gln Leu Thr Glu Lys Arg Met Asp Lys Val Gly Lys Tyr Pro Lys
        675                 680                 685
Glu Leu Arg Lys Cys Cys Glu Asp Gly Met Arg Glu Asn Pro Met Arg
    690                 695                 700
Phe Ser Cys Gln Arg Arg Thr Arg Phe Ile Ser Leu Gly Glu Ala Cys
705                 710                 715                 720
Lys Lys Val Phe Leu Asp Cys Cys Asn Tyr Ile Thr Glu Leu Arg Arg
                725                 730                 735
Gln His Ala Arg Ala Ser His Leu Gly Leu Ala Arg Ser Asn Leu Asp
            740                 745                 750
Glu Asp Ile Ile Ala Glu Glu Asn Ile Val Ser Arg Ser Glu Phe Pro
        755                 760                 765
Glu Ser Trp Leu Trp Asn Val Glu Asp Leu Lys Glu Pro Pro Lys Asn
    770                 775                 780
Gly Ile Ser Thr Lys Leu Met Asn Ile Phe Leu Lys Asp Ser Ile Thr
```

-continued

```
            785                 790                 795                 800
Thr Trp Glu Ile Leu Ala Val Ser Met Ser Asp Lys Gly Ile Cys
                    805                 810                 815

Val Ala Asp Pro Phe Glu Val Thr Val Met Gln Asp Phe Phe Ile Asp
                    820                 825                 830

Leu Arg Leu Pro Tyr Ser Val Arg Asn Glu Gln Val Glu Ile Arg
                    835                 840                 845

Ala Val Leu Tyr Asn Tyr Arg Gln Asn Gln Glu Leu Lys Val Arg Val
        850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                    885                 890                 895

Pro Tyr Val Ile Val Pro Leu Lys Thr Gly Leu Gln Glu Val Glu Val
                    900                 905                 910

Lys Ala Ala Val Tyr His His Phe Ile Ser Asp Gly Val Arg Lys Ser
                    915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                    965                 970                 975

Glu Thr Arg Ile Leu Leu Gln Gly Thr Pro Val Ala Gln Met Thr Glu
                    980                 985                 990

Asp Ala Val Asp Ala Glu Arg Leu  Lys His Leu Ile Val  Thr Pro Ser
        995                 1000                1005

Gly Cys Gly Glu Gln Asn Met  Ile Gly Met Thr Pro  Thr Val Ile
        1010                1015                1020

Ala Val His Tyr Leu Asp Glu  Thr Glu Gln Trp Glu  Lys Phe Gly
        1025                1030                1035

Leu Glu Lys Arg Gln Gly Ala  Leu Glu Leu Ile Lys  Lys Gly Tyr
        1040                1045                1050

Thr Gln Gln Leu Ala Phe Arg  Gln Pro Ser Ser Ala  Phe Ala Ala
        1055                1060                1065

Phe Val Lys Arg Ala Pro Ser  Thr Trp Leu Thr Ala  Tyr Val Val
        1070                1075                1080

Lys Val Phe Ser Leu Ala Val  Asn Leu Ile Ala Ile  Asp Ser Gln
        1085                1090                1095

Val Leu Cys Gly Ala Val Lys  Trp Leu Ile Leu Glu  Lys Gln Lys
        1100                1105                1110

Pro Asp Gly Val Phe Gln Glu  Asp Ala Pro Val Ile  His Gln Glu
        1115                1120                1125

Met Ile Gly Gly Leu Arg Asn  Asn Asn Glu Lys Asp  Met Ala Leu
        1130                1135                1140

Thr Ala Phe Val Leu Ile Ser  Leu Gln Glu Ala Lys  Asp Ile Cys
        1145                1150                1155

Glu Glu Gln Val Asn Ser Leu  Pro Gly Ser Ile Thr  Lys Ala Gly
        1160                1165                1170

Asp Phe Leu Glu Ala Asn Tyr  Met Asn Leu Gln Arg  Ser Tyr Thr
        1175                1180                1185

Val Ala Ile Ala Gly Tyr Ala  Leu Ala Gln Met Gly  Arg Leu Lys
        1190                1195                1200
```

-continued

```
Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Lys Asp Ala Pro Asp His Gln Glu Leu Asn
    1280                1285                1290

Leu Asp Val Ser Leu Gln Leu Pro Ser Arg Ser Ser Lys Ile Thr
    1295                1300                1305

His Arg Ile His Trp Glu Ser Ala Ser Leu Leu Arg Ser Glu Glu
    1310                1315                1320

Thr Lys Glu Asn Glu Gly Phe Thr Val Thr Ala Glu Gly Lys Gly
    1325                1330                1335

Gln Gly Thr Leu Ser Val Val Thr Met Tyr His Ala Lys Ala Lys
    1340                1345                1350

Asp Gln Leu Thr Cys Asn Lys Phe Asp Leu Lys Val Thr Ile Lys
    1355                1360                1365

Pro Ala Pro Glu Thr Glu Lys Arg Pro Gln Asp Ala Lys Asn Thr
    1370                1375                1380

Met Ile Leu Glu Ile Cys Thr Arg Tyr Arg Gly Asp Gln Asp Ala
    1385                1390                1395

Thr Met Ser Ile Leu Asp Ile Ser Met Met Thr Gly Phe Ala Pro
    1400                1405                1410

Asp Thr Asp Asp Leu Lys Gln Leu Ala Asn Gly Val Asp Arg Tyr
    1415                1420                1425

Ile Ser Lys Tyr Glu Leu Asp Lys Ala Phe Ser Asp Arg Asn Thr
    1430                1435                1440

Leu Ile Ile Tyr Leu Asp Lys Val Ser His Ser Glu Asp Asp Cys
    1445                1450                1455

Leu Ala Phe Lys Val His Gln Tyr Phe Asn Val Glu Leu Ile Gln
    1460                1465                1470

Pro Gly Ala Val Lys Val Tyr Ala Tyr Tyr Asn Leu Glu Glu Ser
    1475                1480                1485

Cys Thr Arg Phe Tyr His Pro Glu Lys Glu Asp Gly Lys Leu Asn
    1490                1495                1500

Lys Leu Cys Arg Asp Glu Leu Cys Arg Cys Ala Glu Glu Asn Cys
    1505                1510                1515

Phe Ile Gln Lys Ser Asp Asp Lys Val Thr Leu Glu Glu Arg Leu
    1520                1525                1530

Asp Lys Ala Cys Glu Pro Gly Val Asp Tyr Val Tyr Lys Thr Arg
    1535                1540                1545

Leu Val Lys Val Gln Leu Ser Asn Asp Phe Asp Glu Tyr Ile Met
    1550                1555                1560

Ala Ile Glu Gln Thr Ile Lys Ser Gly Ser Asp Glu Val Gln Val
    1565                1570                1575

Gly Gln Gln Arg Thr Phe Ile Ser Pro Ile Lys Cys Arg Glu Ala
    1580                1585                1590
```

-continued

```
Leu Lys Leu Glu Glu Lys Lys His Tyr Leu Met Trp Gly Leu Ser
    1595                1600                1605

Ser Asp Phe Trp Gly Glu Lys Pro Asn Leu Ser Tyr Ile Ile Gly
    1610                1615                1620

Lys Asp Thr Trp Val Glu His Trp Pro Glu Glu Asp Glu Cys Gln
    1625                1630                1635

Asp Glu Glu Asn Gln Lys Gln Cys Gln Asp Leu Gly Ala Phe Thr
    1640                1645                1650

Glu Ser Met Val Val Phe Gly Cys Pro Asn
    1655                1660

<210> SEQ ID NO 2
<211> LENGTH: 1641
<212> TYPE: PRT
<213> ORGANISM: Homo sapiens

<400> SEQUENCE: 2

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
                20                  25                  30

Val Thr Val Thr Val His Asp Phe Pro Gly Lys Lys Leu Val Leu Ser
            35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Pro Arg Ala Glu Asp Leu Val Gly Lys Ser Leu Tyr Val
    290                 295                 300
```

```
Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
            325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
            355                 360                 365

Val Gln Gly Glu Asp Thr Val Gln Ser Leu Thr Gln Gly Asp Gly Val
    370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
            405                 410                 415

Arg Thr Met Gln Ala Leu Pro Tyr Ser Thr Val Gly Asn Ser Asn Asn
            420                 425                 430

Tyr Leu His Leu Ser Val Leu Arg Thr Glu Leu Arg Pro Gly Glu Thr
        435                 440                 445

Leu Asn Val Asn Phe Leu Leu Arg Met Asp Arg Ala His Glu Ala Lys
450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
            485                 490                 495

Leu Ser Ile Thr Thr Asp Phe Ile Pro Ser Phe Arg Leu Val Ala Tyr
        500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
            565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
        595                 600                 605

Ser Gly Lys Asp Tyr Ala Gly Val Phe Ser Asp Ala Gly Leu Thr Phe
        610                 615                 620

Thr Ser Ser Ser Gly Gln Gln Thr Ala Gln Arg Ala Glu Leu Gln Cys
625                 630                 635                 640

Pro Gln Pro Ala Ala Arg Arg Arg Arg Ser Val Gln Leu Thr Glu Lys
            645                 650                 655

Arg Met Asp Lys Val Gly Lys Tyr Pro Lys Glu Leu Arg Lys Cys Cys
            660                 665                 670

Glu Asp Gly Met Arg Glu Asn Pro Met Arg Phe Ser Cys Gln Arg Arg
        675                 680                 685

Thr Arg Phe Ile Ser Leu Gly Glu Ala Cys Lys Lys Val Phe Leu Asp
        690                 695                 700

Cys Cys Asn Tyr Ile Thr Glu Leu Arg Arg Gln His Ala Arg Ala Ser
705                 710                 715                 720
```

```
His Leu Gly Leu Ala Arg Ser Asn Leu Asp Glu Asp Ile Ile Ala Glu
            725                 730                 735

Glu Asn Ile Val Ser Arg Ser Glu Phe Pro Glu Ser Trp Leu Trp Asn
        740                 745                 750

Val Glu Asp Leu Lys Glu Pro Pro Lys Asn Gly Ile Ser Thr Lys Leu
        755                 760                 765

Met Asn Ile Phe Leu Lys Asp Ser Ile Thr Thr Trp Glu Ile Leu Ala
        770                 775                 780

Val Ser Met Ser Asp Lys Lys Gly Ile Cys Val Ala Asp Pro Phe Glu
785                 790                 795                 800

Val Thr Val Met Gln Asp Phe Phe Ile Asp Leu Arg Leu Pro Tyr Ser
                805                 810                 815

Val Val Arg Asn Glu Gln Val Glu Ile Arg Ala Val Leu Tyr Asn Tyr
            820                 825                 830

Arg Gln Asn Gln Glu Leu Lys Val Arg Val Glu Leu Leu His Asn Pro
        835                 840                 845

Ala Phe Cys Ser Leu Ala Thr Thr Lys Arg Arg His Gln Gln Thr Val
        850                 855                 860

Thr Ile Pro Pro Lys Ser Ser Leu Ser Val Pro Tyr Val Ile Val Pro
865                 870                 875                 880

Leu Lys Thr Gly Leu Gln Glu Val Glu Val Lys Ala Ala Val Tyr His
                885                 890                 895

His Phe Ile Ser Asp Gly Val Arg Lys Ser Leu Lys Val Val Pro Glu
            900                 905                 910

Gly Ile Arg Met Asn Lys Thr Val Ala Val Arg Thr Leu Asp Pro Glu
            915                 920                 925

Arg Leu Gly Arg Glu Gly Val Gln Lys Glu Asp Ile Pro Pro Ala Asp
        930                 935                 940

Leu Ser Asp Gln Val Pro Asp Thr Glu Ser Glu Thr Arg Ile Leu Leu
945                 950                 955                 960

Gln Gly Thr Pro Val Ala Gln Met Thr Glu Asp Ala Val Asp Ala Glu
                965                 970                 975

Arg Leu Lys His Leu Ile Val Thr Pro Ser Gly Cys Gly Glu Gln Asn
            980                 985                 990

Met Ile Gly Met Thr Pro Thr Val Ile Ala Val His Tyr Leu Asp Glu
            995                 1000                1005

Thr Glu Gln Trp Glu Lys Phe Gly Leu Glu Lys Arg Gln Gly Ala
        1010                1015                1020

Leu Glu Leu Ile Lys Lys Gly Tyr Thr Gln Gln Leu Ala Phe Arg
        1025                1030                1035

Gln Pro Ser Ser Ala Phe Ala Ala Phe Val Lys Arg Ala Pro Ser
        1040                1045                1050

Thr Trp Leu Thr Ala Tyr Val Val Lys Val Phe Ser Leu Ala Val
        1055                1060                1065

Asn Leu Ile Ala Ile Asp Ser Gln Val Leu Cys Gly Ala Val Lys
        1070                1075                1080

Trp Leu Ile Leu Glu Lys Gln Lys Pro Asp Gly Val Phe Gln Glu
        1085                1090                1095

Asp Ala Pro Val Ile His Gln Glu Met Ile Gly Gly Leu Arg Asn
        1100                1105                1110

Asn Asn Glu Lys Asp Met Ala Leu Thr Ala Phe Val Leu Ile Ser
        1115                1120                1125

Leu Gln Glu Ala Lys Asp Ile Cys Glu Glu Gln Val Asn Ser Leu
```

```
                1130                1135                1140
Pro Gly Ser Ile Thr Lys Ala Gly Asp Phe Leu Glu Ala Asn Tyr
    1145                1150                1155

Met Asn Leu Gln Arg Ser Tyr Thr Val Ala Ile Ala Gly Tyr Ala
    1160                1165                1170

Leu Ala Gln Met Gly Arg Leu Lys Gly Pro Leu Leu Asn Lys Phe
    1175                1180                1185

Leu Thr Thr Ala Lys Asp Lys Asn Arg Trp Glu Asp Pro Gly Lys
    1190                1195                1200

Gln Leu Tyr Asn Val Glu Ala Thr Ser Tyr Ala Leu Leu Ala Leu
    1205                1210                1215

Leu Gln Leu Lys Asp Phe Asp Phe Val Pro Pro Val Val Arg Trp
    1220                1225                1230

Leu Asn Glu Gln Arg Tyr Tyr Gly Gly Gly Tyr Gly Ser Thr Gln
    1235                1240                1245

Ala Thr Phe Met Val Phe Gln Ala Leu Ala Gln Tyr Gln Lys Asp
    1250                1255                1260

Ala Pro Asp His Gln Glu Leu Asn Leu Asp Val Ser Leu Gln Leu
    1265                1270                1275

Pro Ser Arg Ser Ser Lys Ile Thr His Arg Ile His Trp Glu Ser
    1280                1285                1290

Ala Ser Leu Leu Arg Ser Glu Glu Thr Lys Glu Asn Glu Gly Phe
    1295                1300                1305

Thr Val Thr Ala Glu Gly Lys Gly Gln Gly Thr Leu Ser Val Val
    1310                1315                1320

Thr Met Tyr His Ala Lys Ala Lys Asp Gln Leu Thr Cys Asn Lys
    1325                1330                1335

Phe Asp Leu Lys Val Thr Ile Lys Pro Ala Pro Glu Thr Glu Lys
    1340                1345                1350

Arg Pro Gln Asp Ala Lys Asn Thr Met Ile Leu Glu Ile Cys Thr
    1355                1360                1365

Arg Tyr Arg Gly Asp Gln Asp Ala Thr Met Ser Ile Leu Asp Ile
    1370                1375                1380

Ser Met Met Thr Gly Phe Ala Pro Asp Thr Asp Asp Leu Lys Gln
    1385                1390                1395

Leu Ala Asn Gly Val Asp Arg Tyr Ile Ser Lys Tyr Glu Leu Asp
    1400                1405                1410

Lys Ala Phe Ser Asp Arg Asn Thr Leu Ile Ile Tyr Leu Asp Lys
    1415                1420                1425

Val Ser His Ser Glu Asp Asp Cys Leu Ala Phe Lys Val His Gln
    1430                1435                1440

Tyr Phe Asn Val Glu Leu Ile Gln Pro Gly Ala Val Lys Val Tyr
    1445                1450                1455

Ala Tyr Tyr Asn Leu Glu Glu Ser Cys Thr Arg Phe Tyr His Pro
    1460                1465                1470

Glu Lys Glu Asp Gly Lys Leu Asn Lys Leu Cys Arg Asp Glu Leu
    1475                1480                1485

Cys Arg Cys Ala Glu Glu Asn Cys Phe Ile Gln Lys Ser Asp Asp
    1490                1495                1500

Lys Val Thr Leu Glu Glu Arg Leu Asp Lys Ala Cys Glu Pro Gly
    1505                1510                1515

Val Asp Tyr Val Tyr Lys Thr Arg Leu Val Lys Val Gln Leu Ser
    1520                1525                1530
```

Asn Asp Phe Asp Glu Tyr Ile Met Ala Ile Glu Gln Thr Ile Lys
    1535                1540                1545

Ser Gly Ser Asp Glu Val Gln Val Gly Gln Gln Arg Thr Phe Ile
    1550                1555                1560

Ser Pro Ile Lys Cys Arg Glu Ala Leu Lys Leu Glu Glu Lys Lys
    1565                1570                1575

His Tyr Leu Met Trp Gly Leu Ser Ser Asp Phe Trp Gly Glu Lys
    1580                1585                1590

Pro Asn Leu Ser Tyr Ile Ile Gly Lys Asp Thr Trp Val Glu His
    1595                1600                1605

Trp Pro Glu Glu Asp Glu Cys Gln Asp Glu Glu Asn Gln Lys Gln
    1610                1615                1620

Cys Gln Asp Leu Gly Ala Phe Thr Glu Ser Met Val Val Phe Gly
    1625                1630                1635

Cys Pro Asn
    1640

<210> SEQ ID NO 3
<211> LENGTH: 645
<212> TYPE: PRT
<213> ORGANISM: Homo sapiens

<400> SEQUENCE: 3

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly

```
                    245                 250                 255
Glu Gln Arg Ile Ser Leu Pro Glu Ser Leu Lys Arg Ile Pro Ile Glu
                260                 265                 270

Asp Gly Ser Gly Glu Val Val Leu Ser Arg Lys Val Leu Leu Asp Gly
            275                 280                 285

Val Gln Asn Pro Arg Ala Glu Asp Leu Val Gly Lys Ser Leu Tyr Val
        290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
                340                 345                 350

Phe Val Thr Asn Pro Asp Gly Ser Pro Ala Tyr Arg Val Pro Val Ala
                355                 360                 365

Val Gln Gly Glu Asp Thr Val Gln Ser Leu Thr Gln Gly Asp Gly Val
        370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415

Arg Thr Met Gln Ala Leu Pro Tyr Ser Thr Val Gly Asn Ser Asn Asn
                420                 425                 430

Tyr Leu His Leu Ser Val Leu Arg Thr Glu Leu Arg Pro Gly Glu Thr
                435                 440                 445

Leu Asn Val Asn Phe Leu Leu Arg Met Asp Arg Ala His Glu Ala Lys
        450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
            500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
        595                 600                 605

Ser Gly Lys Asp Tyr Ala Gly Val Phe Ser Asp Ala Gly Leu Thr Phe
    610                 615                 620

Thr Ser Ser Ser Gly Gln Gln Thr Ala Gln Arg Ala Glu Leu Gln Cys
625                 630                 635                 640

Pro Gln Pro Ala Ala
                645

<210> SEQ ID NO 4
```

```
<211> LENGTH: 992
<212> TYPE: PRT
<213> ORGANISM: Homo sapiens

<400> SEQUENCE: 4

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg Ser Asn Leu
65                  70                  75                  80

Asp Glu Asp Ile Ile Ala Glu Glu Asn Ile Val Ser Arg Ser Glu Phe
                85                  90                  95

Pro Glu Ser Trp Leu Trp Asn Val Glu Asp Leu Lys Glu Pro Pro Lys
            100                 105                 110

Asn Gly Ile Ser Thr Lys Leu Met Asn Ile Phe Leu Lys Asp Ser Ile
        115                 120                 125

Thr Thr Trp Glu Ile Leu Ala Val Ser Met Ser Asp Lys Lys Gly Ile
    130                 135                 140

Cys Val Ala Asp Pro Phe Glu Val Thr Val Met Gln Asp Phe Phe Ile
145                 150                 155                 160

Asp Leu Arg Leu Pro Tyr Ser Val Val Arg Asn Glu Gln Val Glu Ile
                165                 170                 175

Arg Ala Val Leu Tyr Asn Tyr Arg Gln Asn Gln Glu Leu Lys Val Arg
            180                 185                 190

Val Glu Leu Leu His Asn Pro Ala Phe Cys Ser Leu Ala Thr Thr Lys
        195                 200                 205

Arg Arg His Gln Gln Thr Val Thr Ile Pro Pro Lys Ser Ser Leu Ser
    210                 215                 220

Val Pro Tyr Val Ile Val Pro Leu Lys Thr Gly Leu Gln Glu Val Glu
225                 230                 235                 240

Val Lys Ala Ala Val Tyr His His Phe Ile Ser Asp Gly Val Arg Lys
                245                 250                 255

Ser Leu Lys Val Val Pro Glu Gly Ile Arg Met Asn Lys Thr Val Ala
            260                 265                 270

Val Arg Thr Leu Asp Pro Glu Arg Leu Gly Arg Glu Gly Val Gln Lys
        275                 280                 285

Glu Asp Ile Pro Pro Ala Asp Leu Ser Asp Gln Val Pro Asp Thr Glu
    290                 295                 300

Ser Glu Thr Arg Ile Leu Leu Gln Gly Thr Pro Val Ala Gln Met Thr
305                 310                 315                 320

Glu Asp Ala Val Asp Ala Glu Arg Leu Lys His Leu Ile Val Thr Pro
                325                 330                 335

Ser Gly Cys Gly Glu Gln Asn Met Ile Gly Met Thr Pro Thr Val Ile
            340                 345                 350

Ala Val His Tyr Leu Asp Glu Thr Glu Gln Trp Glu Lys Phe Gly Leu
        355                 360                 365

Glu Lys Arg Gln Gly Ala Leu Glu Leu Ile Lys Lys Gly Tyr Thr Gln
    370                 375                 380

Gln Leu Ala Phe Arg Gln Pro Ser Ser Ala Phe Ala Ala Phe Val Lys
```

-continued

```
            385                 390                 395                 400
Arg Ala Pro Ser Thr Trp Leu Thr Ala Tyr Val Val Lys Val Phe Ser
                    405                 410                 415

Leu Ala Val Asn Leu Ile Ala Ile Asp Ser Gln Val Leu Cys Gly Ala
                    420                 425                 430

Val Lys Trp Leu Ile Leu Glu Lys Gln Lys Pro Asp Gly Val Phe Gln
                    435                 440                 445

Glu Asp Ala Pro Val Ile His Gln Glu Met Ile Gly Gly Leu Arg Asn
            450                 455                 460

Asn Asn Glu Lys Asp Met Ala Leu Thr Ala Phe Val Leu Ile Ser Leu
465                 470                 475                 480

Gln Glu Ala Lys Asp Ile Cys Glu Glu Gln Val Asn Ser Leu Pro Gly
                    485                 490                 495

Ser Ile Thr Lys Ala Gly Asp Phe Leu Glu Ala Asn Tyr Met Asn Leu
                500                 505                 510

Gln Arg Ser Tyr Thr Val Ala Ile Ala Gly Tyr Ala Leu Ala Gln Met
            515                 520                 525

Gly Arg Leu Lys Gly Pro Leu Leu Asn Lys Phe Leu Thr Thr Ala Lys
        530                 535                 540

Asp Lys Asn Arg Trp Glu Asp Pro Gly Lys Gln Leu Tyr Asn Val Glu
545                 550                 555                 560

Ala Thr Ser Tyr Ala Leu Leu Ala Leu Leu Gln Leu Lys Asp Phe Asp
                    565                 570                 575

Phe Val Pro Pro Val Val Arg Trp Leu Asn Glu Gln Arg Tyr Tyr Gly
                580                 585                 590

Gly Gly Tyr Gly Ser Thr Gln Ala Thr Phe Met Val Phe Gln Ala Leu
            595                 600                 605

Ala Gln Tyr Gln Lys Asp Ala Pro Asp His Gln Glu Leu Asn Leu Asp
            610                 615                 620

Val Ser Leu Gln Leu Pro Ser Arg Ser Ser Lys Ile Thr His Arg Ile
625                 630                 635                 640

His Trp Glu Ser Ala Ser Leu Leu Arg Ser Glu Glu Thr Lys Glu Asn
                    645                 650                 655

Glu Gly Phe Thr Val Thr Ala Glu Gly Lys Gly Gln Gly Thr Leu Ser
                    660                 665                 670

Val Val Thr Met Tyr His Ala Lys Ala Lys Asp Gln Leu Thr Cys Asn
                675                 680                 685

Lys Phe Asp Leu Lys Val Thr Ile Lys Pro Ala Pro Glu Thr Glu Lys
        690                 695                 700

Arg Pro Gln Asp Ala Lys Asn Thr Met Ile Leu Glu Ile Cys Thr Arg
705                 710                 715                 720

Tyr Arg Gly Asp Gln Asp Ala Thr Met Ser Ile Leu Asp Ile Ser Met
                    725                 730                 735

Met Thr Gly Phe Ala Pro Asp Thr Asp Asp Leu Lys Gln Leu Ala Asn
                740                 745                 750

Gly Val Asp Arg Tyr Ile Ser Lys Tyr Glu Leu Asp Lys Ala Phe Ser
            755                 760                 765

Asp Arg Asn Thr Leu Ile Ile Tyr Leu Asp Lys Val Ser His Ser Glu
        770                 775                 780

Asp Asp Cys Leu Ala Phe Lys Val His Gln Tyr Phe Asn Val Glu Leu
785                 790                 795                 800

Ile Gln Pro Gly Ala Val Lys Val Tyr Ala Tyr Tyr Asn Leu Glu Glu
                    805                 810                 815
```

Ser Cys Thr Arg Phe Tyr His Pro Glu Lys Glu Asp Gly Lys Leu Asn
            820                 825                 830

Lys Leu Cys Arg Asp Glu Leu Cys Arg Cys Ala Glu Glu Asn Cys Phe
            835                 840                 845

Ile Gln Lys Ser Asp Asp Lys Val Thr Leu Glu Arg Leu Asp Lys
850                 855                 860

Ala Cys Glu Pro Gly Val Asp Tyr Val Tyr Lys Thr Arg Leu Val Lys
865                 870                 875                 880

Val Gln Leu Ser Asn Asp Phe Asp Glu Tyr Ile Met Ala Ile Glu Gln
            885                 890                 895

Thr Ile Lys Ser Gly Ser Asp Glu Val Gln Val Gly Gln Gln Arg Thr
            900                 905                 910

Phe Ile Ser Pro Ile Lys Cys Arg Glu Ala Leu Lys Leu Glu Lys
            915                 920                 925

Lys His Tyr Leu Met Trp Gly Leu Ser Ser Asp Phe Trp Gly Glu Lys
            930                 935                 940

Pro Asn Leu Ser Tyr Ile Ile Gly Lys Asp Thr Trp Val Glu His Trp
945                 950                 955                 960

Pro Glu Glu Asp Glu Cys Gln Asp Glu Glu Asn Gln Lys Gln Cys Gln
            965                 970                 975

Asp Leu Gly Ala Phe Thr Glu Ser Met Val Val Phe Gly Cys Pro Asn
            980                 985                 990

<210> SEQ ID NO 5
<211> LENGTH: 915
<212> TYPE: PRT
<213> ORGANISM: Homo sapiens

<400> SEQUENCE: 5

Ser Asn Leu Asp Glu Asp Ile Ile Ala Glu Asn Ile Val Ser Arg
1               5                   10                  15

Ser Glu Phe Pro Glu Ser Trp Leu Trp Asn Val Glu Asp Leu Lys Glu
            20                  25                  30

Pro Pro Lys Asn Gly Ile Ser Thr Lys Leu Met Asn Ile Phe Leu Lys
            35                  40                  45

Asp Ser Ile Thr Thr Trp Glu Ile Leu Ala Val Ser Met Ser Asp Lys
50                  55                  60

Lys Gly Ile Cys Val Ala Asp Pro Phe Glu Val Thr Val Met Gln Asp
65                  70                  75                  80

Phe Phe Ile Asp Leu Arg Leu Pro Tyr Ser Val Arg Asn Glu Gln
            85                  90                  95

Val Glu Ile Arg Ala Val Leu Tyr Asn Tyr Arg Gln Asn Gln Glu Leu
            100                 105                 110

Lys Val Arg Val Glu Leu Leu His Asn Pro Ala Phe Cys Ser Leu Ala
            115                 120                 125

Thr Thr Lys Arg Arg His Gln Gln Thr Val Thr Ile Pro Pro Lys Ser
            130                 135                 140

Ser Leu Ser Val Pro Tyr Val Ile Val Pro Leu Lys Thr Gly Leu Gln
145                 150                 155                 160

Glu Val Glu Val Lys Ala Ala Val Tyr His His Phe Ile Ser Asp Gly
            165                 170                 175

Val Arg Lys Ser Leu Lys Val Val Pro Glu Gly Ile Arg Met Asn Lys
            180                 185                 190

Thr Val Ala Val Arg Thr Leu Asp Pro Glu Arg Leu Gly Arg Glu Gly

```
                195                 200                 205
Val Gln Lys Glu Asp Ile Pro Pro Ala Asp Leu Ser Asp Gln Val Pro
210                 215                 220

Asp Thr Glu Ser Glu Thr Arg Ile Leu Leu Gln Gly Thr Pro Val Ala
225                 230                 235                 240

Gln Met Thr Glu Asp Ala Val Asp Ala Glu Arg Leu Lys His Leu Ile
                245                 250                 255

Val Thr Pro Ser Gly Cys Gly Glu Gln Asn Met Ile Gly Met Thr Pro
                260                 265                 270

Thr Val Ile Ala Val His Tyr Leu Asp Glu Thr Glu Gln Trp Glu Lys
                275                 280                 285

Phe Gly Leu Glu Lys Arg Gln Gly Ala Leu Glu Leu Ile Lys Lys Gly
                290                 295                 300

Tyr Thr Gln Gln Leu Ala Phe Arg Gln Pro Ser Ser Ala Phe Ala Ala
305                 310                 315                 320

Phe Val Lys Arg Ala Pro Ser Thr Trp Leu Thr Ala Tyr Val Val Lys
                325                 330                 335

Val Phe Ser Leu Ala Val Asn Leu Ile Ala Ile Asp Ser Gln Val Leu
                340                 345                 350

Cys Gly Ala Val Lys Trp Leu Ile Leu Glu Lys Gln Lys Pro Asp Gly
                355                 360                 365

Val Phe Gln Glu Asp Ala Pro Val Ile His Gln Glu Met Ile Gly Gly
                370                 375                 380

Leu Arg Asn Asn Asn Glu Lys Asp Met Ala Leu Thr Ala Phe Val Leu
385                 390                 395                 400

Ile Ser Leu Gln Glu Ala Lys Asp Ile Cys Glu Glu Gln Val Asn Ser
                405                 410                 415

Leu Pro Gly Ser Ile Thr Lys Ala Gly Asp Phe Leu Glu Ala Asn Tyr
                420                 425                 430

Met Asn Leu Gln Arg Ser Tyr Thr Val Ala Ile Ala Gly Tyr Ala Leu
                435                 440                 445

Ala Gln Met Gly Arg Leu Lys Gly Pro Leu Leu Asn Lys Phe Leu Thr
                450                 455                 460

Thr Ala Lys Asp Lys Asn Arg Trp Glu Asp Pro Gly Lys Gln Leu Tyr
465                 470                 475                 480

Asn Val Glu Ala Thr Ser Tyr Ala Leu Leu Ala Leu Leu Gln Leu Lys
                485                 490                 495

Asp Phe Asp Phe Val Pro Pro Val Val Arg Trp Leu Asn Glu Gln Arg
                500                 505                 510

Tyr Tyr Gly Gly Gly Tyr Gly Ser Thr Gln Ala Thr Phe Met Val Phe
                515                 520                 525

Gln Ala Leu Ala Gln Tyr Gln Lys Asp Ala Pro Asp His Gln Glu Leu
                530                 535                 540

Asn Leu Asp Val Ser Leu Gln Leu Pro Ser Arg Ser Ser Lys Ile Thr
545                 550                 555                 560

His Arg Ile His Trp Glu Ser Ala Ser Leu Leu Arg Ser Glu Glu Thr
                565                 570                 575

Lys Glu Asn Glu Gly Phe Thr Val Thr Ala Glu Gly Lys Gly Gln Gly
                580                 585                 590

Thr Leu Ser Val Val Thr Met Tyr His Ala Lys Ala Lys Asp Gln Leu
                595                 600                 605

Thr Cys Asn Lys Phe Asp Leu Lys Val Thr Ile Lys Pro Ala Pro Glu
                610                 615                 620
```

```
Thr Glu Lys Arg Pro Gln Asp Ala Lys Asn Thr Met Ile Leu Glu Ile
625                 630                 635                 640

Cys Thr Arg Tyr Arg Gly Asp Gln Asp Ala Thr Met Ser Ile Leu Asp
            645                 650                 655

Ile Ser Met Met Thr Gly Phe Ala Pro Asp Thr Asp Leu Lys Gln
        660                 665                 670

Leu Ala Asn Gly Val Asp Arg Tyr Ile Ser Lys Tyr Glu Leu Asp Lys
            675                 680                 685

Ala Phe Ser Asp Arg Asn Thr Leu Ile Ile Tyr Leu Asp Lys Val Ser
        690                 695                 700

His Ser Glu Asp Asp Cys Leu Ala Phe Lys Val His Gln Tyr Phe Asn
705                 710                 715                 720

Val Glu Leu Ile Gln Pro Gly Ala Val Lys Val Tyr Ala Tyr Asn
            725                 730                 735

Leu Glu Glu Ser Cys Thr Arg Phe Tyr His Pro Glu Lys Glu Asp Gly
        740                 745                 750

Lys Leu Asn Lys Leu Cys Arg Asp Glu Leu Cys Arg Cys Ala Glu Glu
            755                 760                 765

Asn Cys Phe Ile Gln Lys Ser Asp Asp Lys Val Thr Leu Glu Glu Arg
770                 775                 780

Leu Asp Lys Ala Cys Glu Pro Gly Val Asp Tyr Val Tyr Lys Thr Arg
785                 790                 795                 800

Leu Val Lys Val Gln Leu Ser Asn Asp Phe Asp Glu Tyr Ile Met Ala
            805                 810                 815

Ile Glu Gln Thr Ile Lys Ser Gly Ser Asp Glu Val Gln Val Gly Gln
        820                 825                 830

Gln Arg Thr Phe Ile Ser Pro Ile Lys Cys Arg Glu Ala Leu Lys Leu
            835                 840                 845

Glu Glu Lys Lys His Tyr Leu Met Trp Gly Leu Ser Ser Asp Phe Trp
850                 855                 860

Gly Glu Lys Pro Asn Leu Ser Tyr Ile Ile Gly Lys Asp Thr Trp Val
865                 870                 875                 880

Glu His Trp Pro Glu Asp Glu Cys Gln Asp Glu Glu Asn Gln Lys
            885                 890                 895

Gln Cys Gln Asp Leu Gly Ala Phe Thr Glu Ser Met Val Val Phe Gly
        900                 905                 910

Cys Pro Asn
        915

<210> SEQ ID NO 6
<211> LENGTH: 77
<212> TYPE: PRT
<213> ORGANISM: Homo sapiens

<400> SEQUENCE: 6

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
```

```
                65                  70                  75

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Thr Asp Phe Tyr Met Asp
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ile Tyr Pro His Asn Gly Gly Thr Thr Tyr Asn Gln Asn Phe Thr
1               5                   10                  15

Gly

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gly Gly Phe Asp Phe Asp Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ala Ser Glu Asn Val Asp Thr Tyr Val Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ala Ser Asn Arg Tyr Thr
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Gly Gln Ser His Ser Tyr Pro Leu Thr
1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ile Tyr Pro His Asn Gly Gly Thr Thr Tyr Asn Gln Gln Phe Thr
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ile Tyr Pro His Asn Ala Gly Thr Thr Tyr Asn Gln Gln Phe Thr
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ile Tyr Pro His Asn Thr Gly Thr Thr Tyr Asn Gln Gln Phe Thr
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Ile Tyr Pro His Glu Gly Gly Thr Thr Tyr Asn Gln Gln Phe Thr
1               5                   10                  15

Gly

<210> SEQ ID NO 17
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 17

Tyr Ile Tyr Pro His Gln Gly Gly Thr Thr Tyr Asn Gln Gln Phe Thr
1               5                   10                  15

Gly

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Gln Gln Ser Gly Pro Glu Leu Val Lys Pro Gly Asp
1               5                   10                  15

Ser Val Lys Met Ser Cys Lys Ala Ser Gly Tyr Thr Phe Thr Asp Phe
            20                  25                  30

Tyr Met Asp Trp Val Lys Gln Ser His Gly Lys Ser Leu Glu Trp Ile
        35                  40                  45

Gly Tyr Ile Tyr Pro His Asn Gly Gly Thr Thr Tyr Asn Gln Asn Phe
    50                  55                  60

Thr Gly Lys Ala Thr Leu Thr Val Asp Lys Ser Ser Asn Thr Ala Tyr
65                  70                  75                  80

Met Glu Leu His Ser Leu Thr Ser Glu Asp Ser Ala Val Tyr Tyr Cys
                85                  90                  95

Ala Arg Arg Gly Gly Phe Asp Phe Asp Tyr Trp Gly Gln Gly Thr Thr
            100                 105                 110

Leu Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asn Ile Val Met Thr Gln Ser Pro Lys Ser Met Ser Leu Ser Val Gly
1               5                   10                  15

Glu Arg Val Thr Leu Arg Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Glu Phe Thr Leu Thr Ile Ser Ser Val Gln Ala
65                  70                  75                  80

Glu Asp Leu Val Gly Tyr His Cys Gly Gln Ser His Ser Tyr Pro Leu
                85                  90                  95

Thr Phe Gly Ala Gly Thr Lys Leu Glu Leu Lys
            100                 105

<210> SEQ ID NO 20
```

<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
        35                  40                  45

Gly Tyr Ile Tyr Pro His Asn Gly Gly Thr Thr Tyr Asn Gln Gln Phe
    50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Phe Asp Phe Asp Tyr Trp Gly Gln Gly Thr Leu
            100                 105                 110

Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
        35                  40                  45

Gly Tyr Ile Tyr Pro His Asn Ala Gly Thr Thr Tyr Asn Gln Gln Phe
    50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Phe Asp Phe Asp Tyr Trp Gly Gln Gly Thr Leu
            100                 105                 110

Val Thr Val Ser Ser
        115

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
        35                  40                  45

Gly Tyr Ile Tyr Pro His Asn Thr Gly Thr Tyr Asn Gln Gln Phe
50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Gly Gly Phe Asp Phe Asp Tyr Trp Gly Gln Gly Thr Leu
            100                 105                 110

Val Thr Val Ser Ser
            115

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
        35                  40                  45

Gly Tyr Ile Tyr Pro His Glu Gly Gly Thr Thr Tyr Asn Gln Gln Phe
50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Gly Gly Phe Asp Phe Asp Tyr Trp Gly Gln Gly Thr Leu
            100                 105                 110

Val Thr Val Ser Ser
            115

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
        35                  40                  45

```
Gly Tyr Ile Tyr Pro His Gln Gly Gly Thr Thr Tyr Asn Gln Gln Phe
         50                  55                  60

Thr Gly Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Gly Phe Asp Phe Asp Tyr Trp Gly Gln Gly Thr Leu
             100                 105                 110

Val Thr Val Ser Ser
            115

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Lys Ala Ser Glu Asn Val Asp Thr Tyr
             20                  25                  30

Val Ser Trp Tyr Gln Gln Lys Pro Gly Lys Ala Pro Lys Leu Leu Ile
         35                  40                  45

Tyr Gly Ala Ser Asn Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr His Cys Gly Gln Ser His Ser Tyr Pro Leu
                 85                  90                  95

Thr Phe Gly Gln Gly Thr Lys Leu Glu Ile Lys
            100                 105

<210> SEQ ID NO 26
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Met Arg Val Pro Ala Gln Leu Leu Gly Leu Leu Leu Leu Trp
 1               5                  10                  15

Leu Arg Gly Ala Arg Cys Gln Val Gln Leu Val Gln Ser Gly Ala Glu
             20                  25                  30

Val Lys Lys Pro Gly Ala Ser Val Lys Val Ser Cys Lys Ala Ser Gly
         35                  40                  45

Tyr Thr Phe Thr Asp Phe Tyr Met Asp Trp Val Arg Gln Ala Pro Gly
 50                  55                  60

Gln Arg Leu Glu Trp Met Gly Tyr Ile Tyr Pro His Asn Gly Gly Thr
 65                  70                  75                  80

Thr Tyr Asn Gln Gln Phe Thr Gly Arg Val Thr Ile Thr Val Asp Lys
                 85                  90                  95

Ser Ala Ser Thr Ala Tyr Met Glu Leu Ser Ser Leu Arg Ser Glu Asp
            100                 105                 110
```

```
Thr Ala Val Tyr Tyr Cys Ala Arg Arg Gly Gly Phe Asp Phe Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Ala Leu
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
    275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 27
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
            35                  40                  45

Gly Tyr Ile Tyr Pro His Asn Gly Gly Thr Thr Tyr Asn Gln Gln Phe
50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Phe Asp Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Ala Leu Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415
```

```
Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 28
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Asp Phe Tyr Met Asp Trp Val Arg Gln Ala Pro Gly
    50                  55                  60

Gln Arg Leu Glu Trp Met Gly Tyr Ile Tyr Pro His Asn Ala Gly Thr
65                  70                  75                  80

Thr Tyr Asn Gln Gln Phe Thr Gly Arg Val Thr Ile Thr Val Asp Lys
                85                  90                  95

Ser Ala Ser Thr Ala Tyr Met Glu Leu Ser Ser Leu Arg Ser Glu Asp
            100                 105                 110

Thr Ala Val Tyr Tyr Cys Ala Arg Arg Gly Gly Phe Asp Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Ala Leu
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335
```

-continued

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 29
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Arg Leu Glu Trp Met
        35                  40                  45

Gly Tyr Ile Tyr Pro His Asn Ala Gly Thr Thr Tyr Asn Gln Gln Phe
    50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Phe Asp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His

```
Thr Cys Pro Cys Pro Ala Pro Ala Leu Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
    435                 440                 445

<210> SEQ ID NO 30
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Glu Asn Val Asp Thr Tyr Val Ser Trp Tyr Gln Gln Lys Pro Gly Lys
    50                  55                  60

Ala Pro Lys Leu Leu Ile Tyr Gly Ala Ser Asn Arg Tyr Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr His Cys Gly Gln
            100                 105                 110

Ser His Ser Tyr Pro Leu Thr Phe Gly Gln Gly Thr Lys Leu Glu Ile
        115                 120                 125
```

```
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 31
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
1               5                   10                  15
Asp Arg Val Thr Ile Thr Cys Lys Ala Ser Glu Asn Val Asp Thr Tyr
            20                  25                  30
Val Ser Trp Tyr Gln Gln Lys Pro Gly Lys Ala Pro Lys Leu Leu Ile
        35                  40                  45
Tyr Gly Ala Ser Asn Arg Tyr Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr His Cys Gly Gln Ser His Ser Tyr Pro Leu
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 32
<211> LENGTH: 1663
<212> TYPE: PRT
<213> ORGANISM: Macaca fascicularis
```

<400> SEQUENCE: 32

```
Met Gly Leu Thr Ser Gly Pro Ser Leu Leu Leu Leu Leu Ile His
1               5                   10                  15

Leu Pro Leu Ala Leu Gly Thr Pro Met Tyr Ser Met Ile Thr Pro Asn
            20                  25                  30

Val Leu Arg Leu Glu Ser Glu Glu Thr Val Val Leu Glu Ala His Asp
        35                  40                  45

Ala Asn Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Ser His Met Gly Ser Val Thr Ile Arg Ile Pro Ala Asn Lys Glu Phe
                85                  90                  95

Lys Ser Glu Lys Gly His Asn Lys Phe Val Thr Val Gln Ala Thr Phe
            100                 105                 110

Gly Ala Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Cys Arg Ile Phe Thr Val Asn His Lys Leu Leu Pro Val Gly
145                 150                 155                 160

Arg Thr Val Val Val Asn Ile Glu Asn Pro Asp Gly Ile Pro Val Lys
                165                 170                 175

Gln Asp Ser Leu Ser Ser Gln Asn Gln Phe Gly Ile Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Gln Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Gln Ile Glu Asp Gly Ser Gly Asp Ala Val Leu Ser Arg
    290                 295                 300

Lys Val Leu Leu Asp Gly Val Gln Asn Pro Arg Pro Glu Asp Leu Val
305                 310                 315                 320

Gly Lys Ser Leu Tyr Val Ser Val Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
    355                 360                 365

Pro Phe Asp Leu Met Val Phe Val Thr Asn Pro Asp Gly Ser Pro Ala
        370                 375                 380

Tyr Arg Val Pro Val Ala Val Gln Gly Glu Asp Ala Val Gln Ser Leu
385                 390                 395                 400

Thr Gln Gly Asp Gly Val Ala Lys Leu Ser Ile Asn Thr His Pro Ser
```

-continued

```
                405                 410                 415
Gln Lys Pro Leu Ser Ile Thr Val Arg Thr Lys Arg Glu Leu Ser
            420                 425                 430

Glu Ala Glu Gln Ala Thr Arg Thr Met Glu Ala Gln Pro Tyr Ser Thr
            435                 440                 445

Val Gly Asn Ser Asn Asn Tyr Leu His Leu Ser Val Pro Arg Ala Glu
450                 455                 460

Leu Arg Pro Gly Glu Thr Leu Asn Val Asn Phe Leu Leu Arg Met Asp
465                 470                 475                 480

Arg Thr Gln Glu Ala Lys Ile Arg Tyr Tyr Thr Tyr Leu Ile Met Asn
                485                 490                 495

Lys Gly Lys Leu Leu Lys Val Gly Arg Gln Val Arg Glu Pro Gly Gln
            500                 505                 510

Asp Leu Val Val Leu Pro Leu Ser Ile Thr Thr Asp Phe Ile Pro Ser
            515                 520                 525

Phe Arg Leu Val Ala Tyr Tyr Thr Leu Ile Gly Ala Asn Gly Gln Arg
            530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Leu
                565                 570                 575

Pro Gly Gln Gln Met Thr Leu Lys Ile Glu Gly Asp His Gly Ala Arg
            580                 585                 590

Val Gly Leu Val Ala Val Asp Lys Gly Val Phe Val Leu Asn Lys Lys
            595                 600                 605

Asn Lys Leu Thr Gln Ser Lys Ile Trp Asp Val Val Glu Lys Ala Asp
610                 615                 620

Ile Gly Cys Thr Pro Gly Ser Gly Lys Asp Tyr Ala Gly Val Phe Ser
625                 630                 635                 640

Asp Ala Gly Leu Thr Phe Ala Ser Ser Ser Gly Gln Gln Thr Ala Gln
                645                 650                 655

Arg Ala Glu Leu Gln Cys Pro Gln Pro Ala Ala Arg Arg Arg Arg Ser
            660                 665                 670

Val Gln Leu Ala Glu Lys Arg Met Asp Lys Val Gly Gln Tyr Pro Lys
            675                 680                 685

Glu Leu Arg Lys Cys Cys Glu His Gly Met Arg Glu Asn Pro Met Arg
            690                 695                 700

Phe Ser Cys Gln Arg Arg Thr Arg Tyr Ile Thr Leu Asp Glu Ala Cys
705                 710                 715                 720

Lys Lys Ala Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
            755                 760                 765

Glu Ser Trp Leu Trp Lys Ile Glu Glu Leu Lys Glu Ala Pro Lys Asn
            770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Leu Ser Asp Lys Lys Gly Ile Cys
                805                 810                 815

Val Ala Asp Pro Phe Glu Val Thr Val Met Gln Asp Phe Phe Ile Asp
            820                 825                 830
```

-continued

```
Leu Arg Leu Pro Tyr Ser Val Val Arg Asn Glu Gln Val Glu Ile Arg
        835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Ala Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Gln Gln Glu Val Glu Val
                900                 905                 910

Lys Ala Ala Val Tyr His Phe Phe Ile Ser Asp Gly Val Arg Lys Ser
                915                 920                 925

Leu Lys Val Val Pro Glu Gly Ile Arg Met Asn Lys Thr Val Ala Val
                930                 935                 940

Arg Thr Leu Asp Pro Glu Arg Leu Gly Gln Glu Gly Val Gln Arg Glu
945                 950                 955                 960

Asp Val Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
                980                 985                 990

Asp Ala Ile Asp Ala Glu Arg Leu Lys His Leu Ile Val Thr Pro Ser
                995                 1000                1005

Gly Cys Gly Glu Gln Asn Met Ile Thr Met Thr Pro Thr Val Ile
    1010                1015                1020

Ala Val His Tyr Leu Asp Glu Thr Glu Gln Trp Glu Lys Phe Gly
    1025                1030                1035

Pro Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Leu Asn Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Thr Gly Gly Phe Arg Asn Thr Asn Glu Lys Asp Met Ala Leu
    1130                1135                1140

Thr Ala Phe Val Leu Ile Ser Leu Gln Glu Ala Lys Glu Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Ala Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Glu Pro Gly Gln Gln Leu Tyr Asn Val Glu Ala Thr
    1220                1225                1230
```

```
Ser Tyr Ala Leu Leu Ala Leu Leu Gln Leu Lys Asp Phe Asp Phe
    1235                1240                1245
Val Pro Pro Val Val Arg Trp Leu Asn Glu Gln Arg Tyr Tyr Gly
    1250                1255                1260
Gly Gly Tyr Gly Ser Thr Gln Ala Thr Phe Met Val Phe Gln Ala
    1265                1270                1275
Leu Ala Gln Tyr Gln Lys Asp Val Pro Asp His Lys Glu Leu Asn
    1280                1285                1290
Leu Asp Val Ser Leu Gln Leu Pro Ser Arg Ser Ser Lys Ile Ile
    1295                1300                1305
His Arg Ile His Trp Glu Ser Ala Ser Leu Leu Arg Ser Glu Glu
    1310                1315                1320
Thr Lys Glu Asn Glu Gly Phe Thr Val Thr Ala Glu Gly Lys Gly
    1325                1330                1335
Gln Gly Thr Leu Ser Val Val Thr Met Tyr His Ala Lys Ala Lys
    1340                1345                1350
Gly Gln Leu Thr Cys Asn Lys Phe Asp Leu Lys Val Thr Ile Lys
    1355                1360                1365
Pro Ala Pro Glu Thr Glu Lys Arg Pro Gln Asp Ala Lys Asn Thr
    1370                1375                1380
Met Ile Leu Glu Ile Cys Thr Arg Tyr Arg Gly Asp Gln Asp Ala
    1385                1390                1395
Thr Met Ser Ile Leu Asp Ile Ser Met Met Thr Gly Phe Val Pro
    1400                1405                1410
Asp Thr Asp Asp Leu Lys Gln Leu Ala Asn Gly Val Asp Arg Tyr
    1415                1420                1425
Ile Ser Lys Tyr Glu Leu Asp Lys Ala Phe Ser Asp Arg Asn Thr
    1430                1435                1440
Leu Ile Ile Tyr Leu Asp Lys Val Ser His Ser Glu Asp Asp Cys
    1445                1450                1455
Ile Ala Phe Lys Val His Gln Tyr Phe Asn Val Glu Leu Ile Gln
    1460                1465                1470
Pro Gly Ala Val Lys Val Tyr Ala Tyr Tyr Asn Leu Ala Glu Ser
    1475                1480                1485
Cys Thr Arg Phe Tyr His Pro Glu Lys Glu Asp Gly Lys Leu Asn
    1490                1495                1500
Lys Leu Cys Arg Asp Glu Leu Cys Arg Cys Ala Glu Glu Asn Cys
    1505                1510                1515
Phe Ile Gln Lys Leu Asp Asp Lys Val Thr Leu Glu Glu Arg Leu
    1520                1525                1530
Asp Lys Ala Cys Glu Pro Gly Val Asp Tyr Val Tyr Lys Thr Arg
    1535                1540                1545
Leu Val Lys Ala Gln Leu Ser Asn Asp Phe Asp Glu Tyr Ile Met
    1550                1555                1560
Ala Ile Glu Gln Ile Ile Lys Ser Gly Ser Asp Glu Val Gln Val
    1565                1570                1575
Gly Gln Gln Arg Thr Phe Ile Ser Pro Ile Lys Cys Arg Glu Ala
    1580                1585                1590
Leu Lys Leu Glu Glu Arg Lys His Tyr Leu Met Trp Gly Leu Ser
    1595                1600                1605
Ser Asp Phe Trp Gly Glu Lys Pro Asn Leu Ser Tyr Ile Ile Gly
    1610                1615                1620
Lys Asp Thr Trp Val Glu His Trp Pro Glu Glu Asp Glu Cys Gln
```

-continued

```
              1625                1630                1635

Asp Glu Glu Asn Gln Lys Gln Cys Gln Asp Leu Gly Thr Phe Thr
    1640                1645                1650

Glu Asn Met Val Val Phe Gly Cys Pro Asn
    1655                1660

<210> SEQ ID NO 33
<211> LENGTH: 1641
<212> TYPE: PRT
<213> ORGANISM: Macaca fascicularis

<400> SEQUENCE: 33

Thr Pro Met Tyr Ser Met Ile Thr Pro Asn Val Leu Arg Leu Glu Ser
1               5                   10                  15

Glu Glu Thr Val Val Leu Glu Ala His Asp Ala Asn Gly Asp Val Pro
                20                  25                  30

Val Thr Val Thr Val His Asp Phe Pro Gly Lys Lys Leu Val Leu Ser
            35                  40                  45

Ser Glu Lys Thr Val Leu Thr Pro Ala Thr Ser His Met Gly Ser Val
    50                  55                  60

Thr Ile Arg Ile Pro Ala Asn Lys Glu Phe Lys Ser Glu Lys Gly His
65                  70                  75                  80

Asn Lys Phe Val Thr Val Gln Ala Thr Phe Gly Ala Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Cys Arg Ile Phe
        115                 120                 125

Thr Val Asn His Lys Leu Leu Pro Val Gly Arg Thr Val Val Val Asn
130                 135                 140

Ile Glu Asn Pro Asp Gly Ile Pro Val Lys Gln Asp Ser Leu Ser Ser
145                 150                 155                 160

Gln Asn Gln Phe Gly Ile Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Gln Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Gln Ile Glu
            260                 265                 270

Asp Gly Ser Gly Asp Ala Val Leu Ser Arg Lys Val Leu Leu Asp Gly
        275                 280                 285

Val Gln Asn Pro Arg Pro Glu Asp Leu Val Gly Lys Ser Leu Tyr Val
    290                 295                 300

Ser Val Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335
```

```
Lys Thr Pro Lys Tyr Phe Lys Pro Gly Met Pro Phe Asp Leu Met Val
                340                 345                 350
Phe Val Thr Asn Pro Asp Gly Ser Pro Ala Tyr Arg Val Pro Val Ala
            355                 360                 365
Val Gln Gly Glu Asp Ala Val Gln Ser Leu Thr Gln Gly Asp Gly Val
        370                 375                 380
Ala Lys Leu Ser Ile Asn Thr His Pro Ser Gln Lys Pro Leu Ser Ile
385                 390                 395                 400
Thr Val Arg Thr Lys Lys Arg Glu Leu Ser Glu Ala Glu Gln Ala Thr
                405                 410                 415
Arg Thr Met Glu Ala Gln Pro Tyr Ser Thr Val Gly Asn Ser Asn Asn
            420                 425                 430
Tyr Leu His Leu Ser Val Pro Arg Ala Glu Leu Arg Pro Gly Glu Thr
        435                 440                 445
Leu Asn Val Asn Phe Leu Leu Arg Met Asp Arg Thr Gln Glu Ala Lys
    450                 455                 460
Ile Arg Tyr Tyr Thr Tyr Leu Ile Met Asn Lys Gly Lys Leu Leu Lys
465                 470                 475                 480
Val Gly Arg Gln Val Arg Glu Pro Gly Gln Asp Leu Val Val Leu Pro
                485                 490                 495
Leu Ser Ile Thr Thr Asp Phe Ile Pro Ser Phe Arg Leu Val Ala Tyr
            500                 505                 510
Tyr Thr Leu Ile Gly Ala Asn Gly Gln Arg Glu Val Val Ala Asp Ser
        515                 520                 525
Val Trp Val Asp Val Lys Asp Ser Cys Val Gly Ser Leu Val Val Lys
    530                 535                 540
Ser Gly Gln Ser Glu Asp Arg Gln Pro Leu Pro Gly Gln Gln Met Thr
545                 550                 555                 560
Leu Lys Ile Glu Gly Asp His Gly Ala Arg Val Gly Leu Val Ala Val
                565                 570                 575
Asp Lys Gly Val Phe Val Leu Asn Lys Lys Asn Lys Leu Thr Gln Ser
            580                 585                 590
Lys Ile Trp Asp Val Val Glu Lys Ala Asp Ile Gly Cys Thr Pro Gly
        595                 600                 605
Ser Gly Lys Asp Tyr Ala Gly Val Phe Ser Asp Ala Gly Leu Thr Phe
    610                 615                 620
Ala Ser Ser Ser Gly Gln Gln Thr Ala Gln Arg Ala Glu Leu Gln Cys
625                 630                 635                 640
Pro Gln Pro Ala Ala Arg Arg Arg Arg Ser Val Gln Leu Ala Glu Lys
                645                 650                 655
Arg Met Asp Lys Val Gly Gln Tyr Pro Lys Glu Leu Arg Lys Cys Cys
            660                 665                 670
Glu His Gly Met Arg Glu Asn Pro Met Arg Phe Ser Cys Gln Arg Arg
        675                 680                 685
Thr Arg Tyr Ile Thr Leu Asp Glu Ala Cys Lys Lys Ala Phe Leu Asp
    690                 695                 700
Cys Cys Asn Tyr Ile Thr Glu Leu Arg Arg Gln His Ala Arg Ala Ser
705                 710                 715                 720
His Leu Gly Leu Ala Arg Ser Asn Leu Asp Glu Asp Ile Ile Ala Glu
                725                 730                 735
Glu Asn Ile Val Ser Arg Ser Glu Phe Pro Glu Ser Trp Leu Trp Lys
            740                 745                 750
Ile Glu Glu Leu Lys Glu Ala Pro Lys Asn Gly Ile Ser Thr Lys Leu
```

-continued

```
            755                 760                 765
Met Asn Ile Phe Leu Lys Asp Ser Ile Thr Thr Trp Glu Ile Leu Ala
            770                 775                 780

Val Ser Leu Ser Asp Lys Lys Gly Ile Cys Val Ala Asp Pro Phe Glu
785                 790                 795                 800

Val Thr Val Met Gln Asp Phe Phe Ile Asp Leu Arg Leu Pro Tyr Ser
                    805                 810                 815

Val Val Arg Asn Glu Gln Val Glu Ile Arg Ala Val Leu Tyr Asn Tyr
                820                 825                 830

Arg Gln Asn Gln Glu Leu Lys Val Arg Val Glu Leu Leu His Asn Pro
            835                 840                 845

Ala Phe Cys Ser Leu Ala Thr Ala Lys Arg Arg His Gln Gln Thr Val
        850                 855                 860

Thr Ile Pro Pro Lys Ser Ser Leu Ser Val Pro Tyr Val Ile Val Pro
865                 870                 875                 880

Leu Lys Thr Gly Gln Gln Glu Val Glu Val Lys Ala Ala Val Tyr His
                    885                 890                 895

Phe Phe Ile Ser Asp Gly Val Arg Lys Ser Leu Lys Val Val Pro Glu
                900                 905                 910

Gly Ile Arg Met Asn Lys Thr Val Ala Val Arg Thr Leu Asp Pro Glu
            915                 920                 925

Arg Leu Gly Gln Glu Gly Val Gln Arg Glu Asp Val Pro Pro Ala Asp
        930                 935                 940

Leu Ser Asp Gln Val Pro Asp Thr Glu Ser Glu Thr Arg Ile Leu Leu
945                 950                 955                 960

Gln Gly Thr Pro Val Ala Gln Met Thr Glu Asp Ala Ile Asp Ala Glu
                    965                 970                 975

Arg Leu Lys His Leu Ile Val Thr Pro Ser Gly Cys Gly Glu Gln Asn
                980                 985                 990

Met Ile Thr Met Thr Pro Thr Val Ile Ala Val His Tyr Leu Asp Glu
            995                 1000                1005

Thr Glu Gln Trp Glu Lys Phe Gly Pro Glu Lys Arg Gln Gly Ala
        1010                1015                1020

Leu Glu Leu Ile Lys Lys Gly Tyr Thr Gln Gln Leu Ala Phe Arg
        1025                1030                1035

Gln Pro Ser Ser Ala Phe Ala Ala Phe Leu Asn Arg Ala Pro Ser
        1040                1045                1050

Thr Trp Leu Thr Ala Tyr Val Val Lys Val Phe Ser Leu Ala Val
        1055                1060                1065

Asn Leu Ile Ala Ile Asp Ser Gln Val Leu Cys Gly Ala Val Lys
        1070                1075                1080

Trp Leu Ile Leu Glu Lys Gln Lys Pro Asp Gly Val Phe Gln Glu
        1085                1090                1095

Asp Ala Pro Val Ile His Gln Glu Met Thr Gly Gly Phe Arg Asn
        1100                1105                1110

Thr Asn Glu Lys Asp Met Ala Leu Thr Ala Phe Val Leu Ile Ser
        1115                1120                1125

Leu Gln Glu Ala Lys Glu Ile Cys Glu Glu Gln Val Asn Ser Leu
        1130                1135                1140

Pro Gly Ser Ile Thr Lys Ala Gly Asp Phe Leu Glu Ala Asn Tyr
        1145                1150                1155

Met Asn Leu Gln Arg Ser Tyr Thr Val Ala Ile Ala Ala Tyr Ala
        1160                1165                1170
```

-continued

```
Leu Ala Gln Met Gly Arg Leu Lys Gly Pro Leu Leu Asn Lys Phe
1175                1180                1185

Leu Thr Thr Ala Lys Asp Lys Asn Arg Trp Glu Glu Pro Gly Gln
1190                1195                1200

Gln Leu Tyr Asn Val Glu Ala Thr Ser Tyr Ala Leu Leu Ala Leu
1205                1210                1215

Leu Gln Leu Lys Asp Phe Asp Phe Val Pro Pro Val Val Arg Trp
1220                1225                1230

Leu Asn Glu Gln Arg Tyr Tyr Gly Gly Gly Tyr Gly Ser Thr Gln
1235                1240                1245

Ala Thr Phe Met Val Phe Gln Ala Leu Ala Gln Tyr Gln Lys Asp
1250                1255                1260

Val Pro Asp His Lys Glu Leu Asn Leu Asp Val Ser Leu Gln Leu
1265                1270                1275

Pro Ser Arg Ser Ser Lys Ile Ile His Arg Ile His Trp Glu Ser
1280                1285                1290

Ala Ser Leu Leu Arg Ser Glu Glu Thr Lys Glu Asn Glu Gly Phe
1295                1300                1305

Thr Val Thr Ala Glu Gly Lys Gly Gln Gly Thr Leu Ser Val Val
1310                1315                1320

Thr Met Tyr His Ala Lys Ala Lys Gly Gln Leu Thr Cys Asn Lys
1325                1330                1335

Phe Asp Leu Lys Val Thr Ile Lys Pro Ala Pro Glu Thr Glu Lys
1340                1345                1350

Arg Pro Gln Asp Ala Lys Asn Thr Met Ile Leu Glu Ile Cys Thr
1355                1360                1365

Arg Tyr Arg Gly Asp Gln Asp Ala Thr Met Ser Ile Leu Asp Ile
1370                1375                1380

Ser Met Met Thr Gly Phe Val Pro Asp Thr Asp Asp Leu Lys Gln
1385                1390                1395

Leu Ala Asn Gly Val Asp Arg Tyr Ile Ser Lys Tyr Glu Leu Asp
1400                1405                1410

Lys Ala Phe Ser Asp Arg Asn Thr Leu Ile Ile Tyr Leu Asp Lys
1415                1420                1425

Val Ser His Ser Glu Asp Asp Cys Ile Ala Phe Lys Val His Gln
1430                1435                1440

Tyr Phe Asn Val Glu Leu Ile Gln Pro Gly Ala Val Lys Val Tyr
1445                1450                1455

Ala Tyr Tyr Asn Leu Ala Glu Ser Cys Thr Arg Phe Tyr His Pro
1460                1465                1470

Glu Lys Glu Asp Gly Lys Leu Asn Lys Leu Cys Arg Asp Glu Leu
1475                1480                1485

Cys Arg Cys Ala Glu Glu Asn Cys Phe Ile Gln Lys Leu Asp Asp
1490                1495                1500

Lys Val Thr Leu Glu Glu Arg Leu Asp Lys Ala Cys Glu Pro Gly
1505                1510                1515

Val Asp Tyr Val Tyr Lys Thr Arg Leu Val Lys Ala Gln Leu Ser
1520                1525                1530

Asn Asp Phe Asp Glu Tyr Ile Met Ala Ile Glu Gln Ile Ile Lys
1535                1540                1545

Ser Gly Ser Asp Glu Val Gln Val Gly Gln Gln Arg Thr Phe Ile
1550                1555                1560
```

-continued

```
Ser Pro Ile Lys Cys Arg Glu Ala Leu Lys Leu Glu Glu Arg Lys
    1565                1570                1575

His Tyr Leu Met Trp Gly Leu Ser Ser Asp Phe Trp Gly Glu Lys
    1580                1585                1590

Pro Asn Leu Ser Tyr Ile Ile Gly Lys Asp Thr Trp Val Glu His
    1595                1600                1605

Trp Pro Glu Glu Asp Glu Cys Gln Asp Glu Glu Asn Gln Lys Gln
    1610                1615                1620

Cys Gln Asp Leu Gly Thr Phe Thr Glu Asn Met Val Val Phe Gly
    1625                1630                1635

Cys Pro Asn
    1640

<210> SEQ ID NO 34
<211> LENGTH: 330
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 35
<211> LENGTH: 330
<212> TYPE: PRT
<213> ORGANISM: Homo sapiens

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys 325                 330

<210> SEQ ID NO 36
<211> LENGTH: 330
<212> TYPE: PRT
<213> ORGANISM: Homo sapiens

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 1663
<212> TYPE: PRT
<213> ORGANISM: Rattus norvegicus

<400> SEQUENCE: 37

```
Met Gly Pro Thr Ser Gly Ser Gln Leu Leu Val Leu Leu Leu Leu
1               5                   10                  15

Ala Ser Ser Leu Leu Ala Leu Gly Ser Pro Met Tyr Ser Ile Ile Thr
            20                  25                  30

Pro Asn Val Leu Arg Leu Glu Ser Glu Thr Phe Ile Leu Glu Ala
            35                  40                  45

His Asp Ala Gln Gly Asp Val Pro Val Thr Val Thr Val Gln Asp Phe
    50                  55                  60

Leu Lys Lys Gln Val Leu Thr Ser Glu Lys Thr Val Leu Thr Gly Ala
65                  70                  75                  80

Thr Gly His Leu Asn Arg Val Phe Ile Lys Ile Pro Ala Ser Lys Glu
                85                  90                  95

Phe Asn Ala Asp Lys Gly His Lys Tyr Val Thr Val Val Ala Asn Phe
            100                 105                 110

Gly Ala Thr Val Val Glu Lys Ala Val Leu Val Ser Phe Gln Ser Gly
            115                 120                 125

Tyr Leu Phe Ile Gln Thr Asp Lys Thr Ile Tyr Thr Pro Gly Ser Thr
    130                 135                 140

Val Phe Tyr Arg Ile Phe Thr Val Asp Asn Asn Leu Leu Pro Val Gly
145                 150                 155                 160

Lys Thr Val Val Ile Val Ile Glu Thr Pro Asp Gly Val Pro Ile Lys
                165                 170                 175

Arg Asp Ile Leu Ser Ser His Asn Gln Tyr Gly Ile Leu Pro Leu Ser
            180                 185                 190

Trp Asn Ile Pro Glu Leu Val Asn Met Gly Gln Trp Lys Ile Arg Ala
        195                 200                 205

Phe Tyr Glu His Ala Pro Lys Gln Thr Phe Ser Ala Glu Phe Glu Val
    210                 215                 220

Lys Glu Tyr Val Leu Pro Ser Phe Glu Val Leu Val Glu Pro Thr Glu
225                 230                 235                 240

Lys Phe Tyr Tyr Ile His Gly Pro Lys Gly Leu Glu Val Ser Ile Thr
                245                 250                 255

Ala Arg Phe Leu Tyr Gly Lys Asn Val Asp Gly Thr Ala Phe Val Ile
            260                 265                 270

Phe Gly Val Gln Asp Glu Asp Lys Lys Ile Ser Leu Ala Leu Ser Leu
        275                 280                 285

Thr Arg Val Leu Ile Glu Asp Gly Ser Gly Glu Ala Val Leu Ser Arg
    290                 295                 300

Lys Val Leu Met Asp Gly Val Arg Pro Ser Ser Pro Glu Ala Leu Val
305                 310                 315                 320

Gly Lys Ser Leu Tyr Val Ser Val Thr Val Ile Leu His Ser Gly Ser
                325                 330                 335

Asp Met Val Glu Ala Glu Arg Ser Gly Ile Pro Ile Val Thr Ser Pro
            340                 345                 350

Tyr Gln Ile His Phe Thr Lys Thr Pro Lys Phe Phe Lys Pro Ala Met
    355                 360                 365

Pro Phe Asp Leu Met Val Phe Val Thr Asn Pro Asp Gly Ser Pro Ala
370                 375                 380

Arg Arg Val Pro Val Val Thr Gln Gly Ser Asp Ala Gln Ala Leu Thr
385                 390                 395                 400

Gln Asp Asp Gly Val Ala Lys Leu Ser Val Asn Thr Pro Asn Asn Arg
                405                 410                 415
```

```
Gln Pro Leu Thr Ile Thr Val Ser Thr Lys Lys Glu Gly Ile Pro Asp
                420                 425                 430

Ala Arg Gln Ala Thr Arg Thr Met Gln Ala Gln Pro Tyr Ser Thr Met
                435                 440                 445

His Asn Ser Asn Tyr Leu His Leu Ser Val Ser Arg Val Glu Leu
    450                 455                 460

Lys Pro Gly Asp Asn Leu Asn Val Asn Phe His Leu Arg Thr Asp Ala
465                 470                 475                 480

Gly Gln Glu Ala Lys Ile Arg Tyr Tyr Thr Tyr Leu Val Met Asn Lys
                485                 490                 495

Gly Lys Leu Leu Lys Ala Gly Arg Gln Val Arg Glu Pro Gly Gln Asp
                500                 505                 510

Leu Val Val Leu Ser Leu Pro Ile Thr Pro Glu Phe Ile Pro Ser Phe
                515                 520                 525

Arg Leu Val Ala Tyr Tyr Thr Leu Ile Gly Ala Asn Gly Gln Arg Glu
530                 535                 540

Val Val Ala Asp Ser Val Trp Val Asp Val Lys Asp Ser Cys Val Gly
545                 550                 555                 560

Thr Leu Val Val Lys Gly Asp Pro Arg Asp Asn Arg Gln Pro Ala Pro
                565                 570                 575

Gly His Gln Thr Thr Leu Arg Ile Glu Gly Asn Gln Gly Ala Arg Val
                580                 585                 590

Gly Leu Val Ala Val Asp Lys Gly Val Phe Val Leu Asn Lys Lys Asn
                595                 600                 605

Lys Leu Thr Gln Ser Lys Ile Trp Asp Val Val Glu Lys Ala Asp Ile
    610                 615                 620

Gly Cys Thr Pro Gly Ser Gly Lys Asn Tyr Ala Gly Val Phe Met Asp
625                 630                 635                 640

Ala Gly Leu Thr Phe Lys Thr Asn Gln Gly Leu Gln Thr Asp Gln Arg
                645                 650                 655

Glu Asp Pro Glu Cys Ala Lys Pro Ala Ala Arg Arg Arg Arg Ser Val
                660                 665                 670

Gln Leu Met Glu Arg Arg Met Asp Lys Ala Gly Gln Tyr Thr Asp Lys
                675                 680                 685

Gly Leu Arg Lys Cys Cys Glu Asp Gly Met Arg Asp Ile Pro Met Pro
                690                 695                 700

Tyr Ser Cys Gln Arg Arg Ala Arg Leu Ile Thr Gln Gly Glu Ser Cys
705                 710                 715                 720

Leu Lys Ala Phe Met Asp Cys Cys Asn Tyr Ile Thr Lys Leu Arg Glu
                725                 730                 735

Gln His Arg Arg Asp His Val Leu Gly Leu Ala Arg Ser Asp Val Asp
                740                 745                 750

Glu Asp Ile Ile Pro Glu Glu Asp Ile Ile Ser Arg Ser His Phe Pro
                755                 760                 765

Glu Ser Trp Leu Trp Thr Ile Glu Glu Leu Lys Glu Pro Glu Lys Asn
                770                 775                 780

Gly Ile Ser Thr Lys Val Met Asn Ile Phe Leu Lys Asp Ser Ile Thr
785                 790                 795                 800

Thr Trp Glu Ile Leu Ala Val Ser Leu Ser Asp Lys Lys Gly Ile Cys
                805                 810                 815

Val Ala Asp Pro Tyr Glu Ile Thr Val Met Gln Asp Phe Phe Ile Asp
                820                 825                 830
```

Leu Arg Leu Pro Tyr Ser Val Val Arg Asn Glu Gln Val Glu Ile Arg
835              840              845

Ala Val Leu Phe Asn Tyr Arg Glu Gln Glu Lys Leu Lys Val Arg Val
850              855              860

Glu Leu Leu His Asn Pro Ala Phe Cys Ser Met Ala Thr Ala Lys Lys
865              870              875              880

Arg Tyr Tyr Gln Thr Ile Glu Ile Pro Pro Lys Ser Ser Val Ala Val
             885              890              895

Pro Tyr Val Ile Val Pro Leu Lys Ile Gly Leu Gln Gly Glu Val
             900              905              910

Lys Ala Ala Val Phe Asn His Phe Ile Ser Asp Gly Val Lys Lys Ile
             915              920              925

Leu Lys Val Val Pro Glu Gly Met Arg Val Asn Lys Thr Val Ala Val
             930              935              940

Arg Thr Leu Asp Pro Glu His Leu Asn Gln Gly Gly Val Gln Arg Glu
945              950              955              960

Asp Val Asn Ala Ala Asp Leu Ser Asp Gln Val Pro Asp Thr Asp Ser
             965              970              975

Glu Thr Arg Ile Leu Leu Gln Gly Thr Pro Val Ala Gln Met Ala Glu
             980              985              990

Asp Ala Val Asp Gly Glu Arg Leu Lys His Leu Ile Val Thr Pro Ser
             995              1000             1005

Gly Cys Gly Glu Gln Asn Met Ile Gly Met Thr Pro Thr Val Ile
    1010             1015             1020

Ala Val His Tyr Leu Asp Gln Thr Glu Gln Trp Glu Lys Phe Gly
    1025             1030             1035

Leu Glu Lys Arg Gln Glu Ala Leu Glu Leu Ile Lys Lys Gly Tyr
    1040             1045             1050

Thr Gln Gln Leu Ala Phe Lys Gln Pro Ile Ser Ala Tyr Ala Ala
    1055             1060             1065

Phe Asn Asn Arg Pro Pro Ser Thr Trp Leu Thr Ala Met Trp Ser
    1070             1075             1080

Arg Ser Phe Ser Leu Ala Ala Asn Leu Ile Ala Ile Asp Ser Gln
    1085             1090             1095

Val Leu Cys Gly Ala Val Lys Trp Leu Ile Leu Glu Lys Gln Lys
    1100             1105             1110

Pro Asp Gly Val Phe Gln Glu Asp Gly Pro Val Ile His Gln Glu
    1115             1120             1125

Met Ile Gly Gly Phe Arg Asn Thr Lys Glu Ala Asp Val Ser Leu
    1130             1135             1140

Thr Ala Phe Val Leu Ile Ala Leu Gln Glu Ala Arg Asp Ile Cys
    1145             1150             1155

Glu Gly Gln Val Asn Ser Leu Pro Gly Ser Ile Asn Lys Ala Gly
    1160             1165             1170

Glu Tyr Leu Glu Ala Ser Tyr Leu Asn Leu Gln Arg Pro Tyr Thr
    1175             1180             1185

Val Ala Ile Ala Gly Tyr Ala Leu Ala Leu Met Asn Lys Leu Glu
    1190             1195             1200

Glu Pro Tyr Leu Thr Lys Phe Leu Asn Thr Ala Lys Asp Arg Asn
    1205             1210             1215

Arg Trp Glu Glu Pro Gly Gln Gln Leu Tyr Asn Val Glu Ala Thr
    1220             1225             1230

Ser Tyr Ala Leu Leu Ala Leu Leu Leu Leu Lys Asp Phe Asp Ser 1235                1240                1245
Val Pro Pro Val Val Arg Trp Leu Asn Asp Glu Arg Tyr Tyr Gly
    1250                1255                1260
Gly Gly Tyr Gly Ser Thr Gln Ala Thr Phe Met Val Phe Gln Ala
    1265                1270                1275
Leu Ala Gln Tyr Arg Ala Asp Val Pro Asp His Lys Asp Leu Asn
    1280                1285                1290
Met Asp Val Ser Leu His Leu Pro Ser Arg Ser Ser Pro Thr Val
    1295                1300                1305
Phe Arg Leu Leu Trp Glu Ser Gly Ser Leu Leu Arg Ser Glu Glu
    1310                1315                1320
Thr Lys Gln Asn Glu Gly Phe Ser Leu Thr Ala Lys Gly Lys Gly
    1325                1330                1335
Gln Gly Thr Leu Ser Val Val Thr Val Tyr His Ala Lys Val Lys
    1340                1345                1350
Gly Lys Thr Thr Cys Lys Lys Phe Asp Leu Arg Val Thr Ile Lys
    1355                1360                1365
Pro Ala Pro Glu Thr Ala Lys Lys Pro Gln Asp Ala Lys Ser Ser
    1370                1375                1380
Met Ile Leu Asp Ile Cys Thr Arg Tyr Leu Gly Asp Val Asp Ala
    1385                1390                1395
Thr Met Ser Ile Leu Asp Ile Ser Met Met Thr Gly Phe Ile Pro
    1400                1405                1410
Asp Thr Asn Asp Leu Glu Leu Leu Ser Ser Gly Val Asp Arg Tyr
    1415                1420                1425
Ile Ser Lys Tyr Glu Met Asp Lys Ala Phe Ser Asn Lys Asn Thr
    1430                1435                1440
Leu Ile Ile Tyr Leu Glu Lys Ile Ser His Ser Glu Glu Asp Cys
    1445                1450                1455
Leu Ser Phe Lys Val His Gln Phe Phe Asn Val Gly Leu Ile Gln
    1460                1465                1470
Pro Gly Ser Val Lys Val Tyr Ser Tyr Tyr Asn Leu Glu Glu Ser
    1475                1480                1485
Cys Thr Arg Phe Tyr His Pro Glu Lys Asp Asp Gly Met Leu Ser
    1490                1495                1500
Lys Leu Cys His Asn Glu Met Cys Arg Cys Ala Glu Glu Asn Cys
    1505                1510                1515
Phe Met His Gln Ser Gln Asp Gln Val Ser Leu Asn Glu Arg Leu
    1520                1525                1530
Asp Lys Ala Cys Glu Pro Gly Val Asp Tyr Val Tyr Lys Thr Lys
    1535                1540                1545
Leu Thr Thr Ile Glu Leu Ser Asp Asp Phe Asp Glu Tyr Ile Met
    1550                1555                1560
Thr Ile Glu Gln Val Ile Lys Ser Gly Ser Asp Glu Val Gln Ala
    1565                1570                1575
Gly Gln Glu Arg Arg Phe Ile Ser His Val Lys Cys Arg Asn Ala
    1580                1585                1590
Leu Lys Leu Gln Lys Gly Lys Gln Tyr Leu Met Trp Gly Leu Ser
    1595                1600                1605
Ser Asp Leu Trp Gly Glu Lys Pro Asn Thr Ser Tyr Ile Ile Gly
    1610                1615                1620
Lys Asp Thr Trp Val Glu His Trp Pro Glu Ala Glu Glu Arg Gln
    1625                1630                1635

```
Asp Gln Lys Asn Gln Lys Gln Cys Glu Asp Leu Gly Ala Phe Thr
    1640                1645                1650
Glu Thr Met Val Val Phe Gly Cys Pro Asn
    1655                1660
```

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gly Tyr Ser Phe Thr Gly Tyr Asn Met Asn
1               5                   10
```

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Asn Ile Asn Pro Tyr Tyr Gly Ser Thr Asn Tyr Asn Gln Lys Phe Lys
1               5                   10                  15
Gly
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gly Tyr Tyr Gly Gly Asn Tyr Pro Phe Ala Tyr
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Arg Ala Ser Glu Asn Ile Tyr Ser Tyr Leu Ala
1               5                   10
```

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Asn Ala Lys Thr Leu Ala Glu
1               5
```

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln His Tyr Tyr Gly Thr Pro Tyr Thr
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Ile Asn Pro Tyr Tyr Asp Ser Thr Ser Tyr Asn Gln Lys Phe Lys
1               5                   10                  15

Gly

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Asn Tyr Asp Phe Val Gly Phe Ala Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Ser Ser Ser Val Ser Tyr Met His
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Thr Ser Asn Leu Ala Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 48

Gln Gln Trp Ser Thr Asn Pro Leu Thr
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Tyr Ser Phe Thr Gly Tyr Asn Met His
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asn Ile Asn Pro Tyr Tyr Gly Thr Thr Asn Ser Asn Gln Lys Phe Glu
1               5                   10                  15

Asp

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ile Tyr Tyr Tyr Gly Thr Gly Tyr Pro Tyr Phe Asp Phe
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Ser Gln Asp Ile Asn Asn Tyr Leu Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Thr Ser Arg Leu His Ser
1               5
```

```
<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Gln Gly Ile Thr Leu Pro Trp Thr
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Tyr Thr Phe Thr Asp Tyr Trp Ile Asn
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ile Tyr Pro Gly Ser Thr Ser Ala Asn Tyr Asn Glu Lys Phe Lys
1               5                   10                  15

Ser

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Gly Tyr Asp Ser Trp Phe Ala Tyr
1               5

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Ser Thr Lys Ser Leu Leu Asn Ser Asp Gly Phe Thr Tyr Leu Asp
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 59

Leu Val Ser Asn Arg Phe Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Phe Gln Ser Asn Tyr Leu Pro Leu Thr
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Tyr Ala Phe Asn Ser Cys Trp Met Asn
1               5                   10

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ile Tyr Pro Gly Asp Gly Asp Thr Asn Tyr Asn Gly Lys Phe Lys
1               5                   10                  15

Gly

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Gly Arg Asn Tyr Gly Tyr Glu Asp Tyr
1               5                   10

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Ala Ser Gln Ser Val Asp Tyr Asp Gly Asp Ser Tyr Met Asn
1               5                   10                  15
```

```
<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Asp Leu Glu Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Ala Asn Glu Asp Pro Arg Thr
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Thr Phe Ser Asn Tyr Ala Met Ser
1               5                   10

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Thr Ile Ser Ser Gly Gly Arg Tyr Thr Tyr Tyr Pro Asp Ser Val
1               5                   10                  15

Lys Gly

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Tyr Tyr Gly Asn Ser Tyr Trp Tyr Phe Asp Val
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 70

Lys Ser Ser Gln Ser Leu Leu Asn Ser Gly Asn Gln Lys His Tyr Leu
1               5                   10                  15

Thr

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ala Ser Thr Arg Gly Ser
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Asn Asp His Ser Tyr Pro Tyr Thr
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Phe Thr Phe Ser Ser Tyr Thr Met Ser
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Ile Ser Ser Gly Gly Gly Thr Thr Tyr Tyr Pro Asp Thr Val Lys
1               5                   10                  15

Gly

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Tyr Tyr Arg Gly Ser Ser Leu Trp Tyr Phe Asp Val
```

```
<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Ser Ser Gln Ser Leu Phe Asn Ser Gly Ser Gln Lys Asn Phe Leu
1               5                   10                  15

Thr

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Ala Ser Thr Arg Glu Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Asn Asp Tyr Ser Tyr Pro Leu Thr
1               5

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Tyr Ser Ile Thr Ser Gly Tyr Ser Leu His
1               5                   10

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Ile His Tyr Ser Gly Ser Thr Asn Tyr Asn Pro Ser Leu Lys Ser
1               5                   10                  15

<210> SEQ ID NO 81
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 81

Ala Trp Asp Tyr Leu Asp Tyr
1               5

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ala Ser Glu Asn Ile Tyr Ser Gln Leu Ala
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Ala Lys Thr Leu Ala Glu
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His His His Phe Gly Ile Leu Tyr Thr
1               5

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Tyr Ser Ile Thr Ser Gly Tyr Tyr Trp Asn
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Ile Arg Tyr Asp Gly Ser Asn Asn Tyr Asn Pro Ser Leu Lys Asn
1               5                   10                  15
```

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Tyr Gly Tyr Asp Gly Gly Ala Phe Asp Phe
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Thr Ser Glu Asn Ile Tyr Asn Tyr Leu Val
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asn Ala Lys Thr Leu Glu Glu
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln His His Tyr Gly Thr Pro Phe Thr
1               5

<210> SEQ ID NO 91
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Asp Ser Leu Thr Ser Glu Asp Ser Ala Val Tyr Tyr Cys
                85                  90                  95

Ala Arg Gly Tyr Tyr Gly Gly Asn Tyr Pro Phe Ala Tyr Trp Gly Gln
            100                 105                 110

Gly Thr Leu Val Thr Val Ser Ala
            115                 120

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Tyr Tyr Gly Thr Pro Tyr
                85                  90                  95

Thr Phe Gly Gly Gly Ser Lys Val Glu Ile Lys
            100                 105

<210> SEQ ID NO 93
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Ile Gln Leu Gln Gln Ser Gly Ala Glu Leu Val Lys Pro Gly Ala
1               5                   10                  15

Ser Val Lys Ile Ser Cys Met Ala Ser Gly Tyr Ser Phe Thr Gly Tyr
                20                  25                  30

Asn Met Asn Trp Val Lys Gln Ser His Gly Lys Gly Leu Glu Trp Ile
            35                  40                  45

Gly Asn Ile Asn Pro Tyr Tyr Asp Ser Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Asn Tyr Asp Phe Val Gly Phe Ala Tyr Trp Gly Gln Gly
            100                 105                 110

Thr Leu Val Thr Val Ser Ala
        115

<210> SEQ ID NO 94
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Phe Gln Gln Lys Pro Gly Ser Ser Pro Lys Pro Trp Ile Tyr
        35                  40                  45

Val Thr Ser Asn Leu Ala Ser Gly Val Pro Pro Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Thr Asn Pro Leu Thr
                85                  90                  95

Phe Gly Ala Gly Thr Lys Leu Glu Leu Lys
            100                 105

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Gln Leu Gln Gln Ser Gly Ala Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met His Trp Val Lys Gln Ser His Gly Lys Ser Leu Glu Trp Ile
        35                  40                  45

Gly Asn Ile Asn Pro Tyr Tyr Gly Thr Thr Asn Ser Asn Gln Lys Phe
    50                  55                  60

Glu Asp Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Ile Tyr Tyr Tyr Gly Thr Gly Tyr Pro Tyr Phe Asp Phe
            100                 105                 110

Trp Gly Gln Gly Thr Thr Leu Thr Val Ser Ser
        115                 120

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Thr Thr Ser Ser Leu Ser Ala Ser Leu Gly

```
            1               5                  10                 15
Asp Arg Val Thr Ile Ser Cys Arg Ala Ser Gln Asp Ile Asn Asn Tyr
                20                  25                  30

Leu Asn Trp Tyr Leu Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Leu Ala Thr Tyr Phe Cys Gln Gln Gly Ile Thr Leu Pro Trp
                85                  90                  95

Thr Phe Gly Gly Gly Thr Lys Leu Glu Ile Lys
            100                 105
```

<210> SEQ ID NO 97
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Gln Val Gln Leu Leu Gln Pro Gly Ala Glu Phe Val Lys Pro Gly Ala
1               5                   10                  15

Ser Val Lys Leu Ser Cys Lys Ala Ser Gly Tyr Thr Phe Thr Asp Tyr
                20                  25                  30

Trp Ile Asn Trp Val Lys Gln Arg Pro Gly Gln Gly Leu Glu Trp Ile
            35                  40                  45

Gly Asn Ile Tyr Pro Gly Ser Thr Ser Ala Asn Tyr Asn Glu Lys Phe
        50                  55                  60

Lys Ser Lys Ala Thr Leu Thr Ile Asp Thr Ser Ser Ile Thr Ala Tyr
65                  70                  75                  80

Met Gln Leu Ser Ser Leu Thr Ser Asp Asp Ser Ala Val Tyr Tyr Cys
                85                  90                  95

Ala Arg Tyr Gly Tyr Asp Ser Trp Phe Ala Tyr Trp Gly Gln Gly Thr
            100                 105                 110

Leu Val Thr Val Ser Ala
        115
```

<210> SEQ ID NO 98
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
                20                  25                  30

Asp Gly Phe Thr Tyr Leu Asp Trp Phe Leu Gln Lys Pro Gly Gln Ser
            35                  40                  45

Pro His Leu Leu Ile Tyr Leu Val Ser Asn Arg Phe Ser Gly Ile Pro
        50                  55                  60

Asp Arg Phe Ser Gly Ser Gly Ser Glu Thr Asp Phe Thr Leu Lys Ile
```

```
                65                  70                  75                  80
Ser Arg Val Glu Ala Glu Asp Leu Gly Val Tyr Tyr Cys Phe Gln Ser
                    85                  90                  95

Asn Tyr Leu Pro Leu Thr Phe Gly Ser Gly Thr Lys Leu Glu Ile Lys
            100                 105                 110

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Asn Ser Cys
                20                  25                  30

Trp Met Asn Trp Val Lys Gln Arg Pro Gly Lys Gly Leu Glu Trp Ile
            35                  40                  45

Gly Arg Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Arg Asn Tyr Gly Tyr Glu Asp Tyr Trp Gly Gln Gly
            100                 105                 110

Thr Thr Leu Thr Val Ser Ser
        115

<210> SEQ ID NO 100
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asp Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ala Asn
                85                  90                  95

Glu Asp Pro Arg Thr Phe Gly Gly Gly Thr Lys Leu Glu Ile Lys
            100                 105                 110

<210> SEQ ID NO 101
<211> LENGTH: 122
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 101

Glu Val Met Leu Val Glu Ser Gly Gly Ala Leu Val Lys Pro Gly Gly
1               5                   10                  15

Ser Leu Lys Leu Ser Cys Thr Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Gln Thr Ile Ser Ser Gly Gly Arg Tyr Thr Tyr Tyr Pro Asp Ser
    50                  55                  60

Val Lys Gly Arg Phe Thr Ile Ser Arg Asp Asn Ala Arg Asn Thr Leu
65                  70                  75                  80

Tyr Leu Gln Met Ser Ser Leu Arg Ser Glu Asp Thr Ala Met Tyr Tyr
                85                  90                  95

Cys Val Arg Arg Tyr Tyr Gly Asn Ser Tyr Trp Tyr Phe Asp Val Trp
            100                 105                 110

Gly Ala Gly Thr Thr Val Thr Val Ser Ser
        115                 120

<210> SEQ ID NO 102
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Val Met Thr Gln Ser Pro Ser Ser Leu Ser Val Ser Ala Gly
1               5                   10                  15

Glu Lys Val Thr Met Asn Cys Lys Ser Ser Gln Ser Leu Leu Asn Ser
            20                  25                  30

Gly Asn Gln Lys His Tyr Leu Thr Trp Tyr Gln Gln Lys Pro Gly Gln
        35                  40                  45

Pro Pro Lys Leu Leu Ile Tyr Gly Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Tyr Thr Phe Gly Gly Gly Thr Lys Leu Glu Ile
            100                 105                 110

Lys

<210> SEQ ID NO 103
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Lys Leu Val Glu Ser Gly Gly Gly Leu Val Gln Pro Gly Gly
1               5                   10                  15

```
Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
50                  55                  60

Lys Gly Arg Phe Thr Val Ser Arg Asp Asn Ala Lys Asn Thr Leu Tyr
65                  70                  75                  80

Leu Gln Met Ser Ser Leu Arg Ser Glu Asp Thr Ala Met Tyr Ser Cys
                85                  90                  95

Ala Arg Arg Tyr Tyr Arg Gly Ser Ser Leu Trp Tyr Phe Asp Val Trp
            100                 105                 110

Gly Ala Gly Thr Thr Val Thr Val Ser Ser
            115                 120
```

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Ser Gln Lys Asn Phe Leu Thr Trp Tyr Gln Gln Arg Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys
```

<210> SEQ ID NO 105
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Leu His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
50                  55                  60

Lys Ser Arg Ile Ser Ile Thr Arg Asp Thr Ser Lys Asn Gln Phe Phe
```

```
65                  70                  75                  80
Leu Lys Leu Asn Ser Val Thr Ser Glu Asp Thr Ala Thr Tyr His Cys
                85                  90                  95
Ala Arg Ala Trp Asp Tyr Leu Asp Tyr Trp Gly Gln Gly Thr Thr Leu
                100                 105                 110
Thr Val Ser Ser
        115

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Gln
                20                  25                  30

Leu Ala Trp Tyr Gln Gln Lys Gln Gly Lys Ser Pro Gln Leu Leu Val
            35                  40                  45

Tyr Asp Ala Lys Thr Leu Ala Glu Gly Val Pro Ser Arg Phe Ser Gly
    50                  55                  60

Ser Gly Ser Asp Thr Gln Phe Ser Leu Lys Ile Ile Ser Leu Gln Pro
65                  70                  75                  80

Glu Asp Phe Gly Arg Tyr Tyr Cys His His Phe Gly Ile Leu Tyr
                85                  90                  95

Thr Phe Gly Gly Gly Thr Lys Leu Glu Met Lys
                100                 105

<210> SEQ ID NO 107
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Arg Tyr Asp Gly Ser Asn Asn Tyr Asn Pro Ser Leu
    50                  55                  60

Lys Asn Arg Ile Ser Ile Thr Arg Asp Thr Ser Lys Asn Gln Val Phe
65                  70                  75                  80

Leu Lys Leu Asn Ser Val Thr Pro Glu Asp Thr Ala Thr Tyr Tyr Cys
                85                  90                  95

Ala Arg His Tyr Gly Tyr Asp Gly Gly Ala Phe Asp Phe Trp Gly Gln
                100                 105                 110

Gly Thr Thr Leu Thr Val Ser Ser
        115                 120
```

-continued

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Asn Tyr
            20                  25                  30

Leu Val Trp Tyr Gln Gln Lys Gln Gly Lys Ser Pro Gln Leu Leu Val
        35                  40                  45

Tyr Asn Ala Lys Thr Leu Glu Glu Gly Val Pro Ser Arg Phe Ser Gly
    50                  55                  60

Ser Gly Ser Gly Thr Gln Phe Ser Leu Lys Val Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys
            100                 105

<210> SEQ ID NO 109
<211> LENGTH: 330
<212> TYPE: PRT
<213> ORGANISM: Homo sapiens

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly

```
                    210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 110
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Cys Leu Glu Trp Met
        35                  40                  45

Gly Tyr Ile Tyr Pro His Asn Gly Gly Thr Thr Tyr Asn Gln Gln Phe
    50                  55                  60

Thr Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Phe Asp Phe Asp Tyr Trp Gly Gln Gly Thr Leu
            100                 105                 110

Val Thr Val Ser Ser
        115

<210> SEQ ID NO 111
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asp Trp Val Arg Gln Ala Pro Gly Gln Cys Leu Glu Trp Met
        35                  40                  45

Gly Tyr Ile Tyr Pro His Asn Ala Gly Thr Thr Tyr Asn Gln Gln Phe
```

```
                    50                  55                  60
Thr Gly Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Arg Gly Gly Phe Asp Phe Asp Tyr Trp Gly Gln Gly Thr Leu
                100                 105                 110

Val Thr Val Ser Ser
            115

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Gln Met Thr Gln Ser Pro Ser Ser Leu Ser Ala Ser Val Gly
  1               5                  10                  15

Asp Arg Val Thr Ile Thr Cys Lys Ala Ser Glu Asn Val Asp Thr Tyr
                 20                  25                  30

Val Ser Trp Tyr Gln Gln Lys Pro Gly Lys Ala Pro Lys Leu Leu Ile
             35                  40                  45

Tyr Gly Ala Ser Asn Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr His Cys Gly Gln Ser His Ser Tyr Pro Leu
                 85                  90                  95

Thr Phe Gly Cys Gly Thr Lys Leu Glu Ile Lys
                100                 105

<210> SEQ ID NO 113
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Asp Ile Gln Met Thr Gln Ser Pro Ser Leu Ser Ala Ser Val
  1               5                  10                  15

Gly Asp Arg Val Thr Ile Thr Cys Lys Ala Ser Glu Asn Val Asp Thr
                 20                  25                  30

Tyr Val Ser Trp Tyr Gln Gln Lys Pro Gly Lys Ala Pro Lys Leu Leu
             35                  40                  45

Ile Tyr Gly Ala Ser Asn Arg Tyr Thr Gly Val Pro Ser Arg Phe Ser
 50                  55                  60

Gly Ser Gly Ser Gly Thr Asp Phe Thr Phe Thr Ile Ser Ser Leu Gln
 65                  70                  75                  80

Pro Glu Asp Ile Ala Thr Tyr His Cys Gly Gln Ser His Ser Tyr Pro
                 85                  90                  95

Leu Thr Phe Gly Cys Gly Thr Lys Leu Glu Ile Lys Gly Gly Gly Gly
                100                 105                 110

Ser Gly Gly Gly Gly Ser Gly Gly Gly Gly Ser Gln Val Gln Leu Val
```

```
            115                 120                 125
Gln Ser Gly Ala Glu Val Lys Lys Pro Gly Ala Ser Val Lys Val Ser
        130                 135                 140

Cys Lys Ala Ser Gly Tyr Thr Phe Thr Asp Phe Tyr Met Asp Trp Val
145                 150                 155                 160

Arg Gln Ala Pro Gly Gln Cys Leu Glu Trp Met Gly Tyr Ile Tyr Pro
                165                 170                 175

His Asn Gly Gly Thr Thr Tyr Asn Gln Gln Phe Thr Gly Arg Val Thr
            180                 185                 190

Ile Thr Val Asp Lys Ser Ala Ser Thr Ala Tyr Met Glu Leu Ser Ser
        195                 200                 205

Leu Arg Ser Glu Asp Thr Ala Val Tyr Tyr Cys Ala Arg Arg Gly Gly
    210                 215                 220

Phe Asp Phe Asp Tyr Trp Gly Gln Gly Thr Leu Val Thr Val Ser Ser
225                 230                 235                 240

<210> SEQ ID NO 114
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Asp Ile Gln Met Thr Gln Ser Pro Ser Ser Leu Ser Ala Ser Val
1               5                   10                  15

Gly Asp Arg Val Thr Ile Thr Cys Lys Ala Ser Glu Asn Val Asp Thr
            20                  25                  30

Tyr Val Ser Trp Tyr Gln Gln Lys Pro Gly Lys Ala Pro Lys Leu Leu
        35                  40                  45

Ile Tyr Gly Ala Ser Asn Arg Tyr Thr Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr His Cys Gly Gln Ser His Ser Tyr Pro
                85                  90                  95

Leu Thr Phe Gly Cys Gly Thr Lys Leu Glu Ile Lys Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
        130                 135                 140

Cys Lys Ala Ser Gly Tyr Thr Phe Thr Asp Phe Tyr Met Asp Trp Val
145                 150                 155                 160

Arg Gln Ala Pro Gly Gln Cys Leu Glu Trp Met Gly Tyr Ile Tyr Pro
                165                 170                 175

His Asn Ala Gly Thr Thr Tyr Asn Gln Gln Phe Thr Gly Arg Val Thr
            180                 185                 190

Ile Thr Val Asp Lys Ser Ala Ser Thr Ala Tyr Met Glu Leu Ser Ser
        195                 200                 205

Leu Arg Ser Glu Asp Thr Ala Val Tyr Tyr Cys Ala Arg Arg Gly Gly
    210                 215                 220

Phe Asp Phe Asp Tyr Trp Gly Gln Gly Thr Leu Val Thr Val Ser Ser
225                 230                 235                 240
```

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gly Gly Gly Ser
1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Gly Gly Gly Ser Gly Gly Gly Gly Ser
1               5                   10

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Gly Gly Gly Ser Gly Gly Gly Gly Ser Gly Gly Gly Gly Ser
1               5                   10                  15

<210> SEQ ID NO 118
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Gly Gly Ser Gly Gly Gly Gly Ser Gly Gly Gly Gly Ser Gly
1               5                   10                  15

Gly Gly Gly Ser
            20

<210> SEQ ID NO 119
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Asp Thr Tyr
            20                  25                  30

Val Ser Trp Tyr Gln Gln Lys Pro Gly Lys Ala Pro Lys Leu Leu Ile
        35                  40                  45

```
Tyr Gly Ala Ser Asn Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr His Cys Gly Gln Ser His Ser Tyr Pro Leu
                 85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gln Val Gln Leu Val Gln
            115                 120                 125

Ser Gly Ala Glu Val Lys Lys Pro Gly Ala Ser Val Lys Val Ser Cys
130                 135                 140

Lys Ala Ser Gly Tyr Thr Phe Thr Asp Phe Tyr Met Asp Trp Val Arg
145                 150                 155                 160

Gln Ala Pro Gly Gln Cys Leu Glu Trp Met Gly Tyr Ile Tyr Pro His
                165                 170                 175

Asn Gly Gly Thr Thr Tyr Asn Gln Gln Phe Thr Gly Arg Val Thr Ile
            180                 185                 190

Thr Val Asp Lys Ser Ala Ser Thr Ala Tyr Met Glu Leu Ser Ser Leu
            195                 200                 205

Arg Ser Glu Asp Thr Ala Val Tyr Tyr Cys Ala Arg Arg Gly Gly Phe
210                 215                 220

Asp Phe Asp Tyr Trp Gly Gln Gly Thr Leu Val Thr Val Ser Ser
225                 230                 235

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Tyr Thr Phe Thr Asp Phe
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Phe Tyr Met Asp
1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Asp Phe Tyr Met Asp
1               5
```

```
<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Tyr Pro His Asn Gly Gly
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Ile Tyr Pro His Asn Gly Gly Thr Thr
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Ile Gly Tyr Ile Tyr Pro His Asn Gly Gly Thr Thr
1               5                   10

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Arg Arg Gly Gly Phe Asp Phe Asp
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Thr Tyr Val Ser Trp Tyr
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128
```

```
Leu Leu Ile Tyr Gly Ala Ser Asn Arg Tyr
1               5                   10

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gln Ser His Ser Tyr Pro Leu
1               5

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Trp Met Gly Tyr Ile Tyr Pro His Asn Gly Gly Thr Thr
1               5                   10

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Pro His Asn Ala Gly
1               5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Ile Tyr Pro His Asn Ala Gly Thr Thr
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Met Gly Tyr Ile Tyr Pro His Asn Ala Gly Thr Thr
1               5                   10

<210> SEQ ID NO 134
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 134

Tyr Pro His Asn Thr Gly
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Ile Tyr Pro His Asn Thr Gly Thr Thr
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Met Gly Tyr Ile Tyr Pro His Asn Thr Gly Thr Thr
1               5                   10

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr Pro His Glu Gly Gly
1               5

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Tyr Ile Tyr Pro His Glu Gly Gly Thr Thr
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Met Gly Tyr Ile Tyr Pro His Glu Gly Gly Thr Thr
1               5                   10
```

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Tyr Pro His Gln Gly Gly
1               5

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Tyr Ile Tyr Pro His Gln Gly Gly Thr Thr
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Trp Met Gly Tyr Ile Tyr Pro His Gln Gly Gly Thr Thr
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Tyr Ser Phe Thr Gly Tyr
1               5

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Tyr Asn Met Asn
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 145

Thr Gly Tyr Asn Met Asn
1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asn Pro Tyr Tyr Gly Ser
1               5

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asn Ile Asn Pro Tyr Tyr Gly Ser Thr Asn
1               5                   10

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asn Ile Asn Pro Tyr Tyr Gly Ser Thr Asn Tyr Asn Gln Lys Phe Lys
1               5                   10                  15

Gly

<210> SEQ ID NO 149
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Trp Ile Gly Asn Ile Asn Pro Tyr Tyr Gly Ser Thr Asn
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Arg Gly Tyr Tyr Gly Gly Asn Tyr Pro Phe Ala
1               5                   10

<210> SEQ ID NO 151
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Tyr Ser Tyr Leu Ala Trp Tyr
1               5

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Leu Val Tyr Asn Ala Lys Thr Leu Ala
1               5                   10

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln His Tyr Tyr Gly Thr Pro Tyr
1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asn Pro Tyr Tyr Asp Ser
1               5

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn Ile Asn Pro Tyr Tyr Asp Ser Thr Ser
1               5                   10

<210> SEQ ID NO 156
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156
```

```
Trp Ile Gly Asn Ile Asn Pro Tyr Tyr Asp Ser Thr Ser
1               5                   10
```

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Ala Arg Glu Asn Tyr Asp Phe Val Gly Phe Ala
1               5                   10
```

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

```
Ser Tyr Met His Trp Phe
1               5
```

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

```
Pro Trp Ile Tyr Val Thr Ser Asn Leu Ala
1               5                   10
```

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

```
Gln Gln Trp Ser Thr Asn Pro Leu
1               5
```

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

```
Gly Tyr Asn Met His
1               5
```

<210> SEQ ID NO 162
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 162

Thr Gly Tyr Asn Met His
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asn Pro Tyr Tyr Gly Thr
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asn Ile Asn Pro Tyr Tyr Gly Thr Thr Asn
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Trp Ile Gly Asn Ile Asn Pro Tyr Tyr Gly Thr Thr Asn
1               5                   10

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Arg Gly Ile Tyr Tyr Tyr Gly Thr Gly Tyr Pro Tyr Phe Asp
1               5                   10                  15

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asn Asn Tyr Leu Asn Trp Tyr
1               5

```
<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Leu Ile Tyr Tyr Thr Ser Arg Leu His
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Gly Ile Thr Leu Pro Trp
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Tyr Thr Phe Thr Asp Tyr
1               5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Tyr Trp Ile Asn
1               5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr Asp Tyr Trp Ile Asn
1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173
```

```
Tyr Pro Gly Ser Thr Ser
1               5
```

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

```
Asn Ile Tyr Pro Gly Ser Thr Ser Ala Asn
1               5                   10
```

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

```
Trp Ile Gly Asn Ile Tyr Pro Gly Ser Thr Ser Ala Asn
1               5                   10
```

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Ala Arg Tyr Gly Tyr Asp Ser Trp Phe Ala
1               5                   10
```

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Leu Asn Ser Asp Gly Phe Thr Tyr Leu Asp Trp Phe
1               5                   10
```

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Leu Leu Ile Tyr Leu Val Ser Asn Arg Phe
1               5                   10
```

<210> SEQ ID NO 179
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 179

Phe Gln Ser Asn Tyr Leu Pro Leu
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Tyr Ala Phe Asn Ser Cys
1               5

<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Cys Trp Met Asn
1               5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asn Ser Cys Trp Met Asn
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Tyr Pro Gly Asp Gly Asp
1               5

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ile Tyr Pro Gly Asp Gly Asp Thr Asn
1               5                   10
```

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Trp Ile Gly Arg Ile Tyr Pro Gly Asp Gly Asp Thr Asn
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Arg Glu Gly Arg Asn Tyr Gly Tyr Glu Asp
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Tyr Asp Gly Asp Ser Tyr Met Asn Trp Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Leu Leu Ile Tyr Ala Ala Ser Asp Leu Glu
1               5                   10

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Gln Ala Asn Glu Asp Pro Arg
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 190

Gly Phe Thr Phe Ser Asn Tyr
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Asn Tyr Ala Met Ser
1               5

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Asn Tyr Ala Met Ser
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Ser Ser Gly Gly Arg Tyr
1               5

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Thr Ile Ser Ser Gly Gly Arg Tyr Thr Tyr
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Val Gln Thr Ile Ser Ser Gly Gly Arg Tyr Thr Tyr
1               5                   10

<210> SEQ ID NO 196
<211> LENGTH: 13
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 196

Val Arg Arg Tyr Tyr Gly Asn Ser Tyr Trp Tyr Phe Asp
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Leu Asn Ser Gly Asn Gln Lys His Tyr Leu Thr Trp Tyr
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Leu Leu Ile Tyr Gly Ala Ser Thr Arg Gly
1               5                   10

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Asn Asp His Ser Tyr Pro Tyr
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Phe Thr Phe Ser Ser Tyr
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Tyr Thr Met Ser
1               5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Ser Tyr Thr Met Ser
1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Ser Gly Gly Gly Thr
1               5

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Tyr Ile Ser Ser Gly Gly Gly Thr Thr Tyr
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Trp Val Ala Tyr Ile Ser Ser Gly Gly Gly Thr Thr Tyr
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Arg Arg Tyr Tyr Arg Gly Ser Ser Leu Trp Tyr Phe Asp
1               5                   10

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 207

Phe Asn Ser Gly Ser Gln Lys Asn Phe Leu Thr Trp Tyr
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Leu Leu Ile Tyr Trp Ala Ser Thr Arg Glu
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Asn Asp Tyr Ser Tyr Pro Leu
1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Tyr Ser Ile Thr Ser Gly Tyr
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Gly Tyr Ser Leu His
1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Thr Ser Gly Tyr Ser Leu His
1               5

<210> SEQ ID NO 213
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

His Tyr Ser Gly Ser
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Tyr Ile His Tyr Ser Gly Ser Thr Asn
1               5

<210> SEQ ID NO 215
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Trp Met Gly Tyr Ile His Tyr Ser Gly Ser Thr Asn
1               5                   10

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Arg Ala Trp Asp Tyr Leu Asp
1               5

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Tyr Ser Gln Leu Ala Trp Tyr
1               5

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Leu Leu Val Tyr Asp Ala Lys Thr Leu Ala
```

```
1               5               10
```

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

His His His Phe Gly Ile Leu Tyr
1               5

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Gly Tyr Tyr Trp Asn
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Ser Gly Tyr Tyr Trp Asn
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Arg Tyr Asp Gly Ser
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Tyr Ile Arg Tyr Asp Gly Ser Asn Asn
1               5

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic

```
                                 peptide

<400> SEQUENCE: 224

Trp Met Gly Tyr Ile Arg Tyr Asp Gly Ser Asn Asn
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Arg His Tyr Gly Tyr Asp Gly Gly Ala Phe Asp
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Asn Tyr Leu Val Trp Tyr
1               5

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Leu Leu Val Tyr Asn Ala Lys Thr Leu Glu
1               5                   10

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln His His Tyr Gly Thr Pro Phe
1               5

<210> SEQ ID NO 229
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Asp Thr Tyr
            20                  25                  30
```

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr His Cys Gln Ser His Ser Tyr Pro Leu
                85                  90                  95

Thr Phe Gly Cys Gly Thr Lys Leu Glu Ile Lys Gly Gly Gly Ser
                100                 105                 110

Gly Gly Gly Gly Ser Gly Gly Gly Ser Gln Val Gln Leu Val Gln
            115                 120                 125

Ser Gly Ala Glu Val Lys Lys Pro Gly Ala Ser Val Lys Val Ser Cys
130                 135                 140

Lys Ala Ser Gly Tyr Thr Phe Thr Asp Phe Tyr Met Asp Trp Val Arg
145                 150                 155                 160

Gln Ala Pro Gly Gln Cys Leu Glu Trp Met Gly Tyr Ile Tyr Pro His
                165                 170                 175

Asn Ala Gly Thr Thr Tyr Asn Gln Gln Phe Thr Gly Arg Val Thr Ile
                180                 185                 190

Thr Val Asp Lys Ser Ala Ser Thr Ala Tyr Met Glu Leu Ser Ser Leu
            195                 200                 205

Arg Ser Glu Asp Thr Ala Val Tyr Tyr Cys Ala Arg Arg Gly Gly Phe
    210                 215                 220

Asp Phe Asp Tyr Trp Gly Gln Gly Thr Leu Val Thr Val Ser Ser
225                 230                 235

<210> SEQ ID NO 230
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ala" repeating units

<400> SEQUENCE: 230

Gly Gly Gly Gly Ala Gly Gly Gly Ala Gly Gly Gly Ala Gly
1               5                   10                  15

Gly Gly Gly Ala
            20

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 231

His His His His His His
1               5

<210> SEQ ID NO 232
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 232

Gly Gly Gly Gly Ser Gly Gly Gly Gly Ser Gly Gly Gly Gly Ser Gly
1               5                   10                  15

Gly Gly Gly Ser
            20
```

US 11,136,381 B2

ANTI-C3 ANTIBODIES

CROSS-REFERENCE TO RELATED APPLICATIONS

This application claims the priority benefit of U.S. provisional application No. 62/652,253, filed Apr. 3, 2018, which is hereby incorporated by reference herein in its entirety.

SEQUENCE LISTING

The present specification is being filed with a computer readable form (CRF) copy of the Sequence Listing. The CRF entitled 47702-0011001_SL.txt, which was created on Mar. 26, 2019 and is 211,214 bytes in size, is identical to the paper copy of the Sequence Listing and is incorporated herein by reference in its entirety.

FIELD OF THE INVENTION

The present disclosure generally relates to agents that bind complement component C3 (C3), particularly antibodies that bind human C3, as well as therapeutic methods of using the agents.

BACKGROUND

The complement cascade is primarily involved in the detection and removal of foreign pathogens such as bacteria. The complement system includes more than 30 cell-associated and circulating proteins (e.g., C1, C1q, C1r, C1s, C2, C3, C3a, C3b, C4, Factor B, Factor D, Factor H, Factor I). There are three main pathways that activate complement, the classical pathway (CP), the lectin pathway (MBL), and the alternative pathway (AP).

The three complement pathways are initiated by different factors, each resulting in the cleavage of complement component C3. The classical complement pathway is activated when the C1 complex binds specific antigen-antibody complexes, often immunoglobulin M (IgM), IgG3, or IgG1. This induces a conformational change in the C1 complex, allowing it to cleave C4 and C2 to generate the C4bC2b complex. C4bC2b acts as the C3 convertase of the classical pathway. The lectin complement pathway is activated when mannose-binding lectin (MBL) binds mannose-containing polysaccharides on microorganisms, initiating the cleavage of C4 and C2 by the MBL-MBL-associated serine protease complex. As in the classical pathway, the C4bC2b complex forms the C3 convertase of the lectin pathway. The oldest evolutionary signaling pathway of the three, the alternative complement pathway acts both independently of, and as an amplification loop for, the classical and lectin pathways. The alternative complement pathway undergoes low-level self-activation through the slow, spontaneous hydrolysis of C3. Once hydrolyzed, $C3(H_2O)$ binds complement Factor B, which is subsequently cleaved by complement Factor D into $C3(H_2O)Bb$, forming the C3 convertase of the alternative complement pathway. These different pathways converge with the cleavage of complement component C3 into C3a and C3b. On host cells, endogenous factors shut down the complement cascade. On pathogens, the complement cascade continues with the cleavage of complement component C5, which triggers cell death via phagocytosis, inflammation, and ultimately membrane attack complex (MAC) activation. (*Immunobiology: The Immune System in Health and Disease. 5th edition; Chapter. The complement system and innate immunity*; New York: Garland Science; 2001.)

Although the complement system is traditionally considered part of the immune system, i.e., protection against foreign pathogens, complement activity also has a role in maintaining healthy tissue. For example, clearance of apoptotic cells is facilitated by the complement pathway. However, inappropriate or excessive complement activation is thought to be a cause or contributing factor to a number of diseases and disorders.

Among the diseases that complement activation is thought to be involved in is aged-related macular degeneration (AMD). AMD is the main cause of vision loss among the elderly in developed countries and globally affects approximately 9% of the world's population. There are two types of AMD, dry (approximately 85-90% of patients) and wet (approximately 10-15% of patients). Wet AMD occurs when abnormal blood vessels (known as choroidal neovascularization or CNV) grow under the retina and macula. These new blood vessels may bleed and leak fluid, causing the macula to bulge or lift up from its normally flat position, thus distorting or destroying central vision. Under these circumstances, vision loss may be rapid and severe. Dry AMD is characterized by formation of drusen under the retina. Geographic atrophy (GA) is the advanced (late) form of dry AMD. GA is characterized by the progressive loss of areas of the retinal pigment epithelium (RPE), loss of photoreceptors (rods and cones), loss of neuroretina, and loss of choriocapillaris. The loss of one or more of these cells and/or tissues results in permanent central vision loss. Although there has been some progress in the development of new therapeutics for wet AMD, particularly the use of VEGF inhibitors, there are no approved treatments for dry AMD and/or GA. Thus, new therapeutic agents and methods of using those agents for treatment of AMD are needed.

BRIEF SUMMARY

The present disclosure provides agents that bind complement component C3 (e.g., SEQ ID NO: 1). The agents include, but are not limited to, polypeptides such as antibodies that specifically bind C3. The agents may be referred to herein as "C3-binding agents". The disclosure provides methods of making and of using a C3-binding agent. In some embodiments, a C3-binding agent inhibits C3 activity. In some embodiments, a C3-binding agent inhibits complement activation. In some embodiments, a C3-binding agent inhibits activation of the classical complement pathway, the alternative complement pathway, or both the classical and alternative complement pathways. In some embodiments, a C3-binding agent is used in a combination therapy. In some embodiments, a C3-binding agent is used in combination with at least one additional therapeutic agent.

The disclosure also provides compositions comprising the C3-binding agents described herein. In some embodiments, the disclosure provides pharmaceutical compositions comprising the C3-binding agents described herein. Polynucleotides and/or vectors encoding the C3-binding agents and methods of making the agents are also provided. Cells comprising or producing the C3-binding agents described herein are provided. Cells comprising the polynucleotides and/or the vectors described herein are also provided.

In one aspect, the present disclosure provides agents that bind C3 (e.g., SEQ ID NO:1). In some embodiments, an agent binds human C3 (e.g., SEQ ID NO:1). In some embodiments, an agent binds cynomolgus monkey ("cyno") C3 (e.g., SEQ ID NO:32). In some embodiments, an agent binds human C3 and cyno C3. In some embodiments, an agent is an antibody. In some embodiments, an agent is an antibody that binds human C3. In some embodiments, an agent is an antibody that binds cyno C3. In some embodiments, an agent is an antibody that binds human C3 and cyno C3. In some embodiments, an agent is an antibody that binds human C3 and does not bind mouse C3. In some embodiments, the agent does not bind mouse C3 at a detectable level. In some embodiments, an agent is an antibody that binds human C3 and does not bind rat C3. In some embodiments, the agent does not bind rat C3 at a detectable level. In some embodiments, an agent is an antibody that binds human C3 and does not bind human C3b. In some embodiments, the agent does not bind human C3b at a detectable level. In some embodiments, an agent is an antibody that binds human C3 with an affinity that is at least 50-fold greater than the antibody's affinity for human C3b. In some embodiments, an agent is an antibody that binds human C3 with an affinity that is at least 100-fold greater than the antibody's affinity for human C3b. In some embodiments, the affinity is measured using surface plasmon resonance (SPR) technology in a Biacore™ system as described herein or as known to those of skill in the art.

In one aspect, the present disclosure provides an agent (e.g., an antibody) that specifically binds human C3 (e.g., SEQ ID NO: 1) and has at least one or more (e.g., 1, 2, 3, 4, 5, 6, 7, 8, 9, 10, 11, 12) of the following properties: (a) binds to cyno C3 (e.g., SEQ ID NO:32), (b) inhibits C3 cleavage, (c) inhibits C3 cleavage and C3a release, (d) inhibits activation of the alternative complement pathway (e.g., as assessed by hemolytic assays), (e) inhibits activation of the classical complement pathway (e.g., as assessed by hemolytic assays), (f) inhibits activation of the alternative complement pathway and classical complement pathway (e.g., as assessed by hemolytic assays), (g) does not detectably bind to Factor Bb, (h) does not detectably bind to C3d, (i) does not detectably bind to C3a, (j) does not detectably bind to C3b, (k) does not detectably bind to iC3b, (1) does not detectably bind to Factor Bb and C3d, (m) does not detectably bind to Factor Bb, C3d, and C3a, (n) does not detectably bind to Factor Bb, C3d, C3a, C3b, and iC3b, (o) binds to human C3 (e.g., SEQ ID NO: 1) with a greater affinity than compstatin, and (p) has a half-life of about 4-5 days in human vitreous humor. In certain embodiments, the C3-binding agent inhibits activation of the classical complement pathway (e.g., as assessed by hemolytic assays). In some embodiments, the C3-binding agent inhibits activation of the alternative complement pathway and classical complement pathway (e.g., as assessed by hemolytic assays). In certain embodiments, the C3-binding agent comprises: (a) a heavy chain CDR1 comprising SEQ ID NO:7, a heavy chain CDR2 comprising SEQ ID NO:8, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12; (b) a heavy chain CDR1 comprising SEQ ID NO:7, a heavy chain CDR2 comprising SEQ ID NO: 13, a heavy chain CDR3 comprising SEQ ID NO:9, a light chain CDR1 comprising SEQ ID NO:10, a light chain CDR2 comprising SEQ ID NO: 11, and a light chain CDR3 comprising SEQ ID NO: 12; (c) a heavy chain CDR1 comprising SEQ ID NO:7, a heavy chain CDR2 comprising SEQ ID NO:14, a heavy chain CDR3 comprising SEQ ID NO:9, a light chain CDR1 comprising SEQ ID NO:10, a light chain CDR2 comprising SEQ ID NO: 11, and a light chain CDR3 comprising SEQ ID NO: 12; (d) a heavy chain CDR1 comprising SEQ ID NO:7, a heavy chain CDR2 comprising SEQ ID NO:15, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12; (e) a heavy chain CDR1 comprising SEQ ID NO:7, a heavy chain CDR2 comprising SEQ ID NO: 16, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12; or (f) a heavy chain CDR1 comprising SEQ ID NO:7, a heavy chain CDR2 comprising SEQ ID NO: 17, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12. In certain embodiments, the C3-binding agent comprises a heavy chain CDR1 comprising SEQ ID NO:7, a heavy chain CDR2 comprising SEQ ID NO: 14, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12. In certain embodiments, the C3-binding agent comprises: (a) a heavy chain variable region comprising SEQ ID NO:20 and a light chain variable region comprising SEQ ID NO:25; (b) a heavy chain variable region comprising SEQ ID NO:21 and a light chain variable region comprising SEQ ID NO:25; (c) a heavy chain variable region comprising SEQ ID NO:22 and a light chain variable region comprising SEQ ID NO:25; (d) a heavy chain variable region comprising SEQ ID NO:23 and a light chain variable region comprising SEQ ID NO:25; or (e) a heavy chain variable region comprising SEQ ID NO:24 and a light chain variable region comprising SEQ ID NO:25. In certain embodiments, the C3-binding agent comprises a heavy chain variable region comprising SEQ ID NO:21 and a light chain variable region comprising SEQ ID NO:25.

In another aspect, the present disclosure provides an agent (e.g., an antibody) that specifically binds human C3 and has at least one or more (e.g., 1, 2, 3, 4, 5, 6, 7, 8, 9, 10, 11, 12) of the following properties: (a) binds to cyno C3 (e.g., SEQ ID NO:32), (b) inhibits C3 cleavage, (c) inhibits C3 cleavage and C3a release, (d) inhibits activation of the alternative complement pathway (e.g., as assessed by hemolytic assays), (e) inhibits activation of the classical complement pathway (e.g., as assessed by hemolytic assays), (f) inhibits activation of the alternative complement pathway and classical complement pathway (e.g., as assessed by hemolytic assays), (g) does not detectably bind to Factor Bb, (h) does not detectably bind to C3d, (i) does not detectably bind to C3a, (j) does not detectably bind to C3b, (k) does not detectably bind to iC3b, (1) does not detectably bind to Factor Bb and C3d, (m) does not detectably bind to Factor Bb, C3d, and C3a, (n) does not detectably bind to Factor Bb, C3d, C3a, C3b, and iC3b, (o) binds to human C3 (e.g., SEQ ID NO:1) with a greater affinity than compstatin, and (p) has a half-life of about 4-5 days in human vitreous humor, wherein the antibody or antigen-binding fragment is for use in the prophylaxis or treatment of a disease selected from AMD, macular degeneration, diabetic retinopathy, retinopathy of prematurity, macular dystrophy, retinal dystrophy, uveitis, keratitis, scleritis, retinitis pigmentosa, choroidal neovascularization, retinal neovascularization, and ocular inflammation. In certain embodiments, the disease is AMD. In certain embodiments, the agent (e.g., an antibody or antigen-binding fragment thereof) inhibits activation of the alternative complement pathway and classical complement pathway (e.g., as assessed by hemolytic assays).

In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHNGGTTYNQNFTG (SEQ ID NO:8), YIYPHNGGTTYNQQFTG (SEQ ID NO: 13), YIYPHNAGTTYNQQFTG (SEQ ID NO: 14), YIYPHNTGTTYNQQFTG (SEQ ID NO:15), YIYPHEGGTTYNQQFTG (SEQ ID NO:16), or YIYPHQGGTTYNQQFTG (SEQ ID NO: 17), and a heavy chain CDR3 comprising RGGFDFDY (SEQ ID NO:9); and/or (b) a light chain CDR1 comprising KASENVDTYVS (SEQ ID NO:10); a light chain CDR2 comprising GASNRYT (SEQ ID NO: 11); and a light chain CDR3 comprising GQSHSYPLT (SEQ ID NO:12). In some embodiments, an agent (e.g., an antibody) that specifically binds C3 comprises a heavy chain CDR1 comprising GYTFTDFYMD (SEQ ID NO:7); a heavy chain CDR2 comprising YIYPHNGGTTYNQNFTG (SEQ ID NO:8), YIYPHNGGTTYNQQFTG (SEQ ID NO: 13), YIYPHNAGTTYNQQFTG (SEQ ID NO: 14), YIYPHNTGTTYNQQFTG (SEQ ID NO:15), YIYPHEGGTTYNQQFTG (SEQ ID NO:16), or YIYPHQGGTTYNQQFTG (SEQ ID NO: 17), and a heavy chain CDR3 comprising RGGFDFDY (SEQ ID NO:9). In some embodiments, an agent (e.g., an antibody) that specifically binds C3 comprises a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO:12). In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHNGGTTYNQNFTG (SEQ ID NO:8), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHNGGTTYNQQFTG (SEQ ID NO: 13), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHNAGTTYNQQFTG (SEQ ID NO: 14), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO:12). In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHNTGTTYNQQFTG (SEQ ID NO: 15), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHEGGTTYNQQFTG (SEQ ID NO: 16), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, an agent (e.g., an antibody) that specifically binds C3 comprises: (a) a heavy chain CDR1 comprising GYTFTDFYMD (SEQ ID NO:7); a heavy chain CDR2 comprising YIYPHQGGTTYNQQFTG (SEQ ID NO: 17), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, the agent is an antibody.

In certain embodiments, an agent (e.g., an antibody) that specifically binds C3 comprises: a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHNGGTTYNQNFTG (SEQ ID NO:8), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO:12). In certain embodiments, an agent (e.g., an antibody) that specifically binds C3 comprises: a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHNGGTTYNQQFTG (SEQ ID NO: 13), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO:12). In certain embodiments, an agent (e.g., an antibody) that specifically binds C3 comprises: a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO: 7), heavy chain CDR2 comprises YIYPHNAGTTYNQQFTG (SEQ ID NO: 14), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO:12). In certain embodiments, an agent (e.g., an antibody) that specifically binds C3 comprises: a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHNTGTTYNQQFTG (SEQ ID NO: 15), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO:12). In certain embodiments, an agent (e.g., an antibody) that specifically binds C3 comprises: a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHEGGT-TYNQQFTG (SEQ ID NO: 16), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO:12). In certain embodiments, an agent (e.g., an antibody) that specifically binds C3 comprises: a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHQGGTTYNQQFTG (SEQ ID NO: 17), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In some embodiments, an agent (e.g., an antibody) that specifically binds C3 further comprises (a) a heavy chain framework region (FR) 1, a heavy chain FR2, a heavy chain FR3, and a heavy chain FR4; and/or (b) a light chain FR1, a light chain FR2, a light chain FR3, and a light chain FR4. In some embodiments, an agent (e.g., an antibody) that specifically binds C3 comprises a heavy chain FR1, a heavy chain FR2, a heavy chain FR3, and a heavy chain FR4. In some embodiments, an agent comprises a light chain FR1, a light chain FR2, a light chain FR3, and a light chain FR4. In some embodiments, an agent (e.g., an antibody) that specifically binds C3 comprises (a) a heavy chain FR1, a heavy chain FR2, a heavy chain FR3, and a heavy chain FR4; and (b) a light chain FR1, a light chain FR2, a light chain FR3, and a light chain FR4

In some embodiments, an agent (e.g., an antibody) that specifically binds C3 comprises: (a) a heavy chain variable region having at least 90% sequence identity to SEQ ID NO:18, SEQ ID NO:20, SEQ ID NO:21, SEQ ID NO:22, SEQ ID NO:23, or SEQ ID NO:24; and/or (b) a light chain variable region having at least 90% sequence identity to SEQ ID NO: 19 or SEQ ID NO:25. In some embodiments, an agent (e.g., an antibody) that specifically binds C3 comprises a heavy chain variable region having at least 95% sequence identity to SEQ ID NO:18 and a light chain variable region having at least 95% sequence identity to SEQ ID NO: 19. In some embodiments, an agent (e.g., an antibody) that specifically binds C3 comprises a heavy chain variable region having at least 95% sequence identity to SEQ ID NO:20 and a light chain variable region having at least 95% sequence identity to SEQ ID NO:25. In some embodiments, an agent (e.g., an antibody) that specifically binds C3 comprises a heavy chain variable region having at least 95% sequence identity to SEQ ID NO:21 and a light chain variable region having at least 95% sequence identity to SEQ ID NO:25. In some embodiments, an agent (e.g., an antibody) that specifically binds C3 comprises a heavy chain variable region having at least 95% sequence identity to SEQ ID NO:22 and a light chain variable region having at least 95% sequence identity to SEQ ID NO:25. In some embodiments, an agent (e.g., an antibody) that specifically binds C3 comprises a heavy chain variable region having at least 95% sequence identity to SEQ ID NO:23 and a light chain variable region having at least 95% sequence identity to SEQ ID NO:25. In some embodiments, an agent (e.g., an antibody) that specifically binds C3 comprises a heavy chain variable region having at least 95% sequence identity to SEQ ID NO:24 and a light chain variable region having at least 95% sequence identity to SEQ ID NO:25. In some embodiments, an agent (e.g., an antibody) that specifically binds C3 comprises a heavy chain variable region comprising SEQ ID NO: 18 and a light chain variable region comprising SEQ ID NO:19. In some embodiments, an agent (e.g., an antibody) that specifically binds C3 comprises a heavy chain variable region comprising SEQ ID NO:20 and a light chain variable region comprising SEQ ID NO:25. In some embodiments, an agent (e.g., an antibody) that specifically binds C3 comprises a heavy chain variable region comprising SEQ ID NO:21 and a light chain variable region comprising SEQ ID NO:25. In some embodiments, an agent (e.g., an antibody) that specifically binds C3 comprises a heavy chain variable region comprising SEQ ID NO:22 and a light chain variable region comprising SEQ ID NO:25. In some embodiments, an agent (e.g., an antibody) that specifically binds C3 comprises a heavy chain variable region comprising SEQ ID NO:23 and a light chain variable region comprising SEQ ID NO:25. In some embodiments, an agent (e.g., an antibody) that specifically binds C3 comprises a heavy chain variable region comprising SEQ ID NO:24 and a light chain variable region comprising SEQ ID NO:25. In some embodiments, the agent is an antibody.

In some embodiments, an agent (e.g., an antibody) that specifically binds C3 comprises the heavy chain CDR1, CDR2, and CDR3, and/or the light chain CDR1, CDR2, and CDR3 from: (a) the antibody designated 38G10 that comprises a heavy chain variable region comprising SEQ ID NO:18 and a light chain variable region comprising SEQ ID NO:19; (b) the antibody designated Hz38G10 that comprises a heavy chain variable region comprising SEQ ID NO:20 and a light chain variable region comprising SEQ ID NO:25; (c) the antibody designated Hz38G10(G56A) that comprises a heavy chain variable region comprising SEQ ID NO:21 and a light chain variable region comprising SEQ ID NO:25; (d) the antibody designated Hz38G10(G56T) that comprises a heavy chain variable region comprising SEQ ID NO:22 and a light chain variable region comprising SEQ ID NO:25; (e) the antibody designated Hz38G10(N55E) that comprises a heavy chain variable region comprising SEQ ID NO:23 and a light chain variable region comprising SEQ ID NO:25, or (f) the antibody designated Hz38G10(N55Q) that comprises a heavy chain variable region comprising SEQ ID NO:24 and a light chain variable region comprising SEQ ID NO:25.

In some embodiments, an agent (e.g., an antibody) that specifically binds C3 comprises the CDR1, CDR2, and CDR3 from a heavy chain variable region and the CDR1, CDR2, and CDR3 from a light chain variable region, wherein each CDR is defined in accordance with the Exemplary definition, the Chothia definition, the AbM definition, the Kabat definition, or the contact definition. Thus, in some embodiments, an agent (e.g., an antibody) that specifically binds C3 comprises the CDR1, CDR2, and CDR3 from a heavy chain variable region comprising SEQ ID NO:18 and the CDR1, CDR2, and CDR3 from a light chain variable region comprising SEQ ID NO:19. In some embodiments, an agent (e.g., an antibody) that specifically binds C3 comprises the CDR1, CDR2, and CDR3 from a heavy chain variable region comprising SEQ ID NO:20 and the CDR1, CDR2, and CDR3 from a light chain variable region comprising SEQ ID NO:25. In some embodiments, an agent (e.g., an antibody) that specifically binds C3 comprises the CDR1, CDR2, and CDR3 from a heavy chain variable region comprising SEQ ID NO:21 and the CDR1, CDR2, and CDR3 from a light chain variable region comprising SEQ ID NO:25. In some embodiments, an agent (e.g., an antibody) that specifically binds C3 comprises the CDR1, CDR2, and CDR3 from a heavy chain variable region comprising SEQ ID NO:22 and the CDR1, CDR2, and CDR3 from a light chain variable region comprising SEQ ID NO:25. In some embodiments, an agent (e.g., an antibody) that specifically binds C3 comprises the CDR1, CDR2, and CDR3 from a heavy chain variable region comprising SEQ ID NO:23 and the CDR1, CDR2, and CDR3 from a light chain variable region comprising SEQ ID NO:25. In some embodiments, an agent (e.g., an antibody) that specifically binds C3 comprises the CDR1, CDR2, and CDR3 from a heavy chain variable region comprising SEQ ID NO:24 and the CDR1, CDR2, and CDR3 from a light chain variable region comprising SEQ ID NO:25.

In some embodiments, a C3-binding agent is an antibody that comprises a heavy chain of SEQ ID NO:27 and/or a light chain of SEQ ID NO:31. In some embodiments, a C3-binding agent is an antibody that comprises a heavy chain of SEQ ID NO:27 and a light chain of SEQ ID NO:31. In some embodiments, a C3-binding agent is an antibody that comprises a heavy chain of SEQ ID NO:29 and/or a light chain of SEQ ID NO:31. In some embodiments, a C3-binding agent is an antibody that comprises a heavy chain of SEQ ID NO:29 and a light chain of SEQ ID NO:31.

In certain embodiments, an agent (e.g., an antibody) that specifically binds C3 comprises heavy chain CDRs 1, 2, and 3 of a heavy chain variable region comprising the amino acid sequence set forth in SEQ ID NO:91. In certain embodiments, an agent (e.g., an antibody) that specifically binds C3 comprises light chain CDRs 1, 2, and 3 of a light chain variable region comprising the amino acid sequence set forth in SEQ ID NO:92. In certain embodiments, an agent (e.g., an antibody) that specifically binds C3 comprises heavy chain CDRs 1, 2, and 3 of a heavy chain variable region comprising the amino acid sequence set forth in SEQ ID NO:91, and light chain CDRs 1, 2, and 3 of a light chain variable region comprising the amino acid sequence set forth in SEQ ID NO:92. In some embodiments, an agent (e.g., an antibody) that specifically binds C3 comprises a heavy chain variable region comprising heavy chain CDRs 1, 2, and 3, wherein heavy chain CDR1 comprises GYSFTGYNMN (SEQ ID NO:38), heavy chain CDR2 comprises NINPYYGSTNYNQKFKG (SEQ ID NO:39), and heavy chain CDR3 comprises GYYGGNYPFAY (SEQ ID NO:40). In some embodiments, an agent (e.g., an antibody) that specifically binds C3 comprises a light chain variable region comprising light chain CDRs 1, 2, and 3, wherein light chain CDR1 comprises RASENIYSYLA (SEQ ID NO:41), light chain CDR2 comprises NAKTLAE (SEQ ID NO:42), and light chain CDR3 comprises QHYYGTPYT (SEQ ID NO:43). In some embodiments, an agent (e.g., an antibody) that specifically binds C3 comprises a heavy chain variable region comprising heavy chain CDRs 1, 2, and 3 and a light chain variable region comprising light chain CDRs 1, 2, and 3, wherein heavy chain CDR1 comprises GYSFTGYNMN (SEQ ID NO:38), heavy chain CDR2 comprises NINPYYGSTNYNQKFKG (SEQ ID NO:39), heavy chain CDR3 comprises GYYGGNYPFAY (SEQ ID NO:40), light chain CDR1 comprises RASENIYSYLA (SEQ ID NO:41), light chain CDR2 comprises NAKTLAE (SEQ ID NO:42), and light chain CDR3 comprises QHYYGTPYT (SEQ ID NO:43).

In certain embodiments, an agent (e.g., an antibody) that specifically binds C3 comprises heavy chain CDRs 1, 2, and 3 of a heavy chain variable region comprising the amino acid sequence set forth in SEQ ID NO:93. In certain embodiments, an agent (e.g., an antibody) that specifically binds C3 comprises light chain CDRs 1, 2, and 3 of a light chain variable region comprising the amino acid sequence set forth in SEQ ID NO:94. In certain embodiments, an agent (e.g., an antibody) that specifically binds C3 comprises heavy chain CDRs 1, 2, and 3 of a heavy chain variable region comprising the amino acid sequence set forth in SEQ ID NO:93, and light chain CDRs 1, 2, and 3 of a light chain variable region comprising the amino acid sequence set forth in SEQ ID NO:94. In some embodiments, an agent (e.g., an antibody) that specifically binds C3 comprises a heavy chain variable region comprising heavy chain CDRs 1, 2, and 3, wherein heavy chain CDR1 comprises GYSFTGYNMN (SEQ ID NO:38), heavy chain CDR2 comprises NINPYYDSTSYNQKFKG (SEQ ID NO:44), and heavy chain CDR3 comprises ENYDFVGFAY (SEQ ID NO:45). In some embodiments, an agent (e.g., an antibody) that specifically binds C3 comprises a light chain variable region comprising light chain CDRs 1, 2, and 3, wherein light chain CDR1 comprises RASSSVSYMH (SEQ ID NO:46), light chain CDR2 comprises VTSNLAS (SEQ ID NO:47), and light chain CDR3 comprises QQWSTNPLT (SEQ ID NO:48). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GYSFTGYNMN (SEQ ID NO:38), heavy chain CDR2 comprises NINPYYDSTSYNQKFKG (SEQ ID NO:44), heavy chain CDR3 comprises ENYDFVGFAY (SEQ ID NO:45), light chain CDR1 comprises RASSSVSYMH (SEQ ID NO:46), light chain CDR2 comprises VTSNLAS (SEQ ID NO:47), and light chain CDR3 comprises QQWSTNPLT (SEQ ID NO:48).

In certain embodiments, an agent (e.g., an antibody) that specifically binds C3 comprises heavy chain CDRs 1, 2, and 3 of a heavy chain variable region comprising the amino acid sequence set forth in SEQ ID NO:95. In certain embodiments, an agent (e.g., an antibody) that specifically binds C3 comprises light chain CDRs 1, 2, and 3 of a light chain variable region comprising the amino acid sequence set forth in SEQ ID NO:96. In certain embodiments, an agent (e.g., an antibody) that specifically binds C3 comprises heavy chain CDRs 1, 2, and 3 of a heavy chain variable region comprising the amino acid sequence set forth in SEQ ID NO:95, and light chain CDRs 1, 2, and 3 of a light chain variable region comprising the amino acid sequence set forth in SEQ ID NO:96. In some embodiments, an agent (e.g., an antibody) that specifically binds C3 comprises a heavy chain variable region comprising heavy chain CDRs 1, 2, and 3, wherein heavy chain CDR1 comprises GYSFTGYNMH (SEQ ID NO:49), heavy chain CDR2 comprises NINPYYGTTNSNQKFED (SEQ ID NO:50), and heavy chain CDR3 comprises GIYYYGTGYPYFDF (SEQ ID NO:51). In some embodiments, an agent (e.g., an antibody) that specifically binds C3 comprises a light chain variable region comprising light chain CDRs 1, 2, and 3, wherein light chain CDR1 comprises RASQDINNYLN (SEQ ID NO:52), light chain CDR2 comprises YTSRLHS (SEQ ID NO:53), and light chain CDR3 comprises QQGITLPWT (SEQ ID NO:54). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GYSFTGYNMH (SEQ ID NO:49), heavy chain CDR2 comprises NINPYYGTTNSNQKFED (SEQ ID NO:50), heavy chain CDR3 comprises GIYYYGTGYPYFDF (SEQ ID NO:51), light chain CDR1 comprises RASQDINNYLN (SEQ ID NO:52), light chain CDR2 comprises YTSRLHS (SEQ ID NO:53), and light chain CDR3 comprises QQGITLPWT (SEQ ID NO:54).

In certain embodiments, an agent (e.g., an antibody) that specifically binds C3 comprises heavy chain CDRs 1, 2, and 3 of a heavy chain variable region comprising the amino acid sequence set forth in SEQ ID NO:97. In certain embodiments, an agent (e.g., an antibody) that specifically binds C3 comprises light chain CDRs 1, 2, and 3 of a light chain variable region comprising the amino acid sequence set forth in SEQ ID NO:98. In certain embodiments, an agent (e.g., an antibody) that specifically binds C3 comprises heavy chain CDRs 1, 2, and 3 of a heavy chain variable region comprising the amino acid sequence set forth in SEQ ID NO:97, and light chain CDRs 1, 2, and 3 of a light chain variable region comprising the amino acid sequence set forth in SEQ ID NO:98. In some embodiments, an agent (e.g., an antibody) that specifically binds C3 comprises a heavy chain variable region comprising heavy chain CDRs 1, 2, and 3, wherein heavy chain CDR1 comprises GYTFTDYWIN (SEQ ID NO:55), heavy chain CDR2 comprises NIYPGSTSANYNEKFKS (SEQ ID NO:56), and heavy chain CDR3 comprises YGYDSWFAY (SEQ ID NO:57). In some embodiments, an agent (e.g., an antibody) that specifically binds C3 comprises a light chain variable region comprising light chain CDRs 1, 2, and 3, wherein light chain CDR1 comprises KSTKSLLNSDGFTYLD (SEQ ID NO:58), light chain CDR2 comprises LVSNRFS (SEQ ID NO:59), and light chain CDR3 comprises FQSNYLPLT (SEQ ID NO:60). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GYTFTDYWIN (SEQ ID NO:55), heavy chain CDR2 comprises NIYPGSTSANYNEKFKS (SEQ ID NO:56), heavy chain CDR3 comprises YGYDSWFAY (SEQ ID NO:57), light chain CDR1 comprises KSTKSLLNSDGFTYLD (SEQ ID NO:58), light chain CDR2 comprises LVSNRFS (SEQ ID NO:59), and light chain CDR3 comprises FQSNYLPLT (SEQ ID NO:60).

In certain embodiments, an agent (e.g., an antibody) that specifically binds C3 comprises heavy chain CDRs 1, 2, and 3 of a heavy chain variable region comprising the amino acid sequence set forth in SEQ ID NO:99. In certain embodiments, an agent (e.g., an antibody) that specifically binds C3 comprises light chain CDRs 1, 2, and 3 of a light chain variable region comprising the amino acid sequence set forth in SEQ ID NO: 100. In certain embodiments, an agent (e.g., an antibody) that specifically binds C3 comprises heavy chain CDRs 1, 2, and 3 of a heavy chain variable region comprising the amino acid sequence set forth in SEQ ID NO:99, and light chain CDRs 1, 2, and 3 of a light chain variable region comprising the amino acid sequence set forth in SEQ ID NO:100. In some embodiments, an agent (e.g., an antibody) that specifically binds C3 comprises a heavy chain variable region comprising heavy chain CDRs 1, 2, and 3, wherein heavy chain CDR1 comprises GYAFNSCWMN (SEQ ID NO:61), heavy chain CDR2 comprises RIYPGDGDTNYNGKFKG (SEQ ID NO:62), and heavy chain CDR3 comprises EGRNYGYEDY (SEQ ID NO:63). In some embodiments, an agent (e.g., an antibody) that specifically binds C3 comprises a light chain variable region comprising light chain CDRs 1, 2, and 3, wherein light chain CDR1 comprises KASQSVDYDGDSYMN (SEQ ID NO:64), light chain CDR2 comprises AASDLES (SEQ ID NO:65), and light chain CDR3 comprises QQANEDPRT (SEQ ID NO:66). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GYAFNSCWMN (SEQ ID NO:61), heavy chain CDR2 comprises RIYPGDGDTNYNGKFKG (SEQ ID NO:62), heavy chain CDR3 comprises EGRNYGYEDY (SEQ ID NO:63), light chain CDR1 comprises KASQSVDYDGDSYMN (SEQ ID NO:64), light chain CDR2 comprises AASDLES (SEQ ID NO:65), and light chain CDR3 comprises QQANEDPRT (SEQ ID NO:66).

In certain embodiments, an agent (e.g., an antibody) that specifically binds C3 comprises heavy chain CDRs 1, 2, and 3 of a heavy chain variable region comprising the amino acid sequence set forth in SEQ ID NO:101. In certain embodiments, an agent (e.g., an antibody) that specifically binds C3 comprises light chain CDRs 1, 2, and 3 of a light chain variable region comprising the amino acid sequence set forth in SEQ ID NO: 102. In certain embodiments, an agent (e.g., an antibody) that specifically binds C3 comprises heavy chain CDRs 1, 2, and 3 of a heavy chain variable region comprising the amino acid sequence set forth in SEQ ID NO: 101, and light chain CDRs 1, 2, and 3 of a light chain variable region comprising the amino acid sequence set forth in SEQ ID NO: 102. In some embodiments, an agent (e.g., an antibody) that specifically binds C3 comprises a heavy chain variable region comprising heavy chain CDRs 1, 2, and 3, wherein heavy chain CDR1 comprises GFTFSNYAMS (SEQ ID NO:67), heavy chain CDR2 comprises QTISSGGRYTYYPDSVKG (SEQ ID NO:68), and heavy chain CDR3 comprises RYYGNSYWYFDV (SEQ ID NO:69). In some embodiments, an agent (e.g., an antibody) that specifically binds C3 comprises a light chain variable region comprising light chain CDRs 1, 2, and 3, wherein light chain CDR1 comprises KSSQSLLNSGNQKHYLT (SEQ ID NO:70), light chain CDR2 comprises GASTRGS (SEQ ID NO:71), and light chain CDR3 comprises QNDHSYPYT (SEQ ID NO:72). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GFTFSNYAMS (SEQ ID NO:67), heavy chain CDR2 comprises QTISSGGRYTYYPDSVKG (SEQ ID NO:68), heavy chain CDR3 comprises RYYGNSYWYFDV (SEQ ID NO:69), light chain CDR1 comprises KSSQSLLNSGNQKHYLT (SEQ ID NO:70), light chain CDR2 comprises GASTRGS (SEQ ID NO:71), and light chain CDR3 comprises QNDHSYPYT (SEQ ID NO:72).

In certain embodiments, an agent (e.g., an antibody) that specifically binds C3 comprises heavy chain CDRs 1, 2, and 3 of a heavy chain variable region comprising the amino acid sequence set forth in SEQ ID NO: 103. In certain embodiments, an agent (e.g., an antibody) that specifically binds C3 comprises light chain CDRs 1, 2, and 3 of a light chain variable region comprising the amino acid sequence set forth in SEQ ID NO: 104. In certain embodiments, an agent (e.g., an antibody) that specifically binds C3 comprises heavy chain CDRs 1, 2, and 3 of a heavy chain variable region comprising the amino acid sequence set forth in SEQ ID NO: 103, and light chain CDRs 1, 2, and 3 of a light chain variable region comprising the amino acid sequence set forth in SEQ ID NO: 104. In some embodiments, an agent (e.g., an antibody) that specifically binds C3 comprises a heavy chain variable region comprising heavy chain CDRs 1, 2, and 3, wherein heavy chain CDR1 comprises GFTFS-SYTMS (SEQ ID NO:73), heavy chain CDR2 comprises YISSGGGTTYYPDTVKG (SEQ ID NO:74), and heavy chain CDR3 comprises RYYRGSSLWYFDV (SEQ ID NO:75). In some embodiments, an agent (e.g., an antibody) that specifically binds C3 comprises a light chain variable region comprising light chain CDRs 1, 2, and 3, wherein light chain CDR1 comprises KSSQSLFNSGSQKNFLT (SEQ ID NO:76), light chain CDR2 comprises WASTRES (SEQ ID NO:77), and light chain CDR3 comprises QNDYSYPLT (SEQ ID NO:78). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GFTFSSYTMS (SEQ ID NO:73), heavy chain CDR2 comprises YISSGGGTTYYPDTVKG (SEQ ID NO:74), heavy chain CDR3 comprises RYYRGSSLWYFDV (SEQ ID NO:75), light chain CDR1 comprises KSSQSLFNSGSQKNFLT (SEQ ID NO:76), light chain CDR2 comprises WASTRES (SEQ ID NO:77), and light chain CDR3 comprises QNDYSYPLT (SEQ ID NO:78).

In certain embodiments, an agent (e.g., an antibody) that specifically binds C3 comprises heavy chain CDRs 1, 2, and 3 of a heavy chain variable region comprising the amino acid sequence set forth in SEQ ID NO: 105. In certain embodiments, an agent (e.g., an antibody) that specifically binds C3 comprises light chain CDRs 1, 2, and 3 of a light chain variable region comprising the amino acid sequence set forth in SEQ ID NO: 106. In certain embodiments, an agent (e.g., an antibody) that specifically binds C3 comprises heavy chain CDRs 1, 2, and 3 of a heavy chain variable region comprising the amino acid sequence set forth in SEQ ID NO: 105, and light chain CDRs 1, 2, and 3 of a light chain variable region comprising the amino acid sequence set forth in SEQ ID NO: 106. In some embodiments, an agent (e.g., an antibody) that specifically binds C3 comprises a heavy chain variable region comprising heavy chain CDRs 1, 2, and 3, wherein heavy chain CDR1 comprises GYSITSGYSLH (SEQ ID NO:79), heavy chain CDR2 comprises YIHYSGSTNYNPSLKS (SEQ ID NO:80), and heavy chain CDR3 comprises AWDYLDY (SEQ ID NO:81). In some embodiments, an agent (e.g., an antibody) that specifically binds C3 comprises a light chain variable region comprising light chain CDRs 1, 2, and 3, wherein light chain CDR1 comprises RASENIYSQLA (SEQ ID NO:82), light chain CDR2 comprises DAKTLAE (SEQ ID NO:83), and light chain CDR3 comprises HHHFGILYT (SEQID NO:84). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GYSITSGYSLH (SEQ ID NO:79), heavy chain CDR2 comprises YIHYSGSTNYNPSLKS (SEQ ID NO:80), heavy chain CDR3 comprises AWDYLDY (SEQ ID NO:81), light chain CDR1 comprises RASENIYSQLA (SEQ ID NO:82), light chain CDR2 comprises DAKTLAE (SEQ ID NO:83), and light chain CDR3 comprises HHHFGILYT (SEQID NO:84).

In certain embodiments, an agent (e.g., an antibody) that specifically binds C3 comprises heavy chain CDRs 1, 2, and 3 of a heavy chain variable region comprising the amino acid sequence set forth in SEQ ID NO: 107. In certain embodiments, an agent (e.g., an antibody) that specifically binds C3 comprises light chain CDRs 1, 2, and 3 of a light chain variable region comprising the amino acid sequence set forth in SEQ ID NO: 108. In certain embodiments, an agent (e.g., an antibody) that specifically binds C3 comprises heavy chain CDRs 1, 2, and 3 of a heavy chain variable region comprising the amino acid sequence set forth in SEQ ID NO: 107, and light chain CDRs 1, 2, and 3 of a light chain variable region comprising the amino acid sequence set forth in SEQ ID NO: 108. In some embodiments, an agent (e.g., an antibody) that specifically binds C3 comprises a heavy chain variable region comprising heavy chain CDRs 1, 2, and 3, wherein heavy chain CDR1 comprises GYSITSGYYWN (SEQ ID NO:85), heavy chain CDR2 comprises YIRYDGSNNYNPSLKN (SEQ ID NO:86), and heavy chain CDR3 comprises HYGYDGGAFDF (SEQ ID NO:87). In some embodiments, an agent (e.g., an antibody) that specifically binds C3 comprises a light chain variable region comprising light chain CDRs 1, 2, and 3, wherein light chain CDR1 comprises RTSENIYNYLV (SEQ ID NO:88), light chain CDR2 comprises NAKTLEE (SEQ ID NO:89), and light chain CDR3 comprises QHHYGTPFT (SEQ ID NO:90). In some embodiments, an agent (e.g., an antibody) that specifically binds C3 comprises a heavy chain variable region comprising heavy chain CDRs 1, 2, and 3, and a light chain variable region comprising light chain CDRs 1, 2, and 3, wherein heavy chain CDR1 comprises GYSITSGYYWN (SEQ ID NO:85), heavy chain CDR2 comprises YIRYDGSNNYNPSLKN (SEQ ID NO:86), heavy chain CDR3 comprises HYGYDGGAFDF (SEQ ID NO:87), light chain CDR1 comprises RTSENIYNYLV (SEQ ID NO:88), light chain CDR2 comprises NAKTLEE (SEQ ID NO:89), and light chain CDR3 comprises QHHYGTPFT (SEQ ID NO:90).

In another aspect of the disclosure, provided herein is an antibody that competes for binding to C3 with any of the C3-binding agents described herein. In some embodiments, provided herein is an antibody that competes for binding to C3 with a reference antibody, wherein the reference antibody comprises: (a) a heavy chain CDR1 comprising GYTFTDFYMD (SEQ ID NO:7); a heavy chain CDR2 comprising YIYPHNGGTTYNQNFTG (SEQ ID NO:8), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, provided herein is an antibody that competes for binding to C3 with a reference antibody, wherein the reference antibody comprises: (a) a heavy chain CDR1 comprising GYTFTDFYMD (SEQ ID NO:7); a heavy chain CDR2 comprising YIYPHNGGTTYNQQFTG (SEQ ID NO: 13), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, provided herein is an antibody that competes for binding to C3 with a reference antibody, wherein the reference antibody comprises: (a) a heavy chain CDR1 comprising GYTFTDFYMD (SEQ ID NO:7); a heavy chain CDR2 comprising YIYPHNAGTTYNQQFTG (SEQ ID NO: 14), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, provided herein is an antibody that competes for binding to C3 with a reference antibody, wherein the reference antibody comprises: (a) a heavy chain CDR1 comprising GYTFTDFYMD (SEQ ID NO:7); a heavy chain CDR2 comprising YIYPHNTGTTYNQQFTG (SEQ ID NO: 15), and a heavy chain CDR3 comprising RGGFDFDY (SEQ ID NO:9); and (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments, provided herein is an antibody that competes for binding to C3 with a reference antibody, wherein the reference antibody comprises: (a) a heavy chain CDR1 comprising GYTFTDFYMD (SEQ ID NO:7); a heavy chain CDR2 comprising YIYPHEGGTTYNQQFTG (SEQ ID NO: 16), and a heavy chain CDR3 comprising RGGFDFDY (SEQ ID NO:9); and/or (b) a light chain CDR1 comprising KASENVDTYVS (SEQ ID NO:10); a light chain CDR2 comprising GASNRYT (SEQ ID NO: 11); and a light chain CDR3 comprising GQSHSYPLT (SEQ ID NO: 12). In some embodiments, provided herein is an antibody that competes for binding to C3 with a reference antibody, wherein the reference antibody comprises: (a) a heavy chain CDR1 comprising GYTFTDFYMD (SEQ ID NO:7); a heavy chain CDR2 comprising YIYPHQGGTTYNQQFTG (SEQ ID NO: 17), and a heavy chain CDR3 comprising RGGFDFDY (SEQ ID NO:9); and/or (b) a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12).

In some embodiments, provided herein is an antibody that competes for binding to C3 with a reference antibody, wherein the reference antibody comprises a heavy chain variable region comprising SEQ ID NO:18, SEQ ID NO:20, SEQ ID NO:21, SEQ ID NO:22, SEQ ID NO:23, or SEQ ID NO:24; and a light chain variable region comprising SEQ ID NO: 19 or SEQ ID NO:25. In some embodiments, a reference antibody comprises a heavy chain variable region comprising SEQ ID NO:18 and a light chain variable region comprising SEQ ID NO:19. In some embodiments, a reference antibody comprises a heavy chain variable region comprising SEQ ID NO:20 and a light chain variable region comprising SEQ ID NO:25. In some embodiments, a reference antibody comprises a heavy chain variable region comprising SEQ ID NO:21 and a light chain variable region comprising SEQ ID NO:25. In some embodiments, a reference antibody comprises a heavy chain variable region comprising SEQ ID NO:22 and a light chain variable region comprising SEQ ID NO:25. In some embodiments, a reference antibody comprises a heavy chain variable region comprising SEQ ID NO:23 and a light chain variable region comprising SEQ ID NO:25. In some embodiments, a reference antibody comprises a heavy chain variable region comprising SEQ ID NO:24 and a light chain variable region comprising SEQ ID NO:25.

In some embodiments, provided herein is a C3-binding agent that binds the same epitope on C3 as an antibody described herein. In some embodiments, provided herein is a C3-binding agent that binds an epitope on C3 that overlaps with the epitope on C3 bound by an antibody described herein. In some embodiments, provided herein is a C3-binding agent that binds the same epitope as an antibody comprising the heavy chain CDR1, CDR2, and CDR3 and the light chain CDR1, CDR2, and CDR3 of an antibody selected from the group consisting of: 38G10, Hz38G10, Hz38G10(N55E), Hz38G10(N55Q), Hz38G10(G56A), or Hz38G10(G56T). In some embodiments, provided herein is a C3-binding agent that binds an epitope that overlaps with the epitope bound by an antibody comprising the heavy chain CDR1, CDR2, and CDR3 and the light chain CDR1, CDR2, and CDR3 of an antibody selected from the group consisting of: 38G10, Hz38G10, Hz38G10(N55E), Hz38G10(N55Q), Hz38G10(G56A), or Hz38G10(G56T). In some embodiments, provided herein is a C3-binding agent that binds the same epitope as an antibody comprising the heavy chain variable region and the light chain variable region from an antibody selected from the group consisting of: 38G10, Hz38G10, Hz38G10(N55E), Hz38G10(N55Q), Hz38G10(G56A), or Hz38G10(G56T). In some embodiments, provided herein is a C3-binding agent that binds an epitope that overlaps with the epitope bound by an antibody comprising the heavy chain variable region and the light chain variable region from an antibody selected from the group consisting of: 38G10, Hz38G10, Hz38G10(N55E), Hz38G10(N55Q), Hz38G10(G56A), or Hz38G10(G56T).

In some embodiments, provided herein is a C3-binding agent that competes with an antibody comprising a heavy chain having the amino acid sequence of SEQ ID NO:27 and a light chain having the amino acid sequence of SEQ ID NO:31 for binding to human C3. In some embodiments, provided herein is a C3-binding agent that competes with an antibody comprising a heavy chain having the amino acid sequence of SEQ ID NO:29 and a light chain having the amino acid sequence of SEQ ID NO:31 for binding to human C3.

In some embodiments of each of the aforementioned aspects and embodiments, as well as other aspects and embodiments described herein, a C3-binding agent is an antibody. In some embodiments, the antibody is a monoclonal antibody. In some embodiments, the antibody is a humanized antibody. In some embodiments, the antibody is a human antibody. In some embodiments, the antibody is a chimeric antibody. In some embodiments, the antibody is a whole or intact antibody. In some embodiments, the antibody is an IgG antibody. In some embodiments, the antibody is an IgG1 antibody, an IgG2 antibody, an IgG3 antibody, or an IgG4 antibody. In some embodiments, the antibody is a bispecific antibody or a multispecific antibody. In some embodiments, the antibody is an antibody fragment (e.g., a C3-binding fragment). In some embodiments, the antibody or antibody fragment is a Fab, Fab', F(ab')2, Fv, scFv, (scFv)$_2$, single chain antibody, dual variable region antibody, single variable region antibody, linear antibody, nanobody, or a V region antibody. In some embodiments, the antibody is a scFv-CH3, a scFv-Fc fusion, a scFv-HSA fusion, a scFv-PEG fusion, or a scFv-XTEN fusion.

In some embodiments, the antibody is a scFv antibody comprising a heavy chain variable region and a light chain variable region. In some embodiments, the antibody is a disulfide-linked scFv (dsscFv) comprising a heavy chain variable region and a light chain variable region. In some embodiments of the dsscFv, the heavy chain variable region comprises the amino acid sequence of SEQ ID NO: 110. In some embodiments of the dsscFv, the heavy chain variable region of the dsscFv comprises the amino acid sequence of SEQ ID NO:111. In some embodiments of the dsscFv, the light chain variable region comprises the amino acid sequence of SEQ ID NO: 112. In some embodiments of the dsscFv, the heavy chain variable region comprises the amino acid sequence of SEQ ID NO: 110 and the light chain variable region comprises the amino acid sequence of SEQ ID NO: 112. In some embodiments of the dsscFv, the heavy chain variable region comprises the amino acid sequence of SEQ ID NO: 111 and the light chain variable region comprises the amino acid sequence of SEQ ID NO: 112. In some embodiments of the dsscFv, the dsscFv comprises the amino acid sequence of SEQ ID NO:113. In some embodiments of the dsscFv, the dsscFv comprises the amino acid sequence of SEQ ID NO: 114. In some embodiments of the dsscFv, the dsscFv comprises the amino acid sequence of SEQ ID NO: 119. In some embodiments of the dsscFv, the dsscFv comprises the amino acid sequence of SEQ ID NO:229.

In some embodiments of each of the aforementioned aspects and embodiments, as well as other aspects and embodiments described herein, a C3-binding agent (e.g., an antibody) described herein is an antagonist of C3. In some embodiments, the C3-binding agent is an antagonistic antibody. In some embodiments, a C3-binding agent (e.g., an antibody) inhibits C3 activity. In some embodiments, a C3-binding agent (e.g., an antibody) inhibits activation of the complement system. In some embodiments, a C3-binding agent (e.g., an antibody) inhibits activation of the classical complement pathway. In some embodiments, a C3-binding agent (e.g., an antibody) inhibits activation of the alternative complement pathway. In some embodiments, a C3-binding agent (e.g., an antibody) inhibits activation of the classical complement pathway and the alternative complement pathway.

In another aspect, the disclosure provides compositions comprising a C3-binding agent (e.g., an antibody) described herein.

In another aspect, the disclosure provides pharmaceutical compositions comprising a C3-binding agent (e.g., an antibody) described herein and a pharmaceutically acceptable carrier.

In some embodiments of each of the aforementioned aspects, as well as other aspects and/or embodiments described elsewhere herein, the C3-binding agent (e.g., an antibody) is isolated. In some embodiments, the C3-binding agent (e.g., an antibody) is substantially pure.

In another aspect, the disclosure provides polynucleotides comprising a polynucleotide that encodes a C3-binding agent described herein. In some embodiments, the polynucleotide is isolated. In some embodiments, a vector comprises a polynucleotide that encodes a C3-binding agent described herein. In some embodiments, an isolated cell comprises a polynucleotide that encodes a C3-binding agent described herein. In some embodiments, an isolated cell comprises a vector comprising a polynucleotide that encodes a C3-binding agent described herein. In some embodiments, the disclosure provides a cell comprising a C3-binding agent described herein. In some embodiments, the disclosure provides a cell producing a C3-binding agent described herein. In some embodiments, a cell produces an anti-C3 antibody described herein. In some embodiments, a cell is a monoclonal cell line. In some embodiments, a cell is a hybridoma.

In another aspect, the disclosure provides methods of using the C3-binding agents (e.g., an antibody) described herein. In some embodiments, a method comprises using a composition comprising a C3-binding agent (e.g., an antibody) described herein. In some embodiments, a method comprises using a pharmaceutical composition comprising a C3-binding agent (e.g., an antibody) described herein.

In some embodiments, a method of treating an eye disorder or eye disease in a subject (e.g., a human) comprises administering to the subject a therapeutically effective amount of a C3-binding agent (e.g., an antibody) described herein. In some embodiments, the eye disorder is selected from the group consisting of: macular degeneration (maculopathy), diabetic retinopathy, retinopathy of prematurity, macular dystrophy, retinal dystrophy, uveitis, keratitis, scleritis, retinitis pigmentosa, choroidal neovascularization, retinal neovascularization, and ocular inflammation. In some embodiments, the eye disorder is macular degeneration. In some embodiments, the eye disorder is age-related macular degeneration (AMD). In some embodiments, a method of treating AMD in a subject (e.g., a human) comprises administering to the subject a therapeutically effective amount of a C3-binding agent (e.g., an antibody) described herein. In some embodiments, the AMD is dry AMD. In some embodiments, the AMD is geographic atrophy. In some embodiments, a method of treating geographic atrophy in a subject (e.g., a human) comprises administering to the subject a therapeutically effective amount of a C3-binding agent (e.g., an antibody) described herein.

In some embodiments, a method of inhibiting or suppressing drusen formation in an eye of a subject (e.g., a human) comprises administering to the subject a therapeutically effective amount of a C3-binding agent (e.g., an antibody) described herein.

In some embodiments, a method of inhibiting or suppressing retinal pigment epithelium atrophy in an eye of a subject (e.g., a human) comprises administering to the subject a therapeutically effective amount of a C3-binding agent (e.g., an antibody) described herein.

In some embodiments, a method of inhibiting complement activation in an eye of a subject (e.g., a human) comprises administering to the subject a therapeutically effective amount of a C3-binding agent (e.g., an antibody) described herein.

In some embodiments of the methods described herein, a C3-binding agent (e.g., an antibody) is administrated to an eye of the subject (e.g., a human) by ocular injection, intraocular injection, or intravitreal injection. In some embodiments, a C3-binding agent (e.g., antibody) is administrated to an eye of the subject by intravitreal injection. In some embodiments of the methods described herein, a C3-binding agent (e.g., an antibody) is administrated to an eye of the subject by topical delivery. In some embodiments, a C3-binding agent is administered to an eye of the subject by eye drops.

In some embodiments of the methods described herein, a C3-binding agent is administered to a subject (e.g., a human) as part of a combination therapy. In some embodiments, the combination therapy comprises photodynamic therapy. In some embodiments, the combination therapy comprises photodynamic therapy with verteporfin. In some embodiments, a C3-binding agent is administered to a subject (e.g., a human), wherein the subject is administered one or more additional therapeutic agents. In some embodiments, an additional therapeutic agent is compstatin or an analog or derivative of compstatin (e.g., POT-4; APL-2). In some embodiments, an additional therapeutic agent is a C5 inhibitor. In some embodiments, a C5 inhibitor is selected from the group including, but not limited to, eculizumab, LFG316, or Zimura™ (anti-C5 aptamer). In some embodiments, an additional therapeutic agent is a properdin inhibitor (e.g., an anti-properdin antibody). In some embodiments, an additional therapeutic agent is a Factor D inhibitor. In some embodiments, a Factor D inhibitor is an anti-Factor D antibody (e.g., lampalizumab). In some embodiments, an additional therapeutic agent is a VEGF inhibitor. In some embodiments, a VEGF inhibitor is selected from the group including, but not limited to, pegaptanib (MACUGEN), ranibizumab (LUCENTIS), bevacizumab (AVASTIN), aflibercept (EYLEA), brolucizumab, and OPT-302. In some embodiments, an additional therapeutic agent is a PDGF inhibitor. In some embodiments, an additional therapeutic agent is a corticosteroid. In some embodiments, an additional therapeutic agent is a neuroprotective agent. In some embodiments, a neuroprotective agent is selected from the group including, but not limited to, ciliary neurotrophic factor (CNTF), tandospirone, and brimonidine.

Also disclosed is the use of a C3-binding agent (e.g., an antibody) described herein in the manufacture of a medicament for treating an eye disorder. Also disclosed is the use of a C3-binding agent (e.g., an antibody) described herein in the manufacture of a medicament for treatment of a C3-associated disease or disorder associated with complement activation.

In some embodiments of each of the aforementioned aspects and embodiments, as well as other aspects and embodiments described herein, the subject is human.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

DETAILED DESCRIPTION

Figure 1:
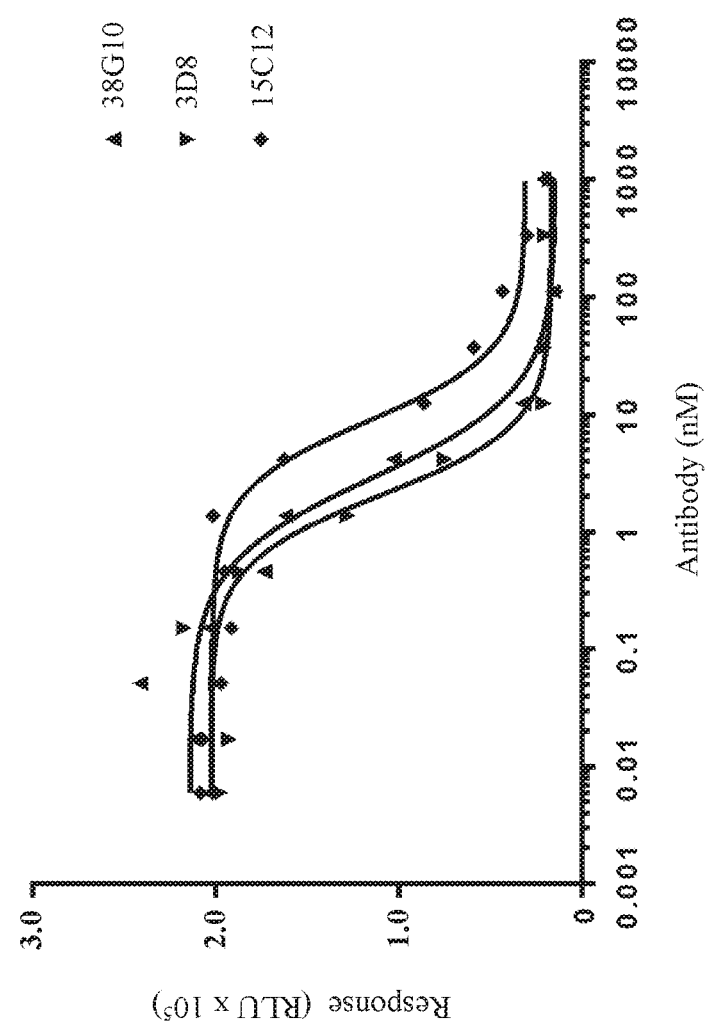
FIG. 1. C3a release assay.

The present disclosure provides novel agents, including but not limited to polypeptides such as antibodies, that bind complement component C3. The C3-binding agents include, but are not limited to, polypeptides, antibodies (including antigen-binding fragments thereof), scaffold proteins, and heterodimeric molecules. C3-binding agents include, but are not limited to, antagonists of C3 activity, inhibitors of C3 activity, and/or agents that modulate C3 activity. Related polypeptides, polynucleotides, vectors, compositions comprising the agents, cells comprising the related polynucleotides or vectors, and methods of making the agents are also provided. Methods of using the novel C3-binding agents are also provided.

I. Definitions

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "binding agent" as used herein refers to a molecule which binds a specific antigen or target (e.g., complement component C3). A binding agent may comprise a protein, peptide, nucleic acid, carbohydrate, lipid, or small molecular weight compound. In some embodiments, a binding agent comprises an antibody or an antigen-binding fragment thereof. In some embodiments, a binding agent is an antibody or an antigen-binding fragment thereof. In some embodiments, a binding agent comprises an alternative protein scaffold or artificial scaffold (e.g., a non-immunoglobulin backbone). In some embodiments, a binding agent is a fusion protein comprising an antigen-binding site. In some embodiments, a binding agent is a bispecific or multispecific molecule comprising at least one antigen-binding site.

The term "antibody" as used herein refers to an immunoglobulin molecule, or antigen-binding fragment thereof, that recognizes and binds a target through at least one antigen-binding site. "Antibody" is used herein in the broadest sense and encompasses various antibody structures, including but not limited to, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, and antibody fragments as long as they exhibit the desired antigen-binding activity.

The term "intact antibody" or "full-length antibody" refers to an antibody having a structure substantially similar to a native antibody structure. This includes, for example, an antibody comprising two light chains each comprising a variable region and a light chain constant region (CL) and two heavy chains each comprising a variable region and at least heavy chain constant regions CH1, CH2, and CH3.

The term "antibody fragment" as used herein refers to a molecule other than an intact antibody that comprises a portion of an antibody and generally an antigen-binding site. Examples of antibody fragments include, but are not limited to, Fab, Fab', F(ab')2, Fv, single chain antibody molecules (e.g., scFv), disulfide-linked scFv (dsscFv), nanobodies, diabodies, tribodies, tetrabodies, minibodies, dual variable domain antibodies (DVD), single variable domain antibodies (e.g., camelid antibodies), and multispecific antibodies formed from antibody fragments.

The term "monoclonal antibody" as used herein refers to a substantially homogenous antibody population involved in the highly specific recognition and binding of a single antigenic determinant or epitope. The term "monoclonal antibody" encompasses intact and full-length monoclonal antibodies as well as antibody fragments (e.g., Fab, Fab', F(ab')2, Fv), single chain antibodies (e.g., scFv), fusion proteins comprising an antibody fragment, and any other modified immunoglobulin molecule comprising at least one antigen-binding site. Furthermore, "monoclonal antibody" refers to such antibodies made by any number of techniques, including but not limited to, hybridoma production, phage library display, recombinant expression, and transgenic animals.

The term "chimeric antibody" refers to an antibody in which a portion of the heavy and/or light chain is derived from a first source or species, while the remainder of the heavy and/or light chain is derived from a different source or species.

The term "humanized antibody" as used herein refers to an antibody that comprises a human heavy chain variable region and a light chain variable region wherein the native CDR residues are replaced by residues from corresponding CDRs from a nonhuman antibody (e.g., mouse, rat, rabbit, or nonhuman primate), wherein the nonhuman antibody has the desired specificity, affinity, and/or activity. In some embodiments, one or more framework region residues of the human heavy chain or light chain variable regions are replaced by corresponding residues from nonhuman antibody. Furthermore, humanized antibodies can comprise residues that are not found in the human antibody or in the nonhuman antibody. In some embodiments, these modifications are made to further refine and/or optimize antibody characteristics. In some embodiments, the humanized antibody comprises at least a portion of an immunoglobulin constant region (e.g., CH1, CH2, CH3, Fc), typically that of a human immunoglobulin.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, recombinant protein production, and B-cell hybridoma technology.

The terms "epitope" and "antigenic determinant" are used interchangeably herein and refer to that portion of an antigen or target capable of being recognized and bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography may be used to characterize an epitope on a target protein by analyzing the amino acid residue interactions of an antigen/antibody complex.

The term "specifically binds" as used herein refers to an agent (e.g., an antibody) that interacts more frequently, more rapidly, with greater duration, with greater affinity, or with some combination of the above to a particular antigen, epitope, protein, or target molecule than with alternative substances. A binding agent (e.g. antibody) that specifically binds an antigen can be identified, for example, by immunoassays, ELISAs, SPR (e.g., Biacore™), or other techniques known to those of skill in the art. In some embodiments, an agent (e.g., an antibody) that specifically binds an antigen (e.g., human C3) can bind related antigens (e.g., cyno C3). A binding agent that specifically binds an antigen can bind the target antigen at a higher affinity than its affinity for a different antigen. The different antigen can be a related antigen. In some embodiments, a binding agent that specifically binds an antigen can bind the target antigen with an affinity that is at least 20 times greater, at least 30 times greater, at least 40 times greater, at least 50 times greater, at least 60 times greater, at least 70 times greater, at least 80 times greater, at least 90 times greater, or at least 100 times greater, than its affinity for a different antigen. In some embodiments, a binding agent that specifically binds a particular antigen binds a different antigen at such a low affinity that binding cannot be detected using an assay described herein or otherwise known in the art. In some embodiments, affinity is measured using SPR technology in a Biacore™ system as described herein or as known to those of skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 20-40, at least about 40-60 nucleotides or amino acid residues, at least about 60-80 nucleotides or amino acid residues in length or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition which is in a form not found in nature. An "isolated" antibody is substantially free of material from the cellular source from which it is derived. In some embodiments, isolated polypeptides, soluble proteins, antibodies, polynucleotides, vectors, cells, or compositions are those which have been purified to a degree that they are no longer in a form in which they are found in nature. In some embodiments, a polypeptide, soluble protein, antibody, polynucleotide, vector, cell, or composition which is isolated is substantially pure. A polypeptide, soluble protein, antibody, polynucleotide, vector, cell, or composition may be isolated from a natural source (e.g., tissue) or from a source such as an engineered cell line.

The term "substantially pure" as used herein refers to material which is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rabbits, rodents, and the like.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject (e.g., a human), together with at least one therapeutic agent (e.g., an antibody), and which is generally safe, non-toxic, and has no effect on the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical formulation" or "pharmaceutical composition" as used herein refers to a preparation which is in such form as to permit the biological activity of the agent (e.g., an antibody) to be effective. A pharmaceutical formulation or composition generally comprises additional components, such as a pharmaceutically acceptable excipient, carrier, adjuvant, buffers, etc.

The term "effective amount" or "therapeutically effective amount" as used herein refers to the amount of an agent (e.g., an antibody) which is sufficient to reduce and/or ameliorate the severity and/or duration of (i) a disease, disorder or condition in a subject (e.g., a human), and/or (ii) a symptom in a subject (e.g., a human). The term also encompasses an amount of an agent necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the binding agents provided herein).

The term "therapeutic effect" as used herein refers to the effect and/or ability of an agent (e.g., an antibody) to reduce and/or ameliorate the severity and/or duration of (i) a disease, disorder, or condition in a subject (e.g., a human), and/or (ii) a symptom in a subject (e.g., a human). The term also encompasses the ability of an agent to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the binding agents provided herein).

The term "treat" or "treatment" or "treating" or "to treat" or "alleviate" or "alleviation" or "alleviating" or "to alleviate" as used herein refers to both (1) therapeutic measures that aim to cure, slow down, lessen symptoms of, and/or halt progression of a pathologic condition or disorder and (2) prophylactic or preventative measures that aim to prevent or slow the development of a targeted pathologic condition or disorder. Thus, those in need of treatment include those already with the disorder, those at risk of having/developing the disorder, and those in whom the disorder is to be prevented.

The term "prevent" or "prevention" or "preventing" as used herein refers to the partial or total inhibition of the development, recurrence, onset, or spread of a disease, disorder, or condition, or a symptom thereof in a subject (e.g., a human).

As used herein, reference to "about" or "approximately" a value or parameter includes (and describes) embodiments that are directed to that value or parameter. For example, a description referring to "about X" includes description of "X".

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. C3-Binding Agents

Amino acid (aa) sequences for human C3 (UniProtKB No. P01024), cynomolgus monkey ("cyno") (NCBI Ref No. XP_005587776.1), and rat C3 (UniProtKB No. P01026) are provided herein as SEQ ID NO:1, SEQ ID NO:32, and SEQ ID NO:37, respectively. As used herein, reference to amino acid positions of C3 refer to the numbering of amino acid sequences including the signal sequence.

The present disclosure provides agents that bind C3. In some embodiments, a C3-binding agent binds a fragment of C3. In some embodiments, a C3-binding agent binds within a specific region of C3. In some embodiments, a C3-binding agent binds an epitope on C3. In some embodiments, a C3-binding agent binds a linear epitope on C3. In some embodiments, a C3-binding agent binds a conformational epitope on C3. In some embodiments, a C3-binding agent binds human C3 (e.g., SEQ ID NO:1). In some embodiments, a C3-binding agent binds cyno C3 (e.g., SEQ ID NO:32). In some embodiments, a C3-binding agent binds human C3 and cyno C3. In some embodiments, a C3-binding agent binds C3 and does not bind C3b. In some embodiments, a C3-binding agent binds C3 and does not bind C3b at a detectable level. In some embodiments, a C3-binding agent binds C3 with an affinity that is at least 50-fold greater than its affinity for C3b. In some embodiments, a C3-binding agent binds C3 with an affinity that is at least 100-fold greater than its affinity for C3b. In some embodiments, the affinity of a C3-binding agent is measured using SPR technology in a Biacore™ system.

In some embodiments, the C3-binding agent binds to human C3 (e.g., SEQ ID NO:1) and has at least one or more of the following properties: (a) binds to cyno C3 (e.g., SEQ ID NO:32), (b) inhibits C3 cleavage and C3a release, (c) inhibits activation of the alternative complement pathway, (d) inhibits activation of the classical complement pathway, (e) inhibits activation of the alternative complement pathway and inhibits activation of the classical complement pathway, (f) does not detectably bind to Factor Bb, (g) does not detectably bind to C3d, and (h) does not detectably bind to C3a. In certain embodiments, the C3-binding agent inhibits activation of the classical complement pathway (e.g., as assessed by hemolytic assays). In some embodiments, the C3-binding agent inhibits activation of the alternative complement pathway and classical complement pathway (e.g., as assessed by hemolytic assays).

Assays for determining inhibition of C3 cleavage and C3a release are known in the art. In certain embodiments, the assay is an assay described herein (see, e.g., Example 2). In certain embodiments, the C3-binding agent inhibits C3 cleavage and C3a release at a concentration of 0.1 to 1000 nM. In certain embodiments, a C3-binding agent inhibits C3 cleavage and C3a release if there is a reduction by at least 10%, at least 20%, at least 30%, at least 40%, at least 50%, at least 60%, at least 70%, at least 80%, at least 90%, or at least 95% in the amount of C3 cleavage and C3a release compared to C3 cleavage and C3a release in the absence of the C3-binding agent.

Assays for determining whether a C3-binding agent inhibits activation of the alternative complement pathway or the classical complement pathway are known in the art. In certain embodiments, the assay is an assay described herein (e.g., hemolysis assays; see, e.g., Example 3).

Assays for determining the binding of a C3-binding agent to factor Bb, C3d, or C3a are known in the art. In certain embodiments, the assay is an assay described herein (e.g., BiaCore™; see, e.g., Example 5). In certain embodiments, a C3-binding agent is determined to not detectably bind to factor Bb, C3d, or C3a if the C3-binding agent does not bind to factor Bb, C3d, or C3a, respectively, at a concentration of up to 1 μM according to an assay described herein (e.g., BiaCore™; see, e.g., Example 5).

In some embodiments, a C3-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody is an antibody fragment comprising an antigen-binding site. In some embodiments, the antibody is a scFv. In some embodiments, the antibody is a disulfide-linked scFv. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody.

In some embodiments, the antibody is isolated. In some embodiments, the antibody is substantially pure.

In some embodiments, a C3-binding agent is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, a C3-binding agent is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, SPR (e.g., BiaCore™), and radioimmunoassay). Once hybridoma cells that produce antibodies of the desired specificity, affinity, and/or activity are identified, the clones may be subcloned by limiting dilution techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are substituted for constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and affinity of a monoclonal antibody.

In some embodiments, a C3-binding agent is a humanized antibody. Various methods for generating humanized antibodies are known in the art. In some embodiments, a humanized antibody comprises one or more amino acid residues that have been introduced into it from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region is used for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

In some embodiments, a C3-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, a C3-binding agent is a scFv antibody. ScFvs are molecules that comprise a variable heavy chain region and a variable light chain region linked to form a single polypeptide. ScFvs can be produced using recombinant technologies known in the art. In some embodiments, a scFv comprises a polypeptide linker between the heavy chain variable region and the light chain variable region. In some embodiments, the scFv comprises an orientation of (from N- to C-terminus) (i) heavy chain variable region, (ii) linker, and (iii) light chain variable region. In some embodiments, the scFv comprises an orientation (from N- to C-terminus) of (i) light chain variable region, (ii) linker, and (iii) heavy chain variable region. In some embodiments, the scFv is a disulfide-linked scFv (dsscFv), which is a scFv comprising an engineered disulfide bond between the light chain variable region and heavy chain variable region of the scFv. In some embodiments, the heavy chain variable region of the dsscFv comprises the amino acid sequence of SEQ ID NO: 110. In some embodiments, the heavy chain variable region of the dsscFv comprises the amino acid sequence of SEQ ID NO:111. In some embodiments, the light chain variable region of the dsscFv comprises the amino acid sequence of SEQ ID NO: 112. In some embodiments, the heavy chain variable region of the dsscFv comprises the amino acid sequence of SEQ ID NO: 110 and the light chain variable region of the dsscFv comprises the amino acid sequence of SEQ ID NO: 112. In some embodiments, the heavy chain variable region of the dsscFv comprises the amino acid sequence of SEQ ID NO: 111 and the light chain variable region of the dsscFv comprises the amino acid sequence of SEQ ID NO: 112. In some embodiments, the dsscFv comprises the amino acid sequence of SEQ ID NO:113. In some embodiments, the dsscFv comprises the amino acid sequence of SEQ ID NO: 114. In some embodiments, the dsscFv comprises the amino acid sequence of SEQ ID NO: 119. In some embodiments, the dsscFv comprises the amino acid sequence of SEQ ID NO:229. In some embodiments, the scFv (e.g., dsscFv) is attached (either directly or indirectly) to a half-life extending moiety such as, e.g., an Fc molecule, a CH3 domain of an immunoglobulin (e.g., CH3 of IgG1), polyethylene glycol (PEG) or a PEG mimetic, XTEN, serum albumin (e.g., human serum albumin), polysicalic acid, N-(2-hydroxypropyl)methacrylamide, or dextran, or is modified by, e.g., hyperglycosylation, to extend the half-life of the scFv (e.g., dsscFv).

A variety of suitable linkers are known to those of skill in the art and are not limited by any specific sequences disclosed herein. In some embodiments, the polypeptide linker is comprised of naturally, or non-naturally, occurring amino acids. In some embodiments, the linker comprises amino acids that allow for flexibility. In some embodiments, the linker comprises amino acids that allow for suitable solubility. In some embodiments, the linker comprises glycine amino acids. In some embodiments, the linker comprises glycine and serine amino acids. In certain embodiments, the linker comprises one or more sets of glycine/serine repeats. In some embodiments, the polypeptide linker is selected from the group consisting of: $(GGGGS)_n$ wherein n=1-4 (SEQ ID NO:232), GGGGS (SEQ ID NO: 115), GGGGSGGGGS (SEQ ID NO: 116), GGGGSGGGGSGGGGS (SEQ ID NO: 117), GGGGSGGGGSGGGGSGGGGS (SEQ ID NO:118), and $(GGGGA)_n$ wherein n=1-4 (SEQ ID NO:230). In some embodiments, the linker comprises GGGGSGGGGSGGGGS (SEQ ID NO:117).

In some embodiments, a scFv comprises a disulfide bond formed between the heavy chain variable region and the light chain variable region. In some embodiments, a scFv comprises a disulfide bond that increases stability of the scFv molecule. In some embodiments, a scFv comprises a disulfide bond that increases thermostability of the scFv molecule.

In some embodiments, a C3-binding agent is a Fv. A Fv comprises a heavy chain variable region and a light chain variable region. In some embodiments, the Fv is attached (either directly or indirectly) to a half-life extending moiety such as, e.g., an Fc molecule, a CH3 domain of an IgG (e.g., CH3 of IgG1), PEG or a PEG mimetic, XTEN, serum albumin (e.g., human serum albumin), polysicalic acid, N-(2-hydroxypropyl)methacrylamide, or dextran, or is modified, e.g., by hyperglycosylation, to extend the half-life of the Fv.

In some embodiments, a C3-binding agent is a Fab. A Fab is one of the molecules that result from digestion of an immunoglobulin antibody with papain. Fabs are monovalent molecules that comprise a light chain, a heavy chain variable region, a CH1 region, and, optionally, a heavy chain constant region hinge region or a portion thereof. Fabs can be produced using recombinant technologies known in the art. In some embodiments, a Fab comprises a polypeptide linker between the light chain constant region and the heavy chain variable region. In some embodiments, a Fab comprises a polypeptide linker between the heavy chain constant region and the light chain variable region. A variety of suitable linkers are known to those of skill in the art and are not limited by any specific sequences disclosed herein. In certain embodiments, the linker is a linker described herein. In some embodiments, the Fab is attached (either directly or indirectly) to a half-life extending moiety such as, e.g., an Fc molecule, a CH3 domain of an IgG (e.g., CH3 of IgG1), PEG or a PEG mimetic, XTEN, serum albumin (e.g., human serum albumin), polysicalic acid, N-(2-hydroxypropyl)methacrylamide, or dextran, or is modified, e.g., by hyperglycosylation, to extend the half-life of the Fab.

In some embodiments, a Fab comprises a disulfide bond formed between the heavy chain variable region and the light chain variable region. In some embodiments, a Fab comprises a disulfide bond that increases stability of the Fab molecule. In some embodiments, a Fab comprises a disulfide bond that increases thermostability of the Fab molecule.

In some embodiments, a C3-binding agent is a F(ab')2. A F(ab')2 is one of the molecules that results from digestion of an immunoglobulin antibody with pepsin. A F(ab')2 is a divalent molecule that comprises a first light chain in association with a first polypeptide comprising a first heavy chain variable region, a first CH1, and a first hinge region, and a second light chain in association with a second polypeptide comprising a second heavy chain variable region, a second CH1, and a second hinge region, wherein the first hinge region is linked to the second hinge region via at least one disulfide bond. F(ab')2s can be produced using recombinant technologies known in the art. In some embodiments, the F(ab')2 is attached (either directly or indirectly) to a half-life extending moiety such as, e.g., a CH3 domain of an IgG (e.g., CH3 of IgG1), PEG or a PEG mimetic, XTEN, serum albumin (e.g., human serum albumin), polysicalic acid, N-(2-hydroxypropyl)methacrylamide, or dextran, or is modified, e.g., by hyperglycosylation, to extend the half-life of the F(ab')2.

In some embodiments, a F(ab')2 comprises a disulfide bond formed between the heavy chain variable region and the light chain variable region. In some embodiments, a F(ab')2 comprises a disulfide bond that increases stability of the F(ab')2 molecule. In some embodiments, a F(ab')2 comprises a disulfide bond that increases thermostability of the F(ab')2 molecule.

In some embodiments, a C3-binding agent is a F(ab'). A F(ab') is a molecule that results from treatment of a F(ab')2 with beta-mercaptoethanol. A F(ab') is a monovalent molecule that comprises a light chain in association with a polypeptide comprising a heavy chain variable region, a CH1, and a hinge region. In some embodiments, the F(ab') is attached (either directly or indirectly) to a half-life extending moiety such as, e.g., an Fc molecule, a CH3 domain of an IgG (e.g., CH3 of IgG1), PEG or a PEG mimetic, XTEN, serum albumin (e.g., human serum albumin), polysicalic acid, N-(2-hydroxypropyl)methacrylamide, or dextran, or is modified, e.g., by hyperglycosylation, to extend the half-life of the F(ab').

In some embodiments, a F(ab') comprises a disulfide bond formed between the heavy chain variable region and the light chain variable region. In some embodiments, a F(ab') comprises a disulfide bond that increases stability of the F(ab') molecule. In some embodiments, a F(ab') comprises a disulfide bond that increases thermostability of the F(ab') molecule.

In some embodiments, a C3-binding agent is a bispecific antibody. Bispecific antibodies are capable of recognizing and binding at least two different antigens or epitopes. The different epitopes can either be within the same molecule (e.g., two epitopes on C3) or on different molecules (e.g., one epitope on C3 and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject (e.g., a human). In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids that are part of the interface between the two heavy chains. These modifications are made to enhance heterodimer formation and generally reduce or eliminate homodimer formation. In some embodiments, the bispecific antibodies are generated using a knobs-into-holes (KIH) strategy. In some embodiments, the bispecific antibodies comprise variant hinge regions incapable of forming disulfide linkages between identical heavy chains (e.g., reduce homodimer formation). In some embodiments, the bispecific antibodies comprise heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

C3-binding agents with more than two valencies are also contemplated. In some embodiments, trispecific or tetraspecific antibodies are generated.

In some embodiments, a C3-binding agent is an antibody that binds C3. In some embodiments, an anti-C3 antibody binds human C3. In some embodiments, an anti-C3 antibody binds cyno C3. In some embodiments, an anti-C3 antibody binds human C3 and cyno C3. In some embodiments, an anti-C3 antibody does not bind rat C3. In some embodiments, an anti-C3 antibody binds a C3 epitope. In some embodiments, an anti-C3 antibody does not bind C3a, C3b, C3c, C3d, or iC3b. In some embodiments, an anti-C3 antibody does not bind C3a, C3b, C3c, C3d, and iC3b. In some embodiments, an anti-C3 antibody does not bind C3a. In some embodiments, an anti-C3 antibody does not bind C3c. In some embodiments, an anti-C3 antibody does not bind C3d. In some embodiments, an anti-C3 antibody does not bind iC3b. In some embodiments, an anti-C3 antibody does not bind C3b. In some embodiments, an anti-C3 antibody does not bind C3a, C3b, C3c, C3d, or iC3b at a detectable level. In some embodiments, an anti-C3 antibody binds C3 with an affinity that is at least 20-fold greater than the antibody's affinity to C3a, C3c, C3d, iC3b or C3b. In some embodiments, an anti-C3 antibody binds C3 with an affinity that is at least 50-fold greater than the antibody's affinity to C3a, C3c, C3d, iC3b or C3b. In some embodiments, an anti-C3 antibody binds C3 with an affinity that is at least 100-fold greater than the antibody's affinity to C3a, C3c, C3d, iC3b or C3b. In some embodiments, an anti-C3 antibody binds C3 and does not bind C3b at a detectable level. In some embodiments, an anti-C3 antibody binds C3 with an affinity that is at least 50-fold greater than the antibody's affinity to C3b. In some embodiments, an anti-C3 antibody binds C3 with an affinity that is at least 100-fold greater than the antibody's affinity to C3b.

In some embodiments, a C3-binding agent is an anti-C3 antibody that comprises one, two, three, four, five, and/or six CDRs of any one of the antibodies described herein. In some embodiments, an anti-C3 antibody comprises (i) one, two, and/or three heavy chain CDRs from Table 1A, and/or (ii) one, two, and/or three light chain CDRs from Table 1A. In some embodiments, an anti-C3 antibody comprises (i) three heavy chain CDRs from Table 1A (i.e., a CDR1, a CDR2, and a CDR3), and (ii) three light chain CDRs from Table 1A. In some embodiments, an anti-C3 antibody comprises (i) one, two, and/or three heavy chain CDRs from Table 1B, and/or (ii) one, two, and/or three light chain CDRs from Table 1B. In some embodiments, an anti-C3 antibody comprises (i) three heavy chain CDRs from Table 1B (i.e., a CDR1, a CDR2, and a CDR3), and (ii) three light chain CDRs from Table 1B. In some embodiments, an anti-C3 antibody comprises (i) one, two, and/or three heavy chain CDRs from Table 1C, and/or (ii) one, two, and/or three light chain CDRs from Table 1C. In some embodiments, an anti-C3 antibody comprises (i) three heavy chain CDRs from Table 1C (i.e., a CDR1, a CDR2, and a CDR3), and (ii) three light chain CDRs from Table 1C. In some embodiments, an anti-C3 antibody comprises (i) one, two, and/or three heavy chain CDRs from Table 2, and/or (ii) one, two, and/or three light chain CDRs from Table 2. In some embodiments, an anti-C3 antibody comprises (i) three heavy chain CDRs from Table 2, and (ii) three light chain CDRs from Table 2. In some embodiments, an anti-C3 antibody comprises (i) one, two, and/or three heavy chain CDRs from Table 3, and/or (ii) one, two, and/or three light chain CDRs from Table 3. In some embodiments, an anti-C3 antibody comprises (i) three heavy chain CDRs from Table 3, and (ii) three light chain CDRs from Table 3. In some embodiments, an anti-C3 antibody comprises (i) one, two, and/or three heavy chain CDRs from Table 4, and/or (ii) one, two, and/or three light chain CDRs from Table 4. In some embodiments, an anti-C3 antibody comprises (i) three heavy chain CDRs from Table 4, and (ii) three light chain CDRs from Table 4. In some embodiments, an anti-C3 antibody comprises (i) one, two, and/or three heavy chain CDRs from Table 5, and/or (ii) one, two, and/or three light chain CDRs from Table 5. In some embodiments, an anti-C3 antibody comprises (i) three heavy chain CDRs from Table 5, and (ii) three light chain CDRs from Table 5. In some embodiments, an anti-C3 antibody comprises (i) one, two, and/or three heavy chain CDRs from Table 6, and/or (ii) one, two, and/or three light chain CDRs from Table 6. In some embodiments, an anti-C3 antibody comprises (i) three heavy chain CDRs from Table 6, and (ii) three light chain CDRs from Table 6. In some embodiments, an anti-C3 antibody comprises (i) one, two, and/or three heavy chain CDRs from Table 7, and/or (ii) one, two, and/or three light chain CDRs from Table 7. In some embodiments, an anti-C3 antibody comprises (i) three heavy chain CDRs from Table 7, and (ii) three light chain CDRs from Table 7. In some embodiments, an anti-C3 antibody comprises (i) one, two, and/or three heavy chain CDRs from Table 8, and/or (ii) one, two, and/or three light chain CDRs from Table 8. In some embodiments, an anti-C3 antibody comprises (i) three heavy chain CDRs from Table 8, and (ii) three light chain CDRs from Table 8. In some embodiments, an anti-C3 antibody comprises (i) one, two, and/or three heavy chain CDRs from Table 9, and/or (ii) one, two, and/or three light chain CDRs from Table 9. In some embodiments, an anti-C3 antibody comprises (i) three heavy chain CDRs from Table 9, and (ii) three light chain CDRs from Table 9. In some embodiments, an anti-C3 antibody comprises (i) one, two, and/or three heavy chain CDRs from Table 10, and/or (ii) one, two, and/or three light chain CDRs from Table 10. In some embodiments, an anti-C3 antibody comprises (i) three heavy chain CDRs from Table 10, and (ii) three light chain CDRs from Table 10. In some embodiments, a C3-binding agent is a humanized anti-C3 antibody that comprises (i) one, two, and/or three heavy chain CDRs, and/or (ii) one, two, and/or three light chain CDRs from any one of Tables 1-10.

TABLE 1A

Antibody 38G10 Sequences

| | Exemplary | Chothia | AbM | Kabat | Contact |
|---|---|---|---|---|---|
| Heavy Chain CDR1 | GYTFTDFYMD (SEQ ID NO: 7) | GYTFTDF (SEQ ID NO: 120) | GYTFTDFYMD (SEQ ID NO: 7) | DFYMD (SEQ ID NO: 121) | TDFYMD (SEQ ID NO: 122) |
| Heavy Chain CDR2 | YIYPHNGGTTYN QNFTG (SEQ ID NO: 8) | YPHNGG (SEQ ID NO: 123) | YIYPHNGGTT (SEQ ID NO: 124) | YIYPHNGGTTYN QNFTG (SEQ ID NO: 8) | WIGYIYPHNGGTT (SEQ ID NO: 125) |
| Heavy Chain CDR3 | RGGFDFDY (SEQ ID NO: 9) | RGGFDFDY (SEQ ID NO: 9) | RGGFDFDY (SEQ ID NO: 9) | RGGFDFDY (SEQ ID NO: 9) | ARRGGFDFD (SEQ ID NO: 126) |
| Light Chain CDR1 | KASENVDTYVS (SEQ ID NO: 10) | KASENVDTYVS (SEQ ID NO: 10) | KASENVDTYVS (SEQ ID NO: 10) | KASENVDTYVS (SEQ ID NO: 10) | DTYVSWY (SEQ ID NO: 127) |
| Light Chain CDR2 | GASNRYT (SEQ ID NO: 11) | GASNRYT (SEQ ID NO: 11) | GASNRYT (SEQ ID NO: 11) | GASNRYT (SEQ ID NO: 11) | LLIYGASNRY (SEQ ID NO: 128) |
| Light Chain CDR3 | GQSHSYPLT (SEQ ID NO: 12) | GQSHSYPLT (SEQ ID NO: 12) | GQSHSYPLT (SEQ ID NO: 12) | GQSHSYPLT (SEQ ID NO: 12) | GQSHSYPL (SEQ ID NO: 129) |

38G10 Heavy chain variable region (SEQ ID NO: 18)
EVQLQQSGPELVKPGDSVKMSCKASGYTFTDFYMDWVKQSHGKSLEWIGYIYPHNGGTTY
NQNFTGKATLTVDKSSNTAYMELHSLTSEDSAVYYCARRGGFDFDYWGQGTTLTVSS 38G10 Light chain variable region (SEQ ID NO: 19)
NIVMTQSPKSMSLSVGERVTLRCKASENVDTYVSWYQQKPEQSPKLLIYGASNRYTGVPD
RFTGSGSATEFTLTISSVQAEDLVGYHCGQSHSYPLTFGAGTKLELK

TABLE 1B

Antibody Hz38G10 Sequences

| | Exemplary | Cho thia | AbM | Kabat | Contact |
|---|---|---|---|---|---|
| Heavy Chain CDR1 | GYTFTDFYMD (SEQ ID NO: 7) | GYTFTDF (SEQ ID NO: 120) | GYTFTDFYMD (SEQ ID NO: 7) | DFYMD (SEQ ID NO: 121) | TDFYMD (SEQ ID NO: 122) |
| Heavy Chain CDR2 | YIYPHNGGTTYN QQFTG (SEQ ID NO: 13) | YPHNGG (SEQ ID NO: 123) | YIYPHNGGTT (SEQ ID NO: 124) | YIYPHNGGTTYN QQFTG (SEQ ID NO: 13) | WMGYIYPHN GGTT (SEQ ID NO: 130) |
| Heavy Chain CDR3 | RGGFDFDY (SEQ ID NO: 9) | RGGFDFDY (SEQ ID NO: 9) | RGGFDFDY (SEQ ID NO: 9) | RGGFDFDY (SEQ ID NO: 9) | ARRGGFDFD (SEQ ID NO: 126) |
| Light Chain CDR1 | KASENVDTYVS (SEQ ID NO: 10) | KASENVDTYVS (SEQ ID NO: 10) | KASENVDTYVS (SEQ ID NO: 10) | KASENVDTYVS (SEQ ID NO: 10) | DTYVSWY (SEQ ID NO: 127) |

TABLE 1B-continued

Antibody Hz38G10 Sequences

| | Exemplary | Chothia | AbM | Kabat | Contact |
|---|---|---|---|---|---|
| Light Chain CDR2 | GASNRYT (SEQ ID NO: 11) | GASNRYT (SEQ ID NO: 11) | GASNRYT (SEQ ID NO: 11) | GASNRYT (SEQ ID NO: 11) | LLIYGASNRY (SEQ ID NO: 128) |
| Light Chain CDR3 | GQSHSYPLT (SEQ ID NO: 12) | GQSHSYPLT (SEQ ID NO: 12) | GQSHSYPLT (SEQ ID NO: 12) | GQSHSYPLT (SEQ ID NO: 12) | GQSHSYPL (SEQ ID NO: 129) |

Hz38G10 Heavy chain variable region (SEQ ID NO: 20)
QVQLVQSGAEVKKPGASVKVSCKASGYTFTDFYMDWVRQAPGQRLEWMGYIYPHNGGTTY
NQQFTGRVTITVDKSASTAYMELSSLRSEDTAVYYCARRGGFDFDYWGQGTLVTVSS Hz38G10 Light chain variable region (SEQ ID NO: 25)
DIQMTQSPSSLSASVGDRVTITCKASENVDTYVSWYQQKPGKAPKLLIYGASNRYTGVPS
RFSGSGSGTDFTFTISSLQPEDIATYHCGQSHSYPLTFGQGTKLEIK

TABLE 1C

Antibody HZ38G10 Variant Sequences

| | Exemplary | Chothia | AbM | Kabat | Contact |
|---|---|---|---|---|---|
| Heavy Chain CDR1 | GYTFTDFYMD (SEQ ID NO: 7) | GYTFTDF (SEQ ID NO: 120) | GYTFTDFYMD (SEQ ID NO: 7) | DFYMD (SEQ ID NO: 121) | TDFYMD (SEQ ID NO: 122) |
| Variant Heavy Chain CDR2 | YIYPHNAGTTYN QQFTG (SEQ ID NO: 14) | YPHNAG (SEQ ID NO: 131) | YIYPHNAGTT (SEQ ID NO: 132) | YIYPHNAGTTYN QQFTG (SEQ ID NO: 14) | WMGYIYPHN AGTT (SEQ ID NO: 133) |
| Variant Heavy Chain CDR2 | YIYPHNTGTTYN QQFTG (SEQ ID NO: 15) | YPHNTG (SEQ ID NO: 134) | YIYPHNTGTT (SEQ ID NO: 135) | YIYPHNTGTTYN QQFTG (SEQ ID NO: 15) | WMGYIYPHN TGTT (SEQ ID NO: 136) |
| Variant Heavy Chain CDR2 | YIYPHEGGTTYN QQFTG (SEQ ID NO: 16) | YPHEGG (SEQ ID NO: 137) | YIYPHEGGTT (SEQ ID NO: 138) | YIYPHEGGTTYN QQFTG (SEQ ID NO: 16) | WMGYIYPHE GGTT (SEQ ID NO: 139) |
| Variant Heavy Chain CDR2 | YIYPHQGGTTYN QQFTG (SEQ ID NO: 17) | YPHQGG (SEQ ID NO: 140) | YIYPHQGGTT (SEQ ID NO: 141) | YIYPHQGGTTYN QQFTG (SEQ ID NO: 17) | WMGYIYPHQ GGTT (SEQ ID NO: 142) |
| Heavy Chain CDR3 | RGGFDFDY (SEQ ID NO: 9) | RGGFDFDY (SEQ ID NO: 9) | RGGFDFDY (SEQ ID NO: 9) | RGGFDFDY (SEQ ID NO: 9) | ARRGGFDFD (SEQ ID NO: 126) |
| Light Chain CDR1 | KASENVDTYVS (SEQ ID NO: 10) | KASENVDTYVS (SEQ ID NO: 10) | KASENVDTYVS (SEQ ID NO: 10) | KASENVDTYVS (SEQ ID NO: 10) | DTYVSWY (SEQ ID NO: 127) |
| Light Chain CDR2 | GASNRYT (SEQ ID NO: 11) | GASNRYT (SEQ ID NO: 11) | GASNRYT (SEQ ID NO: 11) | GASNRYT (SEQ ID NO: 11) | LLIYGASNRY (SEQ ID NO: 128) |
| Light Chain CDR3 | GQSHSYPLT (SEQ ID NO: 12) | GQSHSYPLT (SEQ ID NO: 12) | GQSHSYPLT (SEQ ID NO: 12) | GQSHSYPLT (SEQ ID NO: 12) | GQSHSYPL (SEQ ID NO: 129) |

TABLE 2

Antibody 3D8 Sequences

| | Exemplary | Chothia | AbM | Kabat | Contact |
|---|---|---|---|---|---|
| Heavy Chain CDR1 | GYSFTGYNMN (SEQ ID NO: 38) | GYSFTGY (SEQ ID NO: 143) | GYSFTGYNMN (SEQ ID NO: 38) | GYNMN (SEQ ID NO: 144) | TGYNMN (SEQ ID NO: 145) |
| Heavy Chain CDR2 | NINPYYGSTNYN QKFKG (SEQ ID NO: 39) | NPYYGS (SEQ ID NO: 146) | NINPYYGSTN (SEQ ID NO: 147) | NINPYYGSTNYN QKFKG (SEQ ID NO: 39) | WIGNINPYYGSTN (SEQ ID NO: 149) |
| Heavy Chain CDR3 | GYYGGNYPFAY (SEQ ID NO: 40) | GYYGGNYPFAY (SEQ ID NO: 40) | GYYGGNYPFAY (SEQ ID NO: 40) | GYYGGNYPFAY (SEQ ID NO: 40) | ARGYYGGNYPFA (SEQ ID NO: 150) |

TABLE 2-continued

Antibody 3D8 Sequences

| | Exemplary | Chothia | AbM | Kabat | Contact |
|---|---|---|---|---|---|
| Light Chain CDR1 | RASENIYSYLA (SEQ ID NO: 41) | RASENIYSYLA (SEQ ID NO: 41) | RASENIYSYLA (SEQ ID NO: 41) | RASENIYSYLA (SEQ ID NO: 41) | YSYLAWY (SEQ ID NO: 151) |
| Light Chain CDR2 | NAKTLAE (SEQ ID NO: 42) | NAKTLAE (SEQ ID NO: 42) | NAKTLAE (SEQ ID NO: 42) | NAKTLAE (SEQ ID NO: 42) | LLVYNAKTLA (SEQ ID NO: 152) |
| Light Chain CDR3 | QHYYGTPYT (SEQ ID NO: 43) | QHYYGTPYT (SEQ ID NO: 43) | QHYYGTPYT (SEQ ID NO: 43) | QHYYGTPYT (SEQ ID NO: 43) | QHYYGTPY (SEQ ID NO: 153) |

3D8 Heavy chain variable region (SEQ ID NO: 91)
EIQLQQSGAELVKPGASVKISCKASGYSFTGYNMNWVKQSHGKSLEWIGNINPYYGSTNY
NQKFKGKATLIVDKSSTTAYMQLDSLISEDSAVYYCARGYYGGNYPFAYWGQGTLVTVSA 3D8 Light chain variable region (SEQ ID NO: 92)
DIQMTQSPASLSASVGETVTITCRASENIYSYLAWYQQKQGKSPQLLVYNAKTLAEGVPS
RFSGSGSGTQFSLKINSLQPEDFGSYYCQHYYGTPYTFGGGSKVEIK

TABLE 3

Antibody 3G8 Sequences

| | Exemplary | Chothia | AbM | Kabat | Contact |
|---|---|---|---|---|---|
| Heavy Chain CDR1 | GYSFTGYNMN (SEQ ID NO: 38) | GYSFTGY (SEQ ID NO: 143) | GYSFTGYNMN (SEQ ID NO: 38) | GYNMN (SEQ ID NO: 144) | TGYNMN (SEQ ID NO: 145) |
| Heavy Chain CDR2 | NINPYYDSTSYNQKFKG (SEQ ID NO: 44) | NPYYDS (SEQ ID NO: 154) | NINPYYDSTS (SEQ ID NO: 155) | NINPYYDSTSYNQKFKG (SEQ ID NO: 44) | WIGNINPYYDSTS (SEQ ID NO: 156) |
| Heavy Chain CDR3 | ENYDFVGFAY (SEQ ID NO: 45) | ENYDFVGFAY (SEQ ID NO: 45) | ENYDFVGFAY (SEQ ID NO: 45) | ENYDFVGFAY (SEQ ID NO: 45) | ARENYDFVGFA (SEQ ID NO: 157) |
| Light Chain CDR1 | RASSSVSYMH (SEQ ID NO: 46) | RASSSVSYMH (SEQ ID NO: 46) | RASSSVSYMH (SEQ ID NO: 46) | RASSSVSYMH (SEQ ID NO: 46) | SYMHWF (SEQ ID NO: 158) |
| Light Chain CDR2 | VTSNLAS (SEQ ID NO: 47) | VTSNLAS (SEQ ID NO: 47) | VTSNLAS (SEQ ID NO: 47) | VTSNLAS (SEQ ID NO: 47) | PWIYVTSNLA (SEQ ID NO: 159) |
| Light Chain CDR3 | QQWSTNPLT (SEQ ID NO: 48) | QQWSTNPLT (SEQ ID NO: 48) | QQWSTNPLT (SEQ ID NO: 48) | QQWSTNPLT (SEQ ID NO: 48) | QQWSTNPL (SEQ ID NO: 160) |

3G8 Heavy chain variable region (SEQ ID NO: 93)
EIQLQQSGAELVKPGASVKISCMASGYSFTGYNMNWVKQSHGKGLEWIGNINPYYDSTSY
NQKFKGKATLTVDKSSTTAYMQLNSLTSEDSAVYYCARENYDFVGFAYWGQGTLVTVSA 3G8 Light chain variable region (SEQ ID NO: 94)
QIVLSQSPAILSASPGEKVTMTCRASSSVSYMHWFQQKPGSSPKPWIYVTSNLASGVPPR
FSGSGSGTSYSLTISRVEAEDAATYYCQQWSTNPLTFGAGTKLELK

TABLE 4

Antibody 15C12 Sequences

| | Exemplary | Chothia | AbM | Kabat | Contact |
|---|---|---|---|---|---|
| Heavy Chain CDR1 | GYSFTGYNMH (SEQ ID NO: 49) | GYSFTGY (SEQ ID NO: 143) | GYSFTGYNMH (SEQ ID NO: 49) | GYNMH (SEQ ID NO: 161) | TGYNMH (SEQ ID NO: 162) |
| Heavy Chain CDR2 | NINPYYGTTNSNQKFED (SEQ ID NO: 50) | NPYYGT (SEQ ID NO: 163) | NINPYYGTTN (SEQ ID NO: 164) | NINPYYGTTNSNQKFED (SEQ ID NO: 50) | WIGNINPYYGTTN (SEQ ID NO: 165) |
| Heavy Chain CDR3 | GIYYYGTGYPYFDF (SEQ ID NO: 51) | GIYYYGTGYPYFDF (SEQ ID NO: 51) | GIYYYGTGYPYFDF (SEQ ID NO: 51) | GIYYYGTGYPYFDF (SEQ ID NO: 51) | ARGIYYYGTGYPYFD (SEQ ID NO: 166) |

TABLE 4-continued

Antibody 15C12 Sequences

| | Exemplary | Chothia | AbM | Kabat | Contact |
|---|---|---|---|---|---|
| Light Chain CDR1 | RASQDINNYLN (SEQ ID NO: 52) | RASQDINNYLN (SEQ ID NO: 52) | RASQDINNYLN (SEQ ID NO: 52) | RASQDINNYLN (SEQ ID NO: 52) | NNYLNWY (SEQ ID NO: 167) |
| Light Chain CDR2 | YTSRLHS (SEQ ID NO: 53) | YTSRLHS (SEQ ID NO: 53) | YTSRLHS (SEQ ID NO: 53) | YTSRLHS (SEQ ID NO: 53) | LLIYYTSRLH (SEQ ID NO: 168) |
| Light Chain CDR3 | QQGITLPWT (SEQ ID NO: 54) | QQGITLPWT (SEQ ID NO: 54) | QQGITLPWT (SEQ ID NO: 54) | QQGITLPWT (SEQ ID NO: 54) | QQGITLPW (SEQ ID NO: 169) |

15C12 Heavy chain variable region (SEQ ID NO: 95)
EIQLQQSGAELEKPGASVKISCKASGYSFTGYNMHWVKQSHGKSLEWIGNINPYYGTTNS
NQKFEDKATLTVDKSSSTAYMQLNSLTSEDSAVYYCARGIYYYGTGYPYFDFWGQGTTLT
VSS 15C12 Light chain variable region (SEQ ID NO: 96)
DIQMTQTTSSLSASLGDRVTISCRASQDINNYLNWYLQKPDGTVKLLIYYTSRLHSGVPS
RFSGSGSGTDYSLTISNLEQEDLATYFCQQGITLPWTFGGGTKLEIK

TABLE 5

Antibody 27A8 Sequences

| | Exemplary | Chothia | AbM | Kabat | Contact |
|---|---|---|---|---|---|
| Heavy Chain CDR1 | GYTFTDYWIN (SEQ ID NO: 55) | GYTFTDY (SEQ ID NO: 170) | GYTFTDYWIN (SEQ ID NO: 55) | DYWIN (SEQ ID NO: 171) | TDYWIN (SEQ ID NO: 172) |
| Heavy Chain CDR2 | NIYPGSTSANYN EKFKS (SEQ ID NO: 56) | YPGSTS (SEQ ID NO: 173) | NIYPGSTSAN (SEQ ID NO: 174) | NIYPGSTSANYN EKFKS (SEQ ID NO: 56) | WIGNIYPGSTSAN (SEQ ID NO: 175) |
| Heavy Chain CDR3 | YGYDSWFAY (SEQ ID NO: 57) | YGYDSWFAY (SEQ ID NO: 57) | YGYDSWFAY (SEQ ID NO: 57) | YGYDSWFAY (SEQ ID NO: 57) | ARYGYDSWFA (SEQ ID NO: 176) |
| Light Chain CDR1 | KSTKSLLNSDG FTYLD (SEQ ID NO: 58) | KSTKSLLNSDG FTYLD (SEQ ID NO: 58) | KSTKSLLNSDG FTYLD (SEQ ID NO: 58) | KSTKSLLNSDG FTYLD (SEQ ID NO: 58) | LNSDGFTYLDWF (SEQ ID NO: 177) |
| Light Chain CDR2 | LVSNRFS (SEQ ID NO: 59) | LVSNRFS (SEQ ID NO: 59) | LVSNRFS (SEQ ID NO: 59) | LVSNRFS (SEQ ID NO: 59) | LLIYLVSNRF (SEQ ID NO: 178) |
| Light Chain CDR3 | FQSNYLPLT (SEQ ID NO: 60) | FQSNYLPLT (SEQ ID NO: 60) | FQSNYLPLT (SEQ ID NO: 60) | FQSNYLPLT (SEQ ID NO: 60) | FQSNYLPL (SEQ ID NO: 179) |

27A8 Heavy chain variable region (SEQ ID NO: 97)
QVQLLQPGAEFVKPGASVKLSCKASGYTFTDYWINWVKQRPGQGLEWIGNIYPGSTSANY
NEKFKSKATLTIDTSSITAYMQLSSLTSDDSAVYYCARYGYDSWFAYWGQGTLVTVSA 27A8 Light chain variable region (SEQ ID NO: 98)
DVVLTQTPLSLPVNIGDQASISCKSTKSLLNSDGFTYLDWFLQKPGQSPHLLIYLVSNRF
SGIPDRFSGSGSETDFTLKISRVEAEDLGVYYCFQSNYLPLTFGSGTKLEIK

TABLE 6

Antibody 28C3 Sequences

| | Exemplary | Chothia | AbM | Kabat | Contact |
|---|---|---|---|---|---|
| Heavy Chain CDR1 | GYAFNSCWMN (SEQ ID NO: 61) | GYAFNSC (SEQ ID NO: 180) | GYAFNSCWMN (SEQ ID NO: 61) | SCWMN (SEQ ID NO: 181) | NSCWMN (SEQ ID NO: 182) |
| Heavy Chain CDR2 | RIYPGDGDTNYN GKFKG (SEQ ID NO: 62) | YPGDGD (SEQ ID NO: 183) | RIYPGDGDTN (SEQ ID NO: 184) | RIYPGDGDTNYN GKFKG (SEQ ID NO: 62) | WIGRIYPGDGDTN (SEQ ID NO: 185) |

TABLE 6-continued

Antibody 28C3 Sequences

| | Exemplary | Chothia | AbM | Kabat | Contact |
|---|---|---|---|---|---|
| Heavy Chain CDR3 | EGRNYGYEDY (SEQ ID NO: 63) | EGRNYGYEDY (SEQ ID NO: 63) | EGRNYGYEDY (SEQ ID NO: 63) | EGRNYGYEDY (SEQ ID NO: 63) | AREGRNYGYED (SEQ ID NO: 186) |
| Light Chain CDR1 | KASQSVDYDGDSYMN (SEQ ID NO: 64) | KASQSVDYDGDSYMN (SEQ ID NO: 64) | KASQSVDYDGDSYMN (SEQ ID NO: 64) | KASQSVDYDGDSYMN (SEQ ID NO: 64) | DYDGDSYMNWY (SEQ ID NO: 187) |
| Light Chain CDR2 | AASDLES (SEQ ID NO: 65) | AASDLES (SEQ ID NO: 65) | AASDLES (SEQ ID NO: 65) | AASDLES (SEQ ID NO: 65) | LLIYAASDLE (SEQ ID NO: 188) |
| Light Chain CDR3 | QQANEDPRT (SEQ ID NO: 66) | QQANEDPRT (SEQ ID NO: 66) | QQANEDPRT (SEQ ID NO: 66) | QQANEDPRT (SEQ ID NO: 66) | QQANEDPR (SEQ ID NO: 189) |

28C3 Heavy chain variable region (SEQ ID NO: 99)
QVQLQQSGPELVKPGASVKISCKASGYAFNSCWMNWVKQRPGKGLEWIGRIYPGDGDTNY
NGKFKGKATLTADKSSTTAYMQLSSLTSEDSAVYFCAREGRNYGYEDYWGQGTTLTVSS 28C3 Light chain variable region (SEQ ID NO: 100)
DIVLTQSPASLAVSLGQRATISCKASQSVDYDGDSYMNWYQQKPGQPPKLLIYAASDLES
GIPARFSGSGSGTDFTLNIHPVEEEDAATYYCQQANEDPRTFGGGTKLEIK

TABLE 7

Antibody 38F5 Sequences

| | Exemplary | Chothia | AbM | Kabat | Contact |
|---|---|---|---|---|---|
| Heavy Chain CDR1 | GFTFSNYAMS (SEQ ID NO: 67) | GFTFSNY (SEQ ID NO: 190) | GFTFSNYAMS (SEQ ID NO: 67) | NYAMS (SEQ ID NO: 191) | SNYAMS (SEQ ID NO: 192) |
| Heavy Chain CDR2 | QTISSGGRYTYYPDSVKG (SEQ ID NO: 68) | ISSGGRY (SEQ ID NO: 193) | QTISSGGRYTY (SEQ ID NO: 194) | QTISSGGRYTYYPDSVKG (SEQ ID NO: 68) | WVQTISSGGRYTY (SEQ ID NO: 195) |
| Heavy Chain CDR3 | RYYGNSYWYFDV (SEQ ID NO: 69) | RYYGNSYWYFDV (SEQ ID NO: 69) | RYYGNSYWYFDV (SEQ ID NO: 69) | RYYGNSYWYFDV (SEQ ID NO: 69) | VRRYYGNSYWYFD (SEQ ID NO: 196) |
| Light Chain CDR1 | KSSQSLLNSGNQKHYLT (SEQ ID NO: 70) | KSSQSLLNSGNQKHYLT (SEQ ID NO: 70) | KSSQSLLNSGNQKHYLT (SEQ ID NO: 70) | KSSQSLLNSGNQKHYLT (SEQ ID NO: 70) | LNSGNQKHYLTWY (SEQ ID NO: 197) |
| Light Chain CDR2 | GASTRGS (SEQ ID NO: 71) | GASTRGS (SEQ ID NO: 71) | GASTRGS (SEQ ID NO: 71) | GASTRGS (SEQ ID NO: 71) | LLIYGASTRG (SEQ ID NO: 198) |
| Light Chain CDR3 | QNDHSYPYT (SEQ ID NO: 72) | QNDHSYPYT (SEQ ID NO: 72) | QNDHSYPYT (SEQ ID NO: 72) | QNDHSYPYT (SEQ ID NO: 72) | QNDHSYPY (SEQ ID NO: 199) |

38F5 Heavy chain variable region (SEQ ID NO: 101)
EVMLVESGGALVKPGGSLKLSCTASGFTFSNYAMSWVRQTPEKRLEWVAQTISSGGRYTY
YPDSVKGRFTISRDNARNTLYLQMSSLRSEDTAMYYCVRRYYGNSYWYFDVWGAGTTVTV
SS 38F5 Light chain variable region (SEQ ID NO: 102)
DIVMTQSPSSLSVSAGEKVTMNCKSSQSLLNSGNQKHYLTWYQQKPGQPPKLLIYGASTR
GSGVPDRFTGSGSGTDFTLTISSVQAEDLAVYYCQNDHSYPYTFGGGTKLEIK

TABLE 8

Antibody 62B11 Sequences

| | Exemplary | Chothia | AbM | Kabat | Contact |
|---|---|---|---|---|---|
| Heavy Chain CDR1 | GFTFSSYTMS (SEQ ID NO: 73) | GFTFSSY (SEQ ID NO: 200) | GFTFSSYTMS (SEQ ID NO: 73) | SYTMS (SEQ ID NO: 201) | SSYTMS (SEQ ID NO: 202) |

TABLE 8-continued

Antibody 62B11 Sequences

|  | Exemplary | Chothia | AbM | Kabat | Contact |
|---|---|---|---|---|---|
| Heavy Chain CDR2 | YISSGGGTTYYP DTVKG (SEQ ID NO: 74) | SSGGGT (SEQ ID NO: 203) | YISSGGGTTY (SEQ ID NO: 204) | YISSGGGTTYYP DTVKG (SEQ ID NO: 74) | WVAYISSGGGTTY (SEQ ID NO: 205) |
| Heavy Chain CDR3 | YYRRGSSLWY FDV (SEQ ID NO: 75) | RYYRGSSLWY FDV (SEQ ID NO: 75) | RYYRGSSLWY FDV (SEQ ID NO: 75) | RYYRGSSLWY FDV (SEQ ID NO: 75) | ARRYYRGSSLW YFD (SEQ ID NO: 206) |
| Light Chain CDR1 | SKSQSLFNSGSQ KNFLT (SEQ ID NO: 76) | KSSQSLFNSGSQ KNFLT (SEQ ID NO: 76) | KSSQSLFNSGSQ KNFLT (SEQ ID NO: 76) | KSSQSLFNSGSQ KNFLT (SEQ ID NO: 76) | FNSGSQKNFLTWY (SEQ ID NO: 207) |
| Light Chain CDR2 | WASTRES (SEQ ID NO: 77) | WASTRES (SEQ ID NO: 77) | WASTRES (SEQ ID NO: 77) | WASTRES (SEQ ID NO: 77) | LLIYWASTRE (SEQ ID NO: 208) |
| Light Chain CDR3 | QNDYSYPLT (SEQ ID NO: 78) | QNDYSYPLT (SEQ ID NO: 78) | QNDYSYPLT (SEQ ID NO: 78) | QNDYSYPLT (SEQ ID NO: 78) | QNDYSYPL (SEQ ID NO: 209) |

62B11 Heavy chain variable region (SEQ ID NO: 103)
EVKLVESGGGLVQPGGSLKLSCAASGFTFSSYTMSWVRQTPEKRLEWVAYISSGGGTTYY
PDTVKGRFTVSRDNAKNTLYLQMSSLRSEDTAMYSCARRYYRGSSLWYFDVWGAGTTVTV
SS 62B11 Light chain variable region (SEQ ID NO: 104)
DIVMTQSPSSLTVTAGEKVIMSCKSSQSLFNSGSQKNFLTWYQQRPGQPPKLLIYWASTR
ESGVPDRFTGSGSGTDFTLTISSVQAEDLAVYYCQNDYSYPLTFGAGTKLELK

TABLE 9

Antibody 62F2 Sequences

|  | Exemplary | Chothia | AbM | Kabat | Contact |
|---|---|---|---|---|---|
| Heavy Chain CDR1 | GYSITSGYSLH (SEQ ID NO: 79) | GYSITSGY (SEQ ID NO: 210) | GYSITSGYSLH (SEQ ID NO: 79) | SGYSLH (SEQ ID NO: 211) | TSGYSLH (SEQ ID NO: 212) |
| Heavy Chain CDR2 | YIHYSGSTNYNP SLKS (SEQ ID NO: 80) | HYSGS (SEQ ID NO: 213) | YIHYSGSTN (SEQ ID NO: 214) | YIHYSGSTNYNP SLKS (SEQ ID NO: 80) | WMGYIHYSGSTN (SEQ ID NO: 215) |
| Heavy Chain CDR3 | AWDYLDY (SEQ ID NO: 81) | AWDYLDY (SEQ ID NO: 81) | AWDYLDY (SEQ ID NO: 81) | AWDYLDY (SEQ ID NO: 81) | ARAWDYLD (SEQ ID NO: 216) |
| Light Chain CDR1 | RASENIYSQLA (SEQ ID NO: 82) | RASENIYSQLA (SEQ ID NO: 82) | RASENIYSQLA (SEQ ID NO: 82) | RASENIYSQLA (SEQ ID NO: 82) | YSQLAWY (SEQ ID NO: 217) |
| Light Chain CDR2 | DAKTLAE (SEQ ID NO: 83) | DAKTLAE (SEQ ID NO: 83) | DAKTLAE (SEQ ID NO: 83) | DAKTLAE (SEQ ID NO: 83) | LLVYDAKTLA (SEQ ID NO: 218) |
| Light Chain CDR3 | HHHFGILYT (SEQ ID NO: 84) | HHHFGILYT (SEQ ID NO: 84) | HHHFGILYT (SEQ ID NO: 84) | HHHFGILYT (SEQ ID NO: 84) | HHHFGILY (SEQ ID NO: 219) |

62F2 Heavy chain variable region (SEQ ID NO: 105)
DVQLQESGPDLVKPSQSLSLICTVTGYSITSGYSLHWIRQFPGNKLEWMGYIHYSGSTNY
NPSLKSRISITRDTSKNQFFLKLNSVISEDTATYHCARAWDYLDYWGQGTTLIVSS 62F2 Light chain variable region (SEQ ID NO: 106)
DIQMTQSPASLSASVGETVTITCRASENIYSQLAWYQQKQGKSPQLLVYDAKTLAEGVPS
RFSGSGSDTQFSLKIISLQPEDFGRYYCHHHFGILYTFGGGTKLEMK

TABLE 10

Antibody 63A3 Sequences

|  | Exemplary | Chothia | AbM | Kabat | Contact |
|---|---|---|---|---|---|
| Heavy Chain CDR1 | GYSITSGYYWN (SEQ ID NO: 85) | GYSITSGY (SEQ ID NO: 210) | GYSITSGYYWN (SEQ ID NO: 85) | SGYYWN (SEQ ID NO: 220) | TSGYYWN (SEQ ID NO: 221) |

TABLE 10-continued

Antibody 63A3 Sequences

|  | Exemplary | Chothia | AbM | Kabat | Contact |
|---|---|---|---|---|---|
| Heavy Chain CDR2 | YIRYDGSNNYN PSLKN (SEQ ID NO: 86) | RYDGS (SEQ ID NO: 222) | YIRYDGSNN (SEQ ID NO: 223) | YIRYDGSNNYN PSLKN (SEQ ID NO: 86) | WMGYIRYDGSNN (SEQ ID NO: 224) |
| Heavy Chain CDR3 | HYGYDGGAFDF (SEQ ID NO: 87) | HYGYDGGAFDF (SEQ ID NO: 87) | HYGYDGGAFDF (SEQ ID NO: 87) | HYGYDGGAFDF (SEQ ID NO: 87) | ARHYGYDGGAFD (SEQ ID NO: 225) |
| Light Chain CDR1 | RTSENIYNYLV (SEQ ID NO: 88) | RTSENIYNYLV (SEQ ID NO: 88) | RTSENIYNYLV (SEQ ID NO: 88) | RTSENIYNYLV (SEQ ID NO: 88) | YNYLVWY (SEQ ID NO: 226) |
| Light Chain CDR2 | NAKTLEE (SEQ ID NO: 89) | NAKTLEE (SEQ ID NO: 89) | NAKTLEE (SEQ ID NO: 89) | NAKTLEE (SEQ ID NO: 89) | LLVYNAKTLE (SEQ ID NO: 227) |
| Light Chain CDR3 | QHHYGTPFT (SEQ ID NO: 90) | QHHYGTPFT (SEQ ID NO: 90) | QHHYGTPFT (SEQ ID NO: 90) | QHHYGTPFT (SEQ ID NO: 90) | QHHYGTPF (SEQ ID NO: 228) |

63A3 Heavy chain variable region (SEQ ID NO: 107)
DVQLQESGPGLVKPSQSLSLICSVTGYSITSGYYWNWIRQFPGNKLEWMGYIRYDGSNNY
NPSLKNRISITRDTSKNQVFLKLNSVITEDTATYYCARHYGYDGGAFDFWGQGTTLIVSS 63A3 Light chain variable region (SEQ ID NO: 108)
DIQMTQSPASLSASVGETVTITCRTSENIYNYLVWYQQKQGKSPQLLVYNAKTLEEGVPS
RFSGSGSGTQFSLKVNSLQPEDFGSYYCQHHYGTPFTFGSGTKLEIK In some embodiments, a C3-binding agent comprises a heavy chain CDR1, CDR2, and CDR3 and/or a light chain CDR1, CDR2, CDR3 from an antibody described herein. In some embodiments, a C3-binding agent comprises a humanized version or humanized variant of an antibody described herein. In some embodiments, a C3-binding agent comprises a heavy chain CDR1, CDR2, and CDR3 and/or a light chain CDR1, CDR2, CDR3 from antibody 38G10 or a humanized version thereof. In some embodiments, a C3-binding agent comprises a heavy chain CDR1, CDR2, and CDR3 and a light chain CDR1, CDR2, CDR3 from antibody 38G10 or a humanized version thereof. In some embodiments, a C3-binding agent comprises a heavy chain CDR1, CDR2, and CDR3 and/or a light chain CDR1, CDR2, CDR3 from antibody Hz38G10 or variants thereof. In some embodiments, a C3-binding agent comprises a heavy chain CDR1, CDR2, and CDR3 and a light chain CDR1, CDR2, CDR3 from antibody Hz38G10 or variants thereof. In some embodiments, a C3-binding agent comprises a heavy chain CDR1, CDR2, and CDR3 and a light chain CDR1, CDR2, CDR3 from antibody 38G10, antibody Hz38G10, or Hz38G10 variants.

In some embodiments, a C3-binding agent comprises a heavy chain CDR1, CDR2, and CDR3 and/or a light chain CDR1, CDR2, and CDR3 from antibody 3D8, a humanized version thereof, or variants thereof. In some embodiments, a C3-binding agent comprises a heavy chain CDR1, a heavy chain CDR2, and a heavy chain CDR3 from antibody 3D8. In other embodiments, a C3-binding agent comprises a light chain CDR1, a light chain CDR2, and a light chain CDR3 from antibody 3D8. In certain embodiments, a C3-binding agent comprises a heavy chain CDR1, a heavy chain CDR2, a heavy chain CDR3, a light chain CDR1, light chain CDR2, and a light chain CDR3 from antibody 3D8. In some embodiments, antibody 3D8 is a humanized version of antibody 3D8. In some embodiments, antibody 3D8 is a variant of antibody 3D8.

In some embodiments, a C3-binding agent comprises a heavy chain CDR1, CDR2, and CDR3 and/or a light chain CDR1, CDR2, and CDR3 from antibody 3G8, a humanized version thereof, or variants thereof. In some embodiments, a C3-binding agent comprises a heavy chain CDR1, a heavy chain CDR2, and a heavy chain CDR3 from antibody 3G8. In other embodiments, a C3-binding agent comprises a light chain CDR1, a light chain CDR2, and a light chain CDR3 from antibody 3G8. In certain embodiments, a C3-binding agent comprises a heavy chain CDR1, a heavy chain CDR2, a heavy chain CDR3, a light chain CDR1, light chain CDR2, and a light chain CDR3 from antibody 3G8. In some embodiments, antibody 3G8 is a humanized version of antibody 3G8. In some embodiments, antibody 3G8 is a variant of antibody 3G8.

In some embodiments, a C3-binding agent comprises a heavy chain CDR1, CDR2, and CDR3 and/or a light chain CDR1, CDR2, CDR3 from antibody 15C12, a humanized version thereof, or variants thereof. In some embodiments, a C3-binding agent comprises a heavy chain CDR1, a heavy chain CDR2, and a heavy chain CDR3 from antibody 15C12. In other embodiments, a C3-binding agent comprises a light chain CDR1, a light chain CDR2, and a light chain CDR3 from antibody 15C12. In certain embodiments, a C3-binding agent comprises a heavy chain CDR1, a heavy chain CDR2, a heavy chain CDR3, a light chain CDR1, light chain CDR2, and a light chain CDR3 from antibody 15C12. In some embodiments, antibody 15C12 is a humanized version of antibody 15C12. In some embodiments, antibody 15C12 is a variant of antibody 15C12.

In some embodiments, a C3-binding agent comprises a heavy chain CDR1, CDR2, and CDR3 and/or a light chain CDR1, CDR2, CDR3 from antibody 27A8, a humanized version thereof, or variants thereof. In some embodiments, a C3-binding agent comprises a heavy chain CDR1, a heavy chain CDR2, and a heavy chain CDR3 from antibody 27A8. In other embodiments, a C3-binding agent comprises a light chain CDR1, a light chain CDR2, and a light chain CDR3 from antibody 27A8. In certain embodiments, a C3-binding agent comprises a heavy chain CDR1, a heavy chain CDR2, a heavy chain CDR3, a light chain CDR1, light chain CDR2, and a light chain CDR3 from antibody 27A8. In some embodiments, antibody 27A8 is a humanized version of antibody 27A8. In some embodiments, antibody 27A8 is a variant of antibody 27A8.

In some embodiments, a C3-binding agent comprises a heavy chain CDR1, CDR2, and CDR3 and/or a light chain CDR1, CDR2, CDR3 from antibody 28C3, a humanized version thereof, or variants thereof. In some embodiments, a C3-binding agent comprises a heavy chain CDR1, a heavy chain CDR2, and a heavy chain CDR3 from antibody 28C3. In other embodiments, a C3-binding agent comprises a light chain CDR1, a light chain CDR2, and a light chain CDR3 from antibody 28C3. In certain embodiments, a C3-binding agent comprises a heavy chain CDR1, a heavy chain CDR2, a heavy chain CDR3, a light chain CDR1, light chain CDR2, and a light chain CDR3 from antibody 28C3. In some embodiments, antibody 28C3 is a humanized version of antibody 28C3. In some embodiments, antibody 28C3 is a variant of antibody 28C3.

In some embodiments, a C3-binding agent comprises a heavy chain CDR1, CDR2, and CDR3 and/or a light chain CDR1, CDR2, CDR3 from antibody 38F5, a humanized version thereof, or variants thereof. In some embodiments, a C3-binding agent comprises a heavy chain CDR1, a heavy chain CDR2, and a heavy chain CDR3 from antibody 38F5. In other embodiments, a C3-binding agent comprises a light chain CDR1, a light chain CDR2, and a light chain CDR3 from antibody 38F5. In certain embodiments, a C3-binding agent comprises a heavy chain CDR1, a heavy chain CDR2, a heavy chain CDR3, a light chain CDR1, light chain CDR2, and a light chain CDR3 from antibody 38F5. In some embodiments, antibody 38F5 is a humanized version of antibody 38F5. In some embodiments, antibody 38F5 is a variant of antibody 38F5.

In some embodiments, a C3-binding agent comprises a heavy chain CDR1, CDR2, and CDR3 and/or a light chain CDR1, CDR2, CDR3 from antibody 62B11, a humanized version thereof, or variants thereof. In some embodiments, a C3-binding agent comprises a heavy chain CDR1, a heavy chain CDR2, and a heavy chain CDR3 from antibody 62B11. In other embodiments, a C3-binding agent comprises a light chain CDR1, a light chain CDR2, and a light chain CDR3 from antibody 62B11. In certain embodiments, a C3-binding agent comprises a heavy chain CDR1, a heavy chain CDR2, a heavy chain CDR3, a light chain CDR1, light chain CDR2, and a light chain CDR3 from antibody 62B11. In some embodiments, antibody 62B11 is a humanized version of antibody 62B11. In some embodiments, antibody 62B11 is a variant of antibody 62B11.

In some embodiments, a C3-binding agent comprises a heavy chain CDR1, CDR2, and CDR3 and/or a light chain CDR1, CDR2, CDR3 from antibody 62F2, a humanized version thereof, or variants thereof. In some embodiments, a C3-binding agent comprises a heavy chain CDR1, a heavy chain CDR2, and a heavy chain CDR3 from antibody 62F2. In other embodiments, a C3-binding agent comprises a light chain CDR1, a light chain CDR2, and a light chain CDR3 from antibody 62F2. In certain embodiments, a C3-binding agent comprises a heavy chain CDR1, a heavy chain CDR2, a heavy chain CDR3, a light chain CDR1, light chain CDR2, and a light chain CDR3 from antibody 62F2. In some embodiments, antibody 62F2 is a humanized version of antibody 62F2. In some embodiments, antibody 62F2 is a variant of antibody 62F2.

In some embodiments, a C3-binding agent comprises a heavy chain CDR1, CDR2, and CDR3 and/or a light chain CDR1, CDR2, CDR3 from antibody 63A3, a humanized version thereof, or variants thereof. In some embodiments, a C3-binding agent comprises a heavy chain CDR1, a heavy chain CDR2, and a heavy chain CDR3 from antibody 63A3. In other embodiments, a C3-binding agent comprises a light chain CDR1, a light chain CDR2, and a light chain CDR3 from antibody 63A3. In certain embodiments, a C3-binding agent comprises a heavy chain CDR1, a heavy chain CDR2, a heavy chain CDR3, a light chain CDR1, light chain CDR2, and a light chain CDR3 from antibody 63A3. In some embodiments, antibody 63A3 is a humanized version of antibody 63A3. In some embodiments, antibody 63A3 is a variant of antibody 63A3.

In some embodiments, a C3-binding agent is an antibody. In some embodiments, a variant of an anti-C3 antibody described herein comprises one to thirty conservative amino acid substitutions. In some embodiments, the variant of the anti-C3 antibody comprises one to twenty-five conservative amino acid substitutions. In some embodiments, the variant of the anti-C3 antibody comprises one to twenty conservative amino acid substitutions. In some embodiments, the variant of the anti-C3 antibody comprises one to fifteen conservative amino acid substitutions. In some embodiments, the variant of the anti-C3 antibody comprises one to ten conservative amino acid substitution(s). In some embodiments, the variant of the anti-C3 antibody comprises one to five conservative amino acid substitution(s). In some embodiments, the variant of the anti-C3 antibody comprises one to three conservative amino acid substitution(s). In some embodiments, the conservative amino acid substitution(s) is in a CDR of the antibody. In some embodiments, the conservative amino acid substitution(s) is not in a CDR of the antibody. In some embodiments, the conservative amino acid substitution(s) is in a framework region of the antibody.

CDRs are defined by a variety of methods/systems by those skilled in the art. These systems and/or definitions have been developed and refined over a number of years and include Kabat, Chothia, IMGT, AbM, and Contact. The Kabat definition is based on sequence variability and generally is the most commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis (www.bioinf.org.uk/abysis/sequence_input/key_annotation/key_annotation.cgi)) are available and known to those of skill in the art for analysis of antibody sequences and determination of CDRs.

The specific CDR sequences defined herein are generally based on a combination of Kabat and Chothia definitions (Exemplary system). However, it will be understood that reference to a heavy chain CDR or CDRs and/or a light chain CDR or CDRs of a specific antibody will encompass all CDR definitions as known to those of skill in the art.

In some embodiments, a C3-binding agent (e.g., an antibody) comprises a heavy chain CDR1, CDR2, and CDR3 and a light chain CDR1, CDR2, and CDR3 from the antibody designated 38G10. In some embodiments, a C3-binding agent comprises a heavy chain CDR1, CDR2, and CDR3 from the antibody designated 38G10. In some embodiments, a C3-binding agent comprises a light chain CDR1, CDR2, and CDR3 from the antibody designated 38G10. In some embodiments, a C3-binding agent (e.g., an antibody) comprises a heavy chain CDR1, CDR2, and CDR3 and a light chain CDR1, CDR2, and CDR3 from the antibody designated Hz38G10. In some embodiments, a C3-binding agent comprises a heavy chain CDR1, CDR2, and CDR3 from the antibody designated Hz38G10. In some embodiments, a C3-binding agent (e.g., an antibody) comprises a heavy chain CDR1, CDR2, and CDR3 and a light chain CDR1, CDR2, and CDR3 from the antibody designated Hz38G10(G56A). In some embodiments, a C3-binding agent comprises a heavy chain CDR1, CDR2, and CDR3 from the antibody designated Hz38G10(G56A). In some embodiments, a C3-binding agent (e.g., an antibody) comprises a heavy chain CDR1, CDR2, and CDR3 and a light chain CDR1, CDR2, and CDR3 from the antibody designated Hz38G10(G56T). In some embodiments, a C3-binding agent comprises a heavy chain CDR1, CDR2, and CDR3 from the antibody designated Hz38G10(G56T). In some embodiments, a C3-binding agent (e.g., an antibody) comprises a heavy chain CDR1, CDR2, and CDR3 and a light chain CDR1, CDR2, and CDR3 from the antibody designated Hz38G10(N55E). In some embodiments, a C3-binding agent comprises a heavy chain CDR1, CDR2, and CDR3 from the antibody designated Hz38G10(N55E). In some embodiments, a C3-binding agent (e.g., an antibody) comprises a heavy chain CDR1, CDR2, and CDR3 and a light chain CDR1, CDR2, and CDR3 from the antibody designated Hz38G10(N55Q). In some embodiments, a C3-binding agent comprises a heavy chain CDR1, CDR2, and CDR3 from the antibody designated Hz38G10(N55Q). In some embodiments, a C3-binding agent (e.g., an antibody) comprises a light chain CDR1, CDR2, and CDR3 from the antibody designated Hz38G10, Hz38G10(G56A), Hz38G10(G56T), Hz38G10(N55E), or Hz38G10(N55Q).

In some embodiments, a C3-binding agent (e.g., an antibody) comprises a heavy chain CDR1, CDR2, and CDR3 and a light chain CDR1, CDR2, and CDR3 from Table 1A, Table 1B, or Table 1C.

In certain embodiments, a C3-binding agent (e.g., an antibody) comprises (a) a heavy chain CDR1 comprising SEQ ID NO:7, a heavy chain CDR2 comprising SEQ ID NO:8, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12; (b) a heavy chain CDR1 comprising SEQ ID NO: 120, a heavy chain CDR2 comprising SEQ ID NO: 123, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; (c) a heavy chain CDR1 comprising SEQ ID NO:7, a heavy chain CDR2 comprising SEQ ID NO: 124, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; (d) a heavy chain CDR1 comprising SEQ ID NO: 121, a heavy chain CDR2 comprising SEQ ID NO:8, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; or (e) a heavy chain CDR1 comprising SEQ ID NO: 122, a heavy chain CDR2 comprising SEQ ID NO: 125, a heavy chain CDR3 comprising SEQ ID NO: 126, a light chain CDR1 comprising SEQ ID NO: 127, a light chain CDR2 comprising SEQ ID NO: 128, and a light chain CDR3 comprising SEQ ID NO: 129. In certain embodiments, a C3-binding agent (e.g., an antibody) comprises (a) a heavy chain CDR1 comprising SEQ ID NO:7, a heavy chain CDR2 comprising SEQ ID NO: 13, a heavy chain CDR3 comprising SEQ ID NO:9, a light chain CDR1 comprising SEQ ID NO:10, a light chain CDR2 comprising SEQ ID NO: 11, and a light chain CDR3 comprising SEQ ID NO: 12; (b) a heavy chain CDR1 comprising SEQ ID NO: 120, a heavy chain CDR2 comprising SEQ ID NO: 123, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; (c) a heavy chain CDR1 comprising SEQ ID NO:7, a heavy chain CDR2 comprising SEQ ID NO: 124, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12; (d) a heavy chain CDR1 comprising SEQ ID NO: 121, a heavy chain CDR2 comprising SEQ ID NO: 13, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; or (e) a heavy chain CDR1 comprising SEQ ID NO: 122, a heavy chain CDR2 comprising SEQ ID NO: 130, a heavy chain CDR3 comprising SEQ ID NO: 126, a light chain CDR1 comprising SEQ ID NO: 127, a light chain CDR2 comprising SEQ ID NO: 128, and a light chain CDR3 comprising SEQ ID NO: 129.

In certain embodiments, a C3-binding agent (e.g., an antibody) comprises (a) a heavy chain CDR1 comprising SEQ ID NO:7, a heavy chain CDR2 comprising SEQ ID NO: 14, SEQ ID NO:15, SEQ ID NO:16, or SEQ ID NO:17, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; (b) a heavy chain CDR1 comprising SEQ ID NO: 120, a heavy chain CDR2 comprising SEQ ID NO:131, SEQ ID NO:134, SEQ ID NO: 137, or SEQ ID NO: 140, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO: 12 n; (c) a heavy chain CDR1 comprising SEQ ID NO:7, a heavy chain CDR2 comprising SEQ ID NO: 132, SEQ ID NO: 135, SEQ ID NO: 138, or SEQ ID NO:141, a heavy chain CDR3 comprising SEQ ID NO:9, a light chain CDR1 comprising SEQ ID NO: 10, a light chain CDR2 comprising SEQ ID NO: 11, and a light chain CDR3 comprising SEQ ID NO:12; (d) a heavy chain CDR1 comprising SEQ ID NO:121, a heavy chain CDR2 comprising SEQ ID NO:14, SEQ ID NO:15, SEQ ID NO:16, or SEQ ID NO:17, a heavy chain CDR3 comprising SEQ ID NO:9, a light chain CDR1 comprising SEQ ID NO:10, a light chain CDR2 comprising SEQ ID NO: 11, and a light chain CDR3 comprising SEQ ID NO: 12; or (e) a heavy chain CDR1 comprising SEQ ID NO: 122, a heavy chain CDR2 comprising SEQ ID NO: 133, SEQ ID NO: 136, SEQ ID NO: 139, or SEQ ID NO: 142, a heavy chain CDR3 comprising SEQ ID NO:126, a light chain CDR1 comprising SEQ ID NO:127, a light chain CDR2 comprising SEQ ID NO: 128, and a light chain CDR3 comprising SEQ ID NO: 129.

In some embodiments, a C3-binding agent (e.g., an antibody) comprises: (a) a heavy chain variable region comprising a heavy chain CDR1 comprising GYTFTDFYMD (SEQ ID NO:7), a heavy chain CDR2 comprising YIYPHNGGTTYNQNFTG (SEQ ID NO:8), YIYPHNGGTTYNQQFTG (SEQ ID NO: 13), YIYPHNAGTTYNQQFTG (SEQ ID NO: 14), YIYPHNTGTTYNQQFTG (SEQ ID NO:15), YIYPHEGGTTYNQQFTG (SEQ ID NO:16), or YIYPHQGGTTYNQQFTG (SEQ ID NO: 17), and a heavy chain CDR3 comprising RGGFDFDY (SEQ ID NO:9); and/or (b) a light chain variable region comprising a light chain CDR1 comprising KASENVDTYVS (SEQ ID NO:

10), a light chain CDR2 comprising GASNRYT (SEQ ID NO: 11), and a light chain CDR3 comprising GQSHSYPLT (SEQ ID NO: 12).

In some embodiments, a C3-binding agent comprises (a) a heavy chain CDR1 comprising GYTFTDFYMD (SEQ ID NO:7), a heavy chain CDR2 comprising YIYPHNGGTTYNQNFTG (SEQ ID NO:8), and a heavy chain CDR3 comprising RGGFDFDY (SEQ ID NO:9), and/or (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO:12). In some embodiments, a C3-binding agent comprises a heavy chain CDR1 comprising GYTFTDFYMD (SEQ ID NO:7), a heavy chain CDR2 comprising YIYPHNGGTTYNQNFTG (SEQ ID NO:8), and a heavy chain CDR3 comprising RGGFDFDY (SEQ ID NO:9). In some embodiments, a C3-binding agent comprises a light chain CDR1 comprising KASENVDTYVS (SEQ ID NO:10), a light chain CDR2 comprising GASNRYT (SEQ ID NO: 11), and a light chain CDR3 comprising GQSHSYPLT (SEQ ID NO: 12). In some embodiments, a C3-binding agent comprises (a) a heavy chain CDR1 comprising GYTFTDFYMD (SEQ ID NO:7), a heavy chain CDR2 comprising YIYPHNGGTTYNQNFTG (SEQ ID NO:8), and a heavy chain CDR3 comprising RGGFDFDY (SEQ ID NO:9), and (b) a light chain CDR1 comprising KASENVDTYVS (SEQ ID NO:10), a light chain CDR2 comprising GASNRYT (SEQ ID NO: 11), and a light chain CDR3 comprising GQSHSYPLT (SEQ ID NO: 12).

In some embodiments, a C3-binding agent comprises (a) a heavy chain CDR1 comprising GYTFTDFYMD (SEQ ID NO:7), a heavy chain CDR2 comprising YIYPHNGGTTYNQQFTG (SEQ ID NO: 13), and a heavy chain CDR3 comprising RGGFDFDY (SEQ ID NO:9), and/or (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, a C3-binding agent (e.g., an antibody) comprises a heavy chain CDR1 comprising GYTFTDFYMD (SEQ ID NO:7), a heavy chain CDR2 comprising YIYPHNGGTTYNQQFTG (SEQ ID NO: 13), and a heavy chain CDR3 comprising RGGFDFDY (SEQ ID NO:9). In some embodiments, a C3-binding agent comprises (a) a heavy chain CDR1 comprising GYTFTDFYMD (SEQ ID NO:7), a heavy chain CDR2 comprising YIYPHNGGTTYNQQFTG (SEQ ID NO: 13), and a heavy chain CDR3 comprising RGGFDFDY (SEQ ID NO:9), and (b) a light chain CDR1 comprising KASENVDTYVS (SEQ ID NO:10), a light chain CDR2 comprising GASNRYT (SEQ ID NO: 11), and a light chain CDR3 comprising GQSHSYPLT (SEQ ID NO: 12).

In some embodiments, a C3-binding agent is a variant of an agent described herein. In some embodiments, a C3-binding agent (e.g., an antibody) comprises (a) a heavy chain CDR1 comprising GYTFTDFYMD (SEQ ID NO:7) or a variant thereof comprising 1, 2, 3, or 4 amino acid substitutions; a heavy chain CDR2 comprising YIYPHNGGTTYNQNFTG (SEQ ID NO:8) or YIYPHNGGTTYNQQFTG (SEQ ID NO: 13), or a variant thereof comprising 1, 2, 3, or 4 amino acid substitutions; a heavy chain CDR3 comprising RGGFDFDY (SEQ ID NO:9), or a variant thereof comprising 1, 2, 3, or 4 amino acid substitutions; a light chain CDR1 comprising KASENVDTYVS (SEQ ID NO: 10), or a variant thereof comprising 1, 2, 3, or 4 amino acid substitutions; a light chain CDR2 comprising GASNRYT (SEQ ID NO:11), or a variant thereof comprising 1, 2, 3, or 4 amino acid substitutions; and a light chain CDR3 comprising GQSHSYPLT (SEQ ID NO: 12), or a variant thereof comprising 1, 2, 3, or 4 amino acid substitutions. In some embodiments, the amino acid substitutions are conservative substitutions. In some embodiments, a CDR comprises one conservative amino acid substitution. In some embodiments, a CDR comprises two conservative amino acid substitutions. In some embodiments, a CDR comprises three conservative amino acid substitutions. In some embodiments, a CDR comprises four conservative amino acid substitutions. In some embodiments, the CDR is a heavy chain CDR1. In some embodiments, the CDR is a heavy chain CDR2. In some embodiment, the CDR is a heavy chain CDR3. In some embodiments, the CDR is a light chain CDR1. In some embodiments, the CDR is a light chain CDR2. In some embodiments, the CDR is a light chain CDR3. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, a C3-binding agent (e.g., an antibody) comprises one or more heavy chain or light chain CDRs that have been modified to reduce deamidation within the CDR sequence. Deamidation is a chemical reaction in which an amide functional group in the side chain of the amino acids asparagine (N) or glutamine (Q) is removed or converted to another functional group. Generally, asparagine is converted to aspartic acid or isoaspartic acid and glutamine is converted to glutamic acid or polyglutamic acid. In some situations, deamidation may change the structure, function, and/or stability of a polypeptide, potentially resulting in decreased biological activity.

In some embodiments, a C3-binding agent (e.g., an antibody) comprises (a) a heavy chain CDR1 comprising GYTFTDFYMD (SEQ ID NO:7), a heavy chain CDR2 comprising YIYPHNAGTTYNQQFTG (SEQ ID NO:14), YIYPHNTGTTYNQQFTG (SEQ ID NO: 15), YIYPHEGGTTYNQQFTG (SEQ ID NO: 16), or YIYPHQGGTTYNQQFTG (SEQ ID NO: 17), and a heavy chain CDR3 comprising RGGFDFDY (SEQ ID NO:9), and/or (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, a C3-binding agent comprises (a) a heavy chain CDR1 comprising GYTFTDFYMD (SEQ ID NO:7), a heavy chain CDR2 comprising YIYPHNAGTTYNQQFTG (SEQ ID NO: 14), and a heavy chain CDR3 comprising RGGFDFDY (SEQ ID NO:9). In some embodiments, a C3-binding agent comprises (a) a heavy chain CDR1 comprising GYTFTDFYMD (SEQ ID NO:7), a heavy chain CDR2 comprising YIYPHNAGTTYNQQFTG (SEQ ID NO: 14), and a heavy chain CDR3 comprising RGGFDFDY (SEQ ID NO:9), and (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, a C3-binding agent comprises (a) a heavy chain CDR1 comprising GYTFTDFYMD (SEQ ID NO:7), a heavy chain CDR2 comprising YIYPHNTGTTYNQQFTG (SEQ ID NO: 15), and a heavy chain CDR3 comprising RGGFDFDY (SEQ ID NO:9). In some embodiments, a C3-binding agent comprises (a) a heavy chain CDR1 comprising GYTFTDFYMD (SEQ ID NO:7), a heavy chain CDR2 comprising YIYPHNTGTTYNQQFTG (SEQ ID NO: 15), and a heavy chain CDR3 comprising RGGFDFDY (SEQ ID NO:9), and (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, a C3-binding agent comprises (a) a heavy chain CDR1 comprising GYTFTDFYMD (SEQ ID NO:7), a heavy chain CDR2 comprising YIYPHEGGTTYNQQFTG (SEQ ID NO: 16), and a heavy chain CDR3 comprising RGGFDFDY (SEQ ID NO:9). In some embodiments, a C3-binding agent comprises (a) a heavy chain CDR1 comprising GYTFTDFYMD (SEQ ID NO:7), a heavy chain CDR2 comprising YIYPHEGGTTYNQQFTG (SEQ ID NO: 16), and a heavy chain CDR3 comprising RGGFDFDY (SEQ ID NO:9), and (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, a C3-binding agent comprises (a) a heavy chain CDR1 comprising GYTFTDFYMD (SEQ ID NO:7), a heavy chain CDR2 comprising YIYPHQGGTTYNQQFTG (SEQ ID NO: 17), and a heavy chain CDR3 comprising RGGFDFDY (SEQ ID NO:9). In some embodiments, a C3-binding agent comprises (a) a heavy chain CDR1 comprising GYTFTDFYMD (SEQ ID NO:7), a heavy chain CDR2 comprising YIYPHQGGTTYNQQFTG (SEQ ID NO: 17), and a heavy chain CDR3 comprising RGGFDFDY (SEQ ID NO:9), and (b) a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12).

In certain embodiments, a C3-binding agent comprises a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHNGGTTYNQNFTG (SEQ ID NO:8), heavy chain CDR3 comprises RGGFDFDY (SEQ ID NO:9), light chain CDR1 comprises KASENVDTYVS (SEQ ID NO:10), light chain CDR2 comprises GASNRYT (SEQ ID NO:11), and light chain CDR3 comprises GQSHSYPLT (SEQ ID NO: 12). In certain embodiments, a C3-binding agent comprises a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHNGGTTYNQQFTG (SEQ ID NO: 13), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12). In certain embodiments, a C3-binding agent comprises a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO: 7), heavy chain CDR2 comprises YIYPHNAGTTYNQQFTG (SEQ ID NO: 14), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12). In certain embodiments, a C3-binding agent comprises a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHNTGTTYNQQFTG (SEQ ID NO: 15), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12). In certain embodiments, a C3-binding agent comprises a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHEGGTTYNQQFTG (SEQ ID NO: 16), heavy chain CDR3 comprises RGGFDFDY (SEQ ID NO:9), light chain CDR1 comprises KASENVDTYVS (SEQ ID NO:10), light chain CDR2 comprises GASNRYT (SEQ ID NO:11), and light chain CDR3 comprises GQSHSYPLT (SEQ ID NO: 12). In certain embodiments, a C3-binding agent comprises a heavy chain variable region comprising heavy chain CDRs 1, 2, and 3, and a light chain variable region comprising light chain CDRs 1, 2, and 3, wherein heavy chain CDR1 comprises GYTFTDFYMD (SEQ ID NO:7), heavy chain CDR2 comprises YIYPHQGGTTYNQQFTG (SEQ ID NO: 17), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In some embodiments, a C3-binding agent (e.g., an antibody) comprises a heavy chain variable region having at least about 80% sequence identity to SEQ ID NO:18, SEQ ID NO:20, SEQ ID NO:21, SEQ ID NO:22, SEQ ID NO:23, or SEQ ID NO:24; and/or a light chain variable region having at least 80% sequence identity to SEQ ID NO: 19 or SEQ ID NO:25. In some embodiments, a C3-binding agent (e.g., an antibody) comprises a heavy chain variable region having at least about 85%, at least about 90%, at least about 95%, at least about 97%, or at least about 99% sequence identity to SEQ ID NO: 18. In some embodiments, a C3-binding agent (e.g., an antibody) comprises a light chain variable region having at least about 85%, at least about 90%, at least about 95%, at least about 97%, or at least about 99% sequence identity to SEQ ID NO: 19. In some embodiments, a C3-binding agent (e.g., an antibody) comprises a heavy chain variable region having at least about 85%, at least about 90%, at least about 95%, at least about 97%, or at least about 99% sequence identity to SEQ ID NO:20. In some embodiments, a C3-binding agent (e.g., an antibody) comprises a heavy chain variable region having at least about 85%, at least about 90%, at least about 95%, at least about 97%, or at least about 99% sequence identity to SEQ ID NO:21. In some embodiments, a C3-binding agent (e.g., an antibody) comprises a heavy chain variable region having at least about 85%, at least about 90%, at least about 95%, at least about 97%, or at least about 99% sequence identity to SEQ ID NO:22. In some embodiments, a C3-binding agent (e.g., an antibody) comprises a heavy chain variable region having at least about 85%, at least about 90%, at least about 95%, at least about 97%, or at least about 99% sequence identity to SEQ ID NO:23. In some embodiments, a C3-binding agent (e.g., an antibody) comprises a heavy chain variable region having at least about 85%, at least about 90%, at least about 95%, at least about 97%, or at least about 99% sequence identity to SEQ ID NO:24. In some embodiments, a C3-binding agent (e.g., an antibody) comprises a light chain variable region having at least about 85%, at least about 90%, at least about 95%, at least about 97%, or at least about 99% sequence identity to SEQ ID NO:25.

In some embodiments, a C3-binding agent (e.g., an antibody) comprises a heavy chain variable region having at least about 80% sequence identity to SEQ ID NO: 18 and/or a light chain variable region having at least about 80% sequence identity to SEQ ID NO: 19. In some embodiments, a C3-binding agent (e.g., an antibody) comprises a heavy chain variable region having at least about 80% sequence identity to SEQ ID NO: 18 and a light chain variable region having at least about 80% sequence identity to SEQ ID NO: 19. In some embodiments, a C3-binding agent (e.g., an antibody) comprises a heavy chain variable region having at least about 90% sequence identity to SEQ ID NO: 18 and/or a light chain variable region having at least about 90% sequence identity to SEQ ID NO: 19. In some embodiments, a C3-binding agent (e.g., an antibody) comprises a heavy chain variable region having at least about 90% sequence identity to SEQ ID NO: 18 and a light chain variable region having at least about 90% sequence identity to SEQ ID NO:19. In some embodiments, a C3-binding agent (e.g., an antibody) comprises a heavy chain variable region having at least about 95% sequence identity to SEQ ID NO:18 and/or a light chain variable region having at least about 95% sequence identity to SEQ ID NO:19. In some embodiments, a C3-binding agent (e.g., an antibody) comprises a heavy chain variable region having at least about 95% sequence identity to SEQ ID NO: 18 and a light chain variable region having at least about 95% sequence identity to SEQ ID NO: 19.

In some embodiments, a C3-binding agent (e.g., an antibody) comprises a heavy chain variable region having at least about 90% sequence identity to SEQ ID NO:20, SEQ ID NO:21, SEQ ID NO:22, SEQ ID NO:23, or SEQ ID NO:24; and/or a light chain variable region having at least about 90% sequence identity to SEQ ID NO:25. In some embodiments, a C3-binding agent (e.g., an antibody) comprises a heavy chain variable region having at least about 90% sequence identity to SEQ ID NO:20, SEQ ID NO:21, SEQ ID NO:22, SEQ ID NO:23, or SEQ ID NO:24; and a light chain variable region having at least about 90% sequence identity to SEQ ID NO:25. In some embodiments, a C3-binding agent (e.g., an antibody) comprises a heavy chain variable region having at least about 95% sequence identity to SEQ ID NO:20, SEQ ID NO:21, SEQ ID NO:22, SEQ ID NO:23, or SEQ ID NO:24; and/or a light chain variable region having at least about 95% sequence identity to SEQ ID NO:25. In some embodiments, a C3-binding agent (e.g., an antibody) comprises a heavy chain variable region having at least about 95% sequence identity to SEQ ID NO:20, SEQ ID NO:21, SEQ ID NO:22, SEQ ID NO:23, or SEQ ID NO:24; and a light chain variable region having at least about 95% sequence identity to SEQ ID NO:25. In some embodiments, a C3-binding agent comprises a heavy chain variable region having at least about 95% sequence identity to SEQ ID NO:20 and a light chain variable region having at least about 95% sequence identity to SEQ ID NO:25. In some embodiments, a C3-binding agent comprises a heavy chain variable region having at least about 95% sequence identity to SEQ ID NO:21 and a light chain variable region having at least about 95% sequence identity to SEQ ID NO:25. In some embodiments, a C3-binding agent comprises a heavy chain variable region having at least about 95% sequence identity to SEQ ID NO:22 and a light chain variable region having at least about 95% sequence identity to SEQ ID NO:25. In some embodiments, a C3-binding agent comprises a heavy chain variable region having at least about 95% sequence identity to SEQ ID NO:23 and a light chain variable region having at least about 95% sequence identity to SEQ ID NO:25. In some embodiments, a C3-binding agent comprises a heavy chain variable region having at least about 95% sequence identity to SEQ ID NO:24; and a light chain variable region having at least about 95% sequence identity to SEQ ID NO:25.

In some embodiments, a C3-binding agent (e.g., an antibody) comprises a heavy chain variable region comprising SEQ ID NO:18. In some embodiments, a C3-binding agent comprises a light chain variable region comprising SEQ ID NO:19. In some embodiments, a C3-binding agent comprises a heavy chain variable region comprising SEQ ID NO: 18 and a light chain variable region comprising SEQ ID NO:19.

In some embodiments, a C3-binding agent (e.g., an antibody) comprises a heavy chain variable region comprising SEQ ID NO:20, SEQ ID NO:21, SEQ ID NO:22, SEQ ID NO:23, or SEQ ID NO:24; and/or a light chain variable region comprising SEQ ID NO:25. In some embodiments, a C3-binding agent comprises a heavy chain variable region comprising SEQ ID NO:20. In some embodiments, a C3-binding agent comprises a heavy chain variable region comprising SEQ ID NO:21. In some embodiments, a C3-binding agent comprises a heavy chain variable region comprising SEQ ID NO:22. In some embodiments, a C3-binding agent comprises a heavy chain variable region comprising SEQ ID NO:23. In some embodiments, a C3-binding agent (e.g., an antibody) comprises a heavy chain variable region comprising SEQ ID NO:24. In some embodiments, a C3-binding agent comprises a light chain variable region comprising SEQ ID NO:25. In some embodiments, a C3-binding agent comprises a heavy chain variable region comprising SEQ ID NO:20 and a light chain variable region comprising SEQ ID NO:25. In some embodiments, a C3-binding agent comprises a heavy chain variable region comprising SEQ ID NO:21 and a light chain variable region comprising SEQ ID NO:25. In some embodiments, a C3-binding agent comprises a heavy chain variable region comprising SEQ ID NO:22 and a light chain variable region comprising SEQ ID NO:25. In some embodiments, a C3-binding agent comprises a heavy chain variable region comprising SEQ ID NO:23 and a light chain variable region comprising SEQ ID NO:25. In some embodiments, a C3-binding agent comprises a heavy chain variable region comprising SEQ ID NO:24 and a light chain variable region comprising SEQ ID NO:25.

In some embodiments, a C3-binding agent (e.g., an antibody) comprises a CDR1, CDR2, and CDR3 from a heavy chain variable region having the amino acid sequence of SEQ ID NO:18 and a CDR1, CDR2, and CDR3 from a light chain variable region having the amino acid sequence of SEQ ID NO:19. In some embodiments, a C3-binding agent (e.g., an antibody) comprises a CDR1, CDR2, and CDR3 from a heavy chain variable region having the amino acid sequence of SEQ ID NO:20 and a CDR1, CDR2, and CDR3 from a light chain variable region having the amino acid sequence of SEQ ID NO:25. In some embodiments, a C3-binding agent (e.g., an antibody) comprises a CDR1, CDR2, and CDR3 from a heavy chain variable region having the amino acid sequence of SEQ ID NO:21 and a CDR1, CDR2, and CDR3 from a light chain variable region having the amino acid sequence of SEQ ID NO:25. In some embodiments, a C3-binding agent (e.g., an antibody) comprises a CDR1, CDR2, and CDR3 from a heavy chain variable region having the amino acid sequence of SEQ ID NO:22 and a CDR1, CDR2, and CDR3 from a light chain variable region having the amino acid sequence of SEQ ID NO:25. In some embodiments, a C3-binding agent (e.g., an antibody) comprises a CDR1, CDR2, and CDR3 from a heavy chain variable region having the amino acid sequence of SEQ ID NO:23 and a CDR1, CDR2, and CDR3 from a light chain variable region having the amino acid sequence of SEQ ID NO:25. In some embodiments, a C3-binding agent (e.g., an antibody) comprises a CDR1, CDR2, and CDR3 from a heavy chain variable region having the amino acid sequence of SEQ ID NO:24 and a CDR1, CDR2, and CDR3 from a light chain variable region having the amino acid sequence of SEQ ID NO:25.

In certain embodiments, a C3-binding agent (e.g., an antibody) comprises (a) a heavy chain CDR1 comprising SEQ ID NO:38, a heavy chain CDR2 comprising SEQ ID NO:39, a heavy chain CDR3 comprising SEQ ID NO:40, a light chain CDR1 comprising SEQ ID NO:41, a light chain CDR2 comprising SEQ ID NO:42, and a light chain CDR3 comprising SEQ ID NO:43; (b) a heavy chain CDR1 comprising SEQ ID NO: 143, a heavy chain CDR2 comprising SEQ ID NO: 146, a heavy chain CDR3 comprising SEQ ID NO:40, a light chain CDR1 comprising SEQ ID NO:41, a light chain CDR2 comprising SEQ ID NO:42, and a light chain CDR3 comprising SEQ ID NO:43; (c) a heavy chain CDR1 comprising SEQ ID NO:38, a heavy chain CDR2 comprising SEQ ID NO: 147, a heavy chain CDR3 comprising SEQ ID NO:40, a light chain CDR1 comprising SEQ ID NO:41, a light chain CDR2 comprising SEQ ID NO:42, and a light chain CDR3 comprising SEQ ID NO:43; (d) a heavy chain CDR1 comprising SEQ ID NO: 144, a heavy chain CDR2 comprising SEQ ID NO:39, a heavy chain CDR3 comprising SEQ ID NO:40, a light chain CDR1 comprising SEQ ID NO:41, a light chain CDR2 comprising SEQ ID NO:42, and a light chain CDR3 comprising SEQ ID NO:43; or (e) a heavy chain CDR1 comprising SEQ ID NO: 145, a heavy chain CDR2 comprising SEQ ID NO: 149, a heavy chain CDR3 comprising SEQ ID NO:150, a light chain CDR1 comprising SEQ ID NO:151, a light chain CDR2 comprising SEQ ID NO:152, and a light chain CDR3 comprising SEQ ID NO:153.

In some embodiments, a C3-binding agent (e.g., an antibody) comprises (a) a heavy chain CDR1 comprising GYSFTGYNMN (SEQ ID NO:38), a heavy chain CDR2 comprising NINPYYGSTNYNQKFKG (SEQ ID NO:39), and a heavy chain CDR3 comprising GYYGGNYPFAY (SEQ ID NO:40), and/or (b) a light chain CDR1 comprising RASENIYSYLA (SEQ ID NO:41), a light chain CDR2 comprising NAKTLAE (SEQ ID NO:42), and a light chain CDR3 comprising QHYYGTPYT (SEQ ID NO:43). In some embodiments, a C3-binding agent (e.g., an antibody) comprises (a) a heavy chain CDR1 comprising GYSFTGYNMN (SEQ ID NO:38), a heavy chain CDR2 comprising NINPYYGSTNYNQKFKG (SEQ ID NO:39), and a heavy chain CDR3 comprising GYYGGNYPFAY (SEQ ID NO:40), and (b) a light chain CDR1 comprising RASENIYSYLA (SEQ ID NO:41), a light chain CDR2 comprising NAKTLAE (SEQ ID NO:42), and a light chain CDR3 comprising QHYYGTPYT (SEQ ID NO:43).

In some embodiments, a C3-binding agent (e.g., an antibody) comprises (a) a heavy chain variable region comprising a heavy chain CDR1 comprising GYSFTGYNMN (SEQ ID NO:38), a heavy chain CDR2 comprising NINPYYGSTNYNQKFKG (SEQ ID NO:39), and a heavy chain CDR3 comprising GYYGGNYPFAY (SEQ ID NO:40), and/or (b) a light chain variable region comprising a light chain CDR1 comprising RASENIYSYLA (SEQ ID NO:41), a light chain CDR2 comprising NAKTLAE (SEQ ID NO:42), and a light chain CDR3 comprising QHYYGTPYT (SEQ ID NO:43). In some embodiments, a C3-binding agent (e.g., an antibody) comprises (a) a heavy chain variable region comprising a heavy chain CDR1 comprising GYSFTGYNMN (SEQ ID NO:38), a heavy chain CDR2 comprising NINPYYGSTNYNQKFKG (SEQ ID NO:39), and a heavy chain CDR3 comprising GYYGGNYPFAY (SEQ ID NO:40), and (b) a light chain variable region comprising a light chain CDR1 comprising RASENIYSYLA (SEQ ID NO:41), a light chain CDR2 comprising NAKTLAE (SEQ ID NO:42), and a light chain CDR3 comprising QHYYGTPYT (SEQ ID NO:43).

In certain embodiments, a C3-binding agent comprises heavy chain CDRs 1, 2, and 3, of a heavy chain variable region comprising the amino acid sequence set forth in SEQ ID NO:91. In certain embodiments, a C3-binding agent comprises light chain CDRs 1, 2, and 3 of a light chain variable region comprising the amino acid sequence set forth in SEQ ID NO:92. In certain embodiments, a C3-binding agent comprises heavy chain CDRs 1, 2, and 3 of a heavy chain variable region comprising the amino acid sequence set forth in SEQ ID NO:91, and light chain CDRs 1, 2, and 3, of a light chain variable region comprising the amino acid sequence set forth in SEQ ID NO:92.

In some embodiments, a C3-binding agent (e.g., an antibody) comprises a heavy chain variable region having at least about 80%, about 85%, about 90%, or about 95% sequence identity to SEQ ID NO:91 and/or a light chain variable region having at least about 80%, about 85%, about 90%, or about 95% sequence identity to SEQ ID NO:92. In some embodiments, a C3-binding agent (e.g., an antibody) comprises a heavy chain variable region comprising SEQ ID NO:91 and/or a light chain variable region comprising SEQ ID NO:92. In some embodiments, a C3-binding agent (e.g., an antibody) comprises a heavy chain variable region of SEQ ID NO:91 and a light chain variable region of SEQ ID NO:92.

In certain embodiments, a C3-binding agent (e.g., an antibody) comprises (a) a heavy chain CDR1 comprising SEQ ID NO:38, a heavy chain CDR2 comprising SEQ ID NO:44, a heavy chain CDR3 comprising SEQ ID NO:45, a light chain CDR1 comprising SEQ ID NO:46, a light chain CDR2 comprising SEQ ID NO:47, and a light chain CDR3 comprising SEQ ID NO:48; (b) a heavy chain CDR1 comprising SEQ ID NO: 143, a heavy chain CDR2 comprising SEQ ID NO:154, a heavy chain CDR3 comprising SEQ ID NO:45, a light chain CDR1 comprising SEQ ID NO:46, a light chain CDR2 comprising SEQ ID NO:47, and a light chain CDR3 comprising SEQ ID NO:48; (c) a heavy chain CDR1 comprising SEQ ID NO:38, a heavy chain CDR2 comprising SEQ ID NO:155, a heavy chain CDR3 comprising SEQ ID NO:45, a light chain CDR1 comprising SEQ ID NO:46, a light chain CDR2 comprising SEQ ID NO:47, and a light chain CDR3 comprising SEQ ID NO:48; (d) a heavy chain CDR1 comprising SEQ ID NO: 144, a heavy chain CDR2 comprising SEQ ID NO:44, a heavy chain CDR3 comprising SEQ ID NO:45, a light chain CDR1 comprising SEQ ID NO:46, a light chain CDR2 comprising SEQ ID NO:47, and a light chain CDR3 comprising SEQ ID NO:48; or (e) a heavy chain CDR1 comprising SEQ ID NO:145, a heavy chain CDR2 comprising SEQ ID NO:156, a heavy chain CDR3 comprising SEQ ID NO:157, a light chain CDR1 comprising SEQ ID NO:158, a light chain CDR2 comprising SEQ ID NO:159, and a light chain CDR3 comprising SEQ ID NO:160.

In some embodiments, a C3-binding agent (e.g., an antibody) comprises (a) a heavy chain CDR1 comprising GYSFTGYNMN (SEQ ID NO:38), a heavy chain CDR2 comprising NINPYYDSTSYNQKFKG (SEQ ID NO:44), and a heavy chain CDR3 comprising ENYDFVGFAY (SEQ ID NO:45), and/or (b) a light chain CDR1 comprising RASSSVSYMH (SEQ ID NO:46), a light chain CDR2 comprising VTSNLAS (SEQ ID NO:47), and a light chain CDR3 comprising QQWSTNPLT (SEQ ID NO:48). In some embodiments, a C3-binding agent (e.g., an antibody) comprises (a) a heavy chain CDR1 comprising GYSFTGYNMN (SEQ ID NO:38), a heavy chain CDR2 comprising NINPYYDSTSYNQKFKG (SEQ ID NO:44), and a heavy chain CDR3 comprising ENYDFVGFAY (SEQ ID NO:45), and (b) a light chain CDR1 comprising RASSSVSYMH (SEQ ID NO:46), a light chain CDR2 comprising VTSNLAS (SEQ ID NO:47), and a light chain CDR3 comprising QQWSTNPLT (SEQ ID NO:48).

In some embodiments, a C3-binding agent (e.g., an antibody) comprises (a) a heavy chain variable region comprising a heavy chain CDR1 comprising GYSFTGYNMN (SEQ ID NO:38), a heavy chain CDR2 comprising NINPYYDSTSYNQKFKG (SEQ ID NO:44), and a heavy chain CDR3 comprising ENYDFVGFAY (SEQ ID NO:45), and/or (b) a light chain variable region comprising a light chain CDR1 comprising RASSSVSYMH (SEQ ID NO:46), a light chain CDR2 comprising VTSNLAS (SEQ ID NO:47), and a light chain CDR3 comprising QQWSTNPLT (SEQ ID NO:48). In some embodiments, a C3-binding agent (e.g., an antibody) comprises (a) a heavy chain variable region comprising a heavy chain CDR1 comprising GYSFTGYNMN (SEQ ID NO:38), a heavy chain CDR2 comprising NINPYYDSTSYNQKFKG (SEQ ID NO:44), and a heavy chain CDR3 comprising ENYDFVGFAY (SEQ ID NO:45), and (b) a light chain variable region comprising a light chain CDR1 comprising RASSSVSYMH (SEQ ID NO:46), a light chain CDR2 comprising VTSNLAS (SEQ ID NO:47), and a light chain CDR3 comprising QQWSTNPLT (SEQ ID NO:48).

In certain embodiments, a C3-binding agent comprises heavy chain CDRs 1, 2, and 3 of a heavy chain variable region comprising the amino acid sequence set forth in SEQ ID NO:93. In certain embodiments, a C3-binding agent comprises light chain CDRs 1, 2, and 3 of a light chain variable region comprising the amino acid sequence set forth in SEQ ID NO:94. In certain embodiments, a C3-binding agent comprises heavy chain CDRs 1, 2, and 3 of a heavy chain variable region comprising the amino acid sequence set forth in SEQ ID NO:93, and light chain CDRs 1, 2, and 3 of a light chain variable region comprising the amino acid sequence set forth in SEQ ID NO:94.

In some embodiments, a C3-binding agent (e.g., an antibody) comprises a heavy chain variable region having at least about 80%, about 85%, about 90%, or about 95% sequence identity to SEQ ID NO:93 and/or a light chain variable region having at least about 80%, about 85%, about 90%, or about 95% sequence identity to SEQ ID NO:94. In some embodiments, a C3-binding agent (e.g., an antibody) comprises a heavy chain variable region comprising SEQ ID NO:93 and/or a light chain variable region comprising SEQ ID NO:94. In some embodiments, a C3-binding agent (e.g., an antibody) comprises a heavy chain variable region of SEQ ID NO:93 and a light chain variable region of SEQ ID NO:94.

In certain embodiments, a C3-binding agent (e.g., an antibody) comprises (a) a heavy chain CDR1 comprising SEQ ID NO:49, a heavy chain CDR2 comprising SEQ ID NO:50, a heavy chain CDR3 comprising SEQ ID NO:51, a light chain CDR1 comprising SEQ ID NO:52, a light chain CDR2 comprising SEQ ID NO:53, and a light chain CDR3 comprising SEQ ID NO:54; (b) a heavy chain CDR1 comprising SEQ ID NO: 143, a heavy chain CDR2 comprising SEQ ID NO:163, a heavy chain CDR3 comprising SEQ ID NO:51, a light chain CDR1 comprising SEQ ID NO:52, a light chain CDR2 comprising SEQ ID NO:53, and a light chain CDR3 comprising SEQ ID NO:54; (c) a heavy chain CDR1 comprising SEQ ID NO:49, a heavy chain CDR2 comprising SEQ ID NO: 164, a heavy chain CDR3 comprising SEQ ID NO:51, a light chain CDR1 comprising SEQ ID NO:52, a light chain CDR2 comprising SEQ ID NO:53, and a light chain CDR3 comprising SEQ ID NO:54; (d) a heavy chain CDR1 comprising SEQ ID NO: 161, a heavy chain CDR2 comprising SEQ ID NO:50, a heavy chain CDR3 comprising SEQ ID NO:51, a light chain CDR1 comprising SEQ ID NO:52, a light chain CDR2 comprising SEQ ID NO:53, and a light chain CDR3 comprising SEQ ID NO:54; or (e) a heavy chain CDR1 comprising SEQ ID NO: 162, a heavy chain CDR2 comprising SEQ ID NO: 165, a heavy chain CDR3 comprising SEQ ID NO: 166, a light chain CDR1 comprising SEQ ID NO: 167, a light chain CDR2 comprising SEQ ID NO: 168, and a light chain CDR3 comprising SEQ ID NO: 169.

In some embodiments, a C3-binding agent (e.g., an antibody) comprises (a) a heavy chain CDR1 comprising GYSFTGYNMH (SEQ ID NO:49), a heavy chain CDR2 comprising NINPYYGTTNSNQKFED (SEQ ID NO:50), and a heavy chain CDR3 comprising GIYYYGTGYPYFDF (SEQ ID NO:51), and/or (b) a light chain CDR1 comprising RASQDINNYLN (SEQ ID NO:52), a light chain CDR2 comprising YTSRLHS (SEQ ID NO:53), and a light chain CDR3 comprising QQGITLPWT (SEQ ID NO:54). In some embodiments, a C3-binding agent (e.g., an antibody) comprises (a) a heavy chain CDR1 comprising GYSFTGYNMH (SEQ ID NO:49), a heavy chain CDR2 comprising NINPYYGTTNSNQKFED (SEQ ID NO:50), and a heavy chain CDR3 comprising GIYYYGTGYPYFDF (SEQ ID NO:51), and (b) a light chain CDR1 comprising RASQDINNYLN (SEQ ID NO:52), a light chain CDR2 comprising YTSRLHS (SEQ ID NO:53), and a light chain CDR3 comprising QQGITLPWT (SEQ ID NO:54).

In some embodiments, a C3-binding agent (e.g., an antibody) comprises (a) a heavy chain variable region comprising a heavy chain CDR1 comprising GYSFTGYNMH (SEQ ID NO:49), a heavy chain CDR2 comprising NINPYYGTTNSNQKFED (SEQ ID NO:50), and a heavy chain CDR3 comprising GIYYYGTGYPYFDF (SEQ ID NO:51), and/or (b) a light chain variable region comprising a light chain CDR1 comprising RASQDINNYLN (SEQ ID NO:52), a light chain CDR2 comprising YTSRLHS (SEQ ID NO:53), and a light chain CDR3 comprising QQGITLPWT (SEQ ID NO:54). In some embodiments, a C3-binding agent (e.g., an antibody) comprises (a) a heavy chain variable region comprising a heavy chain CDR1 comprising GYSFTGYNMH (SEQ ID NO:49), a heavy chain CDR2 comprising NINPYYGTTNSNQKFED (SEQ ID NO:50), and a heavy chain CDR3 comprising GIYYYGTGYPYFDF (SEQ ID NO:51), and (b) a light chain variable region comprising a light chain CDR1 comprising RASQDINNYLN (SEQ ID NO:52), a light chain CDR2 comprising YTSRLHS (SEQ ID NO:53), and a light chain CDR3 comprising QQGITLPWT (SEQ ID NO:54).

In certain embodiments, a C3-binding agent comprises heavy chain CDRs 1, 2, and 3 of a heavy chain variable region comprising the amino acid sequence set forth in SEQ ID NO:95. In certain embodiments, a C3-binding agent comprises light chain CDRs 1, 2, and 3 of a light chain variable region comprising the amino acid sequence set forth in SEQ ID NO:96. In certain embodiments, a C3-binding agent comprises heavy chain CDRs 1, 2, and 3 of a heavy chain variable region comprising the amino acid sequence set forth in SEQ ID NO:95, and light chain CDRs 1, 2, and 3 of a light chain variable region comprising the amino acid sequence set forth in SEQ ID NO:96.

In some embodiments, a C3-binding agent (e.g., an antibody) comprises a heavy chain variable region having at least about 80%, about 85%, about 90%, or about 95% sequence identity to SEQ ID NO:95 and/or a light chain variable region having at least about 80%, about 85%, about 90%, or about 95% sequence identity to SEQ ID NO:96. In some embodiments, a C3-binding agent (e.g., an antibody) comprises a heavy chain variable region comprising SEQ ID NO:95 and/or a light chain variable region comprising SEQ ID NO:96. In some embodiments, a C3-binding agent (e.g., an antibody) comprises a heavy chain variable region of SEQ ID NO:95 and a light chain variable region of SEQ ID NO:96.

In certain embodiments, a C3-binding agent (e.g., an antibody) comprises (a) a heavy chain CDR1 comprising SEQ ID NO:55, a heavy chain CDR2 comprising SEQ ID NO:56, a heavy chain CDR3 comprising SEQ ID NO:57, a light chain CDR1 comprising SEQ ID NO:58, a light chain CDR2 comprising SEQ ID NO:59, and a light chain CDR3 comprising SEQ ID NO:60; (b) a heavy chain CDR1 comprising SEQ ID NO: 170, a heavy chain CDR2 comprising SEQ ID NO: 173, a heavy chain CDR3 comprising SEQ ID NO:57, a light chain CDR1 comprising SEQ ID NO:58, a light chain CDR2 comprising SEQ ID NO:59, and a light chain CDR3 comprising SEQ ID NO:60; (c) a heavy chain CDR1 comprising SEQ ID NO:55, a heavy chain CDR2 comprising SEQ ID NO: 174, a heavy chain CDR3 comprising SEQ ID NO:57, a light chain CDR1 comprising SEQ ID NO:58, a light chain CDR2 comprising SEQ ID NO:59, and a light chain CDR3 comprising SEQ ID NO:60; (d) a heavy chain CDR1 comprising SEQ ID NO: 171, a heavy chain CDR2 comprising SEQ ID NO:56, a heavy chain CDR3 comprising SEQ ID NO:57, a light chain CDR1 comprising SEQ ID NO:58, a light chain CDR2 comprising SEQ ID NO:59, and a light chain CDR3 comprising SEQ ID NO:60; or (e) a heavy chain CDR1 comprising SEQ ID NO: 172, a heavy chain CDR2 comprising SEQ ID NO: 175, a heavy chain CDR3 comprising SEQ ID NO: 176, a light chain CDR1 comprising SEQ ID NO: 177, a light chain CDR2 comprising SEQ ID NO: 178, and a light chain CDR3 comprising SEQ ID NO: 179.

In some embodiments, a C3-binding agent (e.g., an antibody) comprises (a) a heavy chain CDR1 comprising GYTFTDYWIN (SEQ ID NO:55), a heavy chain CDR2 comprising NIYPGSTSANYNEKFKS (SEQ ID NO:56), and a heavy chain CDR3 comprising YGYDSWFAY (SEQ ID NO:57), and/or (b) a light chain CDR1 comprising KSTKSLLNSDGFTYLD (SEQ ID NO:58), a light chain CDR2 comprising LVSNRFS (SEQ ID NO:59), and a light chain CDR3 comprising FQSNYLPLT (SEQ ID NO:60). In some embodiments, a C3-binding agent (e.g., an antibody) comprises (a) a heavy chain CDR1 comprising GYTFTDYWIN (SEQ ID NO:55), a heavy chain CDR2 comprising NIYPGSTSANYNEKFKS (SEQ ID NO:56), and a heavy chain CDR3 comprising YGYDSWFAY (SEQ ID NO:57), and (b) a light chain CDR1 comprising KSTKSLLNSDGFTYLD (SEQ ID NO:58), a light chain CDR2 comprising LVSNRFS (SEQ ID NO:59), and a light chain CDR3 comprising FQSNYLPLT (SEQ ID NO:60).

In some embodiments, a C3-binding agent (e.g., an antibody) comprises a heavy chain variable region comprising a heavy chain CDR1 comprising GYTFTDYWIN (SEQ ID NO:55), a heavy chain CDR2 comprising NIYPGSTSANYNEKFKS (SEQ ID NO:56), and a heavy chain CDR3 comprising YGYDSWFAY (SEQ ID NO:57), and/or (b) a light chain variable region comprising a light chain CDR1 comprising KSTKSLLNSDGFTYLD (SEQ ID NO:58), a light chain CDR2 comprising LVSNRFS (SEQ ID NO:59), and a light chain CDR3 comprising FQSNYLPLT (SEQ ID NO:60). In some embodiments, a C3-binding agent (e.g., an antibody) comprises (a) a heavy chain variable region comprising a heavy chain CDR1 comprising GYTFTDYWIN (SEQ ID NO:55), a heavy chain CDR2 comprising NIYPGSTSANYNEKFKS (SEQ ID NO:56), and a heavy chain CDR3 comprising YGYDSWFAY (SEQ ID NO:57), and (b) a light chain variable region comprising a light chain CDR1 comprising KSTKSLLNSDGFTYLD (SEQ ID NO:58), a light chain CDR2 comprising LVSNRFS (SEQ ID NO:59), and a light chain CDR3 comprising FQSNYLPLT (SEQ ID NO:60).

In certain embodiments, a C3-binding agent comprises heavy chain CDRs 1, 2, and 3 of a heavy chain variable region comprising the amino acid sequence set forth in SEQ ID NO:97. In certain embodiments, a C3-binding agent comprises light chain CDRs 1, 2, and 3 of a light chain variable region comprising the amino acid sequence set forth in SEQ ID NO:98. In certain embodiments, a C3-binding agent comprises heavy chain CDRs 1, 2, and 3 of a heavy chain variable region comprising the amino acid sequence set forth in SEQ ID NO:97, and light chain CDRs 1, 2, and 3 of a light chain variable region comprising the amino acid sequence set forth in SEQ ID NO:98.

In some embodiments, a C3-binding agent (e.g., an antibody) comprises a heavy chain variable region having at least about 80%, about 85%, about 90%, or about 95% sequence identity to SEQ ID NO:97 and/or a light chain variable region having at least about 80%, about 85%, about 90%, or about 95% sequence identity to SEQ ID NO:98. In some embodiments, a C3-binding agent (e.g., an antibody) comprises a heavy chain variable region comprising SEQ ID NO:97 and/or a light chain variable region comprising SEQ ID NO:98. In some embodiments, a C3-binding agent (e.g., an antibody) comprises a heavy chain variable region of SEQ ID NO:97 and a light chain variable region of SEQ ID NO:98.

In certain embodiments, a C3-binding agent (e.g., an antibody) comprises (a) a heavy chain CDR1 comprising SEQ ID NO:61, a heavy chain CDR2 comprising SEQ ID NO:62, a heavy chain CDR3 comprising SEQ ID NO:63, a light chain CDR1 comprising SEQ ID NO:64, a light chain CDR2 comprising SEQ ID NO:65, and a light chain CDR3 comprising SEQ ID NO:66; (b) a heavy chain CDR1 comprising SEQ ID NO:180, a heavy chain CDR2 comprising SEQ ID NO:183, a heavy chain CDR3 comprising SEQ ID NO:63, a light chain CDR1 comprising SEQ ID NO:64, a light chain CDR2 comprising SEQ ID NO:65, and a light chain CDR3 comprising SEQ ID NO:66; (c) a heavy chain CDR1 comprising SEQ ID NO:61, a heavy chain CDR2 comprising SEQ ID NO:184, a heavy chain CDR3 comprising SEQ ID NO:63, a light chain CDR1 comprising SEQ ID NO:64, a light chain CDR2 comprising SEQ ID NO:65, and a light chain CDR3 comprising SEQ ID NO:66; (d) a heavy chain CDR1 comprising SEQ ID NO: 181, a heavy chain CDR2 comprising SEQ ID NO:62, a heavy chain CDR3 comprising SEQ ID NO:63, a light chain CDR1 comprising SEQ ID NO:64, a light chain CDR2 comprising SEQ ID NO:65, and a light chain CDR3 comprising SEQ ID NO:66; or (e) a heavy chain CDR1 comprising SEQ ID NO:182, a heavy chain CDR2 comprising SEQ ID NO:185, a heavy chain CDR3 comprising SEQ ID NO:186, a light chain CDR1 comprising SEQ ID NO:187, a light chain CDR2 comprising SEQ ID NO:188, and a light chain CDR3 comprising SEQ ID NO:189.

In some embodiments, a C3-binding agent (e.g., an antibody) comprises (a) a heavy chain CDR1 comprising GYAFNSCWMN (SEQ ID NO:61), a heavy chain CDR2 comprising RIYPGDGDTNYNGKFKG (SEQ ID NO:62), and a heavy chain CDR3 comprising EGRNYGYEDY (SEQ ID NO:63), and/or (b) a light chain CDR1 comprising KASQSVDYDGDSYMN (SEQ ID NO:64), a light chain CDR2 comprising AASDLES (SEQ ID NO:65), and a light chain CDR3 comprising QQANEDPRT (SEQ ID NO:66). In some embodiments, a C3-binding agent (e.g., an antibody) comprises (a) a heavy chain CDR1 comprising GYAFNSCWMN (SEQ ID NO:61), a heavy chain CDR2 comprising RIYPGDGDTNYNGKFKG (SEQ ID NO:62), and a heavy chain CDR3 comprising EGRNYGYEDY (SEQ ID NO:63), and (b) a light chain CDR1 comprising KASQSVDYDGDSYMN (SEQ ID NO:64), a light chain CDR2 comprising AASDLES (SEQ ID NO:65), and a light chain CDR3 comprising QQANEDPRT (SEQ ID NO:66).

In some embodiments, a C3-binding agent (e.g., an antibody) comprises (a) a heavy chain variable region comprising a heavy chain CDR1 comprising GYAFNSCWMN (SEQ ID NO:61), a heavy chain CDR2 comprising RIYPGDGDTNYNGKFKG (SEQ ID NO:62), and a heavy chain CDR3 comprising EGRNYGYEDY (SEQ ID NO:63), and/or (b) a light chain variable region comprising a light chain CDR1 comprising KASQSVDYDGDSYMN (SEQ ID NO:64), a light chain CDR2 comprising AASDLES (SEQ ID NO:65), and a light chain CDR3 comprising QQANEDPRT (SEQ ID NO:66). In some embodiments, a C3-binding agent (e.g., an antibody) comprises (a) a heavy chain variable region comprising a heavy chain CDR1 comprising GYAFNSCWMN (SEQ ID NO:61), a heavy chain CDR2 comprising RIYPGDGDTNYNGKFKG (SEQ ID NO:62), and a heavy chain CDR3 comprising EGRNYGYEDY (SEQ ID NO:63), and (b) a light chain variable region comprising a light chain CDR1 comprising KASQSVDYDGDSYMN (SEQ ID NO:64), a light chain CDR2 comprising AASDLES (SEQ ID NO:65), and a light chain CDR3 comprising QQANEDPRT (SEQ ID NO:66).

In certain embodiments, a C3-binding agent comprises heavy chain CDRs 1, 2, and 3 of a heavy chain variable region comprising the amino acid sequence set forth in SEQ ID NO:99. In certain embodiments, a C3-binding agent comprises light chain CDRs 1, 2, and 3 of a light chain variable region comprising the amino acid sequence set forth in SEQ ID NO: 100. In certain embodiments, a C3-binding agent comprises heavy chain CDRs 1, 2, and 3 of a heavy chain variable region comprising the amino acid sequence set forth in SEQ ID NO:99, and light chain CDRs 1, 2, and 3 of a light chain variable region comprising the amino acid sequence set forth in SEQ ID NO: 100.

In some embodiments, a C3-binding agent (e.g., an antibody) comprises a heavy chain variable region having at least about 80%, about 85%, about 90%, or about 95% sequence identity to SEQ ID NO:99 and/or a light chain variable region having at least about 80%, about 85%, about 90%, or about 95% sequence identity to SEQ ID NO:100. In some embodiments, a C3-binding agent (e.g., an antibody) comprises a heavy chain variable region comprising SEQ ID NO:99 and/or a light chain variable region comprising SEQ ID NO: 100. In some embodiments, a C3-binding agent (e.g., an antibody) comprises a heavy chain variable region of SEQ ID NO:99 and a light chain variable region of SEQ ID NO: 100.

In certain embodiments, a C3-binding agent (e.g., an antibody) comprises (a) a heavy chain CDR1 comprising SEQ ID NO:67, a heavy chain CDR2 comprising SEQ ID NO:68, a heavy chain CDR3 comprising SEQ ID NO:69, a light chain CDR1 comprising SEQ ID NO:70, a light chain CDR2 comprising SEQ ID NO:71, and a light chain CDR3 comprising SEQ ID NO:72; (b) a heavy chain CDR1 comprising SEQ ID NO: 190, a heavy chain CDR2 comprising SEQ ID NO: 193, a heavy chain CDR3 comprising SEQ ID NO:69, a light chain CDR1 comprising SEQ ID NO:70, a light chain CDR2 comprising SEQ ID NO:71, and a light chain CDR3 comprising SEQ ID NO:72; (c) a heavy chain CDR1 comprising SEQ ID NO:67, a heavy chain CDR2 comprising SEQ ID NO: 194, a heavy chain CDR3 comprising SEQ ID NO:69, a light chain CDR1 comprising SEQ ID NO:70, a light chain CDR2 comprising SEQ ID NO:71, and a light chain CDR3 comprising SEQ ID NO:72; (d) a heavy chain CDR1 comprising SEQ ID NO: 191, a heavy chain CDR2 comprising SEQ ID NO:68, a heavy chain CDR3 comprising SEQ ID NO:69, a light chain CDR1 comprising SEQ ID NO:70, a light chain CDR2 comprising SEQ ID NO:71, and a light chain CDR3 comprising SEQ ID NO:72; or (e) a heavy chain CDR1 comprising SEQ ID NO: 192, a heavy chain CDR2 comprising SEQ ID NO: 195, a heavy chain CDR3 comprising SEQ ID NO: 196, a light chain CDR1 comprising SEQ ID NO: 197, a light chain CDR2 comprising SEQ ID NO: 198, and a light chain CDR3 comprising SEQ ID NO: 199.

In some embodiments, a C3-binding agent (e.g., an antibody) comprises (a) a heavy chain CDR1 comprising GFTFSNYAMS (SEQ ID NO:67), a heavy chain CDR2 comprising QTISSGGRYTYYPDSVKG (SEQ ID NO:68), and a heavy chain CDR3 comprising RYYGNSYWYFDV (SEQ ID NO:69), and/or (b) a light chain CDR1 comprising KSSQSLLNSGNQKHYLT (SEQ ID NO:70), a light chain CDR2 comprising GASTRGS (SEQ ID NO:71), and a light chain CDR3 comprising QNDHSYPYT (SEQ ID NO:72). In some embodiments, a C3-binding agent (e.g., an antibody) comprises (a) a heavy chain CDR1 comprising GFTFSNYAMS (SEQ ID NO:67), a heavy chain CDR2 comprising QTISSGGRYTYYPDSVKG (SEQ ID NO:68), and a heavy chain CDR3 comprising RYYGNSYWYFDV (SEQ ID NO:69), and (b) a light chain CDR1 comprising KSSQSLLNSGNQKHYLT (SEQ ID NO:70), a light chain CDR2 comprising GASTRGS (SEQ ID NO:71), and a light chain CDR3 comprising QNDHSYPYT (SEQ ID NO:72).

In some embodiments, a C3-binding agent (e.g., an antibody) comprises (a) a heavy chain variable region comprising a heavy chain CDR1 comprising GFTFSNYAMS (SEQ ID NO:67), a heavy chain CDR2 comprising QTISSGGRYTYYPDSVKG (SEQ ID NO:68), and a heavy chain CDR3 comprising RYYGNSYWYFDV (SEQ ID NO:69), and/or (b) a light chain variable region comprising a light chain CDR1 comprising KSSQSLLNSGNQKHYLT (SEQ ID NO:70), a light chain CDR2 comprising GASTRGS (SEQ ID NO:71), and a light chain CDR3 comprising QNDHSYPYT (SEQ ID NO:72). In some embodiments, a C3-binding agent (e.g., an antibody) comprises (a) a heavy chain variable region comprising a heavy chain CDR1 comprising GFTFSNYAMS (SEQ ID NO:67), a heavy chain CDR2 comprising QTISSGGRYTYYPDSVKG (SEQ ID NO:68), and a heavy chain CDR3 comprising RYYGNSYWYFDV (SEQ ID NO:69), and (b) a light chain variable region comprising a light chain CDR1 comprising KSSQSLLNSGNQKHYLT (SEQ ID NO:70), a light chain CDR2 comprising GASTRGS (SEQ ID NO:71), and a light chain CDR3 comprising QNDHSYPYT (SEQ ID NO:72).

In certain embodiments, a C3-binding agent comprises heavy chain CDRs 1, 2, and 3 of a heavy chain variable region comprising the amino acid sequence set forth in SEQ ID NO: 101. In certain embodiments, a C3-binding agent comprises light chain CDRs 1, 2, and 3 of a light chain variable region comprising the amino acid sequence set forth in SEQ ID NO: 102. In certain embodiments, a C3-binding agent comprises heavy chain CDRs 1, 2, and 3 of a heavy chain variable region comprising the amino acid sequence set forth in SEQ ID NO: 101, and light chain CDRs 1, 2, and 3 of a light chain variable region comprising the amino acid sequence set forth in SEQ ID NO: 102.

In some embodiments, a C3-binding agent (e.g., an antibody) comprises a heavy chain variable region having at least about 80%, about 85%, about 90%, or about 95% sequence identity to SEQ ID NO: 101 and/or a light chain variable region having at least about 80%, about 85%, about 90%, or about 95% sequence identity to SEQ ID NO:102. In some embodiments, a C3-binding agent (e.g., an antibody) comprises a heavy chain variable region comprising SEQ ID NO: 101 and/or a light chain variable region comprising SEQ ID NO: 102. In some embodiments, a C3-binding agent (e.g., an antibody) comprises a heavy chain variable region of SEQ ID NO: 101 and a light chain variable region of SEQ ID NO: 102.

In certain embodiments, a C3-binding agent (e.g., an antibody) comprises (a) a heavy chain CDR1 comprising SEQ ID NO:73, a heavy chain CDR2 comprising SEQ ID NO:74, a heavy chain CDR3 comprising SEQ ID NO:75, a light chain CDR1 comprising SEQ ID NO:76, a light chain CDR2 comprising SEQ ID NO:77, and a light chain CDR3 comprising SEQ ID NO:78; (b) a heavy chain CDR1 comprising SEQ ID NO:200, a heavy chain CDR2 comprising SEQ ID NO:203, a heavy chain CDR3 comprising SEQ ID NO:75, a light chain CDR1 comprising SEQ ID NO:76, a light chain CDR2 comprising SEQ ID NO:77, and a light chain CDR3 comprising SEQ ID NO:78; (c) a heavy chain CDR1 comprising SEQ ID NO:73, a heavy chain CDR2 comprising SEQ ID NO:204, a heavy chain CDR3 comprising SEQ ID NO:75, a light chain CDR1 comprising SEQ ID NO:76, a light chain CDR2 comprising SEQ ID NO:77, and a light chain CDR3 comprising SEQ ID NO:78; (d) a heavy chain CDR1 comprising SEQ ID NO:201, a heavy chain CDR2 comprising SEQ ID NO:74, a heavy chain CDR3 comprising SEQ ID NO:75, a light chain CDR1 comprising SEQ ID NO:76, a light chain CDR2 comprising SEQ ID NO:77, and a light chain CDR3 comprising SEQ ID NO:78; or (e) a heavy chain CDR1 comprising SEQ ID NO:202, a heavy chain CDR2 comprising SEQ ID NO:205, a heavy chain CDR3 comprising SEQ ID NO:206, a light chain CDR1 comprising SEQ ID NO:207, a light chain CDR2 comprising SEQ ID NO:208, and a light chain CDR3 comprising SEQ ID NO:209.

In some embodiments, a C3-binding agent (e.g., an antibody) comprises (a) a heavy chain CDR1 comprising GFTFSSYTMS (SEQ ID NO:73), a heavy chain CDR2 comprising YISSGGGTTYYPDTVKG (SEQ ID NO:74), and a heavy chain CDR3 comprising RYYRGSSLWYFDV (SEQ ID NO:75), and/or (b) a light chain CDR1 comprising KSSQSLFNSGSQKNFLT (SEQ ID NO:76), a light chain CDR2 comprising WASTRES (SEQ ID NO:77), and a light chain CDR3 comprising QNDYSYPLT (SEQ ID NO:78). In some embodiments, a C3-binding agent (e.g., an antibody) comprises (a) a heavy chain CDR1 comprising GFTFS-SYTMS (SEQ ID NO:73), a heavy chain CDR2 comprising YISSGGGTTYYPDTVKG (SEQ ID NO:74), and a heavy chain CDR3 comprising RYYRGSSLWYFDV (SEQ ID NO:75), and (b) a light chain CDR1 comprising KSSQSLFNSGSQKNFLT (SEQ ID NO:76), a light chain CDR2 comprising WASTRES (SEQ ID NO:77), and a light chain CDR3 comprising QNDYSYPLT (SEQ ID NO:78).

In some embodiments, a C3-binding agent (e.g., an antibody) comprises (a) a heavy chain variable region comprising a heavy chain CDR1 comprising GFTFSSYTMS (SEQ ID NO:73), a heavy chain CDR2 comprising YISSGGGT-TYYPDTVKG (SEQ ID NO:74), and a heavy chain CDR3 comprising RYYRGSSLWYFDV (SEQ ID NO:75), and/or (b) a light chain variable region comprising a light chain CDR1 comprising KSSQSLFNSGSQKNFLT (SEQ ID NO:76), a light chain CDR2 comprising WASTRES (SEQ ID NO:77), and a light chain CDR3 comprising QNDYSY-PLT (SEQ ID NO:78). In some embodiments, a C3-binding agent (e.g., an antibody) comprises (a) a heavy chain variable region comprising a heavy chain CDR1 comprising GFTFSSYTMS (SEQ ID NO:73), a heavy chain CDR2 comprising YISSGGGTTYYPDTVKG (SEQ ID NO:74), and a heavy chain CDR3 comprising RYYRGSSLWYFDV (SEQ ID NO:75), and (b) a light chain variable region comprising a light chain CDR1 comprising KSSQSLFNSGSQKNFLT (SEQ ID NO:76), a light chain CDR2 comprising WASTRES (SEQ ID NO:77), and a light chain CDR3 comprising QNDYSYPLT (SEQ ID NO:78).

In certain embodiments, a C3-binding agent comprises heavy chain CDRs 1, 2, and 3 of a heavy chain variable region comprising the amino acid sequence set forth in SEQ ID NO: 103. In certain embodiments, a C3-binding agent comprises light chain CDRs 1, 2, and 3 of a light chain variable region comprising the amino acid sequence set forth in SEQ ID NO: 104. In certain embodiments, a C3-binding agent comprises heavy chain CDRs 1, 2, and 3 of a heavy chain variable region comprising the amino acid sequence set forth in SEQ ID NO: 103, and light chain CDRs 1, 2, and 3 of a light chain variable region comprising the amino acid sequence set forth in SEQ ID NO: 104.

In some embodiments, a C3-binding agent (e.g., an antibody) comprises a heavy chain variable region having at least about 80%, about 85%, about 90%, or about 95% sequence identity to SEQ ID NO: 103 and/or a light chain variable region having at least about 80%, about 85%, about 90%, or about 95% sequence identity to SEQ ID NO:104. In some embodiments, a C3-binding agent (e.g., an antibody) comprises a heavy chain variable region comprising SEQ ID NO: 103 and/or a light chain variable region comprising SEQ ID NO: 104. In some embodiments, a C3-binding agent (e.g., an antibody) comprises a heavy chain variable region of SEQ ID NO: 103 and a light chain variable region of SEQ ID NO: 104.

In certain embodiments, a C3-binding agent (e.g., an antibody) comprises (a) a heavy chain CDR1 comprising SEQ ID NO:79, a heavy chain CDR2 comprising SEQ ID NO:80, a heavy chain CDR3 comprising SEQ ID NO:81, a light chain CDR1 comprising SEQ ID NO:82, a light chain CDR2 comprising SEQ ID NO:83, and a light chain CDR3 comprising SEQ ID NO:84; (b) a heavy chain CDR1 comprising SEQ ID NO:210, a heavy chain CDR2 comprising SEQ ID NO:213, a heavy chain CDR3 comprising SEQ ID NO:81, a light chain CDR1 comprising SEQ ID NO:82, a light chain CDR2 comprising SEQ ID NO:83, and a light chain CDR3 comprising SEQ ID NO:84; (c) a heavy chain CDR1 comprising SEQ ID NO:79, a heavy chain CDR2 comprising SEQ ID NO:214, a heavy chain CDR3 comprising SEQ ID NO:81, a light chain CDR1 comprising SEQ ID NO:82, a light chain CDR2 comprising SEQ ID NO:83, and a light chain CDR3 comprising SEQ ID NO:84; (d) a heavy chain CDR1 comprising SEQ ID NO:211, a heavy chain CDR2 comprising SEQ ID NO:80, a heavy chain CDR3 comprising SEQ ID NO:81, a light chain CDR1 comprising SEQ ID NO:82, a light chain CDR2 comprising SEQ ID NO:83, and a light chain CDR3 comprising SEQ ID NO:84; or (e) a heavy chain CDR1 comprising SEQ ID NO:212, a heavy chain CDR2 comprising SEQ ID NO:215, a heavy chain CDR3 comprising SEQ ID NO:216, a light chain CDR1 comprising SEQ ID NO:217, a light chain CDR2 comprising SEQ ID NO:218, and a light chain CDR3 comprising SEQ ID NO:219.

In some embodiments, a C3-binding agent (e.g., an antibody) comprises (a) a heavy chain CDR1 comprising GYSITSGYSLH (SEQ ID NO:79), a heavy chain CDR2 comprising YIHYSGSTNYNPSLKS (SEQ ID NO:80), and a heavy chain CDR3 comprising AWDYLDY (SEQ ID NO:81), and/or (b) a light chain CDR1 comprising RASENIYSQLA (SEQ ID NO:82), a light chain CDR2 comprising DAKTLAE (SEQ ID NO:83), and a light chain CDR3 comprising HHHFGILYT (SEQ ID NO:84). In some embodiments, a C3-binding agent (e.g., an antibody) comprises (a) a heavy chain CDR1 comprising GYSITSGYSLH (SEQ ID NO:79), a heavy chain CDR2 comprising YIHYSGSTNYNPSLKS (SEQ ID NO:80), and a heavy chain CDR3 comprising AWDYLDY (SEQ ID NO:81), and (b) a light chain CDR1 comprising RASENIYSQLA (SEQ ID NO:82), a light chain CDR2 comprising DAKTLAE (SEQ ID NO:83), and a light chain CDR3 comprising HHHFGILYT (SEQ ID NO:84).

In some embodiments, a C3-binding agent (e.g., an antibody) comprises (a) a heavy chain variable region comprising heavy chain CDR1 comprising GYSITSGYSLH (SEQ ID NO:79), a heavy chain CDR2 comprising YIHYSGSTNYNPSLKS (SEQ ID NO:80), and a heavy chain CDR3 comprising AWDYLDY (SEQ ID NO:81), and/or (b) a light chain variable region comprising a light chain CDR1 comprising RASENIYSQLA (SEQ ID NO:82), a light chain CDR2 comprising DAKTLAE (SEQ ID NO:83), and a light chain CDR3 comprising HHHFGILYT (SEQ ID NO:84). In some embodiments, a C3-binding agent (e.g., an antibody) comprises (a) a heavy chain variable region comprising a heavy chain CDR1 comprising GYSITSGYSLH (SEQ ID NO:79), a heavy chain CDR2 comprising YIHYSGSTNYNPSLKS (SEQ ID NO:80), and a heavy chain CDR3 comprising AWDYLDY (SEQ ID NO:81), and (b) a light chain variable region comprising a light chain CDR1 comprising RASENIYSQLA (SEQ ID NO:82), a light chain CDR2 comprising DAKTLAE (SEQ ID NO:83), and a light chain CDR3 comprising HHHFGILYT (SEQ ID NO:84).

In certain embodiments, a C3-binding agent comprises heavy chain CDRs 1, 2, and 3 of a heavy chain variable region comprising the amino acid sequence set forth in SEQ ID NO: 105. In certain embodiments, a C3-binding agent comprises light chain CDRs 1, 2, and 3 of a light chain variable region comprising the amino acid sequence set forth in SEQ ID NO: 106. In certain embodiments, a C3-binding agent comprises heavy chain CDRs 1, 2, and 3 of a heavy chain variable region comprising the amino acid sequence set forth in SEQ ID NO: 105, and light chain CDRs 1, 2, and 3 of a light chain variable region comprising the amino acid sequence set forth in SEQ ID NO: 106.

In some embodiments, a C3-binding agent (e.g., an antibody) comprises a heavy chain variable region having at least about 80%, about 85%, about 90%, or about 95% sequence identity to SEQ ID NO: 105 and/or a light chain variable region having at least about 80%, about 85%, about 90%, or about 95% sequence identity to SEQ ID NO:106. In some embodiments, a C3-binding agent (e.g., an antibody) comprises a heavy chain variable region comprising SEQ ID NO: 105 and/or a light chain variable region comprising SEQ ID NO: 106. In some embodiments, a C3-binding agent (e.g., an antibody) comprises a heavy chain variable region of SEQ ID NO: 105 and a light chain variable region of SEQ ID NO: 106.

In certain embodiments, a C3-binding agent (e.g., an antibody) comprises (a) a heavy chain CDR1 comprising SEQ ID NO:85, a heavy chain CDR2 comprising SEQ ID NO:86, a heavy chain CDR3 comprising SEQ ID NO:87, a light chain CDR1 comprising SEQ ID NO:88, a light chain CDR2 comprising SEQ ID NO:89, and a light chain CDR3 comprising SEQ ID NO:90; (b) a heavy chain CDR1 comprising SEQ ID NO:210, a heavy chain CDR2 comprising SEQ ID NO:222, a heavy chain CDR3 comprising SEQ ID NO:87, a light chain CDR1 comprising SEQ ID NO:88, a light chain CDR2 comprising SEQ ID NO:89, and a light chain CDR3 comprising SEQ ID NO:90; (c) a heavy chain CDR1 comprising SEQ ID NO:85, a heavy chain CDR2 comprising SEQ ID NO:223, a heavy chain CDR3 comprising SEQ ID NO:87, a light chain CDR1 comprising SEQ ID NO:88, a light chain CDR2 comprising SEQ ID NO:89, and a light chain CDR3 comprising SEQ ID NO:90; (d) a heavy chain CDR1 comprising SEQ ID NO:220, a heavy chain CDR2 comprising SEQ ID NO:86, a heavy chain CDR3 comprising SEQ ID NO:87, a light chain CDR1 comprising SEQ ID NO:88, a light chain CDR2 comprising SEQ ID NO:89, and a light chain CDR3 comprising SEQ ID NO:90; or (e) a heavy chain CDR1 comprising SEQ ID NO:221, a heavy chain CDR2 comprising SEQ ID NO:224, a heavy chain CDR3 comprising SEQ ID NO:225, a light chain CDR1 comprising SEQ ID NO:226, a light chain CDR2 comprising SEQ ID NO:227, and a light chain CDR3 comprising SEQ ID NO:228.

In some embodiments, a C3-binding agent (e.g., an antibody) comprises (a) a heavy chain CDR1 comprising GYSITSGYYWN (SEQ ID NO:85), a heavy chain CDR2 comprising YIRYDGSNNYNPSLKN (SEQ ID NO:86), and a heavy chain CDR3 comprising HYGYDGGAFDF (SEQ ID NO:87), and/or (b) a light chain CDR1 comprising RTSENIYNYLV (SEQ ID NO:88), a light chain CDR2 comprising NAKTLEE (SEQ ID NO:89), and a light chain CDR3 comprising QHHYGTPFT (SEQ ID NO:90). In some embodiments, a C3-binding agent (e.g., an antibody) comprises (a) a heavy chain CDR1 comprising GYSITSGYYWN (SEQ ID NO:85), a heavy chain CDR2 comprising YIRYDGSNNYNPSLKN (SEQ ID NO:86), and a heavy chain CDR3 comprising HYGYDGGAFDF (SEQ ID NO:87), and (b) a light chain CDR1 comprising RTSENIYNYLV (SEQ ID NO:88), a light chain CDR2 comprising NAKTLEE (SEQ ID NO:89), and a light chain CDR3 comprising QHHYGTPFT (SEQ ID NO:90).

In some embodiments, a C3-binding agent (e.g., an antibody) comprises (a) a heavy chain variable region comprising a heavy chain CDR1 comprising GYSITSGYYWN (SEQ ID NO:85), a heavy chain CDR2 comprising YIRYDGSNNYNPSLKN (SEQ ID NO:86), and a heavy chain CDR3 comprising HYGYDGGAFDF (SEQ ID NO:87), and/or (b) a light chain variable region comprising a light chain CDR1 comprising RTSENIYNYLV (SEQ ID NO:88), a light chain CDR2 comprising NAKTLEE (SEQ ID NO:89), and a light chain CDR3 comprising QHHYGTPFT (SEQ ID NO:90). In some embodiments, a C3-binding agent (e.g., an antibody) comprises (a) a heavy chain variable region comprising a heavy chain CDR1 comprising GYSITSGYYWN (SEQ ID NO:85), a heavy chain CDR2 comprising YIRYDGSNNYNPSLKN (SEQ ID NO:86), and a heavy chain CDR3 comprising HYGYDG-GAFDF (SEQ ID NO:87), and (b) a light chain variable region comprising a light chain CDR1 comprising RTSENIYNYLV (SEQ ID NO:88), a light chain CDR2 comprising NAKTLEE (SEQ ID NO:89), and a light chain CDR3 comprising QHHYGTPFT (SEQ ID NO:90).

In certain embodiments, a C3-binding agent comprises heavy chain CDRs 1, 2, and 3 of a heavy chain variable region comprising the amino acid sequence set forth in SEQ ID NO: 107. In certain embodiments, a C3-binding agent comprises light chain CDRs 1, 2, and 3 of a light chain variable region comprising the amino acid sequence set forth in SEQ ID NO: 108. In certain embodiments, a C3-binding agent comprises heavy chain CDRs 1, 2, and 3 of a heavy chain variable region comprising the amino acid sequence set forth in SEQ ID NO: 107, and light chain CDRs 1, 2, and 3 of a light chain variable region comprising the amino acid sequence set forth in SEQ ID NO: 108.

In some embodiments, a C3-binding agent (e.g., an antibody) comprises a heavy chain variable region having at least about 80%, about 85%, about 90%, or about 95% sequence identity to SEQ ID NO: 107 and/or a light chain variable region having at least about 80%, about 85%, about 90%, or about 95% sequence identity to SEQ ID NO:108. In some embodiments, a C3-binding agent (e.g., an antibody) comprises a heavy chain variable region comprising SEQ ID NO: 107 and/or a light chain variable region comprising SEQ ID NO: 108. In some embodiments, a C3-binding agent (e.g., an antibody) comprises a heavy chain variable region of SEQ ID NO: 107 and a light chain variable region of SEQ ID NO: 108.

In some embodiments, a C3-binding agent (e.g., an antibody) is a scFv. In some embodiments, a scFv comprises a heavy chain variable region comprising SEQ ID NO: 110 or SEQ ID NO: 111. In some embodiments, a scFv comprises a light chain variable region comprising SEQ ID NO: 112. In some embodiments, a scFv comprises a heavy chain variable region comprising SEQ ID NO: 110 and a light chain variable region comprising SEQ ID NO: 112. In some embodiments, a scFv comprises a heavy chain variable region comprising SEQ ID NO: 111 and a light chain variable region comprising SEQ ID NO: 112. In some embodiments, a scFv comprises SEQ ID NO:113. In some embodiments, a scFv comprises SEQ ID NO: 114. In some embodiments, a scFv comprises SEQ ID NO: 119. In some embodiments, a scFv comprises SEQ ID NO:229.

Provided in this disclosure are antibodies that compete with one or more of the binding agents described herein for binding to C3. In some embodiments, antibodies provided herein compete with one or more of the C3-binding agents described herein for binding to human C3. In some embodiments, an antibody provided herein binds the same epitope as one of the antibodies described herein. In some embodiments, an antibody provided herein binds an epitope overlapping with an epitope bound by one of the antibodies described herein. Antibodies and antigen-binding fragments that compete with, or bind to the same epitope, as the antibodies described herein are expected to show similar functional properties.

In some embodiments, an antibody competes for binding to C3 with a C3-binding agent (e.g., an antibody) described herein. In some embodiments, antibody competes for binding to human C3 with a C3-binding agent (e.g., an antibody) described herein. In some embodiments, an antibody competes for binding to C3 (e.g., human C3) with a reference antibody, wherein the reference antibody comprises: (a) a heavy chain variable region comprising a heavy chain CDR1 comprising GYTFTDFYMD (SEQ ID NO:7), a heavy chain CDR2 comprising YIYPHNGGT-TYNQNFTG (SEQ ID NO:8), YIYPHNGGTTYNQQFTG (SEQ ID NO: 13), YIYPHNAGTTYNQQFTG (SEQ ID NO: 14), YIYPHNTGTTYNQQFTG (SEQ ID NO:15), YIYPHEGGTTYNQQFTG (SEQ ID NO:16), or YIYPHQGGTTYNQQFTG (SEQ ID NO: 17), and a heavy chain CDR3 comprising RGGFDFDY (SEQ ID NO:9); and/or (b) a light chain variable region comprising a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, an antibody competes for binding to C3 (e.g., human C3) with a reference antibody, wherein the reference antibody comprises (a) a heavy chain variable region comprising a heavy chain CDR1 comprising GYTFTDFYMD (SEQ ID NO:7), a heavy chain CDR2 comprising YIYPHNGGTTYNQNFTG (SEQ ID NO:8), and a heavy chain CDR3 comprising RGGFDFDY (SEQ ID NO:9); and (b) a light chain variable region comprising a light chain CDR1 comprising KASENVDTYVS (SEQ ID NO:10), a light chain CDR2 comprising GASNRYT (SEQ ID NO: 11), and a light chain CDR3 comprising GQSHSYPLT (SEQ ID NO: 12). In some embodiments, an antibody competes for binding to C3 (e.g., human C3) with a reference antibody, wherein the reference antibody comprises (a) a heavy chain variable region comprising a heavy chain CDR1 comprising GYTFTDFYMD (SEQ ID NO:7), a heavy chain CDR2 comprising YIYPHNGGTTYNQQFTG (SEQ ID NO: 13), and a heavy chain CDR3 comprising RGGFDFDY (SEQ ID NO:9); and (b) a light chain variable region comprising a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO:12). In some embodiments, an antibody competes for binding to C3 (e.g., human C3) with a reference antibody, wherein the reference antibody comprises (a) a heavy chain variable region comprising a heavy chain CDR1 comprising GYTFTDFYMD (SEQ ID NO:7), a heavy chain CDR2 comprising YIYPHNAGTTYNQQFTG (SEQ ID NO:14), and a heavy chain CDR3 comprising RGGFDFDY (SEQ ID NO:9); and (b) a light chain variable region comprising a light chain CDR1 comprising KASENVDTYVS (SEQ ID NO:10), a light chain CDR2 comprising GASNRYT (SEQ ID NO: 11), and a light chain CDR3 comprising GQSHSY-PLT (SEQ ID NO: 12). In some embodiments, an antibody competes for binding to C3 (e.g., human C3) with a reference antibody, wherein the reference antibody comprises (a) a heavy chain variable region comprising a heavy chain CDR1 comprising GYTFTDFYMD (SEQ ID NO:7), a heavy chain CDR2 comprising YIYPHNTGTTYNQQFTG (SEQ ID NO: 15), and a heavy chain CDR3 comprising RGGFDFDY (SEQ ID NO:9); and (b) a light chain variable region comprising a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, an antibody competes for binding to C3 (e.g., human C3) with a reference antibody, wherein the reference antibody comprises (a) a heavy chain variable region comprising a heavy chain CDR1 comprising GYTFTDFYMD (SEQ ID NO:7), a heavy chain CDR2 comprising YIYPHEGGTTYNQQFTG (SEQ ID NO: 16), and a heavy chain CDR3 comprising RGGFDFDY (SEQ ID NO:9); and (b) a light chain variable region comprising a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12). In some embodiments, an antibody competes for binding to C3 (e.g., human C3) with a reference antibody, wherein the reference antibody comprises (a) a heavy chain variable region comprising a heavy chain CDR1 comprising GYTFTDFYMD (SEQ ID NO:7), a heavy chain CDR2 comprising YIYPHQGGTTYNQQFTG (SEQ ID NO: 17), and a heavy chain CDR3 comprising RGGFDFDY (SEQ ID NO:9); and (b) a light chain variable region comprising a light chain CDR1 comprising KASENVDTYVS (SEQ ID NO: 10), a light chain CDR2 comprising GASNRYT (SEQ ID NO: 11), and a light chain CDR3 comprising GQSHSYPLT (SEQ ID NO: 12).

In some embodiments, an antibody competes for binding to C3 (e.g., human C3) with a reference antibody, wherein the reference antibody comprises: (a) a heavy chain variable region comprising SEQ ID NO:18 and (b) a light chain variable region comprising SEQ ID NO:19. In some embodiments, an antibody competes for binding to C3 (e.g., human C3) with a reference antibody, wherein the reference antibody comprises: (a) a heavy chain variable region comprising SEQ ID NO:20, SEQ ID NO:21, SEQ ID NO:22, SEQ ID NO:23, or SEQ ID NO:24; and (b) a light chain variable region comprising SEQ ID NO:25. In some embodiments, an antibody competes for specific binding to C3 (e.g., human C3) with a reference antibody, wherein the reference antibody comprises: (a) a heavy chain variable region comprising SEQ ID NO:20 and (b) a light chain variable region comprising SEQ ID NO:25. In some embodiments, an antibody competes for specific binding to C3 (e.g., human C3) with a reference antibody, wherein the reference antibody comprises: (a) a heavy chain variable region comprising SEQ ID NO:21 and (b) a light chain variable region comprising SEQ ID NO:25. In some embodiments, an antibody competes for specific binding to C3 (e.g., human C3) with a reference antibody, wherein the reference antibody comprises: (a) a heavy chain variable region comprising SEQ ID NO:22 and (b) a light chain variable region comprising SEQ ID NO:25. In some embodiments, an antibody competes for specific binding to C3 (e.g., human C3) with a reference antibody, wherein the reference antibody comprises: (a) a heavy chain variable region comprising SEQ ID NO:23 and (b) a light chain variable region comprising SEQ ID NO:25. In some embodiments, an antibody competes for specific binding to C3 (e.g., human C3) with a reference antibody, wherein the reference antibody comprises: (a) a heavy chain variable region comprising SEQ ID NO:24 and (b) a light chain variable region comprising SEQ ID NO:25.

In some embodiments, an antibody competes for binding to C3 (e.g. human C3) with a reference antibody, wherein the reference antibody comprises (a) a heavy chain CDR1 comprising GYSFTGYNMN (SEQ ID NO:38), a heavy chain CDR2 comprising NINPYYGSTNYNQKFKG (SEQ ID NO:39), and a heavy chain CDR3 comprising GYYGG-NYPFAY (SEQ ID NO:40), and/or (b) a light chain CDR1 comprising RASENIYSYLA (SEQ ID NO:41), a light chain CDR2 comprising NAKTLAE (SEQ ID NO:42), and a light chain CDR3 comprising QHYYGTPYT (SEQ ID NO:43). In some embodiments, an antibody competes for binding to C3 (e.g. human C3) with a reference antibody, wherein the reference antibody comprises (a) a heavy chain CDR1 comprising GYSFTGYNMN (SEQ ID NO:38), a heavy chain CDR2 comprising NINPYYDSTSYNQKFKG (SEQ ID NO:44), and a heavy chain CDR3 comprising ENY-DFVGFAY (SEQ ID NO:45), and/or (b) a light chain CDR1 comprising RASSSVSYMH (SEQ ID NO:46), a light chain CDR2 comprising VTSNLAS (SEQ ID NO:47), and a light chain CDR3 comprising QQWSTNPLT (SEQ ID NO:48). In some embodiments, an antibody competes for binding to C3 (e.g. human C3) with a reference antibody, wherein the reference antibody comprises (a) a heavy chain CDR1 comprising GYSFTGYNMH (SEQ ID NO:49), a heavy chain CDR2 comprising NINPYYGTTNSNQKFED (SEQ ID NO:50), and a heavy chain CDR3 comprising GIYYYGTGYPYFDF (SEQ ID NO:51), and/or (b) a light chain CDR1 comprising RASQDINNYLN (SEQ ID NO:52), a light chain CDR2 comprising YTSRLHS (SEQ ID NO:53), and a light chain CDR3 comprising QQGITLPWT (SEQ ID NO:54). In some embodiments, an antibody competes for binding to C3 (e.g. human C3) with a reference antibody, wherein the reference antibody comprises (a) a heavy chain CDR1 comprising GYTFTDYWIN (SEQ ID NO:55), a heavy chain CDR2 comprising NIYPGSTSANYNEKFKS (SEQ ID NO:56), and a heavy chain CDR3 comprising YGYDSWFAY (SEQ ID NO:57), and/or (b) a light chain CDR1 comprising KSTKSLLNSDGFTYLD (SEQ ID NO:58), a light chain CDR2 comprising LVSNRFS (SEQ ID NO:59), and a light chain CDR3 comprising FQSNYLPLT (SEQ ID NO:60). In some embodiments, an antibody competes for binding to C3 (e.g. human C3) with a reference antibody, wherein the reference antibody comprises (a) a heavy chain CDR1 comprising GYAFNSCWMN (SEQ ID NO:61), a heavy chain CDR2 comprising RIYPGDGDTNYNGKFKG (SEQ ID NO:62), and a heavy chain CDR3 comprising EGRNYGYEDY (SEQ ID NO:63), and/or (b) a light chain CDR1 comprising KASQSVDYDGDSYMN (SEQ ID NO:64), a light chain CDR2 comprising AASDLES (SEQ ID NO:65), and a light chain CDR3 comprising QQANEDPRT (SEQ ID NO:66). In some embodiments, an antibody competes for binding to C3 (e.g. human C3) with a reference antibody, wherein the reference antibody comprises (a) a heavy chain CDR1 comprising GFTFSNYAMS (SEQ ID NO:67), a heavy chain CDR2 comprising QTIS-SGGRYTYYPDSVKG (SEQ ID NO:68), and a heavy chain CDR3 comprising RYYGNSYWYFDV (SEQ ID NO:69), and/or (b) a light chain CDR1 comprising KSSQSLLNSGNQKHYLT (SEQ ID NO:70), a light chain CDR2 comprising GASTRGS (SEQ ID NO:71), and a light chain CDR3 comprising QNDHSYPYT (SEQ ID NO:72). In some embodiments, an antibody competes for binding to C3 (e.g. human C3) with a reference antibody, wherein the reference antibody comprises (a) a heavy chain CDR1 comprising GFTFSSYTMS (SEQ ID NO:73), a heavy chain CDR2 comprising YISSGGGTTYYPDTVKG (SEQ ID NO:74), and a heavy chain CDR3 comprising RYYRGSSLWYFDV (SEQ ID NO:75), and/or (b) a light chain CDR1 comprising KSSQSLFNSGSQKNFLT (SEQ ID NO:76), a light chain CDR2 comprising WASTRES (SEQ ID NO:77), and a light chain CDR3 comprising QNDYSYPLT (SEQ ID NO:78). In some embodiments, an antibody competes for binding to C3 (e.g. human C3) with a reference antibody, wherein the reference antibody comprises (a) a heavy chain CDR1 comprising GYSITSGYSLH (SEQ ID NO:79), a heavy chain CDR2 comprising YIHYSGSTNYNPSLKS (SEQ ID NO:80), and a heavy chain CDR3 comprising AWDYLDY (SEQ ID NO:81), and/or (b) a light chain CDR1 comprising RASENIYSQLA (SEQ ID NO:82), a light chain CDR2 comprising DAKT-LAE (SEQ ID NO:83), and a light chain CDR3 comprising HHHFGILYT (SEQ ID NO:84). In some embodiments, an antibody competes for binding to C3 (e.g. human C3) with a reference antibody, wherein the reference antibody comprises (a) a heavy chain CDR1 comprising GYSITSGYYWN (SEQ ID NO:85), a heavy chain CDR2 comprising YIRYDGSNNYNPSLKN (SEQ ID NO:86), and a heavy chain CDR3 comprising HYGYDGGAFDF (SEQ ID NO:87), and/or (b) a light chain CDR1 comprising RTSENIYNYLV (SEQ ID NO:88), a light chain CDR2 comprising NAKTLEE (SEQ ID NO:89), and a light chain CDR3 comprising QHHYGTPFT (SEQ ID NO:90).

In some embodiments, an antibody competes for binding to C3 (e.g., human C3) with a reference antibody, wherein the reference antibody comprises: (a) a heavy chain variable region comprising SEQ ID NO:91 and (b) a light chain variable region comprising SEQ ID NO:92. In some embodiments, an antibody competes for binding to C3 (e.g., human C3) with a reference antibody, wherein the reference antibody comprises: (a) a heavy chain variable region comprising SEQ ID NO:93 and (b) a light chain variable region comprising SEQ ID NO:94. In some embodiments, an antibody competes for binding to C3 (e.g., human C3) with a reference antibody, wherein the reference antibody comprises: (a) a heavy chain variable region comprising SEQ ID NO:95 and (b) a light chain variable region comprising SEQ ID NO:96. In some embodiments, an antibody competes for binding to C3 (e.g., human C3) with a reference antibody, wherein the reference antibody comprises: (a) a heavy chain variable region comprising SEQ ID NO:97 and (b) a light chain variable region comprising SEQ ID NO:98. In some embodiments, an antibody competes for binding to C3 (e.g., human C3) with a reference antibody, wherein the reference antibody comprises: (a) a heavy chain variable region comprising SEQ ID NO:99 and (b) a light chain variable region comprising SEQ ID NO: 100. In some embodiments, an antibody competes for binding to C3 (e.g., human C3) with a reference antibody, wherein the reference antibody comprises: (a) a heavy chain variable region comprising SEQ ID NO:101 and (b) a light chain variable region comprising SEQ ID NO:102. In some embodiments, an antibody competes for binding to C3 (e.g., human C3) with a reference antibody, wherein the reference antibody comprises: (a) a heavy chain variable region comprising SEQ ID NO:103 and (b) a light chain variable region comprising SEQ ID NO:104. In some embodiments, an antibody competes for binding to C3 (e.g., human C3) with a reference antibody, wherein the reference antibody comprises: (a) a heavy chain variable region comprising SEQ ID NO:105 and (b) a light chain variable region comprising SEQ ID NO:106. In some embodiments, an antibody competes for binding to C3 (e.g., human C3) with a reference antibody, wherein the reference antibody comprises: (a) a heavy chain variable region comprising SEQ ID NO:107 and (b) a light chain variable region comprising SEQ ID NO:108.

In some embodiments, a C3-binding agent described herein comprises an antibody in which at least one or more of the constant regions has been modified or deleted. In some embodiments, the antibodies may comprise modifications to one or more of the three heavy chain constant regions (CH1, CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an antibody comprises a variant Fc region. The amino acid sequences of the Fc region of human IgG1, IgG2, IgG3, and IgG4 are known to those of ordinary skill in the art (e.g., a representative human IgG1 is SEQ ID NO:34). In some cases, Fc regions with amino acid variations have been identified in native antibodies. In some embodiments, a variant Fc region is engineered with substitutions at specific amino acid positions as compared to a native Fc region (e.g., SEQ ID NO:35, SEQ ID NO:36, and SEQ ID NO: 109).

In some embodiments, the modified antibodies (e.g., modified Fc region) provide for altered effector functions that, in turn, affect the biological profile of the antibody. For example, in some embodiments, the deletion or inactivation (through point mutations or other means) of a constant region reduces Fc receptor binding of the modified antibody as it circulates. In some embodiments, the constant region modifications increase the serum half-life of the antibody. In some embodiments, the constant region modifications reduce the serum half-life of the antibody. In some embodiments, the constant region modifications decrease or remove ADCC and/or complement dependent cytotoxicity (CDC) of the antibody. In some embodiments, specific amino acid substitutions in a human IgG1 Fc region with corresponding IgG2 or IgG4 residues reduce effector functions (e.g., ADCC and CDC) in the modified antibody. In some embodiments, an antibody does not have one or more effector functions (e.g., "effectorless" antibodies). In some embodiments, the antibody has no ADCC activity and/or no CDC activity. In some embodiments, the antibody does not bind an Fc receptor and/or complement factors. In some embodiments, the antibody has no effector function(s). In some embodiments, the constant region modifications increase or enhance ADCC and/or CDC of the antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

In certain embodiments, a C3-binding agent comprises a heavy chain comprising heavy chain CDRs 1, 2, and 3, and a light chain comprising light chain CDRs 1, 2, and 3, wherein heavy chain CDR1 comprises GYTFTDFYMD (SEQ ID NO:7), heavy chain CDR2 comprises YIYPHNGGTTYNQNFTG (SEQ ID NO:8), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12), wherein the heavy chain comprises at least 80%, at least 85%, at least 90%, at least 95%, at least 97%, or 100% identity to the sequence set forth in SEQ ID NO:27, and wherein the light chain comprises at least 80%, at least 85%, at least 90%, at least 95%, at least 97%, or 100% identity to the sequence set forth in SEQ ID NO:31. In certain embodiments, a C3-binding agent comprises a heavy chain comprising heavy chain CDRs 1, 2, and 3, and a light chain comprising light chain CDRs 1, 2, and 3, wherein heavy chain CDR1 comprises GYTFTDFYMD (SEQ ID NO:7), heavy chain CDR2 comprises YIYPHNGGTTYNQQFTG (SEQ ID NO: 13), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12), wherein the heavy chain comprises at least 80%, at least 85%, at least 90%, at least 95%, at least 97%, or 100% identity to the sequence set forth in SEQ ID NO:27, and wherein the light chain comprises at least 80%, at least 85%, at least 90%, at least 95%, at least 97%, or 100% identity to the sequence set forth in SEQ ID NO:31. In certain embodiments, a C3-binding agent comprises heavy chain CDRs 1, 2, and 3, and a light chain comprising light chain CDRs 1, 2, and 3, wherein heavy chain CDR1 comprises GYTFTDFYMD (SEQ ID NO:7), heavy chain CDR2 comprises YIYPHNAGTTYNQQFTG (SEQ ID NO: 14), heavy chain CDR3 comprises RGGFDFDY (SEQ ID NO:9), light chain CDR1 comprises KASENVDTYVS (SEQ ID NO:10), light chain CDR2 comprises GASNRYT (SEQ ID NO: 11), and light chain CDR3 comprises GQSHSYPLT (SEQ ID NO:12), wherein the heavy chain comprises at least 80%, at least 85%, at least 90%, at least 95%, at least 97%, or 100% identity to the sequence set forth in SEQ ID NO:29, and wherein the light chain comprises at least 80%, at least 85%, at least 90%, at least 95%, at least 97%, or 100% identity to the sequence set forth in SEQ ID NO:31. In certain embodiments, a C3-binding agent comprises a heavy chain comprising heavy chain CDRs 1, 2, and 3, and a light chain comprising light chain CDRs 1, 2, and 3, wherein heavy chain CDR1 comprises GYTFTDFYMD (SEQ ID NO:7), heavy chain CDR2 comprises YIYPHNTGTTYNQQFTG (SEQ ID NO: 15), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12), wherein the heavy chain comprises at least 80%, at least 85%, at least 90%, at least 95%, or at least 97% identity to the sequence set forth in SEQ ID NO:27, and wherein the light chain comprises at least 80%, at least 85%, at least 90%, at least 95%, at least 97%, or 100% identity to the sequence set forth in SEQ ID NO:31. In certain embodiments, a C3-binding agent comprises a heavy chain comprising heavy chain CDRs 1, 2, and 3, and a light chain comprising light chain CDRs 1, 2, and 3, wherein heavy chain CDR1 comprises GYTFTDFYMD (SEQ ID NO:7), heavy chain CDR2 comprises YIYPHEGGTTYNQQFTG (SEQ ID NO: 16), heavy chain CDR3 comprises RGGFDFDY (SEQ ID NO:9), light chain CDR1 comprises KASENVDTYVS (SEQ ID NO:10), light chain CDR2 comprises GASNRYT (SEQ ID NO:11), and light chain CDR3 comprises GQSHSYPLT (SEQ ID NO: 12), wherein the heavy chain comprises at least 80%, at least 85%, at least 90%, at least 95%, or at least 97% identity to the sequence set forth in SEQ ID NO:27, and wherein the light chain comprises at least 80%, at least 85%, at least 90%, at least 95%, at least 97%, or 100% identity to the sequence set forth in SEQ ID NO:31. In certain embodiments, a C3-binding agent comprises a heavy chain comprising heavy chain CDRs 1, 2, and 3, and a light chain comprising light chain CDRs 1, 2, and 3, wherein heavy chain CDR1 comprises GYTFTDFYMD (SEQ ID NO:7), heavy chain CDR2 comprises YIYPHQGGTTYNQQFTG (SEQ ID NO: 17), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12), wherein the heavy chain comprises at least 80%, at least 85%, at least 90%, at least 95%, at least 97%, or 100% identity to the sequence set forth in SEQ ID NO:27, and wherein the light chain comprises at least 80%, at least 85%, at least 90%, at least 95%, at least 97%, or 100% identity to the sequence set forth in SEQ ID NO:31.

In some embodiments, a C3-binding agent is an antibody that comprises a heavy chain of SEQ ID NO:27 and/or a light chain of SEQ ID NO:31. In some embodiments, a C3-binding agent is an antibody that comprises a heavy chain of SEQ ID NO:27. In some embodiments, a C3-binding agent is an antibody that comprises a light chain of SEQ ID NO:31. In some embodiments, a C3-binding agent is an antibody that comprises a heavy chain of SEQ ID NO:27 and a light chain of SEQ ID NO:31. In some embodiments, a C3-binding agent is an antibody that comprises a heavy chain of SEQ ID NO:29 and/or a light chain of SEQ ID NO:31. In some embodiments, a C3-binding agent is an antibody that comprises a heavy chain of SEQ ID NO:29. In some embodiments, a C3-binding agent is an antibody that comprises a light chain of SEQ ID NO:31. In some embodiments, a C3-binding agent is an antibody that comprises a heavy chain of SEQ ID NO:29 and a light chain of SEQ ID NO:31.

Modifications to the constant region of antibodies described herein may be made using well known biochemical or molecular engineering techniques. In some embodiments, antibody variants are prepared by introducing appropriate nucleotide changes into the encoding DNA, and/or by synthesis of the desired antibody or polypeptide. Using these antibody variants it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant are determined by systematically making insertions, deletions, or substitutions in the sequence and testing the resulting variant proteins for activity as compared to the parental antibody.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein, i.e., a fusion protein. In some embodiments, a variant is engineered to be detectable and may comprise a detectable label and/or protein (e.g., an enzyme).

In some embodiments, a cysteine residue not involved in maintaining the proper conformation of an antibody may be substituted or deleted to modulate the antibody's characteristics, for example, to improve oxidative stability and/or prevent aberrant disulfide crosslinking. Conversely, in some embodiments, one or more cysteine residues may be added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) that result in removal of T-cell epitopes without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, C3-binding agents described herein are chemically modified. In some embodiments, the C3-binding agents are anti-C3 antibodies that have been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

The present disclosure encompasses C3-binding agents built upon non-immunoglobulin backbones, wherein the agents bind to the same epitope or essentially the same epitope as an anti-C3 antibody disclosed herein. In some embodiments, a non-immunoglobulin-based binding agent is an agent that competes with an anti-C3 antibody described herein in a competitive binding assay. In some embodiments, alternative C3-binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the $10^{th}$ domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid antiparallel β-strand protein fold; and Kunitz domain inhibitor scaffolds, which are based upon a structure that contains three disulfide bonds and three loops. In some embodiments, a C3-binding agent comprises an engineered scaffold protein comprising a heavy chain CDR1, CDR2, and CDR3 and a light chain CDR1, CDR2, and CDR3 shown in Table 1. In some embodiments, a C3-binding agent comprises an engineered scaffold protein comprising a heavy chain CDR1 comprising GYTFTDFYMD (SEQ ID NO:7), a heavy chain CDR2 comprising YIYPHNGGTTYNQNFTG (SEQ ID NO:8), YIYPHNGGTTYNQQFTG (SEQ ID NO: 13), YIYPHNAGTTYNQQFTG (SEQ ID NO:14), YIYPHNTGTTYNQQFTG (SEQ ID NO: 15), YIYPHEGGTTYNQQFTG (SEQ ID NO: 16), or YIYPHQGGTTYNQQFTG (SEQ ID NO: 17), and a heavy chain CDR3 comprising RGGFDFDY (SEQ ID NO:9); and/or (b) a light chain variable region comprising a light chain CDR1 comprising KASENVDTYVS (SEQ ID NO:10), a light chain CDR2 comprising GASNRYT (SEQ ID NO: 11), and a light chain CDR3 comprising GQSHSYPLT (SEQ ID NO: 12).

In some embodiments, a C3-binding agent comprises an engineered scaffold protein comprising a heavy chain CDR1, CDR2, and CDR3 and a light chain CDR1, CDR2, and CDR3 from antibody 3D8. In some embodiments, a C3-binding agent comprises an engineered scaffold protein comprising a heavy chain CDR1, CDR2, and CDR3 and a light chain CDR1, CDR2, and CDR3 from antibody 3G8. In some embodiments, a C3-binding agent comprises an engineered scaffold protein comprising a heavy chain CDR1, CDR2, and CDR3 and a light chain CDR1, CDR2, and CDR3 from antibody 15C12. In some embodiments, a C3-binding agent comprises an engineered scaffold protein comprising a heavy chain CDR1, CDR2, and CDR3 and a light chain CDR1, CDR2, and CDR3 from antibody 27A8. In some embodiments, a C3-binding agent comprises an engineered scaffold protein comprising a heavy chain CDR1, CDR2, and CDR3 and a light chain CDR1, CDR2, and CDR3 from antibody 28C3. In some embodiments, a C3-binding agent comprises an engineered scaffold protein comprising a heavy chain CDR1, CDR2, and CDR3 and a light chain CDR1, CDR2, and CDR3 from antibody 38F5. In some embodiments, a C3-binding agent comprises an engineered scaffold protein comprising a heavy chain CDR1, CDR2, and CDR3 and a light chain CDR1, CDR2, and CDR3 from antibody 62B11. In some embodiments, a C3-binding agent comprises an engineered scaffold protein comprising a heavy chain CDR1, CDR2, and CDR3 and a light chain CDR1, CDR2, and CDR3 from antibody 62F2. In some embodiments, a C3-binding agent comprises an engineered scaffold protein comprising a heavy chain CDR1, CDR2, and CDR3 and a light chain CDR1, CDR2, and CDR3 from antibody 63A3.

Generally speaking, antigen-antibody interactions are non-covalent and reversible, formed by a combination of hydrogen bonds, hydrophobic interactions, electrostatic and van der Waals forces. When describing the strength of an antigen-antibody complex, the terms affinity and/or avidity are commonly used mentioned. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. In some embodiments, affinity is measured using SPR technology in a BiaCore™ system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, a C3-binding agent (e.g., an antibody) binds C3 (e.g., human C3) with a dissociation constant (KD) of about 1 µM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, a C3-binding agent binds C3 (e.g., human C3) with a KD of about 20 nM or less. In some embodiments, a C3-binding agent binds C3 (e.g., human C3) with a KD of about 10 nM or less. In some embodiments, a C3-binding agent binds C3 (e.g., human C3) with a KD of about 1 nM or less. In some embodiments, a C3-binding agent binds C3 (e.g., human C3) with a KD of about 0.5 nM or less. In some embodiments, a C3-binding agent binds C3 (e.g., human C3) with a KD of about 0.1 nM or less. In some embodiments, a C3-binding agent binds C3 (e.g., human C3) with a KD of about 50 pM or less. In some embodiments, a C3-binding agent binds C3 (e.g., human C3) with a KD of about 25 pM or less. In some embodiments, a C3-binding agent binds C3 (e.g., human C3) with a KD of about 10 pM or less. In some embodiments, a C3-binding agent binds C3 (e.g., human C3) with a KD of about 1 pM or less. In some embodiments, the dissociation constant of the binding agent (e.g., an antibody) for C3 is the dissociation constant determined using a C3 protein immobilized on a BiaCore™ chip and the binding agent flowed over the chip. In some embodiments, the dissociation constant of the binding agent (e.g., an antibody) for C3 is the dissociation constant determined using the binding agent captured by an anti-human IgG antibody on a BiaCore™ chip and soluble C3 flowed over the chip.

In some embodiments, a C3-binding agent (e.g., an antibody) binds C3 (e.g., human C3) with a half maximal effective concentration (EC50) of about 1 µM or less, about 100 nM or less, about 40 nM or less, about 20 nM or less, about 10 nM or less, about 1 nM or less, or about 0.1 nM or less. In some embodiments, a C3-binding agent binds to human C3 with an EC50 of about 1 µM or less, about 100 nM or less, about 40 nM or less, about 20 nM or less, about 10 nM or less, about 1 nM or less, or about 0.1 nM or less. In some embodiments, a C3-binding agent binds cyno C3 and/or human C3 with an EC50 of about 40 nM or less, about 20 nM or less, about 10 nM or less, about 1 nM or less or about 0.1 nM or less.

The C3-binding agents (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In some embodiments, recombinant expression vectors are used to amplify and express DNA encoding antibodies, or fragments thereof, against human C3. For example, recombinant expression vectors can be replicable DNA constructs which have synthetic or cDNA-derived DNA fragments encoding a polypeptide chain of a C3-binding agent, such as an anti-C3 antibody, or antigen-binding fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

The C3-binding agents (e.g., antibodies) of the present disclosure can be expressed from one or more vectors. For example, in some embodiments, a heavy chain polypeptide is expressed by one vector and a light chain polypeptide is expressed by a second vector. In some embodiments, a heavy chain polypeptide and a light chain polypeptide are expressed by one vector.

Suitable host cells for expression of a C3-binding agent (e.g., an antibody) or a C3 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof.

Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the C3-binding agents described herein. In some embodiments, the cells produce the C3-binding agents described herein. In some embodiments, the cells produce an antibody. In some embodiments, the cells produce an antibody that binds human C3. In some embodiments, the cells produce an antibody that binds cyno C3. In some embodiments, the cells produce an antibody that binds human C3 and cyno C3. In some embodiments, the cells produce an antibody designated 38G10. In some embodiments, the cells produce a humanized version of antibody 38G10, referred to as Hz38G10. In some embodiments, the cells produce a variant of Hz38G10, for example, Hz38G10(G56A), Hz38G10(G56T), Hz38G10(N55E), or Hz38G10(N55Q). In some embodiments, the cells produce antibody Hz38G10(G56A). In some embodiments, the cells produce a scFv version of antibody Hz38G10, referred to as dsscFv Hz38G10. In some embodiments, the cells produce a scFv version of antibody Hz38G10(G56A), referred to as dsscFv Hz38G10(G56A). In some embodiments, the cells produce an antibody designated 3D8. In some embodiments, the cells produce a humanized version of antibody 3D8. In some embodiments, the cells produce an antibody designated 3G8. In some embodiments, the cells produce a humanized version of antibody 3G8. In some embodiments, the cells produce an antibody designated 15C12. In some embodiments, the cells produce a humanized version of antibody 15C12. In some embodiments, the cells produce an antibody designated 27A8. In some embodiments, the cells produce a humanized version of antibody 27A8. In some embodiments, the cells produce an antibody designated 28C3. In some embodiments, the cells produce a humanized version of antibody 28C3. In some embodiments, the cells produce an antibody designated 38F5. In some embodiments, the cells produce a humanized version of antibody 38F5. In some embodiments, the cells produce an antibody designated 62B11. In some embodiments, the cells produce a humanized version of antibody 62B11. In some embodiments, the cells produce an antibody designated 62F2. In some embodiments, the cells produce a humanized version of antibody 62F2. In some embodiments, the cells produce an antibody designated 63A3. In some embodiments, the cells produce a humanized version of antibody 63A3. In some embodiments, the cell is a prokaryotic cell (e.g., *E. coli*). In some embodiments, the cell is an eukaryotic cell. In some embodiments, the cell is a mammalian cell. In some embodiments, the cell is a hybridoma cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine (SEQ ID NO:231), maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

Anti-C3 antibodies of the present disclosure may be analyzed for their physical/chemical properties and/or biological activities by various assays known in the art. In some embodiments, an anti-C3 antibody is tested for its ability to bind C3 (e.g., human C3 and/or cyno C3). Binding assays include, but are not limited to, SPR (e.g., BiaCore™) ELISA, and FACS. In some embodiments, an anti-C3 antibody is tested for its ability to inhibit, reduce, or block complement and/or C3 activity. Assays include, but are not limited to, hemolysis assays and C3a release assays. In addition, antibodies may be evaluated for solubility, stability, thermostability, viscosity, expression levels, expression quality, and/or purification efficiency.

In some embodiments, monoclonal antibodies generated against C3 are grouped based upon the epitope each individual antibody recognizes, a process known as "epitope binning". Generally, antibodies are tested in a pairwise combinatorial manner and antibodies that compete with each other are grouped together into bins. For example, in a premix binning assay, a first antibody is immobilized on a surface and a premixed solution of a second antibody and antigen is flowed over the immobilized first antibody. In tandem, the antigen is immobilized on a surface and the two antibodies are flowed over the immobilized antigen and compete to bind. Using these techniques, antibodies that block one another can be identified. A competitive blocking profile is created for each antibody relative to the other antibodies. The blocking results determine which bin each antibody is placed in. High-throughput methods of epitope binning are known in the art and allow for screening and characterization of large numbers of antibodies within a short period of time. Antibodies that bind similar epitopes often share similar functions and/or capabilities. Conversely, antibodies that bind different epitopes may have different functional activities.

Epitope mapping is the process of identifying the binding site, or epitope on a target protein/antigen where an antibody (or other binding agent) binds. A variety of methods are known in the art for mapping epitopes on target proteins. These methods include mutagenesis, including but not limited to, shotgun mutagenesis, site-directed mutagenesis, and alanine scanning; domain or fragment scanning, peptide scanning (e.g., Pepscan technology); display methods (e.g., phage display, microbial display, and ribosome/mRNA display); methods involving proteolysis and mass spectroscopy; and structural determination (e.g., x-ray crystallography and NMR).

In some embodiments, purified anti-C3 antibodies are characterized by assays including, but not limited to, N-terminal sequencing, amino acid analysis, high pressure liquid chromatography (HPLC), mass spectrometry, ion exchange chromatography, and papain digestion.

In some embodiments, assays are provided for identifying anti-C3 antibodies that affect C3 activity. In some embodiments, hemolysis assays are used to assess the functional activity of the complement system. Hemolysis assays have been modified over the years to assess the activity of the different complement pathways and/or individual complement components of the cascade. In some embodiments, a hemolysis assay is used to assess activity of the alternative pathway. In some embodiments, a hemolysis assay is used to assess activity of the classical pathway.

In some embodiments, a C3-binding agent (e.g., an antibody) binds C3 and inhibits C3 activation of the alternative pathway. In some embodiments, a C3-binding agent (e.g., an antibody) binds C3 and inhibits activation of the alternative pathway, wherein the inhibition is evaluated by a hemolysis assay. In certain embodiments, the C3-binding agent (e.g., an antibody) inhibits activation of the alternative pathway by at least about 10%, at least about 20%, at least about 30%, at least about 50%, at least about 75%, at least about 90%, or about 100%. In some embodiments, percent inhibition is used to calculate an $IC_{50}$ (half maximal inhibitory concentration) for the C3-binding agent. In some embodiments, a C3-binding agent that inhibits activation of the alternative pathway is antibody 38G10, antibody Hz38G10, antibody Hz38G10(G56A), antibody Hz38G10(G56T), antibody Hz38G10(N55E), antibody Hz38G10(N55Q), antibody 3D8, antibody 3G8, antibody 15C12, antibody 27A8, antibody 28C3, antibody 38F5, antibody 62B11, antibody 62F2, or antibody 63A3. In some embodiments, a C3-binding agent that inhibits activation of the alternative pathway is antibody 38G10, antibody Hz38G10, or antibody Hz38G10 (G56A). In some embodiments, a C3-binding agent that inhibits activation of the alternative pathway is dsscFv Hz38G10, or dsscFv Hz38G10(G56A).

In some embodiments, a C3-binding agent (e.g., an antibody) described herein binds C3 and inhibits C3 activation of the classical pathway. In some embodiments, a C3-binding agent (e.g., an antibody) binds C3 and inhibits activation of the classical pathway, wherein the inhibition is evaluated by a hemolysis assay. In certain embodiments, the C3-binding agent (e.g., an antibody) inhibits activation of the classical pathway by at least about 10%, at least about 20%, at least about 30%, at least about 50%, at least about 75%, at least about 90%, or about 100%. In some embodiments, a C3-binding agent that inhibits activation of the classical pathway is antibody 38G10, antibody Hz38G10, antibody Hz38G10(G56A), antibody Hz38G10(G56T), antibody Hz38G10(N55E), antibody Hz38G10(N55Q), antibody 3D8, antibody 3G8, antibody 15C12, antibody 27A8, antibody 28C3, antibody 38F5, antibody 62B11, antibody 62F2, or antibody 63A3. In some embodiments, a C3-binding agent that inhibits activation of the classical pathway is antibody 38G10, antibody Hz38G10, or antibody Hz38G10 (G56A). In some embodiments, a C3-binding agent that inhibits activation of the classical pathway is dsscFv Hz38G10, or dsscFv Hz38G10(G56A).

In some embodiments, a C3-binding agent (e.g., an antibody) described herein binds C3 and inhibits C3 activation of the classical and alternative pathways. In some embodiments, a C3-binding agent (e.g., an antibody) binds C3 and inhibits activation of the classical and alternative pathways, wherein the inhibition is evaluated by a hemolysis assay. In certain embodiments, the C3-binding agent (e.g., an antibody) inhibits activation of the classical and alternative pathways by at least about 10%, at least about 20%, at least about 30%, at least about 50%, at least about 75%, at least about 90%, or about 100%. In some embodiments, a C3-binding agent that inhibits activation of the classical and alternative pathway is antibody 38G10, antibody Hz38G10, antibody Hz38G10(G56A), antibody Hz38G10(G56T), antibody Hz38G10(N55E), antibody Hz38G10(N55Q), antibody 3D8, antibody 3G8, antibody 15C12, antibody 27A8, antibody 28C3, antibody 38F5, antibody 62B11, antibody 62F2, or antibody 63A3. In some embodiments, a C3-binding agent that inhibits activation of the classical and alternative pathways is antibody 38G10, antibody Hz38G10, or antibody Hz38G10(G56A). In some embodiments, a C3-binding agent that inhibits activation of the classical and alternative pathways is dsscFv Hz38G10, or dsscFv Hz38G10(G56A).

In some embodiments, an immunochemical assay to determine the presence and/or amount of individual components (e.g., C3a) is used to assess the complement cascade. In some embodiments, a C3-binding agent (e.g., an antibody) described herein binds C3 and inhibits the release of C3a.

The present disclosure also provides conjugates comprising an anti-C3 antibody described herein. In some embodiments, the antibody is attached to a second molecule. In some embodiments, the antibody is conjugated to a cytotoxic agent or moiety. In some embodiments, the antibody is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DM1 and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC 1065. A derivative of any one of these toxins may be used as long as the derivative retains the cytotoxic activity of the parent molecule.

Conjugates comprising an anti-C3 antibody described herein may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, an anti-C3 antibody described herein is conjugated to a detectable substance or molecule that allows the antibody to be used for diagnosis and/or detection. A detectable substance can include but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$CU, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions.

An anti-C3 antibody described herein can also be conjugated to a second antibody to form an antibody heteroconjugate.

An anti-C3 antibody as described herein may be attached to a solid support. Such solid supports include, but are not limited to, glass, cellulose, polyacrylamide, nylon, polystyrene, polyvinyl chloride, or polypropylene. In some embodiments, immobilized anti-C3 antibodies are used in immunoassays. In some embodiments, immobilized anti-C3 antibodies are used in purification of the target antigen.

III Polynucleotides

In some embodiments, the disclosure encompasses polynucleotides comprising polynucleotides that encode a polypeptide (i.e., a C3-binding agent) described herein. The term "polynucleotides that encode a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, the polynucleotide comprises a polynucleotide (e.g., a nucleotide sequence) encoding a polypeptide comprising an amino acid sequence selected from the group consisting of: SEQ ID NOs:18-31, 91-108, 110-114, 119, and 229. In some embodiments, the polynucleotide comprises a polynucleotide encoding a polypeptide comprising an amino acid sequence of SEQ ID NO:26. In some embodiments, the polynucleotide comprises a polynucleotide encoding a polypeptide comprising an amino acid sequence of SEQ ID NO:27. In some embodiments, the polynucleotide comprises a polynucleotide encoding a polypeptide comprising an amino acid sequence of SEQ ID NO:28. In some embodiments, the polynucleotide comprises a polynucleotide encoding a polypeptide comprising an amino acid sequence of SEQ ID NO:29. In some embodiments, the polynucleotide comprises a polynucleotide encoding a polypeptide comprising an amino acid sequence of SEQ ID NO:30. In some embodiments, the polynucleotide comprises a polynucleotide encoding a polypeptide comprising an amino acid sequence of SEQ ID NO:31. In some embodiments, the polynucleotide comprises a polynucleotide encoding a polypeptide comprising an amino acid sequence of SEQ ID NO: 113. In some embodiments, the polynucleotide comprises a polynucleotide encoding a polypeptide comprising an amino acid sequence of SEQ ID NO: 114. In some embodiments, the polynucleotide comprises a polynucleotide encoding a polypeptide comprising an amino acid sequence of SEQ ID NO: 119. In some embodiments, the polynucleotide comprises a polynucleotide encoding a polypeptide comprising an amino acid sequence of SEQ ID NO:229. In some embodiments, the polynucleotide comprises a polynucleotide (e.g., a nucleotide sequence) encoding a polypeptide comprising more than one amino acid sequence selected from the group consisting of: SEQ ID NOs:18-31, 91-108, and 110-112. In some embodiments, the polynucleotide comprises a polynucleotide encoding (i) a polypeptide comprising an amino acid sequence of SEQ ID NO:27 and (ii) a polypeptide comprising an amino acid sequence of SEQ ID NO:31. In some embodiments, the polynucleotide comprises a polynucleotide encoding (i) a polypeptide comprising an amino acid sequence of SEQ ID NO:29 and (ii) a polypeptide comprising an amino acid sequence of SEQ ID NO:31. In some embodiments, the polynucleotide comprises a polynucleotide encoding (i) a polypeptide comprising an amino acid sequence of SEQ ID NO: 110 and (ii) a polypeptide comprising an amino acid sequence of SEQ ID NO: 112. In some embodiments, the polynucleotide comprises a polynucleotide encoding (i) a polypeptide comprising an amino acid sequence of SEQ ID NO: 111 and (ii) a polypeptide comprising an amino acid sequence of SEQ ID NO: 112.

In some embodiments, a polynucleotide comprises a polynucleotide having a nucleotide sequence at least about 80% identical, at least about 85% identical, at least about 90% identical, at least about 95% identical, and in some embodiments, at least about 96%, 97%, 98%, or 99% identical to a polynucleotide encoding an amino acid sequence selected from the group consisting of: SEQ ID NOs:18-31, 91-108, 110-114, 119, and 229. Also provided is a polynucleotide that comprises a polynucleotide that hybridizes to a polynucleotide encoding an amino acid sequence selected from the group consisting of: SEQ ID NOs: 18-31, 91-108, 110-114, 119, and 229. In some embodiments, the hybridization is under conditions of high stringency as is known to those skilled in the art.

In some embodiments, a polynucleotide comprises a polynucleotide having a nucleotide sequence that encodes an amino acid sequence selected from the group consisting of: SEQ ID NOs:26-31. In some embodiments, a polynucleotide comprises a polynucleotide having a nucleotide sequence that encodes an amino acid sequence of SEQ ID NO:26 or SEQ ID NO:27. In some embodiments, a polynucleotide comprises a polynucleotide having a nucleotide sequence that encodes an amino acid sequence of SEQ ID NO:28 or SEQ ID NO:29. In some embodiments, a polynucleotide comprises a polynucleotide having a nucleotide sequence that encodes an amino acid sequence of SEQ ID NO:30 or SEQ ID NO:31.

In certain embodiments, the polynucleotide encodes a heavy chain variable region comprising heavy chain CDRs 1, 2, and 3 of an amino acid sequence set forth in SEQ ID NOs:18, 20, 21, 22, 23, or 24. In certain embodiments, (a) heavy chain CDR1 comprises GYTFTDFYMD (SEQ ID NO:7), heavy chain CDR2 comprises YIYPHNGGTTYNQNFTG (SEQ ID NO:8), and heavy chain CDR3 comprises RGGFDFDY (SEQ ID NO:9); (b) heavy chain CDR1 comprises GYTFTDFYMD (SEQ ID NO:7), heavy chain CDR2 comprises YIYPHNGGTTYNQQFTG (SEQ ID NO: 13), and heavy chain CDR3 comprises RGGFDFDY (SEQ ID NO:9); (c) heavy chain CDR1 comprises GYTFTDFYMD (SEQ ID NO:7), heavy chain CDR2 comprises YIYPHNAGTTYNQQFTG (SEQ ID NO: 14), and heavy chain CDR3 comprises RGGFDFDY (SEQ ID NO:9); (d) heavy chain CDR1 comprises GYTFTDFYMD (SEQ ID NO:7), heavy chain CDR2 comprises YIYPHNTGTTYNQQFTG (SEQ ID NO:15), and heavy chain CDR3 comprises RGGFDFDY (SEQ ID NO:9); (e) heavy chain CDR1 comprises GYTFTDFYMD (SEQ ID NO:7), heavy chain CDR2 comprises YIYPHEGGTTYNQQFTG (SEQ ID NO: 16), heavy chain CDR3 comprises RGGFDFDY (SEQ ID NO:9); or (f) heavy chain CDR1 comprises GYTFTDFYMD (SEQ ID NO:7), heavy chain CDR2 comprises YIYPHQGGTTYNQQFTG (SEQ ID NO: 17), and heavy chain CDR3 comprises RGGFDFDY (SEQ ID NO:9). In certain embodiments, the polynucleotide encodes a light chain variable region comprising light chain CDRs 1, 2, and 3 of an amino acid sequence set forth in SEQ ID NO: 19 or 25. In certain embodiments, light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO:12).

In certain embodiments, the polynucleotide encodes a heavy chain variable region comprising heavy chain CDRs 1, 2, and 3 of an amino acid sequence set forth in SEQ ID NO:91. In certain embodiments, heavy chain CDR1 comprises GYSFTGYNMN (SEQ ID NO:38), heavy chain CDR2 comprises NINPYYGSTNYNQKFKG (SEQ ID NO:39), and heavy chain CDR3 comprises GYYGGNYPFAY (SEQ ID NO:40). In certain embodiments, the polynucleotide encodes a light chain variable region comprising light chain CDRs 1, 2, and 3 of an amino acid sequence set forth in SEQ ID NO:92. In certain embodiments, light chain CDR1 comprises RASENIYSYLA (SEQ ID NO:41), light chain CDR2 comprises NAKTLAE (SEQ ID NO:42), and light chain CDR3 comprises QHYYGTPYT (SEQ ID NO:43).

In certain embodiments, the polynucleotide encodes a heavy chain variable region comprising heavy CDRs 1, 2, and 3 of an amino acid sequence set forth in SEQ ID NO:93. In certain embodiments, heavy chain CDR1 comprises GYSFTGYNMN (SEQ ID NO:38), heavy chain CDR2 comprises NINPYYDSTSYNQKFKG (SEQ ID NO:44), and heavy chain CDR3 comprises ENYDFVGFAY (SEQ ID NO:45). In certain embodiments, the polynucleotide encodes a light chain variable region comprising light chain CDRs 1, 2, and 3 of an amino acid sequence set forth in SEQ ID NO:94. In certain embodiments, light chain CDR1 comprises RASSSVSYMH (SEQ ID NO:46), light chain CDR2 comprises VTSNLAS (SEQ ID NO:47), and light chain CDR3 comprises QQWSTNPLT (SEQ ID NO:48).

In certain embodiments, the polynucleotide encodes a heavy chain variable region comprising heavy chain CDRs 1, 2, and 3 of an amino acid sequence set forth in SEQ ID NO:95. In certain embodiments, heavy chain CDR1 comprises GYSFTGYNMH (SEQ ID NO:49), heavy chain CDR2 comprises NINPYYGTTNSNQKFED (SEQ ID NO:50), and heavy chain CDR3 comprises GIYYYGTGYPYFDF (SEQ ID NO:51). In certain embodiments, the polynucleotide encodes a light chain variable region comprising light chain CDRs 1, 2, and 3 of an amino acid sequence set forth in SEQ ID NO:96. In certain embodiments, light chain CDR1 comprises RASQDINNYLN (SEQ ID NO:52), light chain CDR2 comprises YTSRLHS (SEQ ID NO:53), and light chain CDR3 comprises QQGITLPWT (SEQ ID NO:54).

In certain embodiments, the polynucleotide encodes a heavy chain variable region comprising heavy chain CDRs 1, 2, and 3 of an amino acid sequence set forth in SEQ ID NO:97. In certain embodiments, heavy chain CDR1 comprises GYTFTDYWIN (SEQ ID NO:55), heavy chain CDR2 comprises NIYPGSTSANYNEKFKS (SEQ ID NO:56), and heavy chain CDR3 comprises YGYDSWFAY (SEQ ID NO:57). In certain embodiments, the polynucleotide encodes a light chain variable region comprising light chain CDRs 1, 2, and 3 of an amino acid sequence set forth in SEQ ID NO:98. In certain embodiments, light chain CDR1 comprises KSTKSLLNSDGFTYLD (SEQ ID NO:58), light chain CDR2 comprises LVSNRFS (SEQ ID NO:59), and light chain CDR3 comprises FQSNYLPLT (SEQ ID NO:60).

In certain embodiments, the polynucleotide encodes a heavy chain variable region comprising heavy chain CDRs 1, 2, and 3 of an amino acid sequence set forth in SEQ ID NO:99. In certain embodiments, heavy chain CDR1 comprises GYAFNSCWMN (SEQ ID NO:61), heavy chain CDR2 comprises RIYPGDGDTNYNGKFKG (SEQ ID NO:62), and heavy chain CDR3 comprises EGRNYGYEDY (SEQ ID NO:63). In certain embodiments, the polynucleotide encodes a light chain variable region comprising light chain CDRs 1, 2, and 3 of an amino acid sequence set forth in SEQ ID NO:100. In certain embodiments, light chain CDR1 comprises KASQSVDYDGDSYMN (SEQ ID NO:64), light chain CDR2 comprises AASDLES (SEQ ID NO:65), and light chain CDR3 comprises QQANEDPRT (SEQ ID NO:66).

In certain embodiments, the polynucleotide encodes a heavy chain variable region comprising heavy chain CDRs 1, 2, and 3 of an amino acid sequence set forth in SEQ ID NO:101. In certain embodiments, heavy chain CDR1 comprises GFTFSNYAMS (SEQ ID NO:67), heavy chain CDR2 comprises QTISSGGRYTYYPDSVKG (SEQ ID NO:68), and heavy chain CDR3 comprises RYYGNSYWYFDV (SEQ ID NO:69). In certain embodiments, the polynucleotide encodes a light chain variable region comprising light chain CDRs 1, 2, and 3 of an amino acid sequence set forth in SEQ ID NO:102. In certain embodiments, light chain CDR1 comprises KSSQSLLNSGNQKHYLT (SEQ ID NO:70), light chain CDR2 comprises GASTRGS (SEQ ID NO:71), and light chain CDR3 comprises QNDHSYPYT (SEQ ID NO:72).

In certain embodiments, the polynucleotide encodes a heavy chain variable region comprising heavy chain CDRs 1, 2, and 3 of an amino acid sequence set forth in SEQ ID NO:103. In certain embodiments, heavy chain CDR1 comprises GFTFSSYTMS (SEQ ID NO:73), heavy chain CDR2 comprises YISSGGGTTYYPDTVKG (SEQ ID NO:74), and heavy chain CDR3 comprises RYYRGSSLWYFDV (SEQ ID NO:75). In certain embodiments, the polynucleotide encodes a light chain variable region comprising light chain CDRs 1, 2, and 3 of an amino acid sequence set forth in SEQ ID NO: 104. In certain embodiments, light chain CDR1 comprises KSSQSLFNSGSQKNFLT (SEQ ID NO:76), light chain CDR2 comprises WASTRES (SEQ ID NO:77), and light chain CDR3 comprises QNDYSYPLT (SEQ ID NO:78).

In certain embodiments, the polynucleotide encodes a heavy chain variable region comprising heavy chain CDRs 1, 2, and 3 of an amino acid sequence set forth in SEQ ID NO:105. In certain embodiments, heavy chain CDR1 comprises GYSITSGYSLH (SEQ ID NO:79), heavy chain CDR2 comprises YIHYSGSTNYNPSLKS (SEQ ID NO:80), and heavy chain CDR3 comprises AWDYLDY (SEQ ID NO:81). In certain embodiments, the polynucleotide encodes a light chain variable region comprising light chain CDRs 1, 2, and 3 of an amino acid sequence set forth in SEQ ID NO: 106. In certain embodiments, light chain CDR1 comprises RASENIYSQLA (SEQ ID NO:82), light chain CDR2 comprises DAKTLAE (SEQ ID NO:83), and light chain CDR3 comprises HHHFGILYT (SEQID NO:84).

In certain embodiments, the polynucleotide encodes a heavy chain variable region comprising heavy chain CDRs 1, 2, and 3 of an amino acid sequence set forth in SEQ ID NO:107. In certain embodiments, heavy chain CDR1 comprises GYSITSGYYWN (SEQ ID NO:85), heavy chain CDR2 comprises YIRYDGSNNYNPSLKN (SEQ ID NO:86), and heavy chain CDR3 comprises HYGYDGGAFDF (SEQ ID NO:87). In certain embodiments, the polynucleotide encodes a light chain variable region comprising light chain CDRs 1, 2, and 3 of an amino acid sequence set forth in SEQ ID NO:108. In certain embodiments, light chain CDR1 comprises RTSENIYNYLV (SEQ ID NO:88), light chain CDR2 comprises NAKTLEE (SEQ ID NO:89), and light chain CDR3 comprises QHHYGTPFT (SEQ ID NO:90).

In certain embodiments, the polynucleotide encodes a dsscFv comprising a heavy chain variable region and a light chain variable region, wherein the heavy chain variable region comprises an amino acid sequence set forth in SEQ ID NO:110 or SEQ ID NO: 111, and the light chain variable region comprises an amino acid sequence set forth in SEQ ID NO: 112. In certain embodiments, the dsscFv comprises an amino acid sequence of SEQ ID NO: 113 or SEQ ID NO: 114.

In some embodiments, a polynucleotide comprises the coding sequence for a polypeptide (e.g., an antibody) fused in the same reading frame to a polynucleotide which aids in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine tag (SEQ ID NO:231) (HIS-tag) that allows for efficient purification of the polypeptide fused to the marker. In some embodiments, a marker sequence is a hemagglutinin (HA) tag derived from the influenza hemagglutinin protein when a mammalian host (e.g., COS-7 cells) is used. In some embodiments, the marker sequence is a FLAG™ tag. In some embodiments, a marker may be used in conjunction with other markers or tags.

The present disclosure also provides variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide sequence encoding a polypeptide described herein.

As used herein, the phrase "a polynucleotide having a nucleotide sequence at least about 95% identical to a polynucleotide sequence" is intended to mean that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). In some embodiments, a polynucleotide variant comprises one or more mutated codons comprising one or more (e.g., 1, 2, or 3) substitutions to the codon that change the amino acid encoded by that codon. Methods for introducing one or more substitutions into a codon are known in the art, such as, e.g., PCR mutagenesis and site-directed mutagenesis. Polynucleotide variants can be produced for a variety of reasons, for example, to optimize codon expression for a particular host (e.g., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide is isolated. In some embodiments, a polynucleotide is substantially pure.

Vectors and cells comprising each and every one of the polynucleotides described herein are also provided. In some embodiments, an expression vector comprises a polynucleotide molecule encoding a C3-binding agent described herein. In some embodiments, an expression vector comprises a polynucleotide molecule encoding a polypeptide that is part of a C3-binding agent described herein. In some embodiments, a host cell comprises an expression vector comprising a polynucleotide molecule encoding a C3-binding agent described herein. In some embodiments, a host cell comprises an expression vector comprising a polynucleotide molecule encoding a polypeptide that is part of a C3-binding agent described herein. In some embodiments, a host cell comprises a polynucleotide molecule encoding a C3-binding agent described herein.

IV. Methods of Making Binding Agents

The disclosure provides a method for making the C3-binding agents (e.g., antibodies) described herein. In certain embodiments in which the C3-binding agent is an antibody, the method involves providing a cell comprising a heavy chain and/or light chain of the C3-binding agent, incubating the cell under conditions that permit the expression of the antibody and isolating the antibody. In certain embodiments, the cell comprises one or more vectors (e.g., one or more vectors described herein) encoding the heavy chain and the light chain. For example, in certain embodiments, the cell comprises a first vector encoding the heavy chain and a second vector encoding the light chain. In other embodiments, the cell comprises a vector encoding the heavy chain and the light chain. In certain embodiments, the cell comprises one or more polynucleotides (e.g., one or more polynucleotides described herein) encoding the heavy chain and the light chain. For example, in certain embodiments, the cell comprises a first polynucleotide encoding the heavy chain and a second polynucleotide encoding the light chain. In other embodiments, the cell comprises a polynucleotide encoding the heavy chain and the light chain. In some embodiments, the method comprises purifying the antibody. In certain embodiments, the cell is a CHO cell. In other embodiments, the cell is a 293 cell. In certain embodiments, the cell is a bacterial cell (e.g., E. coli).

In certain embodiments in which the C3-binding agent is an scFv (e.g., a dsscFv), the method involves providing a cell comprising the scFv (e.g., a dsscFv) of the C3-binding agent, incubating the cell under conditions that permit the expression of the scFv and isolating the scFv. In certain embodiments, the cell comprises a vector (e.g., a vector described herein) encoding the scFv. In certain embodiments, the cell comprises a polynucleotide (e.g., a polynucleotide described herein) encoding the scFv. In some embodiments, the method comprises purifying the antibody. In certain embodiments, the cell is a bacterial cell (e.g., E. coli). In certain embodiments, the cell is a yeast cell (e.g., Pichiapastoris). In certain embodiments, the cell is a CHO cell. In other embodiments, the cell is a 293 cell.

V. Methods of Use and Pharmaceutical Compositions

The C3-binding agents (e.g., antibodies) of the disclosure are useful in a variety of applications including, but not limited to, therapeutic treatment methods, such as treatment of diseases or disorders associated with complement activation. In some embodiments, a C3-binding agent described herein is useful in methods for inhibiting complement activation. In some embodiments, a C3-binding agent described herein is useful in methods for inhibiting C3 activity. In some embodiments, a C3-binding agent described herein is useful in methods for treating an eye disorder. In some embodiments, a C3-binding agent described herein is useful in methods for inhibiting or suppressing drusen formation in an eye. In some embodiments, a C3-binding agent described herein is useful in methods for treating macular degeneration. In some embodiments, a C3-binding agent described herein is useful in methods for treating a disorder associated with macular degeneration. In some embodiments, a C3-binding agent described herein is useful in methods for treating age-related macular degeneration (AMD). In some embodiments, a C3-binding agent described herein is useful in methods for treating dry AMD. In some embodiments, a C3-binding agent described herein is useful in methods for treating early AMD. In some embodiments, a C3-binding agent described herein is useful in methods for treating intermediate AMD. In some embodiments, a C3-binding agent described herein is useful in methods for treating advanced dry AMD/geographic atrophy. The terms "advanced dry AMD" and "geographic atrophy" are used interchangeably herein.

In some embodiments, a method of inhibiting complement activation in an eye of a subject (e.g., a human) comprises administering to the subject a therapeutically effective amount of a C3-binding agent described herein. In some embodiments, a method of inhibiting complement activation in an eye of a subject (e.g., a human) comprises administering to the subject a therapeutically effective amount of an anti-C3 antibody described herein. In some embodiments, a method of inhibiting C3 activity in an eye of a subject (e.g., a human) comprises administering to the subject a therapeutically effective amount of a C3-binding agent described herein. In some embodiments, a method of inhibiting C3 activity in an eye of a subject (e.g., a human) comprises administering to the subject a therapeutically effective amount of an anti-C3 antibody described herein. In some embodiments of the methods described herein the C3-binding agent is administered to an eye of the subject. In some embodiments of the methods described herein the anti-C3 antibody is administered to an eye of the subject.

In some embodiments, a method of treating an eye disorder in a subject (e.g., a human) comprises administering to the subject a therapeutically effective amount of a C3-binding agent described herein. In some embodiments, a method of treating an eye disorder in a subject (e.g., a human) comprises administering to the subject a therapeutically effective amount of an anti-C3 antibody described herein. In some embodiments, the eye disorder is selected from the group consisting of: macular degeneration (maculopathy), age-related macular degeneration (AMD), diabetic retinopathy, retinopathy of prematurity, macular dystrophy, retinal dystrophy, uveitis, keratitis, scleritis, retinitis pigmentosa, choroidal neovascularization, retinal neovascularization, and ocular inflammation. In some embodiments, the eye disorder is macular degeneration. In some embodiments, the eye disorder is AMD. In some embodiments, the eye disorder is wet AMD. In some embodiments, the eye disorder is dry AMD. In some embodiments, the eye disorder is early AMD. In some embodiments, the eye disorder is intermediate AMD. In some embodiments, the eye disorder is geographic atrophy.

In the early stages of AMD, the disease is characterized by the presence of drusen, which can manifest with or without retinal pigment epithelium (RPE) irregularities. In the early stages when drusen are small and/or few, vision is generally not affected. As drusen enlarge and multiply in number, patients report that central vision is less sharp. Geographic atrophy (GA) is the advanced form of dry AMD. GA is characterized by the degeneration of RPE, wherein the degeneration of the RPE leads to the death of photoreceptor cells (the rods and cones). Thus, a patient has a spot or area (a "continent") of atrophy surrounded by a "sea" of healthy or healthier-looking retina. Doctors can measure the area of atrophy (often referred to as "GA lesion area") and estimate the loss of visual function. Changes in the GA lesion area can be used to follow progression of the disease over time.

In some embodiments, a method of treating AMD in a subject (e.g., a human) comprises administering to the subject a therapeutically effective amount of a C3-binding agent described herein. In some embodiments, a method of treating AMD in a subject (e.g., a human) comprises administering to the subject a therapeutically effective amount of an antibody that specifically binds C3 (e.g., human C3) described herein. In some embodiments, the AMD is dry AMD. In some embodiments, the AMD is early AMD. In some embodiments, the AMD is intermediate AMD. In some embodiments, the AMD is GA. In some embodiments, a method of treating geographic atrophy in a subject (e.g., a human) comprises administering to the subject a therapeutically effective amount of a C3-binding agent described herein. In some embodiments, a method of treating geographic atrophy in a subject (e.g., a human) comprises administering to the subject a therapeutically effective amount of an antibody that specifically binds C3 described herein.

In some embodiments, a method of inhibiting or suppressing drusen formation in an eye of a subject (e.g., a human) comprises administering to the subject a therapeutically effective amount of a C3-binding agent described herein. In some embodiments, a method of inhibiting or suppressing drusen formation in an eye of a subject (e.g., a human) comprises administering to the subject a therapeutically effective amount of an anti-C3 antibody described herein.

In some embodiments, a method of inhibiting or suppressing retinal pigment epithelium atrophy in an eye of a subject (e.g., a human) comprises administering to the subject a therapeutically effective amount of C3-binding agent described herein. In some embodiments, a method of inhibiting or suppressing retinal pigment epithelium atrophy in an eye of a subject (e.g., a human) comprises administering to the subject a therapeutically effective amount of an anti-C3 antibody described herein.

In some embodiments, a method of treating a subject (e.g., a human) at risk of developing AMD comprises administering to the subject a therapeutically effective amount of a C3-binding agent described herein. In some embodiments, a method of treating a subject (e.g. a human) at risk of developing AMD comprises administering to the subject a therapeutically effective amount of an anti-C3 antibody described herein. In some embodiments, a method of treating a subject (e.g., a human) at risk of developing geographic atrophy comprises administering to the subject a therapeutically effective amount of a C3-binding agent described herein. In some embodiments, a method of treating a subject (e.g., a human) at risk of developing geographic atrophy comprises administering to the subject a therapeutically effective amount of an anti-C3 antibody described herein.

In some embodiments, a method of slowing down or reducing the progression of AMD in a subject (e.g., a human) comprises administering to the subject a therapeutically effective amount of a C3-binding agent described herein. In some embodiments, a method of slowing down or reducing the progression of AMD in a subject (e.g., a human) comprises administering to the subject a therapeutically effective amount of an anti-C3 antibody described herein. In some embodiments, the method slows down or reduces progression of early AMD to intermediate AMD. In some embodiments, the method slows down or reduces progression of intermediate AMD to geographic atrophy. In some embodiments, a method of slowing down or reducing the progression of geographic atrophy in a subject (e.g., a human) comprises administering to the subject a C3-binding agent described herein. In some embodiments, a method of slowing down or reducing the progression of geographic atrophy in a subject (e.g., a human) comprises administering to the subject a therapeutically effective amount of an anti-C3 antibody described herein.

In some embodiments of the methods described herein, a subject (e.g., a human) has AMD or GA. In some embodiments of the methods described herein, a subject (e.g., a human) has been diagnosed with AMD or GA. The criteria for diagnosis of AMD and GA differ across grading systems and may depend upon the imaging modalities that are used. In some embodiments, the criteria for AMD comprises: (1) No AMD—no or a few small (<63 µm in diameter) drusen; (2) Early AMD—intermediate-sized (63-124 µm in diameter) drusen; (3) Intermediate AMD—intermediate-sized drusen and pigmentary changes or at least 1 large (>125 m) drusen; (4) Late AMD (dry)—geographic atrophy or Late AMD (wet)—CNV with signs including subretinal hemorrhage, serous retinal or retinal pigment epithelium detachments, lipid exudates, or fibrovascular scarring. In some embodiments, the criteria for GA comprises an area of pallor in the fundus with visibility of the underlying choroidal blood vessels and sharply defined borders, occupying (1) a diameter >175 µm; (2) a diameter >250 µm; or (3) a diameter of at least 433 µm. Currently, there is no consensus on the minimum diameter for the diagnosis of GA.

There are a number of imaging modalities used by medical practitioners skilled in the art, including but not limited to, color fundus photography (CFP), fundus autofluorescence (FAF), optical coherence tomography (OCT), fluorescein angiography (FA), and indocyanine green angiography (ICGA). Imaging modalities allow for the direct measurement and quantification of GA lesion area.

Thus, in some embodiments, a method of treating geographic atrophy in a subject (e.g., a human) comprises administering to the subject a therapeutically effective amount of an antibody that specifically binds C3 described herein, wherein the treatment reduces growth of the GA lesion area. In some embodiments, the GA lesion area is measured by color fundus photography, fluorescein angiography, and/or optical coherence tomography. In some embodiments, the GA lesion is measured prior to treatment with an anti-C3 antibody and measured again after treatment. In some embodiments, growth of the GA lesion area is reduced by about 20%, about 30%, about 40%, about 50%, about 60%, about 70%, or about 80% or better. In some embodiments, growth of the GA lesion area is reduced by at least 25%. In some embodiments, growth of the GA lesion is reduced by at least 40%. In some embodiments, growth of the GA lesion is reduced by at least 50%. In some embodiments, the GA lesion area is measured about 6 months after treatment, about 1 year after treatment, about 18 months after treatment, and/or about 2 years after treatment. In some embodiments, the GA lesion area is measured every time the C3-binding agent is administered. In some embodiments, the GA lesion area is measured at time points chosen by the medical practitioner.

In some embodiments of the methods described herein, the C3-binding agent (e.g., an anti-C3 antibody) comprises a heavy chain CDR1, CDR2, and CDR3 and a light chain CDR1, CDR2, and CDR3 of antibody 38G10. In some embodiments of the methods described herein, the C3-binding agent (e.g., an anti-C3 antibody) comprises a heavy chain CDR1, CDR2, and CDR3 and a light chain CDR1, CDR2, and CDR3 of antibody Hz38G10. In some embodiments of the methods described herein, the C3-binding agent (e.g., an anti-C3 antibody) comprises a heavy chain CDR1, CDR2, and CDR3 and a light chain CDR1, CDR2, and CDR3 of antibody Hz38G10(G56A). In some embodiments of the methods described herein, the C3-binding agent (e.g., an anti-C3 antibody) comprises a heavy chain CDR1, CDR2, and CDR3 and a light chain CDR1, CDR2, and CDR3 of antibody Hz38G10(G56T). In some embodiments of the methods described herein, the C3-binding agent (e.g. anti-C3 antibody) comprises a heavy chain CDR1, CDR2, and CDR3 and a light chain CDR1, CDR2, and CDR3 of antibody Hz38G10(N55E). In some embodiments of the methods described herein, the C3-binding agent (e.g. anti-C3 antibody) comprises a heavy chain CDR1, CDR2, and CDR3 and a light chain CDR1, CDR2, and CDR3 of antibody Hz38G10(N55Q). In some embodiments of the methods described herein, the C3-binding agent (e.g. anti-C3 antibody) comprises a heavy chain CDR1, CDR2, and CDR3 and a light chain CDR1, CDR2, and CDR3 of antibody 3D8. In some embodiments of the methods described herein, the C3-binding agent (e.g. anti-C3 antibody) comprises a heavy chain CDR1, CDR2, and CDR3 and a light chain CDR1, CDR2, and CDR3 of antibody 3G8. In some embodiments of the methods described herein, the C3-binding agent (e.g. anti-C3 antibody) comprises a heavy chain CDR1, CDR2, and CDR3 and a light chain CDR1, CDR2, and CDR3 of antibody 15C12. In some embodiments of the methods described herein, the C3-binding agent (e.g. anti-C3 antibody) comprises a heavy chain CDR1, CDR2, and CDR3 and a light chain CDR1, CDR2, and CDR3 of antibody 27A8. In some embodiments of the methods described herein, the C3-binding agent (e.g. anti-C3 antibody) comprises a heavy chain CDR1, CDR2, and CDR3 and a light chain CDR1, CDR2, and CDR3 of antibody 28C3. In some embodiments of the methods described herein, the C3-binding agent (e.g. anti-C3 antibody) comprises a heavy chain CDR1, CDR2, and CDR3 and a light chain CDR1, CDR2, and CDR3 of antibody 38F5. In some embodiments of the methods described herein, the C3-binding agent (e.g. anti-C3 antibody) comprises a heavy chain CDR1, CDR2, and CDR3 and a light chain CDR1, CDR2, and CDR3 of antibody 62B11. In some embodiments of the methods described herein, the C3-binding agent (e.g. anti-C3 antibody) comprises a heavy chain CDR1, CDR2, and CDR3 and a light chain CDR1, CDR2, and CDR3 of antibody 62F2. In some embodiments of the methods described herein, the C3-binding agent (e.g. anti-C3 antibody) comprises a heavy chain CDR1, CDR2, and CDR3 and a light chain CDR1, CDR2, and CDR3 of antibody 63A3.

In some embodiments of the methods described herein, the C3-binding agent is a humanized anti-C3 antibody having the above specified CDRs.

In some embodiments of the methods described herein, the anti-C3 antibody comprises a heavy chain CDR1 comprising GYTFTDFYMD (SEQ ID NO:7); a heavy chain CDR2 comprising YIYPHNGGTTYNQQFTG (SEQ ID NO:13), YIYPHNAGTTYNQQFTG (SEQ ID NO: 14), YIYPHNTGTTYNQQFTG (SEQ ID NO: 15), YIYPHEGGTTYNQQFTG (SEQ ID NO: 16), or YIYPHQGGTTYNQQFTG (SEQ ID NO: 17); and a heavy chain CDR3 comprising RGGFDFDY (SEQ ID NO:9), and a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments of the methods described herein, the anti-C3 antibody comprises a heavy chain CDR1 comprising GYTFTDFYMD (SEQ ID NO:7); a heavy chain CDR2 comprising YIYPHNGGTTYNQQFTG (SEQ ID NO: 13), a heavy chain CDR3 comprising RGGFDFDY (SEQ ID NO:9), a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments of the methods described herein, the anti-C3 antibody comprises a heavy chain CDR1 comprising GYTFTDFYMD (SEQ ID NO:7); a heavy chain CDR2 comprising YIYPHNAGTTYNQQFTG (SEQ ID NO: 14); a heavy chain CDR3 comprising RGGFDFDY (SEQ ID NO:9), a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12). In some embodiments of the methods described herein, the anti-C3 antibody comprises a heavy chain CDR1 comprising GYTFTDFYMD (SEQ ID NO:7); a heavy chain CDR2 comprising YIYPHNTGTTYNQQFTG (SEQ ID NO: 15); a heavy chain CDR3 comprising RGGFDFDY (SEQ ID NO:9), a light chain CDR1 comprising KASENVDTYVS (SEQ ID NO: 10); a light chain CDR2 comprising GASNRYT (SEQ ID NO: 11); and a light chain CDR3 comprising GQSHSYPLT (SEQ ID NO: 12).

In some embodiments of the methods described herein, the anti-C3 antibody comprises: (a) a heavy chain variable region of SEQ ID NO:20, SEQ ID NO:21, SEQ ID NO:22, SEQ ID NO:23, or SEQ ID NO:24; and (b) a light chain variable region of SEQ ID NO:25. In some embodiments of the methods described herein, the anti-C3 antibody comprises: (a) a heavy chain variable region of SEQ ID NO:20 and (b) a light chain variable region of SEQ ID NO:25. In some embodiments of the methods described herein, the anti-C3 antibody comprises: (a) a heavy chain variable region of SEQ ID NO:21 and (b) a light chain variable region of SEQ ID NO:25. In some embodiments of the methods described herein, the anti-C3 antibody comprises: (a) a heavy chain variable region of SEQ ID NO:22 and (b) a light chain variable region of SEQ ID NO:25. In some embodiments of the methods described herein, the anti-C3 antibody comprises: (a) a heavy chain variable region of SEQ ID NO:23 and (b) a light chain variable region of SEQ ID NO:25. In some embodiments of the methods described herein, the anti-C3 antibody comprises: (a) a heavy chain variable region of SEQ ID NO:24 and (b) a light chain variable region of SEQ ID NO:25. In some embodiments of the methods described herein, the anti-C3 antibody is Hz38G10. In some embodiments of the methods described herein, the anti-C3 antibody is Hz38G10(G56A). In some embodiments of the methods described herein, the anti-C3 antibody is Hz38G10(G56T). In some embodiments of the methods described herein, the anti-C3 antibody is Hz38G10(N55E). In some embodiments of the methods described herein, the anti-C3 antibody is Hz38G10(N55Q).

In some embodiments of the methods described herein, the anti-C3 antibody comprises a polypeptide of SEQ ID NO:27. In some embodiments of the methods described herein, the anti-C3 antibody comprises a polypeptide of SEQ ID NO:29. In some embodiments of the methods described herein, the anti-C3 antibody comprises a polypeptide of SEQ ID NO:31. In some embodiments of the methods described herein, the anti-C3 antibody comprises a polypeptide of SEQ ID NO:27 and a polypeptide of SEQ ID NO:31. In some embodiments of the methods described herein, the anti-C3 antibody comprises a polypeptide of SEQ ID NO:29 and a polypeptide of SEQ ID NO:31.

In some embodiments of the methods described herein, the anti-C3 antibody comprises a polypeptide of SEQ ID NO: 110 and a polypeptide of SEQ ID NO: 112. In some embodiments of the methods described herein, the anti-C3 antibody comprises a polypeptide of SEQ ID NO: 111 and a polypeptide of SEQ ID NO: 112. In some embodiments of the methods described herein, the anti-C3 antibody comprises a polypeptide of SEQ ID NO: 113. In some embodiments of the methods described herein, the anti-C3 antibody comprises a polypeptide of SEQ ID NO:114. In some embodiments of the methods described herein, the anti-C3 antibody comprises a polypeptide of SEQ ID NO: 119. In some embodiments of the methods described herein, the anti-C3 antibody comprises a polypeptide of SEQ ID NO:229.

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:18, and the light chain variable region comprises light chain CDRs 1, 2, and 3 of an amino acid sequence set forth in SEQ ID NO: 19. In certain embodiments, heavy chain CDR1 comprises GYTFTDFYMD (SEQ ID NO:7), heavy chain CDR2 comprises YIYPHNGGTTYNQNFTG (SEQ ID NO:8), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:20, and the light chain variable region comprises light chain CDRs 1, 2, and 3 of an amino acid sequence set forth in SEQ ID NO:25. In certain embodiments, chain CDR1 comprises GYTFTDFYMD (SEQ ID NO:7), heavy chain CDR2 comprises YIYPHNGGTTYNQQFTG (SEQ ID NO: 13), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:21, and the light chain variable region comprises light chain CDRs 1, 2, and 3 of an amino acid sequence set forth in SEQ ID NO:25. In certain embodiments, heavy chain CDR1 comprises GYTFTDFYMD (SEQ ID NO:7), heavy chain CDR2 comprises YIYPHNAGTTYNQQFTG (SEQ ID NO: 14), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:22, and the light chain variable region comprises light chain CDRs 1, 2, and 3 of an amino acid sequence set forth in SEQ ID NO:25. In certain embodiments, heavy chain CDR1 comprises GYTFTDFYMD (SEQ ID NO:7), heavy chain CDR2 comprises YIYPHNTGTTYNQQFTG (SEQ ID NO: 15), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:23, and the light chain variable region comprises light chain CDRs 1, 2, and 3 of an amino acid sequence set forth in SEQ ID NO:25. In certain embodiments, heavy chain CDR1 comprises GYTFTDFYMD (SEQ ID NO:7), heavy chain CDR2 comprises YIYPHEGGTTYNQQFTG (SEQ ID NO: 16), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:24, and the light chain variable region comprises light chain CDRs 1, 2, and 3 of an amino acid sequence set forth in SEQ ID NO:25. In certain embodiments, heavy chain CDR1 comprises GYTFTDFYMD (SEQ ID NO:7), heavy chain CDR2 comprises YIYPHQGGTTYNQQFTG (SEQ ID NO: 17), heavy chain CDR3 comprises RGGFDFDY (SEQ ID NO:9), light chain CDR1 comprises KASENVDTYVS (SEQ ID NO: 10), light chain CDR2 comprises GASNRYT (SEQ ID NO: 11), and light chain CDR3 comprises GQSHSYPLT (SEQ ID NO: 12).

In certain embodiments of the methods described herein, the C3-binding agent comprises which comprises a heavy chain variable region and a light chain variable region, wherein the heavy chain variable region comprises heavy chain CDRs 1, 2, and 3 of an amino acid sequence set forth in SEQ ID NO:91, and the light chain variable region comprises light chain CDRs 1, 2, and 3 of an amino acid sequence set forth in SEQ ID NO:92. In certain embodiments, heavy chain CDR1 comprises GYSFTGYNMN (SEQ ID NO:38), heavy chain CDR2 comprises NINPYYG-STNYNQKFKG (SEQ ID NO:39), heavy chain CDR3 comprises GYYGGNYPFAY (SEQ ID NO:40), light chain CDR1 comprises RASENIYSYLA (SEQ ID NO:41), light chain CDR2 comprises NAKTLAE (SEQ ID NO: 42), and light chain CDR3 comprises QHYYGTPYT (SEQ ID NO:43).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:93, and the light chain variable region comprises light chain CDRs 1, 2, and 3 of an amino acid sequence set forth in SEQ ID NO:94. In certain embodiments, heavy chain CDR1 comprises GYSFTGYNMN (SEQ ID NO:38), heavy chain CDR2 comprises NINPYYDSTSYNQKFKG (SEQ ID NO:44), heavy chain CDR3 comprises ENYDFVGFAY (SEQ ID NO:45), light chain CDR1 comprises RASSSVSYMH (SEQ ID NO:46), light chain CDR2 comprises VTSNLAS (SEQ ID NO:47), and light chain CDR3 comprises QQWSTNPLT (SEQ ID NO:48).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:95, and the light chain variable region comprises light chain CDRs 1, 2, and 3 of an amino acid sequence set forth in SEQ ID NO:96. In certain embodiments, heavy chain CDR1 comprises GYSFTGYNMH (SEQ ID NO:49), heavy chain CDR2 comprises NINPYYGTTNSNQKFED (SEQ ID NO:50), heavy chain CDR3 comprises GIYYYGTGY-PYFDF (SEQ ID NO:51), light chain CDR1 comprises RASQDINNYLN (SEQ ID NO:52), light chain CDR2 comprises YTSRLHS (SEQ ID NO:53), and light chain CDR3 comprises QQGITLPWT (SEQ ID NO:54).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:97, and the light chain variable region comprises light chain CDRs 1, 2, and 3 of an amino acid sequence set forth in SEQ ID NO:98. In certain embodiments, heavy chain CDR1 comprises GYTFTDYWIN (SEQ ID NO:55), heavy chain CDR2 comprises NIYPGSTSANYNEKFKS (SEQ ID NO:56), heavy chain CDR3 comprises YGYDSWFAY (SEQ ID NO:57), light chain CDR1 comprises KSTKSLLNSDGFTYLD (SEQ ID NO:58), light chain CDR2 comprises LVSNRFS (SEQ ID NO:59), and light chain CDR3 comprises FQSNYLPLT (SEQ ID NO:60).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:99, and the light chain variable region comprises light chain CDRs 1, 2, and 3 of an amino acid sequence set forth in SEQ ID NO: 100. In certain embodiments, heavy chain CDR1 comprises GYAFNSCWMN (SEQ ID NO:61), heavy chain CDR2 comprises RIYPGDGDTNYNGKFKG (SEQ ID NO:62), heavy chain CDR3 comprises EGRNYGYEDY (SEQ ID NO:63), light chain CDR1 comprises KASQSVDYDGDSYMN (SEQ ID NO:64), light chain CDR2 comprises AASDLES (SEQ ID NO:65), and light chain CDR3 comprises QQANEDPRT (SEQ ID NO:66).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:101, and the light chain variable region comprises light chain CDRs 1, 2, and 3 of an amino acid sequence set forth in SEQ ID NO:102. In certain embodiments, heavy chain CDR1 comprises GFTFSNYAMS (SEQ ID NO:67), heavy chain CDR2 comprises QTISSGGRYTYYPDSVKG (SEQ ID NO:68), heavy chain CDR3 comprises RYYGNSYWYFDV (SEQ ID NO:69), light chain CDR1 comprises KSSQSLLNSGNQKHYLT (SEQ ID NO:70), light chain CDR2 comprises GASTRGS (SEQ ID NO:71), and light chain CDR3 comprises QNDHSYPYT (SEQ ID NO:72).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:103, and the light chain variable region comprises light chain CDRs 1, 2, and 3 of an amino acid sequence set forth in SEQ ID NO:104. In certain embodiments, heavy chain CDR1 comprises GFTFSSYTMS (SEQ ID NO:73), heavy chain CDR2 comprises YISSGGGTTYYPDTVKG (SEQ ID NO:74), heavy chain CDR3 comprises RYYRGSSLWYFDV (SEQ ID NO:75), light chain CDR1 comprises KSSQSLFNSGSQKNFLT (SEQ ID NO:76), light chain CDR2 comprises WASTRES (SEQ ID NO:77), and light chain CDR3 comprises QNDYSYPLT (SEQ ID NO:78).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:105, and the light chain variable region comprises light chain CDRs 1, 2, and 3 of an amino acid sequence set forth in SEQ ID NO:106. In certain embodiments, heavy chain CDR1 comprises GYSITSGYSLH (SEQ ID NO:79), heavy chain CDR2 comprises YIHYSGSTNYNPSLKS (SEQ ID NO:80), heavy chain CDR3 comprises AWDYLDY (SEQ ID NO:81), light chain CDR1 comprises RASENIYSQLA (SEQ ID NO:82), light chain CDR2 comprises DAKTLAE (SEQ ID NO:83), and light chain CDR3 comprises HHHFGILYT (SEQID NO:84).

In certain embodiments of the methods described herein, the C3-binding agent comprises a heavy chain variable region and a light chain variable region, wherein the heavy chain variable region comprises heavy chain CDRs 1, 2, and 3 of an amino acid sequence set forth in SEQ ID NO:107, and the light chain variable region comprises light chain CDRs 1, 2, and 3 of an amino acid sequence set forth in SEQ ID NO:108. In certain embodiments, heavy chain CDR1 comprises GYSITSGYYWN (SEQ ID NO:85), heavy chain CDR2 comprises YIRYDGSNNYNPSLKN (SEQ ID NO:86), heavy chain CDR3 comprises HYGYDGGAFDF (SEQ ID NO:87), light chain CDR1 comprises RTSENIY-NYLV (SEQ ID NO:88), light chain CDR2 comprises NAKTLEE (SEQ ID NO:89), and light chain CDR3 comprises QHHYGTPFT (SEQ ID NO:90).

In certain embodiments of the methods described herein, the C3-binding agent comprises a dsscFv comprising a heavy chain variable region and a light chain variable region. In certain embodiments, the heavy chain variable region comprises an amino acid sequence set forth in SEQ ID NO:110 or SEQ ID NO:111, and the light chain variable region comprises an amino acid sequence set forth in SEQ ID NO:112. In certain embodiments, the dsscFv comprises an amino acid sequence of SEQ ID NO:113. In certain embodiments, the dsscFv comprises an amino acid sequence of SEQ ID NO:114. In certain embodiments, the dsscFv comprises an amino acid sequence of SEQ ID NO:119. In certain embodiments, the dsscFv comprises an amino acid sequence of SEQ ID NO:229.

In some embodiments of the methods described herein, a method comprises administering a C3-binding agent (e.g., an antibody) described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments, the combination of a C3-binding agent (e.g., an antibody) described herein and at least one additional therapeutic agent results in additive or synergistic results. In some embodiments, the combination therapy results in an increase in the therapeutic index of the C3-binding agent. In some embodiments, the combination therapy results in an increase in the therapeutic index of the additional therapeutic agent(s). In some embodiments, the combination therapy results in a decrease in the toxicity and/or side effects of the C3-binding agent. In some embodiments, the combination therapy results in a decrease in the toxicity and/or side effects of the additional therapeutic agent(s).

In some embodiments, a combination treatment comprises one additional therapeutic agent or two or more additional therapeutic agents. In some embodiments, treatment with a C3-binding agent can occur prior to, concurrently with, or subsequent to administration of the additional therapeutic agents. In some embodiments, combined administration includes co-administration, either in a single pharmaceutical formulation or using separate formulations, or consecutive administration in either order but generally within a time period such that all active agents can exert their biological activities. In some embodiments, preparation of agents and/or dosing schedules for additional therapeutic agents are according to manufacturers' instructions or as determined empirically by the skilled practitioner.

In some embodiments of the methods described herein, a C3-binding agent (e.g., an antibody) is administered to a subject (e.g., a human) as part of a combination therapy. In some embodiments, the combination therapy comprises photodynamic therapy. In some embodiments, the combination therapy comprises photodynamic therapy with verteporfin. In some embodiments, a C3-binding agent (e.g., an antibody) is administered to a subject (e.g., a human), wherein the subject is administered one or more additional therapeutic agents. In some embodiments, an additional therapeutic agent is compstatin or an analog or derivative of compstatin (e.g., POT-4; APL-2). In some embodiments, an additional therapeutic agent is a C5 inhibitor. In some embodiments, a C5 inhibitor is selected from the group including, but not limited to, eculizumab, LFG316, or Zimura™ (anti-05 aptamer). In some embodiments, an additional therapeutic agent is a properdin inhibitor (e.g., an anti-properdin antibody). In some embodiments, an additional therapeutic agent is a Factor D inhibitor. In some embodiments, a Factor D inhibitor is an anti-Factor D antibody (e.g., lampalizumab). In some embodiments, an additional therapeutic agent is a VEGF inhibitor. In some embodiments, a VEGF inhibitor is selected from the group including, but not limited to, pegaptanib (MACUGEN), ranibizumab (LUCENTIS), bevacizumab (AVASTIN), aflibercept (EYLEA), brolucizumab, and OPT-302. In some embodiments, an additional therapeutic agent is a PDGF inhibitor. In some embodiments, an additional therapeutic agent is a corticosteroid. In some embodiments, an additional therapeutic agent is a neuroprotective agent. In some embodiments, a neuroprotective agent is selected from the group including, but not limited to, ciliary neurotrophic factor (CNTF), tandospirone, and brimonidine.

It will be appreciated that the combination of a C3-binding agent (e.g., an antibody) described herein and at least one additional therapeutic agent may be administered in any order or concurrently. In some embodiments, a C3-binding agent is administered to subjects (e.g., humans) that have previously undergone treatment with a therapeutic agent. In some embodiments, a C3-binding agent and a second therapeutic agent are administered substantially simultaneously or concurrently. For example, a subject (e.g., a human) may be given a C3-binding agent while undergoing a course of treatment with a second therapeutic agent (e.g., an angiogenesis inhibitor). In some embodiments, a C3-binding agent is administered within 1 year of the treatment with a second therapeutic agent. In some embodiments, a C3-binding agent is administered within 10, 8, 6, 4, or 2 months of any treatment with a second therapeutic agent. In some embodiments, a C3-binding agent is administered within 4, 3, 2, or 1 weeks of any treatment with a second therapeutic agent. In some embodiments, a C3-binding agent is administered within 5, 4, 3, 2, or 1 days of any treatment with a second therapeutic agent. It will further be appreciated that the two (or more) agents or treatments can be administered to the subject within a matter of hours or minutes (i.e., substantially simultaneously).

For the treatment of a disease, the appropriate dosage of a C3-binding agent (e.g., an antibody) of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. A C3-binding agent can be administered one time or over a series of treatments lasting from several days to several months, or until a cure is effected or a diminution of the disease state is achieved.

The dose of a C3-binding agent (e.g., an antibody) described herein may vary depending on the nature and/or severity of the disease or disorder, as well as the condition of the subject. In some embodiments, the dose of a C3-binding agent depends on the site of administration (e.g., into the vitreous cavity). In some embodiments, the dose of a C3-binding agent depends on the delivery system (e.g., eye drops). In some embodiments, a dose of a C3-binding agent (e.g., an antibody) described herein is from about 0.1 mg to about 20 mg. In some embodiments, a dose of a C3-binding agent (e.g., an antibody) described herein is from about 0.1 mg to about 20 mg into the vitreous cavity. In some embodiments, a dose of a C3-binding agent (e.g., an antibody) described herein is from about 0.1 mg to about 20 mg delivered by eye drop. In some embodiments, a dose of a C3-binding agent described herein is from about 1.0 mg to about 10 mg. In some embodiments, a dose of a C3-binding agent described herein is about 0.1, 0.25, 0.5, 1.0, 1.25, 2.0, 2.5, 3.0, 4.0, 5.0, 6.0, 7.0, 7.5, 8.0, 9.0, 10.0, 11.0, 12.0, 12.5, 13.0, 14.0, or 15 mg into the vitreous cavity. In some embodiments, a dose of a C3-binding agent described herein is about 0.1, 0.25, 0.5, 1.0, 1.25, 2.0, 2.5, 3.0, 4.0, 5.0, 6.0, 7.0, 7.5, 8.0, 9.0, 10.0, 11.0, 12.0, 12.5, 13.0, 14.0, or 15 mg delivered by eye drop.

In some embodiments, the C3-binding agent (e.g., an antibody) described herein is dosed once a month, once every 2 months, or once every 3 months. In some embodiments, the C3-binding agent is dosed once a month. In some embodiments, the C3-binding agent is dosed once every 6 weeks. In some embodiments, the C3-binding agent is dosed once every 2 months. In some embodiments, the C3-binding agent is dosed once every 10 weeks. In some embodiments, the C3-binding agent is dosed once every 3 months.

In some embodiments, the C3-binding agent (e.g., an antibody) is dosed using a 30 gauge needle. In some embodiments, the C3-binding agent is dosed using a 30+ gauge needle. In some embodiments, the C3-binding agent is injected in a formulation of about 25 to about 100 uL (per an eye). In some embodiments, the C3-binding agent is injected in a formulation of about 50 uL (per an eye). In some embodiments, the C3-binding agent is injected in a formulation of about 75 uL (per an eye). In some embodiments, the C3-binding agent is injected in a formulation of about 100 uL (per an eye).

In some embodiments, the C3-binding agent (e.g., an antibody) is delivered by eye drops. In some embodiments, the C3-binding agent is delivered in a formulation of about 25 to about 100 uL (per an eye). In some embodiments, the C3-binding agent is delivered in a formulation of about 50 uL (per an eye). In some embodiments, the C3-binding agent is delivered in a formulation of about 75 uL (per an eye). In some embodiments, the C3-binding agent is delivered in a formulation of about 100 uL (per an eye).

In some embodiments, the C3-binding agent (e.g., an antibody) is delivered topically. In certain embodiments of topical administration, the C3-binding agent (e.g., an antibody) is administered in combination with a cell penetrating peptide. In certain embodiments, the C3-binding agent (e.g., an antibody) and the cell penetrating peptide are delivered as part of a single pharmaceutical composition. Cell penetrating peptides are known in the art (see, e.g., de Cogan et al., 2017, Investigative Opthamology & Visual Science, 58(5): 2578-2590). Nonlimiting examples of cell penetrating peptides are described in US Patent Publication Nos. 2019/0015521, 2017/0355730, 2018/0346531, and 2012/0065124.

The present disclosure provides compositions comprising a C3-binding agent (e.g., an antibody) described herein. The present disclosure also provides pharmaceutical compositions comprising a C3-binding agent described herein and a pharmaceutically acceptable vehicle.

Formulations are prepared for storage and use by combining a purified antibody or agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol. (Remington: The Science and Practice of Pharmacy, $22^{nd}$ Edition, 2012, Pharmaceutical Press, London.). In some embodiments, the formulation is in the form of an aqueous solution. In some embodiments, the formulation is stored in a lyophilized or in an alternative dried form.

The binding agents of the present disclosure can be formulated in any suitable form for delivery to a target cell/tissue. In some embodiments, a C3-binding agent (e.g., an antibody) can be formulated as a liposome, microparticle, microcapsule, albumin microsphere, microemulsion, nanoparticle, nanocapsule, or macroemulsion. In some embodiments, the pharmaceutical formulation includes an agent of the present disclosure complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, a C3-binding agent (e.g., an antibody) is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), intracranial (e.g., intrathecal or intraventricular), ocular, intraocular, or intravitreal.

In some embodiments of the methods described herein, a C3-binding agent (e.g., an antibody) described herein is administered by ocular injection. In some embodiments of the methods described herein, a C3-binding agent is administered by intraocular injection. In some embodiments of the methods described herein, a C3-binding agent is administered by intravitreal injection.

EXAMPLES

Example 1

Generation of Antibodies

Anti-C3 antibodies were generated using human C3 as the immunogen. Single cell suspensions of lymphocytes were obtained from the spleens and lymph nodes of immunized mice after the individual animals had been determined to have suitable antibody titers. Lymphocytes were fused with murine myeloma cells by standard methods. Cells were dispersed into 96-well plates in HAT-containing selection media. Cell supernatants (approximately 10,000) were screened by ELISA for binding to human C3 and cyno C3. Approximately 1600 cell clones were selected based on binding assay results.

Example 2

C3 Alternative Pathway Biochemical Assay

Anti-C3 antibodies identified in C3 binding assays were tested for their ability to inhibit the in vitro generation of C3a. C3a is produced by the cleavage of C3 by the C3 convertase complex. The C3a assay was based upon a previously described method (Loyet et al., 2014, J Pharmacol and Exp Ther; 351:527-537). Briefly, 20 µL of solution of 50 nM human C3 (Complement Technologies) in GVB (bovine skin gelatin in veronal buffer) was mixed with 20 test anti-C3 antibodies or controls diluted in GVB for 10 minutes. Controls included (i) no C3; (ii) no Factor B and Factor D; (iii) no inhibitor; and (iv) compstatin as positive control. 100 nM human Factor B and human 100 nM Factor D (Complement Technologies) in 0.05 M EGTA/0.1 M MgCl2/GVB were added to the C3/Ab samples and the mixtures were incubated for an additional 10 minutes. 20 uL of 50% rabbit serum (diluted 1:2 in GVB) was added and incubated for 10 minutes, followed by addition of 20 µL of 0.5M EDTA to quench the reaction. The addition of rabbit serum cleaves C3a produced by C3 convertase in the reaction mixtures to C3a des Arg (C3a des Arg has been found to be more stable than C3a). C3 des Arg concentrations were subsequently measured by ELISA. Briefly, a mouse anti-C3a/C3a des Arg antibody (ThermoFisher) was coated on ELISA plates at 1.0 µg/mL and incubated overnight at 4° C. The following day, the plates were washed and 60 uL of SuperBlock™ blocking buffer (Pierce) was added to the plates and incubated for 60 minutes at room temperature. Prior to adding samples, blocking buffer was decanted from the wells. Samples from the C3/Ab reactions were diluted, added to the plates, and incubated for 90 minutes. The plates were washed, biotinylated anti-human C3/C3a/C3a des Arg antibody (Biolegend) was added to the wells (0.5 µg/mL), and the plates were incubated for 60 minutes. The plates were washed, 20 uL poly-HRP streptavidin (Pierce) was added to each well and the plates were incubated for 30 minutes. For detection, SuperSignal™ PICO ELISA chemiluminescent substrate (ThermoFisher Scientific) was added to each well. The plates were read in a luminometer with a 0.2 second read time per well at 425 nm.

Under these assay conditions, test anti-C3 antibodies were ranked for their ability to inhibit C3a des Arg production. Several dozen exemplary antibodies were observed to strongly inhibit C3 cleavage and C3a release. The activities of three exemplary antibodies, 38G10, 3D8, and 15C12, at concentrations ranging from 0.1 to 1000 nM, are shown in FIG. 1.

Example 3

Alternative and Classical Pathway-Dependent Hemolysis Assays

Hemolytic assays have traditionally been used to assess the functional activity of the complement system. For the alternative pathway (AP) assay, rabbit erythrocytes were included with C3-depleted human serum and 50 nM of human C3 in the presence of increasing concentrations of anti-C3 antibodies 38G10, 3D8, and 15C12. For the classical pathway (CP), IgM-coated sheep erythrocytes were incubated with C3-depleted human serum and increasing concentration of anti-C3 antibodies 38G10, 3D8, and 15C12 in the presence of 10 nM human C3. Hemolysis was determined by reading the absorbance of the supernatant at 412 nm. Results were expressed as a percentage of hemolysis observed in control samples without any inhibitor and can be calculated into IC50s. These assays were duplicated using cyno serum as a source of C3.

Figure 2:
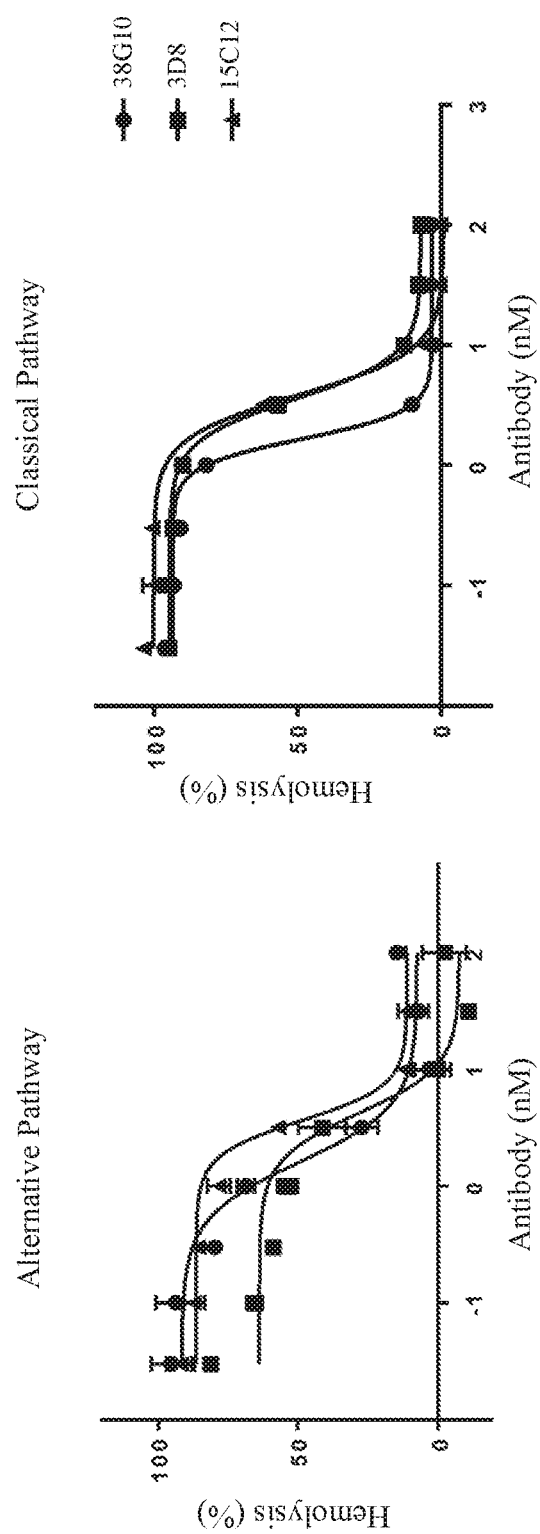
FIG. 2. Alternative Pathway and Classical Pathway Hemolysis Assays. Antibodies 38G10, 3D8, and 15C12 were tested for their ability to inhibit complement activation.

Results of the AP and CP assays using human C3 and cyno C3 for a set of exemplary antibodies are summarized in Table 11 ($IC_{50}$) and shown in FIG. 2 for antibodies 38G10, 3D8, and 15C12 (% hemolysis).

TABLE 11

| | Hemolytic Assay $IC_{50}$ (nM) | | | |
|---|---|---|---|---|
| Antibody | Human AP | Human CP | Cyno AP | Cyno CP |
| 3D8 | 4.2 | 3.6 | 5.5 | ND |
| 3G8 | 6.8 | 10.4 | 20.9 | 102.5 |
| 15C12 | 3.7 | 3.8 | 8.8 | ND |
| 27A8 | 8.5 | 7.6 | 9.6 | ND |
| 28C3 | 8.0 | 6.5 | 7.8 | 3.4 |
| 38F5 | 9.2 | 6.7 | 12.9 | 2.3 |
| 38G10 | 1.9 | 1.7 | 3.5 | ND |
| 62B11 | 6.6 | 4.2 | ~11.0 | ~1.0 |
| 62F2 | 5.7 | 5.0 | 8.7 | 5.3 |
| 63A3 | 6.5 | 4.1 | 3.4 | 1.6 |

ND—Not determined

These results showed that the anti-C3 antibodies inhibited activation of both the alternative and classical pathways as demonstrated by the inhibition of hemolysis.

Example 4

Binding Affinity

The binding affinities of exemplary anti-C3 antibodies to human C3 and cyno C3 were measured using a BiaCore™ system (GE Healthcare LifeSciences). Briefly, anti-Fe antibody (Sigma-Aldrich) was immobilized on all four flow cells of a CM5 chip using amine coupling reagents (GE Healthcare LifeSciences). Antibodies were captured on flow cells 2, 3, and 4 using flow cell 1 as a reference. Concentrations ranging from 0.62-40 nM of human C3 or cyno C3 were injected at a flow rate of 50 µL/min at 37° C. Kinetic data were collected over time and fit using the simultaneous global fit equation to yield affinity constants (KD values) for each antibody.

Table 12 shows the binding affinities for antibodies 38G10, 3D8, and 15C12.

TABLE 12

| | Binding Affinity $K_D$ (nM) | |
|---|---|---|
| Antibody | Human C3 | Cyno C3 |
| 38G10 | 0.19 | 0.16 |
| 3D8 | 1.90 | 1.40 |
| 15C12 | 0.13 | 0.13 |

Example 5

Binding Profile

The anti-C3 antibodies described herein were characterized for their ability to bind a number of other components of the complement cascade. Antibodies were screened for binding to C3, C3a, C3b, C3c, C3d, iC3b, and Factor Bb. A representative set of the results is shown in Table 13. All the anti-C3 antibodies included in Table 13 were able to block complement activation. The data are relative to the binding of the negative control mIgG2 antibody.

TABLE 13

| | C3 | C3a | C3b | C3c | C3d | iC3b | Factor Bb |
|---|---|---|---|---|---|---|---|
| 3D8 | 0.47 | −0.01 | 0.38 | 0.17 | 0.01 | 0.29 | −0.01 |
| 3G8 | 0.37 | −0.01 | 0.33 | 0.22 | 0.00 | 0.25 | 0.00 |
| 28C3 | 0.66 | 0.11 | 0.09 | 0.28 | 0.01 | 0.01 | 0.00 |
| 38F5 | 0.83 | 0.00 | 0.66 | 0.45 | 0.01 | 0.45 | −0.01 |
| 38G10 | 0.53 | 0.02 | 0.06 | 0.13 | 0.00 | 0.06 | 0.01 |
| 62B11 | 0.83 | −0.03 | 0.76 | 0.49 | −0.02 | 0.54 | −0.02 |
| 62F2 | 0.7 | −0.04 | 0.61 | 0.43 | 0.01 | 0.49 | 0.00 |
| 63A3 | 0.95 | −0.02 | 0.83 | 0.55 | 0.01 | 0.72 | 0.00 |
| Control mIgG2 | 0.00 | 0.00 | 0.00 | 0.00 | 0.00 | 0.00 | 0.00 |

These data indicated that antibody 38G10 had a unique C3 binding profile, in that it bound preferentially to C3 with no detectable or very limited binding to any of the fragments of the complement cascade.

Example 6

Sequence Analyses of Anti-C3 Antibodies

Antibodies 3D8, 3G8, 15C12, 27A8, 28C3, 38F5, 38G10, 62B11, 62F2, and 63A3 were sequenced and the heavy chain variable region and light chain variable region amino acid sequences are disclosed herein and summarized in Table 14.

TABLE 14

| Antibody | Heavy Chain Variable Region | Light Chain Variable Region |
|---|---|---|
| 3D8 | SEQ ID NO: 91 | SEQ ID NO: 92 |
| 3G8 | SEQ ID NO: 93 | SEQ ID NO: 94 |
| 15C12 | SEQ ID NO: 95 | SEQ ID NO: 96 |
| 27A8 | SEQ ID NO: 97 | SEQ ID NO: 98 |
| 28C3 | SEQ ID NO: 99 | SEQ ID NO: 100 |
| 38F5 | SEQ ID NO: 101 | SEQ ID NO: 102 |
| 38G10 | SEQ ID NO: 18 | SEQ ID NO: 19 |
| 62B11 | SEQ ID NO: 103 | SEQ ID NO: 104 |
| 62F2 | SEQ ID NO: 105 | SEQ ID NO: 106 |
| 63A3 | SEQ ID NO: 107 | SEQ ID NO: 108 |

The heavy chain and light chain CDRs for the individual antibodies are disclosed in Tables 1-10 and as SEQ ID NOs:7-12, 38-90, and 120-228.

Based on the antibody characterization data as well as additional studies, antibody 38G10 was selected for humanization (CDRs disclosed in Table 1A and heavy chain variable region and light chain variable region amino acid sequences disclosed herein as SEQ ID NO: 18 and SEQ ID NO:19, respectively).

Example 7

Generation of Humanized Antibody

Antibody 38G10 was humanized by methods known to those skilled in the art and humanized 38G10 is referred to herein as Hz38G10. Antibody 38G10 was found to have a potential glycosylation site in CDR2 of the heavy chain variable region, YIYPHNGGTTYNQNFTG (SEQ ID NO:8). The consensus glycosylation site for N-linked glycans is N-X-S/T, wherein X can be any amino acid except proline. During the humanization process, the heavy chain CDR2 was reengineered to remove the glycosylation site resulting in antibody Hz38G10 comprising a heavy chain CDR2 comprising YIYPHNGGTTYNQQFTG (SEQ ID NO:13). The heavy chain variable sequence of antibody Hz38G10 is SEQ ID NO:20 and the light chain variable sequence is SEQ ID NO:25; CDRs are disclosed in Table 1B.

Example 8

Characterization of Hz38G10

The binding affinity of Hz38G10 was determined using a BiaCore™ system as described herein and compared with the binding affinity of the parental 38G10 antibody. Antibody Hz38G10 had a binding affinity to human C3 of 0.3 nM and to cyno C3 of 1.8 nM as compared to the parental antibody's binding affinity of approximately 0.1 nM to both human and cyno C3 (at 37° C.). These results demonstrated that the humanization process for antibody 38G10, as well as the removal of a glycosylation site within CDR2 of the heavy chain, did not have a significant effect on the binding capabilities to human C3 or cyno C3. Hz38G10 was formulated in two different buffers and evaluated for viscosity at high concentrations. The first buffer formulation was 10 mM sodium phosphate, 40 mM sodium chloride, 0.03% polysorbate 20, and 5% sucrose at pH 6.2. Hz38G10 was concentrated to 164 mg/mL with a viscosity of 15.2 mPa·s (by RheoSense). The second buffer formulation was 10 mM histidine HCl, 10% α,α trehalose dihydrate, and 0.01% polysorbate 20 at pH 5.5. Hz38G10 was concentrated to 152 mg/mL with a viscosity of 17.6 mPa·s. These results demonstrated that Hz38G10 retained acceptable viscosity at high formulation concentrations.

Due to a lack of anti-C3 antibodies in the clinic or FDA-licensed, the binding affinity of Hz38G10 to human C3 was compared against compstatin, a 13-residue cyclic peptide with potent C3 inhibitory activity that was identified several years ago (Morikis et al., 1998, Protein Science; 7:619-627). More recently, a number of compstatin analogs and derivatives have been generated and studied. The binding affinity of Hz38G10 to human C3 was compared to the binding affinity of a compstatin derivative (referred to herein as "COMP") and a pegylated version of the compstatin derivative (referred to herein as "COMP-PEG"). A BiaCore™ system was used to assess the binding affinities of the different molecules to human C3. Binding affinity of Hz38G10 to human C3 at 25° C. and 37° C. was carried out as described in Example 4. Evaluation of COMP or COMP-PEG binding to human C3 was carried out as follows. Human C3 was immobilized on flow cell 2 of a CM5 chip using amine-coupling reagents (GE Healthcare Life-Sciences) and flow cell 1 (immobilized with a similar amount of human IgG) was used as a reference. Concentrations ranging from 1.56-100 nM of COMP were injected at a flow rate of 50 μL/min for evaluation of binding affinity at 25° C. and 37° C. Similar experiments were set up with COMP-PEG (concentration range of 25-400 nM) for evaluation at 37° C. COMP-PEG binding to human C3 was also evaluated at 25° C. with modifications. Briefly, rat anti-PEG antibody (Abcam Inc.) was immobilized on a CM5 chip surface using amine coupling reagents and COMP-PEG was captured on flow cell 2. Human C3 (concentration range 12-100 nM) was injected at a flow rate of 50 μL/min. Kinetic data were collected over time and fit using the simultaneous global fit equation to yield affinity constants (KD values) for each antibody.

A set of representative results is shown in Table 15.

TABLE 15

|  | Hz38G10 | COMP | COMP-PEG |
|---|---|---|---|
| $K_D$ (25° C.), nM | <0.1 | 7.1 | 55 |
| $K_D$ (37° C.), nM | 0.28 | 21 | 490 |

These results suggest that antibody Hz38G10 binds to human C3 with a significantly greater affinity than a compstatin derivative or the pegylated version (ranging from approximately 50-80 times greater).

To confirm that the humanized version of antibody 38G10 retained the ability to inhibit complement activation, Hz38G10 was assessed in alternative and classical pathway-dependent hemolysis assays as described herein and compared to COMP and COMP-PEG. Hz38G10 and COMP or antibody Hz38G10 and COMP-PEG were tested for their respective abilities to inhibit hemolysis in the assays.

Figure 3:
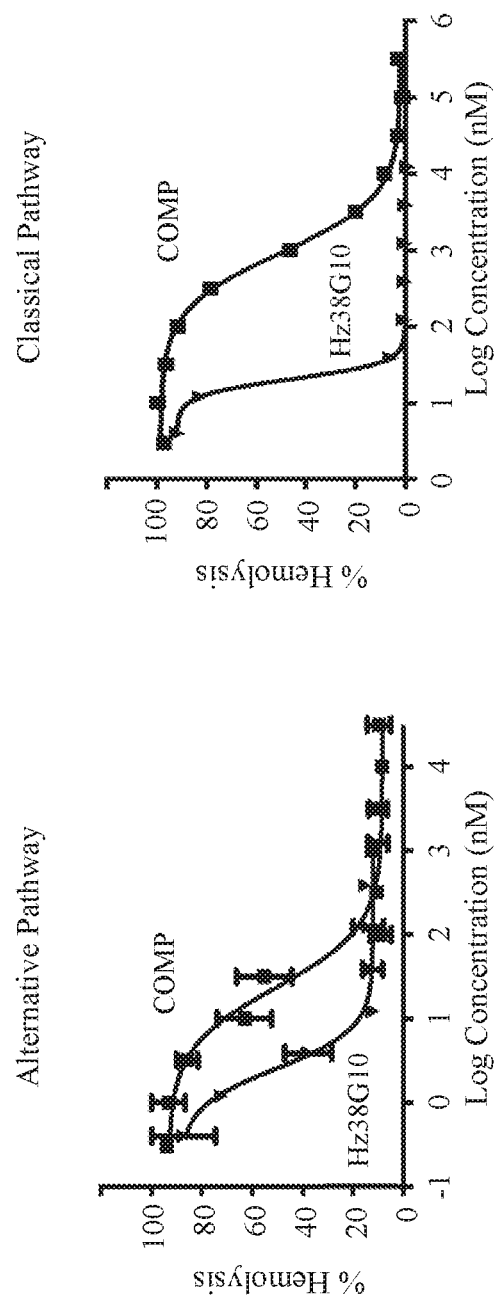
FIG. 3. Alternative Pathway and Classical Pathway Hemolysis Assays. Antibody Hz38G10 and compstatin derivative (COMP) were tested for their ability to inhibit complement activation.
Figure 4:
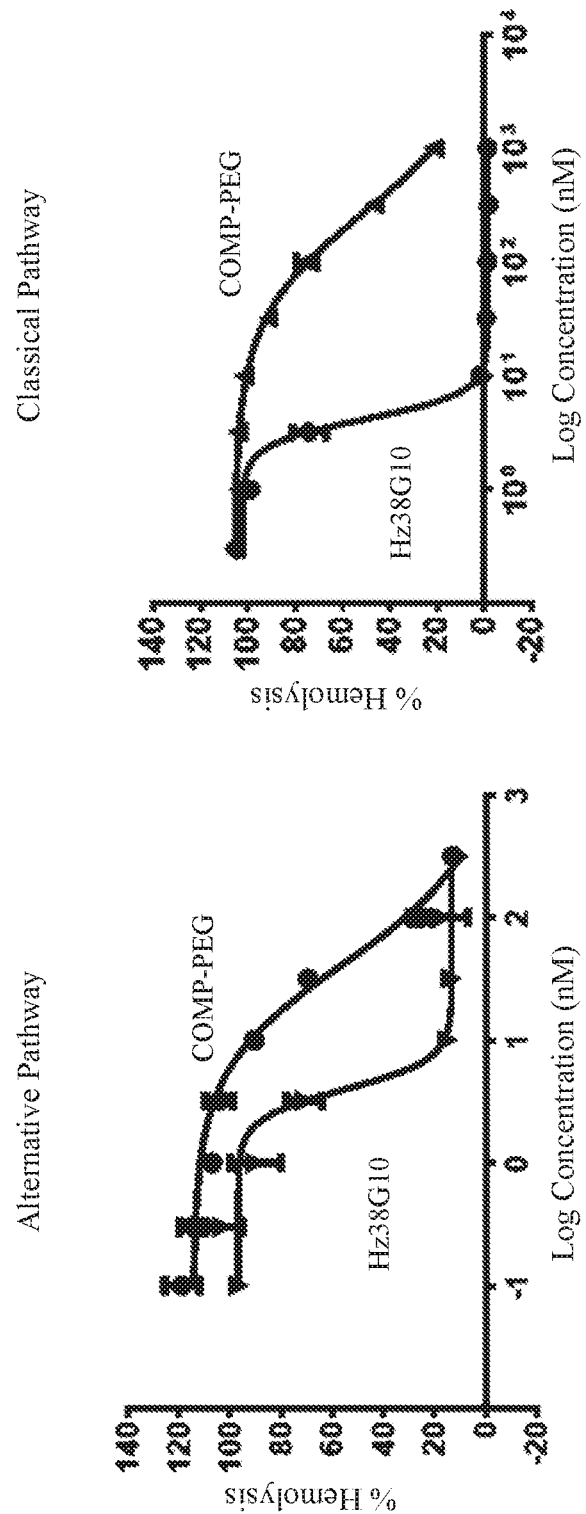
FIG. 4. Alternative Pathway and Classical Pathway Hemolysis Assays. Antibody Hz38G10 and a pegylated version of the compstatin derivative (COMP-PEG) were tested for their ability to inhibit complement activation.

As shown in FIGS. 3 and 4 and Table 16, the results of these experiments indicated that antibody Hz38G10 was more effective at inhibiting complement activation than a compstatin derivative or a pegylated version of the compstatin derivative. Antibody Hz38G10 had similar inhibitory activity on both the classical and alternative pathways. In contrast, COMP and COMP-PEG appeared to have greater activity on the alternative pathway than the classical pathway. Antibody Hz38G10 was approximately 10-fold more effective than COMP or COMP-PEG in inhibiting the alternative pathway and approximately 40- to 60-fold more effective than the compstatin derivatives on inhibiting the classical pathway.

TABLE 16

|  | Classical Pathway IC50 (nM) | Alternative Pathway IC50 (nM) |
|---|---|---|
| Hz38G10 | 2 | 2.5 |
| COMP | 90 | 23 |
| Hz38G10 | 4.1 | 4.0 |
| COMP-PEG | 272 | 41.8 |

An additional experiment was undertaken to determine whether antibody Hz38G10 and the compstatin derivative (COMP) bound to the same or similar region on human C3. COMP was immobilized on a CM5 chip using amine coupling reagents (GE Healthcare LifeSciences) at a high density (approx. 3000 RUs). In separate reactions in a 96-well plate, human C3 (5 nM) was titrated with increasing concentrations of antibody Hz38G10 or COMP (0.05-100 nM). After an incubation of approximately 3 hours at room temperature, the C3-COMP or C3-Hz38G10 reactions were injected over the COMP-coated surface.

Figure 5:
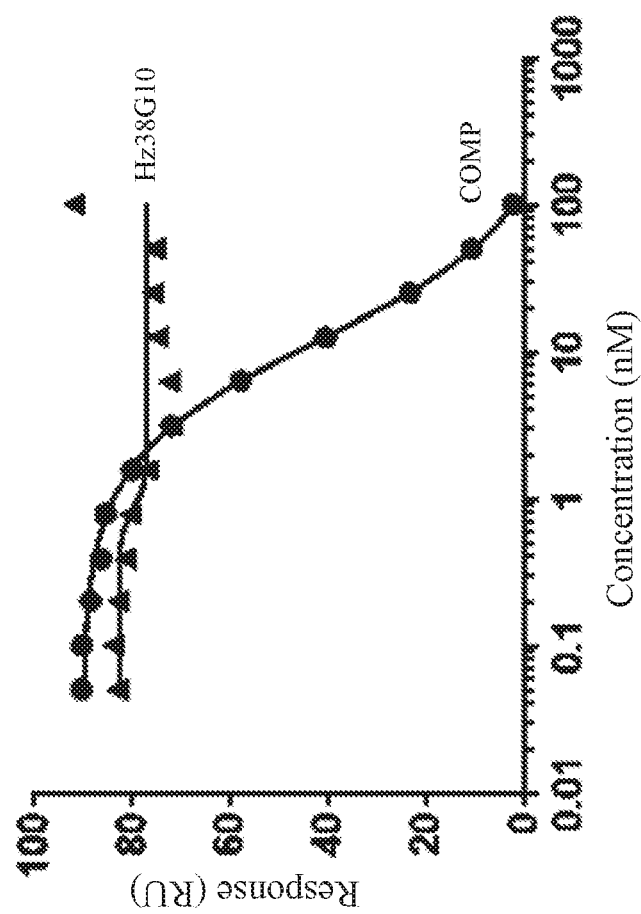
FIG. 5. Binding Site Analysis. Hz38G10 and a compstatin derivative were tested in a competitive binding assay to assess whether the molecules bind to the same or different epitopes.

As shown in FIG. 5, increasing concentrations of COMP reduced binding of C3 to COMP surface due to self-blocking (positive control). However, increasing concentration of Hz38G10 did not prevent C3 from binding to the COMP-coated chip surface. The results of this experiment indicated that antibody Hz38G10 and COMP bind different epitopes on human C3.

Example 9

Generation and Characterization of Hz38G10 Variants

Sequence analysis of the heavy chain CDRs of antibody Hz38G10 identified a potential spot for deamidation within CDR2, YIYPHNGGTTYNQQFTG (SEQ ID NO:13). An elevated pH stress test was performed at pH 8.5 and deamidation at the asparagine (N55 of SEQ ID NO:20) was determined to be 29.75% on Day 0 and 48.23% on Day 7 (an increase of 18.5%). A variant of antibody Hz38G10 was generated with a N55D mutation in the heavy chain CDR2, a change that would mimic a fully deamidated molecule. This antibody, Hz38G10(N55D), was assayed for binding to human C3 using a BiaCore™ system as described herein and was shown to have reduced binding as compared to Hz38G10.

Four additional Hz38G10 variants were generated with amino acid substitutions within the heavy chain CDR2 at N55 or G56 of SEQ ID NO:20. The Hz38G10 variants contained (i) a N55E mutation, heavy chain CDR2 YIYPHEGGTTYNQQFTG (SEQ ID NO: 16); (ii) a N55Q mutation, heavy chain CDR2 YIYPHQGGTTYNQQFTG (SEQ ID NO: 17); (iii) a G56A mutation, heavy chain CDR2 YIYPHNAGTTYNQQFTG (SEQ ID NO: 14); or (iv) a G56T mutation, heavy chain CDR2 YIYPHNTGT-TYNQQFTG (SEQ ID NO: 15). The heavy chain variable region sequence of antibody Hz38G10(G56A) is SEQ ID NO:21, Hz38G10(G56T) is SEQ ID NO:22, Hz38G10(N55E) is SEQ ID NO:23, and Hz38G10(N55Q) is SEQ ID NO:24; the light chain variable region sequence for all variants is SEQ ID NO:25; CDRs are disclosed in Table 1C.

These antibodies, Hz38G10(N55E), Hz38G10(N55Q), Hz38G10(G56A), and Hz38G10(G56T) were assayed for binding to human C3 using a BiaCore™ system as described herein and compared to antibody Hz38G10. The results are shown in Table 17.

TABLE 17

| Antibody | Binding KD (nM) |
| --- | --- |
| Hz38G10 | 0.30 |
| Hz38G10(N55E) | 6.20 |
| Hz38G10(N55Q) | 0.82 |
| Hz38G10(G56A) | 0.27 |
| Hz38G10(G56T) | 0.23 |

These results indicated that a mutation at position G56 retained binding affinity to a greater extent than a mutation at position N55.

To determine if the substitution of alanine for glycine at position 56 of the heavy chain variable region (SEQ ID NO:20) reduced deamidation within the CDR2, a pH stress test was performed with antibody Hz38G10(G56A) as described above. For this variant, deamidation at N55 of Hz38G10(G56A) (SEQ ID NO:21) was determined to be 0.66% on Day 0 and 1.0% on Day 7. These results showed that antibody Hz38G10(G56A) was very stable under deamidation stressed conditions.

To determine whether antibody Hz38G10(G56A) retained the ability to inhibit complement activation, the antibody was assessed in alternative and classical pathway hemolysis assays as described herein and compared to antibody Hz38G10. Hz38G10 and Hz38G10(G56A) were tested for their ability to inhibit hemolysis in the assays.

As shown in Table 18, antibody Hz38G10(G56A) showed almost identical inhibition activity when compared to antibody Hz38G10 for human C3 and cyno C3.

TABLE 18

| Antibody | Classical Pathway IC50 (nM) | Alternative Pathway IC50 (nM) |
| --- | --- | --- |
| | Human C3 | |
| Hz38G10 | 5.2 | 3.9 |
| Hz38G10(G56A) | 5.4 | 3.9 |
| | Cyno C3 | |
| Hz38G10 | 0.7 | 4.8 |
| Hz38G10(G56A) | 0.6 | 4.8 |

Example 10

Pharmacokinetics of Antibody Hz38G10

The pharmacokinetics (PK) of anti-C3 antibody Hz38G10 were assessed in New Zealand White rabbits at a dose of 1 mg or 7.5 mg. Antibody Hz38G10 was administered by intravitreal injection (IVT) as a single dose of 50 µL/eye. Samples were taken at 1 and 8 hours and on days 2, 4, 8, 15 and 22 (4 eyes/time point). The concentration of Hz38G10 was evaluated in the vitreous humor, aqueous humor, and retina.

As shown in Table 19, the half-life of Hz38G10 in the vitreous humor was approximately 4-5 days.

TABLE 19

| Hz38G10 Dose | Cmax (ug/mL) | AUC (day ug/mL) | $T_{1/2}$ (day) |
| --- | --- | --- | --- |
| 1.0 mg | 541 | 3140 | 4.1 |
| 7.5 mg | 5680 | 33049 | 5.3 |

The PK of Hz38G10 is similar to the reported PKs of bevacizumab and aflibercept in vitreous humor of rabbits. In addition, the distribution of Hz38G10 to the retina was estimated to be approximately 20% of the vitreous humor for both Cmax and AUC.

Example 11

Generation of Hz38G10 scFv

A scFv version of an exemplary anti-C3 antibody was generated. scFv molecules based on the heavy chain variable region (VH) and the light chain variable region (VL) of Hz38G10 were designed in two orientations and with or without disulfide stabilization. The four molecules were (i) VL-linker-VH scFv, (ii) VH-linker-VL scFv, (iii) VL-linker-VH dsscFv; and (iv) VH-linker-VL dsscFv, wherein dsscFv indicates a scFv with an engineered disulfide bond between the VL and VH regions. These four molecules were tested in an *E. coli* expression system and based on several parameters, for example, expression titer and percent monomer, the VL-linker-VH dsscFv molecule was selected for additional studies and characterization. The sequence of Hz38G10 dsscFv is disclosed herein as SEQ ID NO:113.

Hz38G10 dsscFv antibodies were produced via expression as inclusion bodies. BL21(DE3) *E. coli* were transformed with a plasmid encoding Hz38G10 VL-linker-VH dsscFv, referred to hereafter as Hz38G10 dsscFv. Transformed BL21(DE3) *E. coli* were harvested by low speed centrifugation. The bacterial pellet was resuspended by magnetic stirring in 50 mM Tris-HCl pH 7.5 for 15 minutes at room temperature. For cell disruption, the suspension was passed 3 times through a microfluidizer at 200 Bar. Inclusion bodies were recovered from broken cells by centrifugation at 4° C. in a fixed angle rotor operating at 13,000×g for 45 minutes. The resulting inclusion body pellet was washed with cold Milli-Q® water until the lipid and cell wall layers were removed. The washed inclusion body pellet was resuspended in 5 volumes of Milli-Q® water by magnetic stirring and collected by centrifugation at 13,000×g for 30 minutes. Washed inclusion bodies were solubilized in 10 volumes of 8 M guanidine-HCl, 50 mM Tris-HCl pH 7.5, 1 mM TCEP using magnetic stirring and incubated overnight at 4° C. The following day, a dounce homogenizer with loose pestle was used to resuspend any remaining solid inclusion body particles. Solubilized inclusion bodies were diluted dropwise 1:25 into refold buffer (3 M urea, 50 mM Tris-HCl pH 8.0, 160 mM L-arginine, 1 mM cysteine, 3 mM cystamine) under gentle magnetic stirring at room temperature to a final concentration of 0.1 mg/ml. Refolding was carried out for 48 hours at 4° C. and disulfide bond formation was monitored by SDS-PAGE under non-reducing conditions. The solution containing the refolded dsscFv was concentrated 5-fold by ultrafiltration/diafiltration (UF/DF) on a 0.22 m² 10,000 Da NMWCO tangential flow filtration membrane. The concentrate was cleared of misfolded dsscFv by rapid acidification to pH 2.8 with 4 volumes of 100 mM glycine pH 2.5. The solution was held at pH 2.8 as the solution was further concentrated 5-fold. After 15 minutes, the pH was quickly returned to neutral with addition of concentrated Tris-HCl solution. The resulting acid-treated solution was buffer-exchanged with diavolumes of Protein-L affinity binding buffer (50 mM Tris-HCl pH 7.5, 50 mM NaCl). Recovered diafiltration product was cleared of precipitate by centrifugation at 13,000×g for 45 minutes at 4° C. and subsequently filtered using a 0.2 μm membrane.

Hz38G10 dsscFv antibodies were purified in two chromatography steps: (i) a Protein L affinity column for capture and (ii) a cation exchange (CEX) column for polishing. For Protein L affinity chromatography, the suspension containing Hz38G10 dsscFv was applied to a 5 mL MiniChrom TOYOPEARL® AF-rProtein L-650F column (Tosoh Bioscience), washed extensively with Tris-buffered saline, and eluted with a step gradient of 100 mM glycine pH 2.5. The resulting elution pool (Pool M) was dialyzed against CEX binding buffer (20 mM sodium acetate pH 5.0). Dialyzed Pool M was applied to a HiTrap® SP HP cation exchange column (GE Healthcare), washed with 20 mM sodium acetate, pH 5.0, and eluted with an isocratic gradient of 50 mM sodium chloride in 20 mM sodium acetate, pH 5.0. Hz38G10 dsscFv-enriched fractions were pooled and evaluated by SDS-PAGE and analytical SEC methods. Subsequently, a Hz38G10(G56A) dsscFv antibody (SEQ ID NO: 114) was generated following the same general methods.

Example 12

Characterization of Hz38G10 dsscFv

The solubility parameters of Hz38G10 dsscFv were investigated. The purified antibodies were dialyzed into buffer consisting of 10 mM sodium phosphate, 40 mM sodium chloride, 0.03% polysorbate 20, and 5% sucrose, pH 6.2. The solution was micro-concentrated using 10,000 Da NMWCO spin concentrator at 3,000×g at room temperature. Protein concentration was measured on an Agilent Cary 60 UV-VIS Solo VPE spectrophotometer. Protein concentration reached 229 mg/ml with no visible aggregation.

Hz38G10 dsscFv were compared to Hz38G10 intact antibody and a Fab version of Hz38G10 in several assays. Binding affinity to human C3 was assessed using a BiaCore™ system as described herein. In addition, inhibition of the alternative pathway and classical pathway by the three antibodies was assessed in hemolysis assays as described herein.

The results are summarized in Table 20.

TABLE 20

| Antibody Hz38G10 | $K_D$ (pM) | AP human C3 $IC_{50}$ (nM) | CP human C3 $IC_{50}$ (nM) |
|---|---|---|---|
| Intact antibody | 27 | 5.9 | 4.0 |
| Fab | ND | 16 | 17.8 |
| dsscFv | 35 | 19.5 | 15.3 |

These results showed that Hz38G10 dsscFv had a similar $K_D$ as compared to the intact antibody. In addition, Hz38G10 dsscFv had a similar level of inhibition of hemolytic activity in both the AP and CP pathways as compared to the intact antibody or the Fab version. It should be noted that the intact Hz38G10 antibody has two antigen-binding sites, while the Fab and dsscFv antibodies have only one antigen-binding site.

Example 13

In Vivo Inhibition of C3 Activation

To evaluate the ability of anti-C3 antibodies to block activation of C3 in the eye, Hz38G10 was tested in an LPS-induced complement activation model in cynomolgus monkeys. In normal cynomolgus monkeys, C3 activation is minimal and thus the inhibitory effects of an anti-C3 antibody on C3 activation cannot be reliably evaluated in this setting. It is known that LPS can activate the complement system and a pilot study confirmed that complement C3 was activated by intravitreal injection (IVT) of LPS. Using this LPS-induced C3 activation model, the effects of Hz38G10 on activation of C3 was evaluated.

Twelve normal female cynomolgus monkeys (ages ranging from 8 to 17 years old) were assigned to 2 groups with 6 animals per group. A baseline sampling of aqueous humor was conducted on Day −3. On Day 1, animals were treated in both eyes with a single IVT dose of either vehicle or Hz38G10 at 5 mg/eye at a dose volume of 67 μl/eye. On Day 3, animals were injected intravitreously with LPS at 30 ng/eye at a volume of 50 μl/eye. On Days 5, 8, 13, and 18 aqueous humor samples were taken. C3a concentrations in the aqueous humor were determined using a Complement C3a Human ELISA Kit (Invitrogen) following the manufacturer's instructions.

Figure 6:
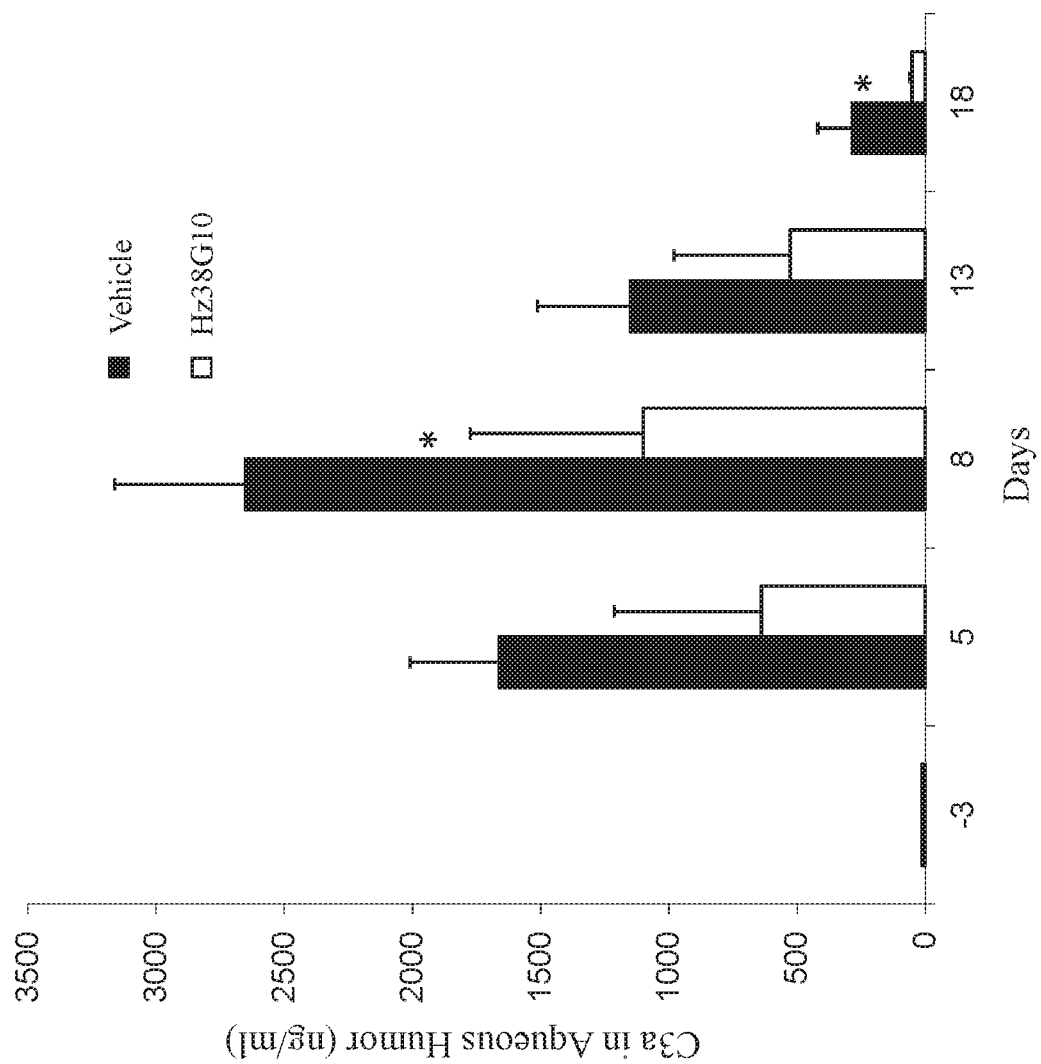
FIG. 6. Complement Activation Inhibition. Antibody Hz38G10 was tested for its ability to inhibit complement activation in the eye.

As shown in FIG. 6, LPS induced a significant increase of C3a in the aqueous humor in both groups of animals as compared to baseline (Day −3). Significantly lower levels of C3a were observed in the Hz38G10-treated animals as compared to animals treated with vehicle.

These results demonstrate that an anti-C3 antibody is capable of functionally inhibiting complement activation in the eye.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are sequences disclosed in the application. CDR sequences are listed in Tables 1-10.

```
Human C3 amino acid sequence with predicted signal sequence underlined
                                                      (SEQ ID NO: 1)
MGPTSGPSLLLLLLTHLPLALGSPMYSIITPNILRLESEETMVLEAHDAQGDVPVTVIVH

DFPGKKLVLSSEKTVLTPATNHMGNVTFTIPANREFKSEKGRNKFVTVQATFGTQVVEKV

VLVSLQSGYLFIQTDKTIYTPGSTVLYRIFTVNHKLLPVGRTVMVNIENPEGIPVKQDSL

SSQNQLGVLPLSWDIPELVNMGONKIRAYYENSPQQVFSTEFEVKEYVLPSFEVIVEPTE

KFYYIYNEKGLEVTITARFLYGKKVEGTAFVIFGIQDGEQRISLPESLKRIPIEDGSGEV

VLSRKVLLDGVQNPRAEDLVGKSLYVSATVILHSGSDMVQAERSGIPIVISPYQIHFIKT

PKYFKPGMPFDLMVFVTNPDGSPAYRVPVAVQGEDTVQSLTQGDGVAKLSINTHPSQKPL

SITVRTKKQELSEAEQATRTMQALPYSTVGNSNNYLHLSVLRTELRPGETLNVNFLLRMD

RAHEAKIRYYTYLIMNKGRLLKAGRQVREPGQDLVVLPLSITTDFIPSFRLVAYYTLIGA

SGQREVVADSVWVDVKDSCVGSLVVKSGQSEDRQPVPGQQMTLKIEGDHGARVVLVAVDK

GVFVLNKKNKLTQSKIWDVVEKADIGCTPGSGKDYAGVFSDAGLTFTSSSGQQTAQRAEL

QCPQPAARRRSVQLTEKRMDKVGKYPKELRKCCEDGMRENPMRFSCQRRTRFISLGEAC

KKVFLDCCNYITELRRQHARASHLGLARSNLDEDIIAEENIVSRSEFPESWLWNVEDLKE

PPKNGISTKLMNIFLKDSITTWEILAVSMSDKKGICVADPFEVTVMQDFFIDLRLPYSVV

RNEQVEIRAVLYNYRQNQELKVRVELLHNPAFCSLATTKRRHQQTVTIPPKSSLSVPYVI

VPLKTGLQEVEVKAAVYHHFISDGVRKSLKVVPEGIRMNKTVAVRTLDPERLGREGVQKE

DIPPADLSDQVPDTESETRILLQGTPVAQMTEDAVDAERLKHLIVITSGCGEQNMIGMTP

TVIAVHYLDETEQWEKFGLEKRQGALELIKKGYTQQLAFRQPSSAFAAFVKRAPSTWLTA

YVVKVFSLAVNLIAIDSQVLCGAVKWLILEKQKPDGVFQEDAPVIHQEMIGGLRNNNEKD

MALTAFVLISLQEAKDICEEQVNSLPGSITKAGDFLEANYMNLQRSYTVAIAGYALAQMG

RLKGPLLNKFLTTAKDKNRWEDPGKQLYNVEATSYALLALLQLKDFDFVPPVVRWLNEQR

YYGGGYGSTQATFMVFQALAQYQKDAPDHQELNLDVSLQLPSRSSKITHRIHWESASLLR

SEETKENEGFTVTAEGKGQGTLSVVTMYHAKAKDQLTCNKFDLKVTIKPAPETEKRPQDA

KNIMILEICTRYRGDQDATMSILDISMMTGFAPDTDDLKQLANGVDRYISKYELDKAFSD

RNTLIIYLDKVSHSEDDCLAFKVHQYFNVELIQPGAVKVYAYYNLEESCTRFYHPEKEDG

KLNKLCRDELCRCAEENCFIQKSDDKVTLEERLDKACEPGVDYVYKTRLVKVQLSNDFDE

YIMAIEQTIKSGSDEVQVGQQRTFISPIKCREALKLEEKKHYLMWGLSSDFWGEKPNLSY

IIGKDTWVEHWPEEDECQDEENQKQCQDLGAFTESMVVFGCPN

Human C3 amino acid sequence without predicted signal sequence
                                                      (SEQ ID NO: 2)
SPMYSIITPNILRLESEETMVLEAHDAQGDVPVTVTVHDFPGKKLVLSSEKTVLTPATNH

MGNVTFTIPANREFKSEKGRNKFVTVQATFGTQVVEKVVLVSLQSGYLFIQTDKTIYTPG
```

-continued

STVLYRIFTVNHKLLPVGRTVMVNIENPEGIPVKQDSLSSQNQLGVLPLSWDIPELVNMG

QWKIRAYYENSPQQVFSTEFEVKEYVLPSFEVIVEPTEKFYYIYNEKGLEVTITARFLYG

KKVEGTAFVIFGIQDGEQRISLPESLKRIPIEDGSGEVVLSRKVLLDGVQNPRAEDLVGK

SLYVSATVILHSGSDMVQAERSGIPIVISPYQIHFIKTPKYFKPGMPFDLMVFVTNPDGS

PAYRVPVAVQGEDTVQSLTQGDGVAKLSINTHPSQKPLSITVRTKKQELSEAEQATRTMQ

ALPYSTVGNSNNYLHLSVLRTELRPGETLNVNFLLRMDRAHEAKIRYYTYLIMNKGRLLK

AGRQVREPGQDLVVLPLSITTDFIPSFRLVAYYTLIGASGQREVVADSVWVDVKDSCVGS

LVVKSGQSEDRQPVPGQQMTLKIEGDHGARVVLVAVDKGVFVLNKKNKLTQSKIWDVVEK

ADIGCTPGSGKDYAGVFSDAGLTFTSSSGQQTAQRAELQCPQPAARRRRSVQLTEKRMDK

VGKYPKELRKCCEDGMRENPMRFSCQRRTRFISLGEACKKVFLDCCNYITELRRQHARAS

HLGLARSNLDEDIIAEENIVSRSEFPESWLWNVEDLKEPPKNGISTKLMNIFLKDSITTW

EILAVSMSDKKGICVADPFEVTVMQDFFIDLRLPYSVVRNEQVEIRAVLYNYRQNQELKV

RVELLHNPAFCSLATTKRRHQQTVTIPPKSSLSVPYVIVPLKTGLQEVEVKAAVYHHFIS

DGVRKSLKVVPEGIRMNKTVAVRTLDPERLGREGVQKEDIPPADLSDQVPDTESETRILL

QGTPVAQMTEDAVDAERLKHLIVTPSGCGEQNMIGMTPTVIAVHYLDETEQWEKFGLEKR

QGALELIKKGYTQQLAFRQPSSAFAAFVKRAPSTWLTAYVVKVFSLAVNLIAIDSQVLCG

AVKWLILEKQKPDGVFQEDAPVIHQEMIGGLRNNNEKDMALTAFVLISLQEAKDICEEQV

NSLPGSITKAGDFLEANYMNLQRSYTVAIAGYALAQMGRLKGPLLNKFLTTAKDKNRWED

PGKQLYNVEATSYALLALLQLKDFDFVPPVVRWLNEQRYYGGGYGSTQATFMVFQALAQY

QKDAPDHQELNLDVSLQLPSRSSKITHRIHWESASLLRSEETKENEGFTVTAEGKGQGTL

SVVTMYHAKAKDQLTCNKFDLKVTIKPAPETEKRPQDAKNTMILEICTRYRGDQDATMSI

LDISMMTGFAPDTDDLKQLANGVDRYISKYELDKAFSDRNTLIIYLDKVSHSEDDCLAFK

VHQYFNVELIQPGAVKVYAYYNLEESCTRFYHPEKEDGKLNKLCRDELCRCAEENCFIQK

SDDKVTLEERLDKACEPGVDYVYKTRLVKVQLSNDFDEYIMAIEQTIKSGSDEVQVGQQR

TFISPIKCREALKLEEKKHYLMWGLSSDFWGEKPNLSYIIGKDTWVEHWPEEDECQDEEN

QKQCQDLGAFTESMVVFGCPN

Human C3 and C3b beta chain (amino acids 23-667)
(SEQ ID NO: 3)
SPMYSIITPNILRLESEETMVLEAHDAQGDVPVTVTVHDFPGKKLVLSSEKTVLTPATNH

MGNVTFTIPANREFKSEKGRNKFVTVQATFGTQVVEKVVLVSLQSGYLFIQTDKTIYTPG

STVLYRIFTVNHKLLPVGRTVMVNIENPEGIPVKQDSLSSQNQLGVLPLSWDIPELVNMG

QWKIRAYYENSPQQVFSTEFEVKEYVLPSFEVIVEPTEKFYYIYNEKGLEVTITARFLYG

KKVEGTAFVIFGIQDGEQRISLPESLKRIPIEDGSGEVVLSRKVLLDGVQNPRAEDLVGK

SLYVSATVILHSGSDMVQAERSGIPIVISPYQIHFIKTPKYFKPGMPFDLMVFVTNPDGS

PAYRVPVAVQGEDTVQSLTQGDGVAKLSINTHPSQKPLSITVRTKKQELSEAEQATRTMQ

ALPYSTVGNSNNYLHLSVLRTELRPGETLNVNFLLRMDRAHEAKIRYYTYLIMNKGRLLK

AGRQVREPGQDLVVLPLSITTDFIPSFRLVAYYTLIGASGQREVVADSVWVDVKDSCVGS

LVVKSGQSEDRQPVPGQQMTLKIEGDHGARVVLVAVDKGVFVLNKKNKLTQSKIWDVVEK

ADIGCTPGSGKDYAGVFSDAGLTFTSSSGQQTAQRAELQCPQPAA

Human C3 alpha chain (amino acids 672-1663)
(SEQ ID NO: 4)
SVQLTEKRMDKVGKYPKELRKCCEDGMRENPMRFSCQRRTRFISLGEACKKVFLDCCNYI

TELRRQHARASHLGLARSNLDEDIIAEENIVSRSEFPESWLWNVEDLKEPPKNGISTKLM

-continued

```
NIFLKDSITIMEILAVSMSDKKGICVADPFEVTVMQDFFIDLRLPYSVVRNEQVEIRAVL

YNYRQNQELKVRVELLHNPAFCSLATTKRRHQQTVTIPPKSSLSVPYVIVPLKTGLQEVE

VKAAVYHHFISDGVRKSLKVVPEGIRMNKTVAVRTLDPERLGREGVQKEDIPPADLSDQV

PDTESETRILLQGTPVAQMTEDAVDAERLKHLIVTPSGCGEQNMIGMTPTVIAVHYLDET

EQWEKFGLEKRQGALELIKKGYTQQLAFRQPSSAFAAFVKRAPSTWLTAYVVKVFSLAVN

LIAIDSQVLCGAVKWLILEKQKPDGVFQEDAPVIHQEMIGGLRNNNEKDMALTAFVLISL

QEAKDICEEQVNSLPGSITKAGDFLEANYMNLQRSYTVAIAGYALAQMGRLKGPLLNKFL

TTAKDKNRWEDPGKQLYNVEATSYALLALLQLKDFDFVPPVVRWLNEQRYYGGGYGSTQA

TFMVFQALAQYQKDAPDHQELNLDVSLQLPSRSSKITHRIHWESASLLRSEETKENEGFT

VTAEGKGQGTLSVVIMYHAKAKDQLTCNKFDLKVTIKPAPETEKRPQDAKNTMILEICTR

YRGDQDATMSILDISMMTGFAPDTDDLKQLANGVDRYISKYELDKAFSDRNTLIIYLDKV

SHSEDDCLAFKVHQYFNVELIQPGAVKVYAYYNLEESCTRFYHPEKEDGKLNKLCRDELC

RCAEENCFIQKSDDKVTLEERLDKACEPGVDYVYKTRLVKVQLSNDFDEYIMAIEQTIKS

GSDEVQVGQQRTFISPIKCREALKLEEKKHYLMWGLSSDFWGEKPNLSYIIGKDTWVEHW

PEEDECQDEENQKQCQDLGAFTESMVVFGCPN
```

Human C3b alpha chain (amino acids 749-1663)  (SEQ ID NO: 5)

```
SNLDEDIIAEENIVSRSEFPESWLWNVEDLKEPPKNGISTKLMNIFLKDSITTWEILAVS

MSDKKGICVADPFEVTVMQDFFIDLRLPYSVVRNEQVEIRAVLYNYRQNQELKVRVELLH

NPAFCSLATTKRRHQQTVTIPPKSSLSVPYVIVPLKTGLQEVEVKAAVYHHFISDGVRKS

LKVVPEGIRMNKTVAVRTLDPERLGREGVQKEDIPPADLSDQVPDTESETRILLQGTPVA

QMTEDAVDAERLKHLIVTPSGCGEQNMIGMTPTVIAVHYLDETEQWEKFGLEKRQGALEL

IKKGYTQQLAFRQPSSAFAAFVKRAPSTWLTAYVVKVFSLAVNLIAIDSQVLCGAVKWLI

LEKQKPDGVFQEDAPVIHQEMIGGLRNNNEKDMALTAFVLISLQEAKDICEEQVNSLPGS

ITKAGDFLEANYMNLQRSYTVAIAGYALAQMGRLKGPLLNKFLTTAKDKNRWEDPGKQLY

NVEATSYALLALLQLKDFDFVPPVVRWLNEQRYYGGGYGSTQATFMVFQALAQYQKDAPD

HQELNLDVSLQLPSRSSKITHRIHWESASLLRSEETKENEGFTVTAEGKGQGTLSVVTMY

HAKAKDQLTCNKFDLKVTIKPAPETEKRPQDAKNTMILEICTRYRGDQDATMSILDISMM

TGFAPDTDDLKQLANGVDRYISKYELDKAFSDRNTLIIYLDKVSHSEDDCLAFKVHQYFN

VELIQPGAVKVYAYYNLEESCTRFYHPEKEDGKLNKLCRDELCRCAEENCFIQKSDDKVT

LEERLDKACEPGVDYVYKTRLVKVQLSNDFDEYIMAIEQTIKSGSDEVQVGQQRTFISPI

KCREALKLEEKKHYLMWGLSSDFWGEKPNLSYIIGKDTWVEHWPEEDECQDEENQKQCQD

LGAFTESMVVFGCPN
```

Human C3a (amino acids 672-748)  (SEQ ID NO: 6)
```
SVQLTEKRMDKVGKYPKELRKCCEDGMRENPMRFSCQRRTRFISLGEACKKVFLDCCNYI
TELRRQHARASHLGLAR
```

38G10 Heavy chain CDR1  (SEQ ID NO: 7)
GYTFTDFYMD

38G10 Heavy chain CDR2  (SEQ ID NO: 8)
YIYPHNGGTTYNQNFTG

38G10 Heavy chain CDR3  (SEQ ID NO: 9)
RGGFDFDY

38G10 Light chain CDR1
(SEQ ID NO: 10)
KASENVDTYVS

38G10 Light chain CDR2
(SEQ ID NO: 11)
GASNRYT

38G10 Light chain CDR3
(SEQ ID NO: 12)
GQSHSYPLT

Hz38G10 Heavy chain CDR2
(SEQ ID NO: 13)
YIYPHNGGTTYNQQFTG

Hz38G10 G56A Heavy chain CDR2
(SEQ ID NO: 14)
YIYPHNAGTTYNQQFTG

Hz38G10 G56T Heavy chain CDR2
(SEQ ID NO: 15)
YIYPHNTGTTYNQQFTG

Hz38G10 N55E Heavy chain CDR2
(SEQ ID NO: 16)
YIYPHEGGTTYNQQFTG

Hz38G10 N55Q Heavy chain CDR2
(SEQ ID NO: 17)
YIYPHQGGTTYNQQFTG

38G10 Heavy chain variable region amino acid sequence
(SEQ ID NO: 18)
EVQLQQSGPELVKPGDSVKMSCKASGYTFTDFYMDWVKQSHGKSLEWIGYIYPHNGGTTY
NQNFTGKATLTVDKSSNTAYMELHSLTSEDSAVYYCARRGGFDFDYWGQGTTLTVSS 38G10 Light chain variable region amino acid sequence
(SEQ ID NO: 19)
NIVMTQSPKSMSLSVGERVTLRCKASENVDTYVSWYQQKPEQSPKLLIYGASNRYTGVPD
RFTGSGSATEFTLTISSVQAEDLVGYHCGQSHSYPLTFGAGTKLELK Hz38G10 Heavy chain variable region amino acid sequence
(SEQ ID NO: 20)
QVQLVQSGAEVKKPGASVKVSCKASGYTFTDFYMDWVRQAPGQRLEWMGYIYPHNGGTTY
NQQFTGRVTITVDKSASTAYMELSSLRSEDTAVYYCARRGGFDFDYWGQGTLVTVSS Hz38G10(G56A) Heavy chain variable region amino acid sequence
(SEQ ID NO: 21)
QVQLVQSGAEVKKPGASVKVSCKASGYTFTDFYMDWVRQAPGQRLEWMGYIYPHNAGTTY
NQQFTGRVTITVDKSASTAYMELSSLRSEDTAVYYCARRGGFDFDYWGQGTLVTVSS Hz38G10(G56T) Heavy chain variable region amino acid sequence
(SEQ ID NO: 22)
QVQLVQSGAEVKKPGASVKVSCKASGYTFTDFYMDWVRQAPGQRLEWMGYIYPHNTGTTY
NQQFTGRVTITVDKSASTAYMELSSLRSEDTAVYYCARRGGFDFDYWGQGTLVTVSS Hz38G10(N55E) Heavy chain variable region amino acid sequence
(SEQ ID NO: 23)
QVQLVQSGAEVKKPGASVKVSCKASGYTFTDFYMDWVRQAPGQRLEWMGYIYPHEGGTTY
NQQFTGRVTITVDKSASTAYMELSSLRSEDTAVYYCARRGGFDFDYWGQGTLVTVSS Hz38G10(N55Q) Heavy chain variable region amino acid sequence
(SEQ ID NO: 24)
QVQLVQSGAEVKKPGASVKVSCKASGYTFTDFYMDWVRQAPGQRLEWMGYIYPHQGGTTY
NQQFTGRVTITVDKSASTAYMELSSLRSEDTAVYYCARRGGFDFDYWGQGTLVTVSS Hz38G10 Light chain variable region amino acid sequence
(SEQ ID NO: 25)
DIQMTQSPSSLSASVGDRVTITCKASENVDTYVSWYQQKPGKAPKLLIYGASNRYTGVPS
RFSGSGSGTDFTFTISSLQPEDIATYHCGQSHSYPLTFGQGTKLEIK Hz38G10 Heavy chain amino acid sequence with signal sequence underlined
(SEQ ID NO: 26)
<u>MDMRVPAQLLGLLLLWLRGARC</u>QVQLVQSGAEVKKPGASVKVSCKASGYTFTDFYMDWVR

QAPGQRLEWMGYIYPHNGGTTYNQQFTGRVTITVDKSASTAYMELSSLRSEDTAVYYCAR

RGGFDFDYWGQGTLVTVSSASTKGPSVFPLAPSSKSTSGGTAALGCLVKDYFPEPVTVSW

-continued

NSGALTSGVHTFPAVLQSSGLYSLSSVVTVPSSSLGTQTYICNVNHKPSNTKVDKKVEPK

SCDKTHTCPPCPAPALAGGPSVFLFPPKPKDTLMISRIPEVTCVVVDVSHEDPEVKFNWY

VDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Hz38G10 Heavy chain amino acid sequence without signal sequence
(SEQ ID NO: 27)
QVQLVQSGAEVKKPGASVKVSCKASGYTFTDFYMDWVRQAPGQRLEWMGYIYPHNGGTTY

NQQFTGRVTITVDKSASTAYMELSSLRSEDTAVYYCARRGGFDFDYWGQGTLVTVSSAST

KGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPALAGGPSV

FLFPPKPKDTLMISRIPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKLTVDKSRWQQG

NVFSCSVMHEALHNHYTQKSLSLSPGK

Hz38G10(G56A) Heavy chain amino acid sequence with signal sequence
underlined
(SEQ ID NO: 28)
<u>MDMRVPAQLLGLLLLWLRGARC</u>QVQLVQSGAEVKKPGASVKVSCKASGYTFTDFYMDWVR

QAPGQRLEWMGYIYPHNAGTTYNQQFTGRVTITVDKSASTAYMELSSLRSEDTAVYYCAR

RGGFDFDYWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKKVEPK

SCDKTHTCPPCPAPALAGGPSVFLFPPKPKDTLMISRIPEVTCVVVDVSHEDPEVKFNWY

VDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Hz38G10(G56A) Heavy chain amino acid sequence without signal sequence
(SEQ ID NO: 29)
QVQLVQSGAEVKKPGASVKVSCKASGYTFTDFYMDWVRQAPGQRLEWMGYIYPHNAGTTY

NQQFTGRVTITVDKSASTAYMELSSLRSEDTAVYYCARRGGFDFDYWGQGTLVTVSSAST

KGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPALAGGPSV

FLFPPKPKDTLMISRIPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKLTVDKSRWQQG

NVFSCSVMHEALHNHYTQKSLSLSPGK

Hz38G10 Light chain amino acid sequence with signal sequence underlined
(SEQ ID NO: 30)
<u>MDMRVPAQLLGLLLLWLRGARC</u>DIQMTQSPSSLSASVGDRVTITCKASENVDTYVSWYQQ

KPGKAPKLLIYGASNRYTGVPSRFSGSGSGTDFTFTISSLQPEDIATYHCGQSHSYPLTF

GQGTKLEIKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRGEC

Hz38G10 Light chain amino acid sequence without signal sequence
(SEQ ID NO: 31)
DIQMTQSPSSLSASVGDRVTITCKASENVDTYVSWYQQKPGKAPKLLIYGASNRYTGVPS

RFSGSGSGTDFTFTISSLQPEDIATYHCGQSHSYPLTFGQGTKLEIKRTVAAPSVFIFPP

-continued

SDEQLKSGTASVVCLLNNFYPREAKVQWKVDNALQSGNSQESVTEQDSKDSTYSLSSILT

LSKADYEKHKVYACEVTHQGLSSPVTKSFNRGEC

Cynomolgus monkey C3 amino acid sequence with predicted signal sequence
underlined
(SEQ ID NO: 32)

<u>MGLTSGPSLLLLLLIHLPLALG</u>TPMYSMITPNVLRLESEETVVLEAHDANGDVPVTVTVH

DFPGKKLVLSSEKTVLTPATSHMGSVTIRIPANKEFKSEKGHNKFVTVQATFGAQVVEKV

VLVSLQSGYLFIQTDKTIYTPGSTVLCRIFTVNHKLLPVGRTVVVNIENPDGIPVKQDSL

SSQNQFGILPLSWDIPELVNMGQWKIRAYYENSPQQVFSTEFEVKEYVLPSFEVIVEPTE

KFYYIYNQKGLEVTITARFLYGKKVEGTAFVIFGIQDGEQRISLPESLKRIQIEDGSGDA

VLSRKVLLDGVQNPRPEDLVGKSLYVSVIVILHSGSDMVQAERSGIPIVISPYQIHFIKT

PKYFKPGMPFDLMVFVTNPDGSPAYRVPVAVQGEDAVQSLTQGDGVAKLSINTHPSQKPL

SITVRTKKRELSEAEQATRTMEAQPYSTVGNSNNYLHLSVPRAELRPGETLNVNFLLRMD

RTQEAKIRYYTYLIMNKGKLLKVGRQVREPGQDLVVLPLSITTDFIPSFRLVAYYTLIGA

NGQREVVADSVWVDVKDSCVGSLVVKSGQSEDRQPLPGQQMTLKIEGDHGARVGLVAVDK

GVFVLNKKNKLTQSKIWDVVEKADIGCTPGSGKDYAGVFSDAGLTFASSSGQQTAQRAEL

QCPQPAARRRRSVQLAEKRMDKVGQYPKELRKCCEHGMRENPMRFSCQRRTRYITLDEAC

KKAFLDCCNYITELRRQHARASHLGLARSNLDEDIIAEENIVSRSEFPESWLWKIEELKE

APKNGISTKLMNIFLKDSITTWEILAVSLSDKKGICVADPFEVTVMQDFFIDLRLPYSVV

RNEQVEIRAVLYNYRQNQELKVRVELLHNPAFCSLATAKRRHQQTVTIPPKSSLSVPYVI

VPLKTGQQEVEVKAAVYHFFISDGVRKSLKVVPEGIRMNKTVAVRTLDPERLGQEGVQRE

DVPPADLSDQVPDTESETRILLQGTPVAQMTEDAIDAERLKHLIVITSGCGEQNMITMTP

TVIAVHYLDETEQWEKFGPEKRQGALELIKKGYTQQLAFRQPSSAFAAFLNRAPSTWLTA

YVVKVFSLAVNLIAIDSQVLCGAVKWLILEKQKPDGVFQEDAPVIHQEMTGGFRNTNEKD

MALTAFVLISLQEAKEICEEQVNSLPGSITKAGDFLEANYMNLQRSYTVAIAAYALAQMG

RLKGPLLNKFLTTAKDKNRWEEPGQQLYNVEATSYALLALLQLKDFDFVPPVVRWLNEQR

YYGGGYGSTQATFMVFQALAQYQKDVPDHKELNLDVSLQLPSRSSKIIHRIHWESASLLR

SEETKENEGFTVTAEGKGQGTLSVVTMYHAKAKGQLTCNKFDLKVTIKPAPETEKRPQDA

KNIMILEICTRYRGDQDATMSILDISMMTGFVPDTDDLKQLANGVDRYISKYELDKAFSD

RNTLIIYLDKVSHSEDDCIAFKVHQYFNVELIQPGAVKVYAYYNLAESCTRFYHPEKEDG

KLNKLCRDELCRCAEENCFIQKLDDKVTLEERLDKACEPGVDYVYKTRLVKAQLSNDFDE

YIMAIEQIIKSGSDEVQVGQQRTFISPIKCREALKLEERKHYLMWGLSSDFWGEKPNLSY

IIGKDTWVEHWPEEDECQDEENQKQCQDLGTFTENMVVFGCPN

Cynomolgus monkey C3 amino acid sequence without predicted signal
sequence
(SEQ ID NO: 33)

TPMYSMITPNVLRLESEETVVLEAHDANGDVPVTVTVHDFPGKKLVLSSEKTVLTPATSH

MGSVTIRIPANKEFKSEKGHNKFVTVQATFGAQVVEKVVLVSLQSGYLFIQTDKTIYTPG

STVLCRIFTVNHKLLPVGRTVVVNIENPDGIPVKQDSLSSQNQFGILPLSWDIPELVNMG

QWKIRAYYENSPQQVFSTEFEVKEYVLPSFEVIVEPTEKFYYIYNQKGLEVTITARFLYG

KKVEGTAFVIFGIQDGEQRISLPESLKRIQIEDGSGDAVLSRKVLLDGVQNPRPEDLVGK

SLYVSVTVILHSGSDMVQAERSGIPIVISPYQIHFIKTPKYFKPGMPFDLMVFVTNPDGS

PAYRVPVAVQGEDAVQSLTQGDGVAKLSINTHPSQKPLSITVRTKKRELSEAEQATRIME

AQPYSTVGNSNNYLHLSVPRAELRPGETLNVNFLLRMDRTQEAKIRYYTYLIMNKGKLLK

-continued

```
VGRQVREPGQDLVVLPLSITTDFIPSFRLVAYYTLIGANGQREVVADSVWVDVKDSCVGS
LVVKSGQSEDRQPLPGQQMTLKIEGDHGARVGLVAVDKGVFVLNKKNKLTQSKIWDVVEK
ADIGCTPGSGKDYAGVFSDAGLTFASSSGQQTAQRAELQCPQPAARRRRSVQLAEKRMDK
VGQYPKELRKCCEHGMRENPMRFSCQRRTRYITLDEACKKAFLDCCNYITELRRQHARAS
HLGLARSNLDEDIIAEENIVSRSEFPESWLWKIEELKEAPKNGISTKLMNIFLKDSITTW
EILAVSLSDKKGICVADPFEVTVMQDFFIDLRLPYSVVRNEQVEIRAVLYNYRQNQELKV
RVELLHNPAFCSLATAKRRHQQTVTIPPKSSLSVPYVIVPLKTGQQEVEVKAAVYHFFIS
DGVRKSLKVVPEGIRMNKTVAVRTLDPERLGQEGVQREDVPPADLSDQVPDTESETRILL
QGTPVAQMTEDAIDAERLKHLIVTPSGCGEQNMITMTPTVIAVHYLDETEQWEKFGPEKR
QGALELIKKGYTQQLAFRQPSSAFAAFLNRAPSTWLTAYVVKVFSLAVNLIAIDSQVLCG
AVKWLILEKQKPDGVFQEDAPVIHQEMTGGFRNTNEKDMALTAFVLISLQEAKEICEEQV
NSLPGSITKAGDFLEANYMNLQRSYTVAIAAYALAQMGRLKGPLLNKFLTTAKDKNRWEE
PGQQLYNVEATSYALLALLQLKDFDFVPPVVRWLNEQRYYGGGYGSTQATFMVFQALAQY
QKDVPDHKELNLDVSLQLPSRSSKIIHRIHWESASLLRSEETKENEGFTVTAEGKGQGTL
SVVTMYHAKAKGQLTCNKFDLKVTIKPAPETEKRPQDAKNTMILEICTRYRGDQDATMSI
LDISMMTGFVPDTDDLKQLANGVDRYISKYELDKAFSDRNTLIIYLDKVSHSEDDCIAFK
VHQYFNVELIQPGAVKVYAYYNLAESCTRFYHPEKEDGKLNKLCRDELCRCAEENCFIQK
LDDKVTLEERLDKACEPGVDYVYKTRLVKAQLSNDFDEYIMAIEQIIKSGSDEVQVGQQR
TFISPIKCREALKLEERKHYLMWGLSSDFWGEKPNLSYIIGKDTWVEHWPEEDECQDEEN
QKQCQDLGTFTENMVVFGCPN
```

Human IgG1 constant region
(SEQ ID NO: 34)
```
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK
```

Human IgG1 constant region E233A/L235A
(SEQ ID NO: 35)
```
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPALAGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK
```

Human IgG1 constant region L234A/L235A
(SEQ ID NO: 36)
```
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPEAAGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
```

```
MTKNQVSLTCLVKGFYPSDIAVEWESNGQPENNYKTTPPVLDSDGSFFLYSKLTVDKSRW

QQGNVFSCSVMHEALHNHYTQKSLSLSPGK
```

Rat C3 amino acid sequence with predicted signal sequence underlined
(SEQ ID NO: 37)

```
MGPTSGSQLLVLLLLASSLLALGSPMYSIITPNVLRLESEETFILEAHDAQGDVPVTVT

VQDFLKKQVLTSEKTVLTGATGHLNRVFIKIPASKEFNADKGHKYVTVVANFGATVVEKA

VLVSFQSGYLFIQTDKTIYTPGSTVFYRIFTVDNNLLPVGKTVVIVIETPDGVPIKRDIL

SSHNQYGILPLSWNIPELVNMGQWKIRAFYEHAPKQTFSAEFEVKEYVLPSFEVLVEPTE

KFYYIHGPKGLEVSITARFLYGKNVDGTAFVIFGVQDEDKKISLALSLTRVLIEDGSGEA

VLSRKVLMDGVRPSSPEALVGKSLYVSVTVILHSGSDMVEAERSGIPIVISPYQIHFIKT

PKFFKPAMPFDLMVFVTNPDGSPARRVPVVTQGSDAQALTQDDGVAKLSVNTPNNRQPLT

ITVSTKKEGIPDARQATRTMQAPYSTMHNSNNYLHLSVSRVELKPGDNLNVNFHLRTDA

GQEAKIRYYTYLVMNKGKLLKAGRQVREPGQDLVVLSLPITPEFIPSFRLVAYYTLIGAN

GQREVVADSVWVDVKDSCVGTLVVKGDPRDNRQPAPGHQTTLRIEGNQGARVGLVAVDKG

VFVLNKKNKLTQSKIWDVVEKADIGCTPGSGKNYAGVFMDAGLTFKTNQGLQTDQREDPE

CAKPAARRRSVQLMERRMDKAGQYTDKGLRKCCEDGMRDIPMPYSCQRRARLITQGESC

LKAFMDCCNYITKLREQHRRDHVLGLARSDVDEDIIPEEDIISRSHFPESWLWTIEELKE

PEKNGISTKVMNIFLKDSITTWEILAVSLSDKKGICVADPYEITVMQDFFIDLRLPYSVV

RNEQVEIRAVLFNYREQEKLKVRVELLHNPAFCSMATAKKRYYQTIEIPPKSSVAVPYVI

VPLKIGLQEVEVKAAVFNHFISDGVKKILKVVPEGMRVNKTVAVRTLDPEHLNQGGVQRE

DVNAADLSDQVPDTDSETRILLQGTPVAQMAEDAVDGERLKHLIVTPSGCGEQNMIGMTP

TVIAVHYLDQTEQWEKFGLEKRQEALELIKKGYTQQLAFKQPISAYAAFNNRPPSTWLTA

MWSRSFSLAANLIAIDSQVLCGAVKWLILEKQKPDGVFQEDGPVIHQEMIGGFRNTKEAD

VSLTAFVLIALQEARDICEGQVNSLPGSINKAGEYLEASYLNLQRPYTVAIAGYALALMN

KLEEPYLTKFLNTAKDRNRWEEPGQQLYNVEATSYALLALLLLKDFDSVPPVVRWLNDER

YYGGGYGSTQATFMVFQALAQYRADVPDHKDLNMDVSLHLPSRSSPTVFRLLWESGSLLR

SEETKQNEGFSLTAKGKGQGTLSVVTVYHAKVKGKTICKKFDLRVTIKPAPETAKKPQDA

KSSMILDICTRYLGDVDATMSILDISMMTGFIPDTNDLELLSSGVDRYISKYEMDKAFSN

KNTLIIYLEKISHSEEDCLSFKVHQFFNVGLIQPGSVKVYSYYNLEESCTRFYHPEKDDG

MLSKLCHNEMCRCAEENCFMHQSQDQVSLNERLDKACEPGVDYVYKTKLTTIELSDDFDE

YIMTIEQVIKSGSDEVQAGQERRFISHVKCRNALKLQKGKQYLMWGLSSDLWGEKPNTSY

IIGKDTWVEHWPEAEERQDQKNQKQCEDLGAFTETMVVFGCPN
```

3D8 Heavy chain variable region amino acid sequence
(SEQ ID NO: 91)
```
EIQLQQSGAELVKPGASVKISCKASGYSFTGYNMNWVKQSHGKSLEWIGNINPYYGSTNY
NQKFKGKATLTVDKSSTTAYMQLDSLTSEDSAVYYCARGYYGGNYPFAYWGQGTLVTVSA
```

3D8 Light chain variable region amino acid sequence
(SEQ ID NO: 92)
```
DIQMTQSPASLSASVGETVTITCRASENIYSYLAWYQQKQGKSPQLLVYNAKTLAEGVPS
RFSGSGSGTQFSLKINSLQPEDFGSYYCQHYYGTPYTFGGGSKVEIK
```

3G8 Heavy chain variable region amino acid sequence
(SEQ ID NO: 93)
```
EIQLQQSGAELVKPGASVKISCMASGYSFTGYNMNWVKQSHGKGLEWIGNINPYYDSTSY
NQKFKGKATLTVDKSSSTAYMQLNSLTSEDSAVYYCARENYDFVGFAYWGQGTLVTVSA
```

3G8 Light chain variable region amino acid sequence
(SEQ ID NO: 94)
```
QIVLSQSPAILSASPGEKVTMTCRASSSVSYMHWFQQKPGSSPKPWIYVTSNLASGVPPR
FSGSGSGTSYSLTISRVEAEDAATYYCQQWSTNPLTFGAGTKLELK
```

-continued

15C12 Heavy chain variable region amino acid sequence
(SEQ ID NO: 95)
EIQLQQSGAELEKPGASVKISCKASGYSFTGYNMHWVKQSHGKSLEWIGNINPYYGTTNS
NQKFEDKATLTVDKSSSTAYMQLNSLTSEDSAVYYCARGIYYYGTGYPYFDFWGQGTTLT
VSS 15C12 Light chain variable region amino acid sequence
(SEQ ID NO: 96)
DIQMTQTTSSLSASLGDRVTISCRASQDINNYLNWYLQKPDGTVKLLIYYTSRLHSGVPS
RFSGSGSGTDYSLTISNLEQEDLATYFCQQGITLPWTFGGGTKLEIK 27A8 Heavy chain variable region amino acid sequence
(SEQ ID NO: 97)
QVQLLQPGAEFVKPGASVKLSCKASGYTFTDYWINWVKQRPGQGLEWIGNIYPGSTSANY
NEKFKSKATLTIDTSSITAYMQLSSLTSDDSAVYYCARYGYDSWFAYWGQGTLVTVSA 27A8 Light chain variable region amino acid sequence
(SEQ ID NO: 98)
DVVLTQTPLSLPVNIGDQASISCKSTKSLLNSDGFTYLDWFLQKPGQSPHLLIYLVSNRF
SGIPDRFSGSGSETDFTLKISRVEAEDLGVYYCFQSNYLPLTFGSGTKLEIK 28C3 Heavy chain variable region amino acid sequence
(SEQ ID NO: 99)
QVQLQQSGPELVKPGASVKISCKASGYAFNSCWMNWVKQRPGKGLEWIGRIYPGDGDTNY
NGKFKGKATLTADKSSTTAYMQLSSLTSEDSAVYFCAREGRNYGYEDYWGQGTTLTVSS 28C3 Light chain variable region amino acid sequence
(SEQ ID NO: 100)
DIVLTQSPASLAVSLGQRATISCKASQSVDYDGDSYMNWYQQKPGQPPKLLIYAASDLES
GIPARFSGSGSGTDFTLNIHPVEEEDAATYYCQQANEDPRTFGGGTKLEIK 38F5 Heavy chain variable region amino acid sequence
(SEQ ID NO: 101)
EVMLVESGGALVKPGGSLKLSCTASGFTFSNYAMSWVRQTPEKRLEWVAQTISSGGRYTY
YPDSVKGRFTISRDNARNTLYLQMSSLRSEDTAMYYCVRRYYGNSYWYFDVWGAGTTVTV
SS 38F5 Light chain variable region amino acid sequence
(SEQ ID NO: 102)
DIVMTQSPSSLSVSAGEKVIMNCKSSQSLLNSGNQKHYLTWYQQKPGQPPKLLIYGASTR
GSGVPDRFTGSGSGTDFTLTISSVQAEDLAVYYCQNDHSYPYTFGGGTKLEIK 62B11 Heavy chain variable region amino acid sequence
(SEQ ID NO: 103)
EVKLVESGGGLVQPGGSLKLSCAASGFTFSSYTMSWVRQTPEKRLEWVAYISSGGGTTYY
PDTVKGRFTVSRDNAKNTLYLQMSSLRSEDTAMYSCARRYYRGSSLWYFDVWGAGTTVTV
SS 62B11 Light chain variable region amino acid sequence
(SEQ ID NO: 104)
DIVMTQSPSSLTVTAGEKVIMSCKSSQSLFNSGSQKNFLTWYQQRPGQPPKLLIYWASTR
ESGVPDRFTGSGSGTDFTLTISSVQAEDLAVYYCQNDYSYPLTFGAGTKLELK 62F2 Heavy chain variable region amino acid sequence
(SEQ ID NO: 105)
DVQLQESGPDLVKPSQSLSLICTVTGYSITSGYSLHWIRQFPGNKLEWMGYIHYSGSTNY
NPSLKSRISITRDTSKNQFFLKLNSVISEDTATYHCARAWDYLDYWGQGTTLIVSS 62F2 Light chain variable region amino acid sequence
(SEQ ID NO: 106)
DIQMTQSPASLSASVGETVTITCRASENIYSQLAWYQQKQGKSPQLLVYDAKTLAEGVPS
RFSGSGSDTQFSLKIISLQPEDFGRYYCHHHFGILYTFGGGTKLEMK 63A3 Heavy chain variable region amino acid sequence
(SEQ ID NO: 107)
DVQLQESGPGLVKPSQSLSLICSVTGYSITSGYYWNWIRQFPGNKLEWMGYIRYDGSNNY
NPSLKNRISITRDTSKNQVFLKLNSVTPEDTATYYCARHYGYDGGAFDFWGQGTTLTVSS 63A3 Light chain variable region amino acid sequence
(SEQ ID NO: 108)
DIQMTQSPASLSASVGETVTITCRTSENIYNYLVWYQQKQGKSPQLLVYNAKTLEEGVPS
RFSGSGSGTQFSLKVNSLQPEDFGSYYCQHHYGTPFTFGSGTKLEIK Human IgG1 constant region L234A/L235A/P329G
(SEQ ID NO: 109)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALGAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Hz38G10 dsscFv heavy chain variable region
(SEQ ID NO: 110)
QVQLVQSGAEVKKPGASVKVSCKASGYTFTDFYMDWVRQAPGQCLEWMGYIYPHNGGTTY
NQQFTGRVTITVDKSASTAYMELSSLRSEDTAVYYCARRGGFDFDYWGQGTLVTVSS Hz38G10(G56A) dsscFv heavy chain variable region
(SEQ ID NO: 111)
QVQLVQSGAEVKKPGASVKVSCKASGYTFTDFYMDWVRQAPGQCLEWMGYIYPHNAGTTY
NQQFTGRVTITVDKSASTAYMELSSLRSEDTAVYYCARRGGFDFDYWGQGTLVTVSS Hz38G10 dsscFv light chain variable region
(SEQ ID NO: 112)
DIQMTQSPSSLSASVGDRVTITCKASENVDTYVSWYQQKPGKAPKLLIYGASNRYTGVPS
RFSGSGSGTDFTFTISSLQPEDIATYHCGQSHSYPLTFGCGTKLEIK Hz38G10 dsscFv
(SEQ ID NO: 113)
MDIQMTQSPSSLSASVGDRVTITCKASENVDTYVSWYQQKPGKAPKLLIYGASNRYTGVP

SRFSGSGSGTDFTFTISSLQPEDIATYHCGQSHSYPLTFGCGTKLEIKGGGGSGGGGSGG

GGSQVQLVQSGAEVKKPGASVKVSCKASGYTFTDFYMDWVRQAPGQCLEWMGYIYPHNGG

TTYNQQFTGRVTITVDKSASTAYMELSSLRSEDTAVYYCARRGGFDFDYWGQGTLVTVSS

Hz38G10(G56A) dsscFv
(SEQ ID NO: 114)
MDIQMTQSPSSLSASVGDRVTITCKASENVDTYVSWYQQKPGKAPKLLIYGASNRYTGVP

SRFSGSGSGTDFTFTISSLQPEDIATYHCGQSHSYPLTFGCGTKLEIKGGGGSGGGGSGG

GGSQVQLVQSGAEVKKPGASVKVSCKASGYTFTDFYMDWVRQAPGQCLEWMGYIYPHNAG

TTYNQQFTGRVTITVDKSASTAYMELSSLRSEDTAVYYCARRGGFDFDYWGQGTLVTVSS

Linker
(SEQ ID NO: 115)
GGGGS

Linker
(SEQ ID NO: 116)
GGGGSGGGGS

Linker
(SEQ ID NO: 117)
GGGGSGGGGSGGGGS

Linker
(SEQ ID NO: 118)
GGGGSGGGGSGGGGSGGGGS

Hz38G10 dsscFv
(SEQ ID NO: 119)
DIQMTQSPSSLSASVGDRVTITCKASENVDTYVSWYQQKPGKAPKLLIYGASNRYTGVPS

RFSGSGSGTDFTFTISSLQPEDIATYHCGQSHSYPLTFGCGTKLEIKGGGGSGGGGSGGG

GSQVQLVQSGAEVKKPGASVKVSCKASGYTFTDFYMDWVRQAPGQCLEWMGYIYPHNGGT

TYNQQFTGRVTITVDKSASTAYMELSSLRSEDTAVYYCARRGGFDFDYTNGQGTLVTVSS

Hz38G10(G56A) dsscFv
(SEQ ID NO: 229)
DIQMTQSPSSLSASVGDRVTITCKASENVDTYVSWYQQKPGKAPKLLIYGASNRYTGVPS

RFSGSGSGTDFTFTISSLQPEDIATYHCGQSHSYPLTFGCGTKLEIKGGGGSGGGGSGGG

GSQVQLVQSGAEVKKPGASVKVSCKASGYTFTDFYMDWVRQAPGQCLEWMGYIYPHNAGT

TYNQQFTGRVTITVDKSASTAYMELSSLRSEDTAVYYCARRGGFDFDYTNGQGTLVTVSS

What is claimed:

1. An antibody that specifically binds human complement component C3 (SEQ ID NO:2), wherein the antibody comprises:
   a heavy chain variable region (VH) comprising VH complementarity determining region (CDR)1, VH CDR2, and VH CDR3 from the amino acid sequence set forth in SEQ ID NO:21, and
   a light chain variable region (VL) comprising VL CDR1, VL CDR2, and VL CDR3 from the amino acid sequence set forth in SEQ ID NO:25.

2. An antibody that specifically binds human complement component C3 (SEQ ID NO:2), wherein the antibody comprises:
   (a) (i) a VH comprising a VH CDR1 comprising the amino acid sequence set forth in SEQ ID NO:7, a VH CDR2 comprising the amino acid sequence set forth in SEQ ID NO:14, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;
   (b) (i) a VH comprising a VH CDR1 comprising the amino acid sequence set forth in SEQ ID NO:120, a VH CDR2 comprising the amino acid sequence set forth in SEQ ID NO:131, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;
   (c) (i) a VH comprising a VH CDR1 comprising the amino acid sequence set forth in SEQ ID NO:7, a VH CDR2 comprising the amino acid sequence set forth in SEQ ID NO:132, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;
   (d) (i) a VH comprising a VH CDR1 comprising the amino acid sequence set forth in SEQ ID NO:121, a VH CDR2 comprising the amino acid sequence set forth in SEQ ID NO:14, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12; or
   (e) (i) a VH comprising a VH CDR1 comprising the amino acid sequence set forth in SEQ ID NO:122, a VH CDR2 comprising the amino acid sequence set forth in SEQ ID NO:133, and a VH CDR3 comprising the amino acid sequence set forth in SEQ ID NO:126; and (ii) a VL comprising a VL CDR1 comprising the amino acid sequence set forth in SEQ ID NO:127, a VL CDR2 comprising the amino acid sequence set forth in SEQ ID NO:128, and a VL CDR3 comprising the amino acid sequence set forth in SEQ ID NO:129.

3. The antibody of claim 1, wherein:
   (i) the VH has at least 80% sequence identity to the amino acid sequence set forth in SEQ ID NO:21;
   (ii) the VL has at least 80% sequence identity to the amino acid sequence set forth in SEQ ID NO:25; or
   (iii) the VH has at least 80% sequence identity to the amino acid sequence set forth in SEQ ID NO:21 and the VL has at least 80% sequence identity to the amino acid sequence set forth in SEQ ID NO:25.

4. The antibody of claim 1, wherein:
   (i) the VH has at least 90% sequence identity to the amino acid sequence set forth in SEQ ID NO:21;
   (ii) the VL has at least 90% sequence identity to the amino acid sequence set forth in SEQ ID NO:25; or
   (iii) the VH has at least 90% sequence identity to the amino acid sequence set forth in SEQ ID NO:21 and the VL has at least 90% sequence identity to the amino acid sequence set forth in SEQ ID NO:25.

5. The antibody of claim 1, which is a chimeric or humanized antibody.

6. The antibody of claim 1, which is a bispecific antibody or a multispecific antibody.

7. The antibody of claim 1, which is a Fab, Fab', F(ab')$_2$, Fv, scFv, (scFv)$_2$, single chain antibody, dual variable region antibody, diabody, or nanobody.

8. The antibody of claim 1, which is an scFv comprising the VH and the VL, wherein the VH comprises the amino acid sequence set forth in SEQ ID NO:111 and the VL comprises the amino acid sequence set forth in SEQ ID NO:112.

9. The antibody of claim 1, which is an IgG1 antibody, an IgG2 antibody, or an IgG4 antibody.

10. The antibody of claim 1, which has at least one or more of the following properties:
   (i) does not bind C3b at a detectable level;
   (ii) binds C3 with an affinity that is at least 50-fold greater than the antibody's affinity to C3b;
   (iii) binds C3 with an affinity that is at least 100-fold greater than the antibody's affinity to C3b;
   (iv) is an antagonist of C3;
   (v) inhibits C3 activity;
   (vi) inhibits complement activation;
   (v) inhibits activation of the classical complement pathway;
   (vi) inhibits activation of the alternative complement pathway; and
   (vii) inhibits activation of the classical complement pathway and the alternative complement pathway.

11. An antibody that specifically binds human complement component C3 (SEQ ID NO:2), wherein the antibody comprises a VH comprising the amino acid sequence set forth in SEQ ID NO:21 and a VL comprising the amino acid sequence set forth in SEQ ID NO:25.

12. An antibody that specifically binds human complement component C3 (SEQ ID NO:2), wherein the antibody comprises a heavy chain comprising the amino acid sequence set forth in SEQ ID NO:29 and a light chain comprising the amino acid sequence set forth in SEQ ID NO:31.

13. A single chain variable fragment (scFv), comprising the amino acid sequence set forth in SEQ ID NO:114.

14. A single chain variable fragment (scFv), comprising the amino acid sequence set forth in SEQ ID NO:229.

15. A pharmaceutical composition comprising the antibody of claim 1 and a pharmaceutically acceptable carrier.

16. A pharmaceutical composition comprising the antibody of claim 2 and a pharmaceutically acceptable carrier.

17. A pharmaceutical composition comprising the antibody of claim 8 and a pharmaceutically acceptable carrier.

18. A pharmaceutical composition comprising the antibody of claim 11 and a pharmaceutically acceptable carrier.

19. A pharmaceutical composition comprising the antibody of claim 12 and a pharmaceutically acceptable carrier.

20. A pharmaceutical composition comprising the scFv of claim 13 and a pharmaceutically acceptable carrier.

21. A pharmaceutical composition comprising the scFv of claim 14 and a pharmaceutically acceptable carrier.

22. An antibody that specifically binds human complement component C3 (SEQ ID NO:2), wherein the antibody comprises:
   (a) a VH comprising VH CDR1, VH CDR2, and VH CDR3 from the amino acid sequence set forth in SEQ ID NO:18, and a VL comprising VL CDR1, VL CDR2, and VL CDR3 from the amino acid sequence set forth in SEQ ID NO:19;
   (b) a VH comprising VH CDR1, VH CDR2, and VH CDR3 from the amino acid sequence set forth in SEQ ID NO:20, and a VL comprising VL CDR1, VL CDR2, and VL CDR3 from the amino acid sequence set forth in SEQ ID NO:25;
   (c) a VH comprising VH CDR1, VH CDR2, and VH CDR3 from the amino acid sequence set forth in SEQ ID NO:23, and a VL comprising VL CDR1, VL CDR2, and VL CDR3 from the amino acid sequence set forth in SEQ ID NO:25;
   (d) a VH comprising VH CDR1, VH CDR2, and VH CDR3 from the amino acid sequence set forth in SEQ ID NO:24, and a VL comprising VL CDR1, VL CDR2, and VL CDR3 from the amino acid sequence set forth in SEQ ID NO:25; or
   (e) a VH comprising VH CDR1, VH CDR2, and VH CDR3 from the amino acid sequence set forth in SEQ ID NO:22, and a VL comprising VL CDR1, VL CDR2, and VL CDR3 from the amino acid sequence set forth in SEQ ID NO:25.

23. An antibody that specifically binds human complement component C3 (SEQ ID NO:2), wherein the antibody comprises:
   (a) (1) (i) a VH comprising a VH CDR1 comprising the amino acid sequence set forth in SEQ ID NO:7, a VH CDR2 comprising the amino acid sequence set forth in SEQ ID NO:8, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;
   (2) (i) a VH comprising a VH CDR1 comprising the amino acid sequence set forth in SEQ ID NO:120, a VH CDR2 comprising the amino acid sequence set forth in SEQ ID NO:123, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;
   (3) (i) a VH comprising a VH CDR1 comprising the amino acid sequence set forth in SEQ ID NO:7, a VH CDR2 comprising the amino acid sequence set forth in SEQ ID NO:124, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;
   (4) (i) a VH comprising a VH CDR1 comprising the amino acid sequence set forth in SEQ ID NO:121, a VH CDR2 comprising the amino acid sequence set forth in SEQ ID NO:8, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12; or
   (5) (i) a VH comprising a VH CDR1 comprising the amino acid sequence set forth in SEQ ID NO:122, a VH CDR2 comprising the amino acid sequence set forth in SEQ ID NO:125, and a VH CDR3 comprising the amino acid sequence set forth in SEQ ID NO:126; and (ii) a VL comprising a VL CDR1 comprising the amino acid sequence set forth in SEQ ID NO:127, a VL CDR2 comprising the amino acid sequence set forth in SEQ ID NO:128, and a VL CDR3 comprising the amino acid sequence set forth in SEQ ID NO:129;
   (b) (1) (i) a VH comprising a VH CDR1 comprising the amino acid sequence set forth in SEQ ID NO:7, a VH CDR2 comprising the amino acid sequence set forth in SEQ ID NO:13, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(2) (i) a VH comprising a VH CDR1 comprising the amino acid sequence set forth in SEQ ID NO:120, a VH CDR2 comprising the amino acid sequence set forth in SEQ ID NO:123, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(3) (i) a VH comprising a VH CDR1 comprising the amino acid sequence set forth in SEQ ID NO:7, a VH CDR2 comprising the amino acid sequence set forth in SEQ ID NO:124, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(4) (i) a VH comprising a VH CDR1 comprising the amino acid sequence set forth in SEQ ID NO:121, a VH CDR2 comprising the amino acid sequence set forth in SEQ ID NO:13, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12; or (5) (i) a VH comprising a VH CDR1 comprising the amino acid sequence set forth in SEQ ID NO:122, a VH CDR2 comprising the amino acid sequence set forth in SEQ ID NO:130, and a VH CDR3 comprising the amino acid sequence set forth in SEQ ID NO:126; and (ii) a VL comprising a VL CDR1 comprising the amino acid sequence set forth in SEQ ID NO:127, a VL CDR2 comprising the amino acid sequence set forth in SEQ ID NO:128, and a VL CDR3 comprising the amino acid sequence set forth in SEQ ID NO:129;

(c) (1) (i) a VH comprising a VH CDR1 comprising the amino acid sequence set forth in SEQ ID NO:7, a VH CDR2 comprising the amino acid sequence set forth in SEQ ID NO:16, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(2) (i) a VH comprising a VH CDR1 comprising the amino acid sequence set forth in SEQ ID NO:120, a VH CDR2 comprising the amino acid sequence set forth in SEQ ID NO:137, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(3) (i) a VH comprising a VH CDR1 comprising the amino acid sequence set forth in SEQ ID NO:7, a VH CDR2 comprising the amino acid sequence set forth in SEQ ID NO:138, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(4) (i) a VH comprising a VH CDR1 comprising the amino acid sequence set forth in SEQ ID NO:121, a VH CDR2 comprising the amino acid sequence set forth in SEQ ID NO:16, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12; or (5) (i) a VH comprising a VH CDR1 comprising the amino acid sequence set forth in SEQ ID NO:122, a VH CDR2 comprising the amino acid sequence set forth in SEQ ID NO:139, and a VH CDR3 comprising the amino acid sequence set forth in SEQ ID NO:126; and (ii) a VL comprising a VL CDR1 comprising the amino acid sequence set forth in SEQ ID NO:127, a VL CDR2 comprising the amino acid sequence set forth in SEQ ID NO:128, and a VL CDR3 comprising the amino acid sequence set forth in SEQ ID NO:129;

(d) (1) (i) a VH comprising a VH CDR1 comprising the amino acid sequence set forth in SEQ ID NO:7, a VH CDR2 comprising the amino acid sequence set forth in SEQ ID NO:17, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(2) (i) a VH comprising a VH CDR1 comprising the amino acid sequence set forth in SEQ ID NO:120, a VH CDR2 comprising the amino acid sequence set forth in SEQ ID NO:140, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(3) (i) a VH comprising a VH CDR1 comprising the amino acid sequence set forth in SEQ ID NO:7, a VH CDR2 comprising the amino acid sequence set forth in SEQ ID NO:141, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(4) (i) a VH comprising a VH CDR1 comprising the amino acid sequence set forth in SEQ ID NO:121, a VH CDR2 comprising the amino acid sequence set forth in SEQ ID NO:17, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12; or (5) (i) a VH comprising a VH CDR1 comprising the amino acid sequence set forth in SEQ ID NO:122, a VH CDR2 comprising the amino acid sequence set forth in SEQ ID NO:142, and a VH CDR3 comprising the amino acid sequence set forth in SEQ ID NO:126; and (ii) a VL comprising a VL CDR1 comprising the amino acid sequence set forth in SEQ ID NO:127, a VL CDR2 comprising the amino acid sequence set forth in SEQ ID NO:128, and a VL CDR3 comprising the amino acid sequence set forth in SEQ ID NO:129; or (e) (1) a VH comprising a VH CDR1 comprising the amino acid sequence set forth in SEQ ID NO:7, a VH CDR2 comprising the amino acid sequence set forth in SEQ ID NO:15, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(2) (i) a VH comprising a VH CDR1 comprising the amino acid sequence set forth in SEQ ID NO:120, a VH CDR2 comprising the amino acid sequence set forth in SEQ ID NO:134, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(3) (i) a VH comprising a VH CDR1 comprising the amino acid sequence set forth in SEQ ID NO:7, a VH CDR2 comprising the amino acid sequence set forth in SEQ ID NO:135, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12;

(4) (i) a VH comprising a VH CDR1 comprising the amino acid sequence set forth in SEQ ID NO:121, a VH CDR2 comprising the amino acid sequence set forth in SEQ ID NO:15, and a VH CDR3 comprising the amino acid sequence set forth in SEQ ID NO:9; and (ii) a VL comprising a VL CDR1 comprising the amino acid sequence set forth in SEQ ID NO:10, a VL CDR2 comprising the amino acid sequence set forth in SEQ ID NO:11, and a VL CDR3 comprising the amino acid sequence set forth in SEQ ID NO:12; or (5) (i) a VH comprising a VH CDR1 comprising the amino acid sequence set forth in SEQ ID NO:122, a VH CDR2 comprising the amino acid sequence set forth in SEQ ID NO:136, and a VH CDR3 comprising the amino acid sequence set forth in SEQ ID NO:126; and (ii) a VL comprising a VL CDR1 comprising the amino acid sequence set forth in SEQ ID NO:127, a VL CDR2 comprising the amino acid sequence set forth in SEQ ID NO:128, and a VL CDR3 comprising the amino acid sequence set forth in SEQ ID NO:129.

24. The antibody of claim 22, wherein:
(i) the VH has at least 80% sequence identity to the amino acid sequence set forth in SEQ ID NO:18;
(ii) the VH has at least 80% sequence identity to the amino acid sequence set forth in SEQ ID NO:20;
(iii) the VH has at least 80% sequence identity to the amino acid sequence set forth in SEQ ID NO:23;
(iv) the VH has at least 80% sequence identity to the amino acid sequence set forth in SEQ ID NO:24;
(v) the VH has at least 80% sequence identity to the amino acid sequence set forth in SEQ ID NO:22;
(vi) the VL has at least 80% sequence identity to the amino acid sequence set forth in SEQ ID NO:19;
(vii) the VL has at least 80% sequence identity to the amino acid sequence set forth in SEQ ID NO:25;
(viii) the VH has at least 80% sequence identity to the amino acid sequence set forth in SEQ ID NO:18 and the VL has at least 80% sequence identity to the amino acid sequence set forth in SEQ ID NO:19;
(ix) the VH has at least 80% sequence identity to the amino acid sequence set forth in SEQ ID NO:20 and the VL has at least 80% sequence identity to the amino acid sequence set forth in SEQ ID NO:25;
(x) the VH has at least 80% sequence identity to the amino acid sequence set forth in SEQ ID NO:23 and the VL has at least 80% sequence identity to the amino acid sequence set forth in SEQ ID NO:25;
(xi) the VH has at least 80% sequence identity to the amino acid sequence set forth in SEQ ID NO:24 and the VL has at least 80% sequence identity to the amino acid sequence set forth in SEQ ID NO:25; or
(xii) the VH has at least 80% sequence identity to the amino acid sequence set forth in SEQ ID NO:22 and the VL has at least 80% sequence identity to the amino acid sequence set forth in SEQ ID NO:25.

25. The antibody of claim 22, wherein:
(i) the VH has at least 90% sequence identity to the amino acid sequence set forth in SEQ ID NO:18;
(ii) the VH has at least 90% sequence identity to the amino acid sequence set forth in SEQ ID NO:20;
(iii) the VH has at least 90% sequence identity to the amino acid sequence set forth in SEQ ID NO:23;
(iv) the VH has at least 90% sequence identity to the amino acid sequence set forth in SEQ ID NO:24;
(v) the VH has at least 90% sequence identity to the amino acid sequence set forth in SEQ ID NO:22;
(vi) the VL has at least 90% sequence identity to the amino acid sequence set forth in SEQ ID NO:19;
(vii) the VL has at least 90% sequence identity to the amino acid sequence set forth in SEQ ID NO:25;
(viii) the VH has at least 90% sequence identity to the amino acid sequence set forth in SEQ ID NO:18 and the VL has at least 90% sequence identity to the amino acid sequence set forth in SEQ ID NO:19;
(ix) the VH has at least 90% sequence identity to the amino acid sequence set forth in SEQ ID NO:20 and the VL has at least 90% sequence identity to the amino acid sequence set forth in SEQ ID NO:25;

(x) the VH has at least 90% sequence identity to the amino acid sequence set forth in SEQ ID NO:23 and the VL has at least 90% sequence identity to the amino acid sequence set forth in SEQ ID NO:25;
(xi) the VH has at least 90% sequence identity to the amino acid sequence set forth in SEQ ID NO:24 and the VL has at least 90% sequence identity to the amino acid sequence set forth in SEQ ID NO:25; or
(xii) the VH has at least 90% sequence identity to the amino acid sequence set forth in SEQ ID NO:22 and the VL has at least 90% sequence identity to the amino acid sequence set forth in SEQ ID NO:25.

26. The antibody of claim 22, wherein:
the VH comprises the amino acid sequence set forth in SEQ ID NO:18 and the VL comprises the amino acid sequence set forth in SEQ ID NO:19;
(ii) the VH comprises the amino acid sequence set forth in SEQ ID NO:20 and the VL comprises the amino acid sequence set forth in SEQ ID NO:25;
(iii) the VH comprises the amino acid sequence set forth in SEQ ID NO:23 and the VL comprises the amino acid sequence set forth in SEQ ID NO:25; or
(iv) the VH comprises the amino acid sequence set forth in SEQ ID NO:24 and the VL comprises the amino acid sequence set forth in SEQ ID NO:25.

27. The antibody of claim 22, which is an scFv comprising the VH and the VL, wherein the VH comprises the amino acid sequence set forth in SEQ ID NO:110 and the VL comprises the amino acid sequence set forth in SEQ ID NO:112.

28. The antibody of claim 22, which is an scFv comprising the amino acid sequence of SEQ ID NO:113 or SEQ ID NO:119.

29. The antibody of claim 22, which is a chimeric or humanized antibody.

30. The antibody of claim 22, which is a bispecific antibody or a multispecific antibody.

31. The antibody of claim 22, which is a Fab, Fab', F(ab')$_2$, Fv, scFv, (scFv)$_2$, single chain antibody, dual variable region antibody, diabody, or nanobody.

32. The antibody of claim 22, which is an IgG1 antibody, an IgG2 antibody, or an IgG4 antibody.

33. The antibody of claim 22, which has at least one or more of the following properties:
(i) does not bind C3b at a detectable level;
(ii) binds C3 with an affinity that is at least 50-fold greater than the antibody's affinity to C3b;
(iii) binds C3 with an affinity that is at least 100-fold greater than the antibody's affinity to C3b;
(iv) is an antagonist of C3;
(v) inhibits C3 activity;
(vi) inhibits complement activation;
(v) inhibits activation of the classical complement pathway;
(vi) inhibits activation of the alternative complement pathway; and
(vii) inhibits activation of the classical complement pathway and the alternative complement pathway.

34. An antibody that specifically binds human complement component C3 (SEQ ID NO:2), wherein the antibody comprises a VH comprising the amino acid sequence set forth in SEQ ID NO:22 and a VL comprising the amino acid sequence set forth in SEQ ID NO:25.

35. An antibody that specifically binds human complement component C3 (SEQ ID NO:2), wherein the antibody comprises a heavy chain and a light chain, wherein:
(a) the heavy chain comprises a VH comprising the amino acid sequence set forth in any one of SEQ ID NOs:20 and 22-24 and a heavy chain constant region comprising the amino acid sequence set forth in any one of SEQ ID NOs: 34-36 and 109; and
(b) the light chain comprises the amino acid sequence of SEQ ID NO: 31.

36. A pharmaceutical composition comprising the antibody of claim 22 and a pharmaceutically acceptable carrier.

37. A pharmaceutical composition comprising the antibody of claim 23 and a pharmaceutically acceptable carrier.

38. A pharmaceutical composition comprising the antibody of claim 26 and a pharmaceutically acceptable carrier.

39. A pharmaceutical composition comprising the antibody of claim 34 and a pharmaceutically acceptable carrier.

40. A pharmaceutical composition comprising the antibody of claim 35 and a pharmaceutically acceptable carrier.

41. The antibody of claim 2, wherein: (i) the VH comprises the VH CDR1 comprising the amino acid sequence set forth in SEQ ID NO:121, the VH CDR2 comprising the amino acid sequence set forth in SEQ ID NO:14, and the VH CDR3 comprising the amino acid sequence set forth in SEQ ID NO:9; and (ii) the VL comprises the VL CDR1 comprising the amino acid sequence set forth in SEQ ID NO:10, the VL CDR2 comprising the amino acid sequence set forth in SEQ ID NO:11, and the VL CDR3 comprising the amino acid sequence set forth in SEQ ID NO:12.

42. A pharmaceutical composition comprising the antibody of claim 41.

43. The antibody of claim 2, wherein: (i) the VH comprises the VH CDR1 comprising the amino acid sequence set forth in SEQ ID NO:7, the VH CDR2 comprising the amino acid sequence set forth in SEQ ID NO:14, and the VH CDR3 comprising the amino acid sequence set forth in SEQ ID NO:9; and (ii) the VL comprises the VL CDR1 comprising the amino acid sequence set forth in SEQ ID NO:10, the VL CDR2 comprising the amino acid sequence set forth in SEQ ID NO:11, and the VL CDR3 comprising the amino acid sequence set forth in SEQ ID NO:12.

44. A pharmaceutical composition comprising the antibody of claim 43.

* * * * *

UNITED STATES PATENT AND TRADEMARK OFFICE
CERTIFICATE OF CORRECTION

PATENT NO. : 11,136,381 B2
APPLICATION NO. : 16/371684
DATED : October 5, 2021
INVENTOR(S) : Dana Yen Mei Duey et al.

It is certified that error appears in the above-identified patent and that said Letters Patent is hereby corrected as shown below:

On the Title Page

Line 10, In item (56) "Other Publications":
Delete "complemetarity-determining" and insert -- complementarity-determining --, therefor.

In the Claims

Column 307, Line 11, In Claim 10:
Delete "(v)" and insert -- (vii) --, therefor.

Column 307, Line 13, In Claim 10:
Delete "(vi)" and insert -- (viii) --, therefor.

Column 307, Line 15, In Claim 10:
Delete "(vii)" and insert -- (ix) --, therefor.

Column 313, Line 14, in Claim 26:
Before "the VH" insert -- (i) --.

Column 313, Line 53, in Claim 33:
Delete "(v)" and insert -- (vii) --, therefor.

Column 314, Line 1, In Claim 33:
Delete "(vi)" and insert -- (viii) --, therefor.

Column 314, Line 3, In Claim 33:
Delete "(vii)" and insert -- (ix) --, therefor.

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*